US007563775B2

(12) United States Patent
Villafuerte

(10) Patent No.: US 7,563,775 B2
(45) Date of Patent: Jul. 21, 2009

(54) INSULIN-RESPONSIVE DNA BINDING PROTEIN-1 AND METHODS TO REGULATE INSULIN-RESPONSIVE GENES

(75) Inventor: Betty C. Villafuerte, 3611 Brownsboro Rd., #5A, Louisville, KY (US) 40207

(73) Assignee: Betty C. Villafuerte, Lousiville, KY (US)

( * ) Notice: Subject to any disclaimer, the term of this patent is extended or adjusted under 35 U.S.C. 154(b) by 3 days.

(21) Appl. No.: 10/310,002

(22) Filed: Dec. 4, 2002

(65) Prior Publication Data

US 2003/0125296 A1 Jul. 3, 2003

Related U.S. Application Data

(63) Continuation-in-part of application No. 09/703,559, filed on Nov. 1, 2000, now abandoned.

(60) Provisional application No. 60/336,585, filed on Dec. 4, 2001, provisional application No. 60/390,000, filed on Jun. 18, 2002.

(51) Int. Cl.
*A01N 43/04* (2006.01)
*A01N 63/00* (2006.01)
*A61K 31/70* (2006.01)
*A61K 48/00* (2006.01)

(52) U.S. Cl. ........................................ 514/44; 424/93.2

(58) Field of Classification Search ................. 514/342, 514/212.01, 309, 412, 593, 866, 44; 424/93.2
See application file for complete search history.

(56) References Cited

U.S. PATENT DOCUMENTS 3,912,807 A * 10/1975 Alburn et al. ................. 514/11
5,972,973 A * 10/1999 Whitcomb .................. 514/342

OTHER PUBLICATIONS

Guyton, "Insulin, Glucagon and Diabetes Mellitus" in Textbook of Medical Physiology, W.B. Saunders Co., Philadelphia, 1991.*
"Definition, Diagnosis and Classification of Diabetes Mellitus", Report of a WHO Consultation, ā World Health Organization 1999, available at http://www.staff.ncl.ac.uk/philip.home/who_dmc.htm. *
Skolnick et al. (2000) Trends Biotechnol. 18:34-39.*
Smith et al. (1997) Nature Biotechnol. 15:1222-1223.*
Villafuerte et al. (2004) J. Biol. Chem. 279:36650-36659.*
Richards (1997) Cell Mol. Life Sci. 53:790-802.*
Nicholson et al. (2002) Cell. Signal. 14:381-395.*
Arbabi et al. (2002) Crit. Care. Med. 30:S74-S79.*
Verma et al. (1997) Nature vol. 389: 239-242.*
Orkin et al. (1995) Report and recommendations of the panel to assess the NIH investment in research on gene therapy. Available at http://www.nih.gov/news/panelrep.html.*
Eck et al. (1996) Goodman & Gilman's The Pharmacological Basis of Therapeutics, 9th Edition, Chapter 5, McGraw-Hill, NY.*
Ross et al. (1996) Human gene Therapy, vol. 7, pp. 1781-1790.*
Rubanyi (2001) Mol. Aspects Med. 22:113-142.*
UniProtKB/Swiss-Prot entry P31749, 2006.*
UniProtKB/Swiss-Prot entry P28482, 2006.*
Marshall (1995) Science 269:1050-1055.*
Xing et al. (2005) PLoS Genetics 4:0323-0328.*
Van de Peer (2006) Heredity 96:204-205.*
Gibbs et al. Nature, 2004, 428:493-521.*
"Cloning and characterization of three human forkhead gene that comprise an FKHR-like gene subfamily"; Anderson, M.J., Viars, C.S., Czekay, S., Cavenee, W.K. & Arden, J.C., Genomics 47, 187-199 (1998).
"Notches signaling in the nervous system. Pieces still missing from the puzzle"; Baker, N.E., BioEssays 22, 264-273 (2000).
"CAP defines a second signaling pathway required for insulin-stimulated glucose transport"; Baumann, C.A., et al., Nature 407, 202-207 (2000).
"Protein kinase B/Akt-mediated phosphorylation promotes nuclear exclusion of the winged helix transcription factor FKHR1"; Biggs, I.W.A., Meisenhelder, J., Hunter, T., Cavenee, W.K. & Arden, K.C., Proc. Natl. Acad. Sci. USA 96., 7421-7426 (1999).
"Preferential Measurement of Insulin-Like Growth Factor (IGF) I-Related Peptides in Serum with the Aid of IGF-Binding Proteins (IGF BPs) Produced by Rat Liver in Culture. Estimation of Serum IGF BP Levels*"; Binoux, et al., J. Clin. Endocrinol. Metab. 59:453-462 (1984).
"Inhibitory Diffusible Factor 45 Bifunctional Activity"; Blat, et al., J. Biol. Chem. 264(21): 12449-12454 (1989).
"A Specific Radioimmunoassay for the Growth Hormone (GH)-Dependent Somatomedin-Binding Protein: Its Use for Diagnosis of GH Deficiency"; Blum, et al., J. Clin. Endocrinol. Metab. 70: 1292-1298 (1990).
"Insulin-Like Growth Factor I (IGF-I)-Binding Protein Complex Is a Better Mitogen than Free IGF-I"; Blum, et al., Endocrinol. 125: 766-772 (1989).

(Continued)

*Primary Examiner*—Michael C. Wilson
(74) *Attorney, Agent, or Firm*—Intellectual Property Connections, Inc.; Hsiu-Ming Saunders

(57) ABSTRACT

The present invention relates to the novel protein Insulin-Responsive DNA Binding Protein-1 (IRDBP-1) and nucleotide sequences that encode it. IRDBP-1 binds to nucleic acid regions of genes that respond when cells are exposed to insulin. IRDBP-1 regulates genes important in mediating the insulin response in mammals and in regulating conditions such as diabetes, obesity, insulin-resistant syndrome and cell proliferative disorders. The present invention provides nucleic acids useful as probes for detecting nucleic acids encoding regions of the IRDBP-1 protein. Within the scope of the present invention are recombinant cells, tissues and animals containing non-naturally occurring recombinant nucleic acid molecules encoding IRDBP-1, including expression vectors, antibodies specific for IRDBP-1, assays for IRDBP-1 polypeptide, and methods relating to all of the foregoing, the development of therapeutic and diagnostic agents that mimic, facilitate or inhibit the action of IRDBP-1, and/or are based on relationships to the structure and action of IRDBP-1.

17 Claims, 88 Drawing Sheets

OTHER PUBLICATIONS

"Induction of the growth inhibitor IGF-binding protein 3 by p53"; Buckbinder, et al., Nature 37: 646-649 (1995).

"Purified Preparations of the Amniotic Fluid-Derived Insulin-Like Growth Factor-Binding Protein Contain Multimeric Forms that Are Biologically Active"; Busby, et al., Endocrinol. 125(2): 773-776 (1989).

"REST: A Mammalian Silencer Protein That Restricts Sodium Channel Gene Expression to Neurons"; Chong, et al., Cell 80: 949-957 (1995).

"Protein Kinase B/Akt Mediates Effects of Insulin on Hepatic Insulin-like Growth Factor-binding Protein-1 Gene Expression through a Conserved Insulin Response Sequence"; Cichy, et al., J. Biol. Chem. 273: 6483-6487 (1998).

"Pathogenesis of NIDDM"; Defronzo, et al., Diabetes Care 15: 318-368 (1992).

"A Multifaceted Syndrome Responsible for NIDDM, Obesity, Hypertension, Dyslipidemia, and Atherosclerotic Cardiovascular Disease"; Defronzo & Ferrannini, Diabetes Care 14: 173-194 (1991).

"Early Metabolic Defects in Persons at Increased Risk for Non-Insulin-Dependent Diabetes Mellitus"; Eriksson, et al., N. Eng. J. Med. 321(6): 337-343 (1989).

"The protein kinase encoded by the Akt proto-oncogene is a target of the PDGF-activated phosphatidylinositol 3-kinase"; Franke, T.F., et al., Cell 81, 727-736 (1995).

"Alphavirus-based expression vectors: Strategies and applications"; Frolov, et al., Proc. Natl. Acad. Sci. 93: 11371-11377 (1996)

"Proteolytic Degradation of Insulin-Like Growth Factor (IGF)-Binding Protein-3 by Porcine Ovarian Granulosa Cells in Culture: Regulation by IGF-I*"; Grimes & Hammond, Endocrinol. 134: 337-343 (1994).

"Undiagnosed NIDDM: Clinical and Public Health Issues"; Harris, Diabetes Care 16: 642-652 (1993).

"Physical Activity and Reduced Occurrence of Non-Insulin-Dependent Diabetes Mellitus"; Helmrich, et al., N. Eng. J. Med. 325: 147-152 (1991).

"A ten-minute DNA preparation from yeast efficiently releases autonomous plasmids for transformation of *Escherichia coli*"; Hoffman & Winston, Gene 57: 267-272 (1987).

"Evidence of Enzymatic Degradation of Insulin-Like Growth Factor-Binding Proteins in the 150K Complex during Pregnancy"; Hossenlopp, et al., J. Clin. Endocrinol. & Metab. 71: 797-805 (1990).

"Estradiol and Antiestrogens Regulate a Growth Inhibitory Insulin-like Growth Factor Binding Protein 3 Autocrine Loop in Human Breast Cancer Cells"; Huynh, et al., J. Biol. Chem. 271(2): 1016-1021 (1996).

"A Consensus Insulin Response Element Is Activated by an ETS-related Transcription Factor"; Jacob, et al., J. Biol. Chem. 270: 27773-27779 (1995).

"Insulin Action, Diabetogenes, and the Cause of Type II Diabetes"; Kahn, Diabetes 43: 1066-1084 (1994).

"Differential regulation of insulin receptor substrates-1 and -2 (IRS-1 and IRS-2) and phosphatidylinositol 3-kinase isoforms in liver and muscle of the obese diabetic (ob/ob) mouse"; Kerouz, N.J., Horsch, D., Pons, S., Kahn, C.R., J. Clin. Invest. 100: 3164-3172 (1997).

"Notch/LIN-12 signaling: transduction by regulated protein splicing"; Kimble, J., Henderson, S. & Crittenden, S., TIBS 23, 353-357 (1998).

"Expression of a constitutively active Akt Ser/Thr kinase in 3T3-L1 adipocytes stimulates glucose uptake and glucose transporter 4 translocation"; Kohn, A.D., Summers, S.A., Birnbaum, M.J. & Roth, R.A., J. Biol. Chem. 271, 31372-31378 (1996).

"Forced unfolding of the fibronectin type III module reveals a tensile molecular recognition switch"; Krammer, A., Lu, H., Isralewitz, B., Schulten, J. & Vogel, V., Proc. Natl. Acad. Sci. USA 96, 1351-1356 (1999).

"Raf-1 activates MAP kinase-kinase"; Kyriakis, et al., Nature 358: 417-421 (1992).

"Targeted oncogene activation by site-specific recombination in transgenic mice"; Lakso, et al., Proc. Natl. Acad. Sci. 89: 6232-6236 (1992).

"Nuclear Transport of Insulin-Like Growth Factor-I and Insulin-Like Growth Factor Binding Protein-3 in Opossum Kidney Cells"; Li, et al., Endocrinol. 138: 1763-1766 (1997).

"Isolation of *ORC6*, a Component of the Yeast Origin Recognition Complex by a One-Hybrid System"; Li & Herskowitz, Science 1252: 1870-1873 (1993).

"Impaired Glucose Tolerance As A Disorder of Insulin Action"; Lillioja, et al., N. Eng. J. Med. 318(19): 1217-1225 (1988).

"The SH2 and SH3 Domain-Containing Protein GRB2 Links Receptor Tyrosine Kinases to ras Signaling"; Lowenstein, et al., Cell 70: 431-442 (1992).

"Insulin selectively stimulates nuclear phosphoinositide-specific phospholipase C (PI-PLC) β1 activity through a mitrogen-activated protein (MAP) kinase-dependent serine phosphorylation"; Martelli, A.M., et al., FEBS Letters 486, 230-236 (2000).

"Insulin-Like Growth Factor-I (IGF-I) and Transforming Growth Factor-β1 Release IGF-Binding Protein-3 from Human Fibroblasts by Different Mechanisms"; Martin, et al., Endocrinol. 131: 1703-1710 (1992).

"Insulin-like Growth Factor-binding Protein from Human Plasma"; Martin & Baxter, J. Biol. Chem. 261: 8754-8760 (1986).

"Abnormal Regulation of Protein Tyrosine Phosphatase Activities in Skeletal Muscle of Insulin-Resistant Humans"; McGuire, et al., Diabetes 40: 939-942 (1991).

"Translocation and activation of Akt2 in response to stimulation by insulin"; Mitsuuchi, Y., Johnson, S.W., Moonblatt, S. & Testa, J.R., J. Cell. Biochem. 70, 433-441 (1998).

"Genetically engineered poxviruses for recombinant gene expression, vaccination, and safety"; Moss, Proc. Natl. Acad. Sci. 93: 11341-11348 (1996).

"Potential Convergence of Insulin and cAMP Signal Transduction Systems at the Phosphoenolpyruvate Carboxykinase (PEPCK) Gene Promoter through CCAAT/Enhancer Binding Protein (C/EBP)*"; O'Brien, et al., J. Biol. Chem. 269: 30419-30428 (1994).

"Transforming Growth Factor-β-induced Cell Growth Inhibition in Human Breast Cancer Cells Is Mediated through Insulin-like Growth Factor-binding Protein-3 Action"; Oh, et al., J. Biol. Chem. 270: 13589-13592 (1995).

"PPARγ and the treatment of insulin resistance"; Olefsky, J.M., Saltiel, A.R., TEM 11: 362-367 (2000).

"Tissue- and site-specific DNA recombination in transgenic mice"; Orban, et al., Proc. Natl. Acad. Sci. 89: 6861-6865 (1992).

"Applications of pox virus vectors to vaccination: An update"; Paoletti, E., Proc. Natl. Acad. Sci. 93: 11349-11353 (1996).

"A Novel Transforming Protein (SHC) with an SH2 Domain Is Implicated in Mitogenic Signal Transduction"; Pellicci, et al., Cell 70: 93-104 (1992).

"Molecular basis of insulin-stimulated GLUT4 vesicle trafficking. Location! Location! Location!"; Pessin, J.E., Thurmond, D.C., Elmendord, J.S., Coker, K.J. & Okada, S. J. Biol. Chem. 274, 2593-9596 (1999).

"Insulin-like Growth Factor (IGF)-binding Protein-3 Induces Apoptosis and Mediates the Effects of Transforming Growth Factor-β1 on Programmed Cell Death through a p53-and IGF-independent Mechanism"; Rajah, et al., J. Biol. Chem. 272(18): 12181-12188 (1997).

"The function of herpes simplex virus genes: A primer for genetic engineering of novel vectors"; Roizman, Proc. Natl. Acad. Sci. 93: 11307-11302 (1996).

"Phosphorylation of the transcription factor forkhead family member FKHR by protein kinase"; Rena, G., Guo, S., Unterman, T.G. & Cohen, P., J. Biol. Chem. 274, 17179-17183 (1999).

"Insulin-Like Growth Factor Carrier Proteins in Neonatal and Adult Rat Serum Are Immunologically Different: Demonstration Using a New Radioimmunassay for the Carrier Protein from BRL-3A Rat Liver Cells"; Romanus, et al., Endocrinol. 118: 1743-1758 (1986).

"Health Care Expenditures for People with Diabetes Mellitus, 1992*"; Rubin, et al., J. Clin. Endocrinol. 78: 809A-809F (1994).

"Impaired Activation of Glycogen Synthase in People at Increased Risk for Developing NIDDM"; Schanlin-Jantti, et al., Diabetes 41: 598-604 (1992).

"Glucose transporters and insulin action: implications for insulin resistance and diabetes mellitus"; Shepherd, P.R. & Kahn, B.B. N. Eng. J. Med. 341, 248-257 (1999).

"Identification of Five Different Insulin-like Growth Factor Binding Proteins (IGFBPs) from Adult Rat Serum and Molecular Cloning of a Novel IGFBP-5 in Rat and Human*"; Shimasaki, et al., J. Biol. Chem. 266: 10646-10653 (1991).

"Troglitazone not only increases GLUT4 but also induces its translocation in rat adipocytes"; Shintani, M., et al., Diabetes 50, 2296-2300 (2001).

"Cloning of PI3 Kinase-Associated p85 Utilizing a Novel Method for Expression/Cloning of Target Proteins for Receptor Tyrosine Kinases"; Skolnik, et al., Cell 65: 83-90 (1991).

"Insulin-stimulated MAP-2 kinase phosphorylates and activates ribosomal protein S6 kinase II"; Sturgill, et al., Nature 334: 715-718 (1988).

"Expression and function of IRS-1 in insulin signal transmission"; Sun, X.L., Miralpeix, M., Myers, Jr., M.G., Glasheen, E.M., Backer, J.M., Kahn, C.R., White, M.F., J. Biol. Chem. 2657: 22662-22672 (1992).

"Structure of the insulin receptor substrate IRS-1 defines a unique signal transduction protein"; Sun, X.L., Rothenberg, P., Kahn, C.R., Backer, J.M., Araki, E., Wilden, P.A., Cahill, D.A., Goldstein, B.J., White, M.F., Nature 352: 73-77 (1991).

"Negative regulation of the forkhead transcription factor FKHR by Akt"; J. Biol. Chem. 274, 16741-16746 (1999).

"Insulin Resistance or Insulin Deficiency—Which Is the Primary Cause of NIDDM?"; Taylor, et al., Diabetes 43: 735-774 (1994).

"Potential role of protein kinase B in insulin-induced glucose transport, glycogen synthesis, and protein systhesis"; Ueki, K., et al., J. Biol. Chem. 273, 5315-5322 (1998).

"Multihormonal Regulation of Insulin-Like Growth Factor-Binding Protein-1 in Rat H4IIE Hepatoma Cells: The Dominant Role of Insulin*"; Unterman, et al., Endocrinol. 128: 2693-2701 (1991).

"Glucocorticoid Regulation of Insulin-Like Growth Factor-Binding Protein-3"; Villafuerte, et al., Endocrinol. 136: 1928-1933 (1995).

"Identification of an Insulin-responsive Element in the Rat Insulin-like Growth Factor-binding Protein-3 Gene"; Villafuerte, et al., J. Biol. Chem. 272: 5024-5030 (1997).

"Insulin and Insulin-Like Growth Factor-I Regulate Hepatic Insulin-Like Growth Factor Binding Protein-3 by Different Mechanisms"; Villafuerte, et al., Mol. Endocrinol. 10: 622-630 (1996).

"Molecular cloning of the olfactory neuronal transcription factor Olf-1 by genetic selection in yeast"; Wang & Reed, Nature 364: 121-126 (1993).

"ras Mediates Nerve Growth Factor Receptor Modulation of Three Signal-Transducing Protein Kinases: MAP Kinase, Raf-1, and RSK"; Wood, et al., Cell 68: 1041-1050 (1992).

"Troglitazone induces GLUT4 translocation in L6 myocytes"; Yonemitsu, S., Nishimura, H., Shintani, M., Inoue, R., Yamamoto, Y., Masuzaki, H., Ogawa, Y., Hosoda, K., Inoue, G., Hayashi, T., Nakao, K, Diabetes 50: 1093-1101 (2001).

"The 16-kDa Proteolytic Fragment of Insulin-like Growth Factor (IGF) Binding Protein-3 Inhibits the Mitogenic Action of Fibroblast Growth Factor on Mouse Fibroblasts with a Targeted Disruption of the Type 1 IGF Receptor Gene"; Zadeh & Binoux, Endocrinol. 138: 3069-3072 (1997).

"Insulin Receptor Substrate-2 (IRS-2) Can Mediate the Action of Insulin to Stimulate Translocation of GLUT4 to the Cell Surface in Rate Adipose Cells"; Zhou, et al., J. Biol. Chem. 272: 29829-29833 (1997).

* cited by examiner

SEQ ID NO: 2

CTTAGATCATGTTTCACTACATGCCCTTTGACCTCTCACCACTTCCTTCTGTCCATTCCT
LeuArgSerCysPheThrThrCysProLeuThrSerHisHisPheLeuLeuSerIlePro
CATCCAGGGCCTTTGCCTCCAGCAAACCTGACTGCCTCTCGAGTCACAGCGACCTCTGCC
HisProGlyProLeuProProAlaAsnLeuThrAlaSerArgValThrAlaThrSerAla
CATATGGTCTGGGACCCGCCCACTCCAGGCATCTCACTGGAGGCTTACGTCATCAATGTG
HisMetValTrpAspProProThrProGlyIleSerLeuGluAlaTyrValIleAsnVal
ACCACCAGTCAGAATACCAAGAGCCGCTACATCCCCAATGGGAAGCTGGTGTCCTATACG
ThrThrSerGlnAsnThrLysSerArgTyrIleProAsnGlyLysLeuValSerTyrThr
GTGCGTGATCTGATGCCAGGTCGGCGGTACCAGCTCTCGGTCACAGCGGTGCAGAGCACA
ValArgAspLeuMetProGlyArgArgTyrGlnLeuSerValThrAlaValGlnSerThr
GAGCAGGGCCAGCTGCACAGTGAGCCTGCGCACCTCTACATCATCACCTGTGAGTTAGTT
GluGlnGlyGlnLeuHisSerGluProAlaHisLeuTyrIleIleThrCysGluLeuVal
CCCTGA
Pro
CAGGACGGCCTGGGATGCTGTTCAAACCCACGGCTGCTGTTTGCTGCTGTTGGGGTGTGG
GATCCTTGCCCAGAAGAGGCAGCATAGACAACTTGCATGGGCCATTCCTCGGAACAGAGA
TGTAGGCATAAGGGTGAGGAAGGACAGTTGACAGCATGAGCCTCATCTTACACTGTTTTA
CCAGTCCAATCCCAGCAGGCTTAGCAGCAAATACAGGACCTCACCGTGAAAGAGCTACCA
AGCAGGCAGCAATGCCGAGGCCCAGGCCTGACCCAAAAGGGGCCACTGGGCATGAACACC
AGAGGGCGGGGCAAGAGACTACAAGTAGCTGGGTAGGGCAGGAAGGGTAAGAATGAAAAG
CTGGGGTGTAGACATTCAGGTGGCCACATTAACAACCTCACTCTATTCCCAAGGTGACAG
GGCACTCAGCTGGAGCCCAAAAGTGTCCTGTGTGCCCCTTATTACCTTCTCAAACCTTAC
GTGAGGTGCTGTATGAGAGAGTTTCAGGAGTGCAGGGAGCAGAACTCAGCGAGAAAACAA
GCAGAAGGTGCACAAGAAAACAAGACAGCGGGTCGACGCGGCCGCG

*Fig. 1*

SEQ ID NO: 3

```
Leu Arg Ser Cys Phe Thr Thr Cys Pro Leu Thr Ser His His Phe Leu
 1              5                   10                  15
Leu Ser Ile Pro His Pro Gly Pro Leu Pro Pro Ala Asn Leu Thr Ala
            20                  25                  30
Ser Arg Val Thr Ala Thr Ser Ala His Met Val Trp Asp Pro Pro Thr
        35                  40                  45
Pro Gly Ile Ser Leu Glu Ala Tyr Val Ile Asn Val Thr Thr Ser Gln
    50                  55                  60
Asn Thr Lys Ser Arg Tyr Ile Pro Asn Gly Lys Leu Val Ser Tyr Thr
65                  70                  75                  80
Val Arg Asp Leu Met Pro Gly Arg Arg Tyr Gln Leu Ser Val Thr Ala
                85                  90                  95
Val Gln Ser Thr Glu Gln Gly Gln Leu His Ser Glu Pro Ala His Leu
            100                 105                 110
Tyr Ile Ile Thr Cys Glu Leu Val Pro
        115                 120
```

*Fig. 2*

SEQ ID NO: 4

TCGAGTCACAGCGACCTCTGCCCATATGGTCTGGGACCCGCCCACTCCAGGCATCTCACT
GGAGGCTTACGTCATCAATGTGACCACCAGTCAGAATACCAAGAGCCGCTACATCCCCAA
TGGGAAGCTGGTGTCCCGGTGCGTGATCTGATGCCAGGTCGGCGGTAC

*Fig. 3*

SEQ ID NO: 5

FIG. 4A, PART 1 (SEQ ID NO: 8)

TGCCTGAATGGAGGCTGTTGTGTTGACCTGGTTGGAAACTACAGCTGTATTTGTGTGGAG
CysLeuAsnGlyGlySerCysValAspLeuValGlyAsnTyrSerCysIleCysValGlu
CCCTTTGAAGGACCTCAGTGCGAGACAGGAAGCTACGTGGTGCCTTCGCCCTGCCTCTCC
ProPheGluGlyProGlnCysGluThrGlySerTyrValValProSerProCysLeuSer
AACCCCTGCCTGAACGGGGGCACCTGTGTGGATGCTGACCAGGGATACGTGTGCGAATGC
AsnProCysLeuAsnGlyGlyThrCysValAspAlaAspGlnGlyTyrValCysGluCys
CCTGAAGGTTTCATGGGCTTGGACTGCAGAGAGAGAATTCTCAATGACTGTGATTGCCGG
ProGluGlyPheMetGlyLeuAspCysArgGluArgIleLeuAsnAspCysAspCysArg
AATGGAGGCAGATGCCTGGGTGCCAACACCACCATCTGCCAGTGTCCTCCAGGCTCCTTT
AsnGlyGlyArgCysLeuGlyAlaAsnThrThrIleCysGlnCysProProGlySerPhe
GGGCTCCTCTGTGAATTTGAAGTCACAGCCACGCCCTGCAACATGAACACACAGTGTCCA
GlyLeuLeuCysGluPheGluValThrAlaThrProCysAsnMetAsnThrGlnCysPro
GATGGAGGVTACTGCATGGAGTATGGCGGAAGCTACCTATGTGTCTGCCACACGGACCAC
AspGlyGlyTyrCysMetGluTyrGlyGlySerTyrLeuCysValCysHisThrAspHis
AACATCAGCCATTCTCTGCCCTCGCCCTGCGACTCAGACCCATGCTTTAATGGAGGTTCC
AsnIleSerHisSerLeuProSerProCysAspSerAspProCysPheAsnGlyGlySer
TGTGACGCCCACGAGGACTCCTACACGTGCGAGTGCCCTCGTGGATTCCATGGCAGGCAC
CysAspAlaHisGluAspSerTyrThrCysGluCysProArgGlyPheHisGlyArgHis
TGCGAGAAAGCCCGGCCACACCTGTGCAGCTCAGGGCCCTGCCGGAATGGGGGCACATAC
CysGluLysAlaArgProHisLeuCysSerSerGlyProCysArgAsnGlyGlyThrTyr
AAGGAGACTGGTGACGAGTACCGCTGCACCTGCCCTTACCGGTTCACTGGGAGACACTGT
LysGluThrGlyAspGluTyrArgCysThrCysProTyrArgPheThrGlyArgHisCys
GAGATTGGAAAGCCAGACTCCTGTGCCTCTGGCCCCTGTCACAACGGTGGCACTTGTTTC
GluIleGlyLysProAspSerCysAlaSerGlyProCysHisAsnGlyGlyThrCysPhe
CACTACATTGGCAAATACAAGTGTGACTGCCCTCCAGGCTTCTCTGGTCGGCACTGTGAG
HisTyrIleGlyLysTyrLysCysAspCysProProGlyPheSerGlyArgHisCysGlu
ATAGCCCCCTCCCCCTGCTTCCGGAGCCCATGTATGAATGGGGGTATCTGCGAGGATCTA
IleAlaProSerProCysPheArgSerProCysMetAsnGlyGlyIleCysGluAspLeu
GGAACAGATTTCTCCTGCCACTGCCAACCAGGATATACAGGACACCGGTGTCAGGCAGAG
GlyThrAspPheSerCysHisCysGlnProGlyTyrThrGlyHisArgCysGlnAlaGlu
GTGGACTGCGGTCAGCCTGAGGAGGTAAAACATGCTACCATGCGTCTCAATGGAACTCGC
ValAspCysGlyGlnProGluGluValLysHisAlaThrMetArgLeuAsnGlyThrArg
ATGGGCTCGGTGGCCCTGTACACATGTGACCCCGGCTTCAGCCTGAGCGTCCTCAGCCAT
MetGlySerValAlaLeuTyrThrCysAspProGlyPheSerLeuSerValLeuSerHis
ATGCGTGTCTGTCAGCCACAAGGTGTCTGGAGCCAGCCTCCCCAGTGCATTGAAGTAGAT
MetArgValCysGlnProGlnGlyValTrpSerGlnProProGlnCysIleGluValAsp
GAGTGCCAGTCTCAGCCATACCTGCATAAAGGCTCCTGCCAGGACCTCATTGCTGGTTAC
GluCysGlnSerGlnProTyrLeuHisLysGlySerCysGlnAspLeuIleAlaGluTyr
CAGTGCCTCTGCAGCCCGGGGTACGAAGGAGTCCACTGTGAGCTAGAGACAGACGAGTGC
GlnCysLeuCysSerProGlyTyrGluGlyValHisCysGluLeuGluThrAspGluCys
CAAGCACAGCCCTGCAGAAATGGAGGCTCCTGCAGGGACCTCCCCGGGGCTTTCATCTGC
GlnAlaGlnProCysArgAsnGlyGlySerCysArgAspLeuProGlyAlaPheIleCys
CAGTGCCCTGAAGGTTTTGTTGGAACCCACTATGAAACAGAGGTGGATGCCTGTGCCTCC
GlnCysProGluGlyPheValGlyThrHisTyrGluThrGluValAspAlaCysAlaSer
AGCCCCTGCCAGCACGGAGGCCGGTGTGAGGACGGTGGTGGGGCCTACCTGTGCGTTTGT
SerProCysGlnHisGlyGlyArgCysGluAspGlyGlyGlyAlaTyrLeuCysValCys
CCAGAGGGCTTCTTCGGCTACAACTGTGAGACAGTGAGTAACCCCTGCTTCTCTAGCCCC
ProGluGlyPhePheGlyTyrAsnCysGluThrValSerAsnProCysPheSerSerPro
TGTGGGGGCCGCGGCTACTGCTTGGCCAGCAACGGGTCCCACAGCTGTACCTGCAAAGTG
CysGlyGlyArgGlyTyrCysLeuAlaSerAsnGlySerHisSerCysThrCysLysVal
GGCTACACAGGCAAGGACTGCACCAAAGAGCTCCTCCCACCAACAGCCCTCAGGGTAGAA

FIG. 4A (CONTINUED, PART 2)

GlyTyrThrGlyLysAspCysThrLysGluLeuLeuProProThrAlaLeuArgValGlu
AGGGTGGAGGAGAGTGGGGTCTCCATCTCCTGGAGCCCACCCGAGGGCACCACGGCCAGA
ArgValGluGluSerGlyValSerIleSerTrpSerProProGluGlyThrThrAlaArg
CAGGTGCTGGACGGCTATGCAGTCACCTATGCCTCCTCGGATGGATCGTCCAGGCGCACG
GlnValLeuAspGlyTyrAlaValThrTyrAlaSerSerAspGlySerSerArgArgThr
GACTTTGTGGACCGGAGCCGCTCCTCTCACCAGCTTCGGGCCCTGGCAGCCGGCCGTGCC
AspPheValAspArgSerArgSerSerHisGlnLeuArgAlaLeuAlaAlaGlyArgAla
TACAACATCTCTGTTTTCTCAGTCAAGAGAAACACTAACAACAAAAATGACATCAGCAGG
TyrAsnIleSerValPheSerValLysArgAsnThrAsnAsnLysAsnAspIleSerArg
CCTGCAGCCCTGCTCACCCGCACCCGACCCCGCCCTATTGAAGACTTCGAGGTCACCAAC
ProAlaAlaLeuLeuThrArgThrArgProArgProIleGluAspPheGluValThrAsn
ATTTCAGCCAATGCCATCTCAGTGCAGTGGGCTCTTCATAGGATCCAGCATGCCACTGTC
IleSerAlaAsnAlaIleSerValGlnTrpAlaLeuHisArgIleGlnHisAlaThrVal
AGCAGGGTTCGAGTGTCTGTCCTCTACCCTGAGGACACTGTGGTCCAGTCCACGGAGGTG
SerArgValArgValSerValLeuTyrProGluAspThrValValGlnSerThrGluVal
GACAGGAGTGTGGACCGCCTCACATTTGGGGACCTGCTGCCAGGGAGAAGATACAGTGTG
AspArgSerValAspArgLeuThrPheGlyAspLeuLeuProGlyArgArgTyrSerVal
CGGCTAACCACCCTCAGTGGGCCTGGAGGAGCTGAATATCCTACAGAGAGCCTGGCCTCA
ArgLeuThrThrLeuSerGlyProGlyGlyAlaGluTyrProThrGluSerLeuAlaSer
GCTCCGCTGAACGTGTGGACCCGGCCTTTGCCTCCAGCAAACCTGACTGCCTCTCGAGTC
AlaProLeuAsnValTrpThrArgProLeuProProAlaAsnLeuThrAlaSerArgVal
ACAGCGACCTCTGCCCATATGGTCTGGGACCCGCCCACTCCAGGCATCTCACTGGAGGCT
ThrAlaThrSerAlaHisMetValTrpAspProProThrProGlyIleSerLeuGluAla
TACGTCATCAATGTGACCACCAGTCAGAATACCAAGAGCCGCTACATCCCCAATGGGAAG
TyrValIleAsnValThrThrSerGlnAsnThrLysSerArgTyrIleProAsnGlyLys
CTGGTGTCCTATACGGTGCGTGATCTGATGCCAGGTCGGCGGTACCAGCTCTCGGTCACA
LeuValSerTyrThrValArgAspLeuMetProGlyArgArgTyrGlnLeuSerValThr
GCGGTGCAGAGCACAGAGCAGGGCCAGCTGCACAGTGAGCCTGCGCACCTCTACATCATC
AlaValGlnSerThrGluGlnGlyGlnLeuHisSerGluProAlaHisLeuTyrIleIle
ACCTCCCCCAGGGATGGCACCGACAGGCGCTGGCACCAGGGAGGACACCACTCACGGATG
ThrSerProArgAspGlyThrAspArgArgTrpHisGlnGlyGlyHisHisSerArgMet
CTCAGAAATAGGCCGGCCCCTTTGCGCCTGCCAGAACTGCGCCTCCTCAATGACCACGGT
LeuArgAsnArgProAlaProLeuArgLeuProGluLeuArgLeuLeuAsnAspHisGly
GCCCCTGAAACACCAACCCAGCCACCCAGGTTCTCAGAGCTTGTAGACGGAAGAGCAAGA
AlaProGluThrProThrGlnProProArgPheSerGluLeuValAspGlyArgAlaArg
GTGAGTGCCAGGTTTGGTGGATTGCCCAGCAGAGCAGTAACTGTGAGATCACAACCCACT
ValSerAlaArgPheGlyGlyLeuProSerArgAlaValThrValArgSerGlnProThr
ACTCCGGTGCCGCTCAAGAACACAGAGGCCCCTGAGCAGGCCCGTCTGGCCCTTCAGCTA
ThrProValProLeuLysAsnThrGluAlaProGluGlnAlaArgLeuAlaLeuGlnLeu
CCCAAGAACAACAGCAAGGACACAGAAAGTACCCCTGGCAGCTGTTCAGAAGACACCTGT
ProLysAsnAsnSerLysAspThrGluSerThrProGlySerCysSerGluAspThrCys
CAGAATGGAGGCACCTGTGTCCCAGGTGCCAATGCCCACAGCTGTGACTGCAGGCCTGGG
GlnAsnGlyGlyThrCysValProGlyAlaAsnAlaHisSerCysAspCysArgProGly
TTCAAAGGCAGACACTGTGAGCTTGCCTGTGAAAAAGTGCCCCGCCCCTGCACACGGCTG
PheLysGlyArgHisCysGluLeuAlaCysGluLysValProArgProCysThrArgLeu
TTCTCTGAGACCAAGTCATTTCCTGTCTGGGAAGGAGATGTCTGCCACCATGTGTATAAG
PheSerGluThrLysSerPheProValTrpGluGlyAspValCysHisHisValTyrLys
AAAGTCTACAAAGTTCACCAGGACGTGTGTTTTAAGGAGCGCTGCCAGAGCACAAGCCTC
LysValTyrLysValHisGlnAspValCysPheLysGluArgCysGlnSerThrSerLeu
AAAAGCTCAAACAGGAATCAAATTAA
LysLysLeuLysGlnGluSerAsn

FIG. 4B

CAGTCAAACACTGAAGAAATCTTAAGGTACATTCTCCTTCATACCAAGATCT
GTTGAGAACTGGAGACACCATCATACCCAGCACCTTGGACAACTGATGGTGCAAACTTAG
CACTGTGCTATTACAGACCCAACCAGGAAGGTTCCAGAATTCCCTGTCTATAGCCTCCCA
ATAGACATAACCTGGTCTGGCCTTCCATATGAATCCACTTTCAGGTGGAAATGACTCTCT
GGGGGAGGGGCAAATGCAGACCAGTTACAATGAGGCACAAGAATCACCTGGCCCCTTCAG
GACAGTGGGCCTGGGTGTTAGATGGATCAAGGATGCCAAACAATCCTGGGGGTGCTAGGA
AGGACCTAAGGACATACCCTCAAGCCCTATGAATAGCATTCTACTGGTGGAAAAGGGCGG
GAGCCTTGTCATGTAACCTGCAGGTGATCCTAAATAGAGCCTCTCACTGGGAGAGATATC
ATGGATCCTGGAATTCTAAGCACTAATAACCCTGAAGTGAAAGAAACTTTGCCTGCTTGA
TCCAGCATGTCCCACCCCACCCTCCCCATACATAAACTGTGAGATGTCAAAGGGCATTGG
AAAATTTTTTTCACAAGCCTGGGAAATACTGGGTTACACTACAGAGATCCCTGTATAGCC
TGAACTCAGCCCCAACACTGACTTACTGATGGGACATCAATTGGAAACGAGAGACTGGCT
GGCCAGAGACATTTCACTCCTCTCCCTTGGAGGAGCCAGAACAGTACATCTGTGCAGTGG
TGGGAGAGAGGCAGATCTGGAAGCCTGCCACTCCAGGAGTGAATCACCTTTGTTCTACAG
TGTAGGACGTGAAGGAGAAATGTCACCCAAAGGCCTAAGAACAAAGAAGAGCAAAGCAGT
TCTGGGCGAAGGTCATCCGAAGAGAAAAGTGTCTACAGTAAAAGGCAGGGCATCAGGAGA
GCGGGCTCTCAGACAGGCCTAAGCAGGGCCTGTGCATCTTGACCATTTCAGATGTGAAGA
CTGCAGGAAGAGCAGCTGACCAGACTCAAATCCTGTCTACTTAACAGCATCACCTTTTCA
CCTCAGCCCCCAAAAATGCACACAACACCCTCCAACACATGTGAGCAACTTCATTCTGGC
AAAGATCAAAAATCCACAAATTATTTGGTTTTAAAATATTTACATGGCAGTAAGTCAGAT
GAAATATTAATGCAAAAAAAGAAATATTAATGCATCCTTTAAGAACTCACAGAAAACTCA
TTTTTAGAAAAAAAAATGAGAATCCCTAGGTACTTATCACATAATGGCTTATAGAAAACC
TATTCTCAAAGCAACACACACACACACACACACACCCCATACGTACGTACATACATACATCT
AACACACACATGTGTGTGTATATATATATATATATATATATATATATATATATGACACAC
ACAAAGCAAAAATAATTATATCTTTTTAAAGATATATATTTTCTTTTAGGAAACAGTAAT
TACTGACAACGCTGCATTTGAAATACTCAAAAAGATACTACCGTTACAAAACTCCAGTTT
CTCAGGGACAGGTTTGGTATTGCCAGCTAAGAATCCCAAGGAGGAGACTGAGCTGCTTAA
GTCGGAGGGAGCAACAGTAATGGCCAAGTCGCCTGAGCCTCCTTCACAGTCACAGGATTC
AGAAAATGGATACATCAATGTGACTTCTCTAAAGGAGACATACCACACACAAGGGGACCG
GAAGCCAAAACTATGACCTCACGGGATCTGAAACAATACTAATCATGCCTACTAAGTCAG
AGCCTGGGTACAGAGGTGCAAACTGAGCTGGAGACGTCTCACAGAACACCCTGGACATCA
ACAAGGAGTCTTCAAAATCGCTTTTTAAACAGTCATTAAAATTTTTC

SEQ ID NO: 6

FIG. 5A

AATACCAAGAGCCGCTACATCCCCAATGGGAAGCTGGTGTCCTATACGGTGCGTGATCTG
AsnThrLysSerArgTyrIleProAsnGlyLysLeuValSerTyrThrValArgAspLeu
ATGCCAGGTCGGCGGTACCAGCTCTCGGTCACAGCGGTGCAGAGCACAGAGCAGGGCCAG
MetProGlyArgArgTyrGlnLeuSerValThrAlaValGlnSerThrGluGlnGlyGln
CTGCACAGTGAGCCTGCGCACCTCTACATCATCACCTCCCCCAGGGATGGCACCGACAGG
LeuHisSerGluProAlaHisLeuTyrIleIleThrSerProArgAspGlyThrAspArg
CGCTGGCACCAGGGAGGACACCACTCACGGATGCTCAGAAATAGGCCGGCCCCTTTGCGC
ArgTrpHisGlnGlyGlyHisHisSerArgMetLeuArgAsnArgProAlaProLeuArg
CTGCCAGAACTGCGCCTCCTCAATGACCACGGTGCCCCTGAAACACCAACCCAGCCACCC
LeuProGluLeuArgLeuLeuAsnAspHisGlyAlaProGluThrProThrGlnProPro
AGGTTCTCAGAGCTTGTAGACGGAAGAGCAAGAGTGAGTGCCAGGTTTGGTGGATTGCCC
ArgPheSerGluLeuValAspGlyArgAlaArgValSerAlaArgPheGlyGlyLeuPro
AGCAGAGCAGTAACTGTGAGATCACAACCCACTACTCCGGTGCCGCTCAAGAACACAGAG
SerArgAlaValThrValArgSerGlnProThrThrProValProLeuLysAsnThrGlu
GCCCCTGAGCAGGCCCGTCTGGCCCTTCAGCTACCCAAGAACAACAGCAAGGACACAGAA
AlaProGluGlnAlaArgLeuAlaLeuGlnLeuProLysAsnAsnSerLysAspThrGlu
AGTACCCCTGGCAGCTGTTCAGAAGACACCTGTCAGAATGGAGGCACCTGTGTCCCAGGT
SerThrProGlySerCysSerGluAspThrCysGlnAsnGlyGlyThrCysValProGly
GCCAATGCCCACAGCTGTGACTGCAGGCCTGGGTTCAAAGGCAGACACTGTGAGCTTGCC
AlaAsnAlaHisSerCysAspCysArgProGlyPheLysGlyArgHisCysGluLeuAla
TGTGAAAAAGTGCCCCGCCCCTGCACACGGCTGTTCTCTGAGACCAAGTCATTTCCTGTC
CysGluLysValProArgProCysThrArgLeuPheSerGluThrLysSerPheProVal
TGGGAAGGAGATGTCTGCCACCATGTGTATAAGAAAGTCTACAAAGTTCACCAGGACGTG
TrpGluGlyAspValCysHisHisValTyrLysLysValTyrLysValHisGlnAspVal
TGTTTTAAGGAGCGCTGCCAGAGCACAAGCCTCAAAAAGCTCAAACAGGAATCAAATTAA
CysPheLysGluArgCysGlnSerThrSerLeuLysLysLeuLysGlnGluSerAsn

FIG. 5B (PART 1)

CAGTCAAACACTGAAGAAATCTTAAGGTACATTCTCCTTCATACCAAGATCTGTTGAGAA
CTGGAGACACCATCATACCCAGCACCTTGGACAACTGATGGTGCAAACTTAGCACTGTGC
TATTACAGACCCAACCAGGAAGGTTCCAGAATTCCCTGTCTATAGCCTCCCAATAGACAT
AACCTGGTCTGGCCTTCCATATGAATCCACTTTCAGGTGGAAATGACTCTCTGGGGGAGG
GGCAAATGCAGACCAGTTACAATGTGGATCAAGGATGCCAAACAATCCTGGGGGTGCTAG
GAAGGACCTAAGGACATACCCTCAAGCCCTATGAATAGCATTCTACTGGTGGAAAAGGGC
GGGAGCCTTGTCATGTAACCTGCAGGTGATCCTAAATAGAGCCTCTCACTGGGAGAGATA
TCATGGATCCTGGAATTCTAAGCACTAATAACCCTGAAGTGAAAGAAACTTTGCCTGCTT
GATCCAGCATGTCCCACCCCACCCTCCCCATACATAAACTGTGAGATGTCAAAGGGCATT
GGAAAATTTTTTTCACAAGCCTGGGAAATACTGGGTTACACTACAGAGATCCCTGTATAG
CCTGAACTCAGCCCCAACACTGACTTACTGATGGGACATCAATTGGAAACGAGAGACTGG
CTGGCCAGAGACATTTCACTCCTCTCCCTTGGAGGAGCCAGAACAGTACATCTGTGCAGT
GGTGGGAGAGAGGCAGATCTGGAAGCCTGCCACTCCAGGAGTGAATCACCTTTGTTCTAC
AGTGTAGGACGTGAAGGAGAAATGTCACCCAAAGGCCTAAGAACAAAGAAGAGCAAAGCA
GTTCTGGGCGAAGGTCATCCGAAGAGAAAAGTGTCTACAGTAAAAGGCAGGGCATCAGGA
GAGCGGGCTCTCAGACAGGCCTAAGCAGGGCCTGTGCATCTTGACCATTTCAGATGTGAA
GACTGCAGGAAGAGCAGCTGACCAGACTCAAATCCTGTCTACTTAACAGCATCACCTTTT
ACCTCAGCCCCCAAAAATGCACACAACACCCTCCAACACATGTGAGCAACTTCATTCTGG
CAAAGATCAAAAATCCACAAATTATTTGGTTTTAAAATATTTACATGGCAGTAAGTCAGA
TGAAATATTAATGCAAAAAAAGAAATATTAATGCATCCTTTAAGAACTCACAGAAAACTC
ATTTTTAGAAAAAAAAATGAGAATCCCTAGGTACTTATCACATAATGGCTTATAGAAAAC
CTATTCTCAAAGCAACACACACACACACACACACACACACACACACACATCACACACACCCC
TTCTCTTTCTGAAGAAACCAGAATTCGCCATCCACAGCTGCCCTGAGAAAATGAGCAGTG
CCACCCGCCCCTAAGGAAAGGCAGCAGAGGACCAGCAAGCAGCAAACTTAAAGCCGGAGG

FIG. 5B (CONTINUED, PART 2)

CTGATCGCAAGTGTCCTAAGAGGTGCGTGTGTCCCTTCCATCCCGCCCTGCATCACAGCC
AGCTGGAATTCTGGCTCCTGGGGACAATGCCTGCTGCCTCCAGAGAAAGACTGGATATAA
AGAGGAGTGTGCCTCAGTTCACTGTTACTCCTTTTGTCAAAAGGACCGGCATGTGCTGGT
AATTCTGTCCACACCTCAAGGATTTCCAAAACCCAGGAAATGAGGTTCAAAACTTAAACG
CCAAGCTCCCAGCAGTAGGCAGTCTCCCCGAGATCTCTGTCCTCCAAATTCTAGAAAAGA
GACAGCCAGACATGCACACCCAAAGGACTCCTGCCAGGGAAGCAACAATGCACCCTGCTG
CAACCCAGGGTTGCTGTTTCCGCAGTTCTGGTCAATCCCTCTGTGGAGAGTTACCTGTGT
TACCAGGCTCTTTGTGATGCTTCTGTGCTCAGAAACCCACATCCAGATCCCAGTGCCAAG
AAAAAGACTCAGCTTTCACAAGAGATGCAAGAGAGGCTGTGCAGAAATAGATGGGCTCTA
CCCTGCTCCTCTTCTCATTTATACTGATGACCTAAAGAAGTGCTAATTCTACTATGGTGG
GGCTTAGACACTTGGTCTACAACTCAGGGGTGGCAGGGCAGGCAGATGCTCAGGCAGGAT
TTTGGGCTCCGCAGGTAGGATGACTTGTACCTCTGGCACACACCCAACCCTGCTACTGTA
CTGCCAACACCATCACAGATGTAGATAGCATAGCTGTGTCCCAATGAGACTGCATTTACA
AAAACAGGCAGCAGGCCATAGCTGGCAGCTTTATAAGATGATCTAGACCTCAGCCTTCCT
TCTGCGGAGAAAACCATCCTGAATGACAAGTTGGCATCAAGACATGAAAGACCCCTGAAC
TTTCATACAAGAAAAGCGATCAAGACCCCTGCTCTGAAACCTGAGGTAAACTTACACCCA
GAGCAGGAAGAGCTACCTGTTCAAACCTGTGACACAGGGCAGGCTGGCTCCAGGAGACAG
GGTCCAAGGCTTCTTGTAAGCTGTGCCCCAACTAGACAGCTGTGGTTCACCAAAACAAAA
ATATTTTACACAGCCTCCGCTTTCCATCCCACTCCGAACAAGGCTGTAAACAGCTGTCCT
CTCCCTGCAGTAACATCACAATCAGAAAAGCCGACATACCCTGACTCCTTGCTCCAGCCT
GAGCAGAGCTGACTAGAGATCCAGCACCAAGAACTACATCCCAACCAGAGAGGCCTCCTG
CCCTTCAGAGGTCATAAAAACACAGTTTGAAGCATAACCTTTTAAGTTTTATTCTCACTA
AAAACTTCTGAACCTATGTTATCACATAATTTTTTTCTCTTTCAAAAACTCACTACTGTA
CCTTAGATACTCGCTAGAGTCCTGGAGACCGCATAAGCTACAGCGTTAGCAGGGAGTTGC
AAGCTCAGGTGGCATCACTGAAGAGCAGATGGGATCTTTGTACTTTACTACTAACCTCAG
GGCCCTCACCGCCAGGCCGATGCTGCCACATTCCCATTTCCAGTTGGAGCCTGTGTTTCA
AACAAGAGTCAGCCTGCTGACTGCTGAGTGTGGAGTGGAGAAAGACTCGCTGGTGCTGAG
GAATTAGTGTATGACATTCCACACATGCGGTCTCTGCTTTCTTACATGCCTTTCTTATGC
AGACTAATTAAATCCCTCAAAACAGTCACTGTCCACTTAAGAAATGTCACAGTGGGGTT
GGGCATTTAGCTCAGTGGTAGAGGGCTTGCCTAGGAAGCGCAAGGCCCTGGGTTCAGTCC
CCAGCTCCGAAAAAAAAGAACCAAAAAAAAAAAAAAAAAA

FIG. 6A
SEQ ID NO: 7
GGAGAACGGCTCTGCGGTGTGTGTGTGCCAGGCCGGATACACCGGAGCAGCCTGCGAG

FIG. 6B (PART 1)
SEQ ID NO: 9

ATG
Met
GATGTGGACGACTGCAGCCCTGACCCCTGCCTGAATGGAGGCTCTTGTGTTGACCTAGTG
AspValAspAspCysSerProAspProCysLeuAsnGlyGlySerCysValAspLeuVal
GGGAATTACACCTGCTTGTGTGCCGAGCCCTTCAAGGGACTTCGCTGTGAGACAGGAGAC
GlyAsnTyrThrCysLeuCysAlaGluProPheLysGlyLeuArgCysGluThrGlyAsp
CATCCAGTGCCAGACGCCTGCCTCTCGGCCCCTTGCCACAATGGGGGCACCTGTGTGGAT
HisProValProAspAlaCysLeuSerAlaProCysHisAsnGlyGlyThrCysValAsp
GCGGACCAGGGCTACGTGTGCGAGTGCCCCGAAGGCTTCATGGGCCTGGACTGCAGGGAG
AlaAspGlnGlyTyrValCysGluCysProGluGlyPheMetGlyLeuAspCysArgGlu
AGAGTCCCCGATGACTGTGAGTGCCGCAACGGAGGCAGATGCCTGGGCGCCAACACCACC
ArgValProAspAspCysGluCysArgAsnGlyGlyArgCysLeuGlyAlaAsnThrThr
CTCTGCCAGTGCCCCCTGGGATTCTTTGGCTTCTCTGTGAATTTGAAATCACAGCCATG
LeuCysGlnCysProLeuGlyPhePheGlyLeuLeuCysGluPheGluIleThrAlaMet
CCCTGCAACATGAACACACAGTGCCCAGATGGGGGCTACTGCATGGAGCACGGCGGGAGC
ProCysAsnMetAsnThrGlnCysProAspGlyGlyTyrCysMetGluHisGlyGlySer
TACCTCTGCGTCTGCCACACCGACCACAATGCCAGCCACTCCCTGCCATCACCCTGCGAC
TyrLeuCysValCysHisThraspHisAsnAlaSerHisSerLeuProSerProCysAsp
TCGGACCCCTGCTTCAACGGAGGCTCCTGCGATGCCCATGACGACTCCTACACCTGCGAG
SerAspProCysPheAsnGlyGlySerCysAspAlaHisAspAspSerTyrThrCysGlu
TGCCCGCGCGGGTTCCACGGCAAGCACTGCGAGAAAGCCCGGCCACACCTGTGCAGCTCA
CysProArgGlyPheHisGlyLysHisCysGluLysAlaArgProHisLeuCysSerSer
GGGCCCTGCCGGAACGGGGGCACGTGCAAGGAGGCGGGCGGCGAGTACCACTGCAGCTGC
GlyProCysArgAsnGlyGlyThrCysLysGluAlaGlyGlyGluTyrHisCysSerCys
CCCTACCGCTTCACTGGGAGGCACTGTGAGATCGGGAAGCCAGACTCGTGTGCCTCTGGC
ProTyrArgPheThrGlyArgHisCysGluIleGlyLysProAspSerCysAlaSerGly
CCCTGTCACAACGGCGGCACCTGCTTCCACTACATTGGCAAATACAAGTGTGACTGTCCC
ProCysHisAsnGlyGlyThrCysPheHisTyrIleGlyLysTyrLysCysAspCysPro
CCAGGCTTCTCCGGGCGGCACTGCGAGATAGCCCCCTCCCCCTGCTTCCGGAGCCCGTGT
ProGlyPheSerGlyArgHisCysGluIleAlaProSerProCysPheArgSerProCys
GTGAATGGGGGCACCTGCGAGGACCGGGACACGGATTTCTTCTGCCACTGCCAAGCAGGG
ValAsnGlyGlyThrCysGluAspArgAspThrAspPhePheCysHisCysGlnAlaGly
TACATGGGACGCCGGTGCCAGGCAGAGGTGGACTGCGGCCCCCCGGAGGAGGTGAAGCAC
TyrMetGlyArgArgCysGlnAlaGluValAspCysGlyProProGluGluValLysHis
GCCACACTGCGCTTCAACGGCACGCGGCTGGGCGCGGTGGCCCTGTATGCATGTGACCGT
AlaThrLeuArgPheAsnGlyThrArgLeuGlyAlaValAlaLeuTyrAlaCysAspArg
GGCTACAGCCTGAGCGCCCCCAGCCGCATCCGGGTCTGCCAGCCACACGGTGTCTGGAGT
GlyTyrSerLeuSerAlaProSerArgIleArgValCysGlnProHisGlyValTrpSer
GAGCCTCCCCAGTGCCTTGAAATCGATGAGTGCCGGTCTCAGCCGTGCCTGCATGGGGGC
GluProProGlnCysLeuGluIleAspGluCysArgSerGlnProCysLeuHisGlyGly
TCTTGTCAGGACCGCGTTGCTGGGTACCTGTGCCTCTGCAGCACAGGCTATGAGGGCGCC
SerCysGlnAspArgValAlaGlyTyrLeuCysLeuCysSerThrGlyTyrGluGlyAla
CACTGTGAGCTGGAGAGGGATGAGTGCCGAGCTCACCCGTGCAGAAATGGAGGGTCCTGC
HisCysGluLeuGluArgAspGluCysArgAlaHisproCysArgAsnGlyGlySerCys
AGGAACCTCCCAGGGGCCTATGTCTGCCGGTGCCCTGCAGGCTTCGTTGGAGTCCACTGT
ArgAsnLeuProGluAlaTyrValCysArgCysProAlaGlyPheValGlyValHisCys

FIG. 6B (CONTINUED, PART 2)

GAGACAGAGGTGGACGCCTGCGACTCCAGCCCCTGCCAGCATGGAGGCCGGTGTGAGAGC
GluThrGluValaspAlaCysAspSerSerProCysGlnHisGlyGlyArgCysGluSer
GGCGGCGGGGCCTACCTGTGCGTCTGCCCAGAGAGCTTCTTCGGCTACCACTGCGAGACA
GlyGlyGlyAlaTyrLeuCysValCysProGluSerPhePheGlyTyrHisCysGluThr
GTGAGTGACCCCTGCTTCTCCAGCCCCTGTGGGGGCCGTGGCTATTGCCTGGCCAGCAAC
ValSerAspProCysPheSerSerProCysGlyGlyArgGlyTyrCysLeuAlaSerAsn
GGCTCCCACAGCTGCACCTGCAAAGTGGGCTACACGGGCGAGGACTGCGCCAAAGAGCTC
GlySerHisSerCysThrCysLysValGlyTyrThrGlyGluAspCysAlaLysGluLeu
TTCCCACCGACGGCCCTCAAGATGGAGAGAGTGGAGGAGAGTGGGGTCTCTATCTCCTGG
PheProProThrAlaLeuLysMetGluArgValGluGluSerGlyValSerIleSerTrp
AACCCGCCCAATGGTCCAGCCGCCAGGCAGATGCTTGATGGCTACGCGGTCACCTACGTC
AsnProProAsnGlyProAlaAlaArgGlnMetLeuAspGlyTyrAlaValThrTyrVal
TCCTCCGACGGCTCCTACCGCCGCACAGACTTTGTGGACAGGACCCGCTCCTCGCACCAG
SerSerAspGlySerTyrArgArgThrAspPheValAspArgThrArgSerSerHisGln
CTCCAGGCCCTGGCGGCCGGCAGGGCCTACAACATCTCCGTCTTCTCAGTGAAGCGAAAC
LeuGlnAlaLeuAlaAlaGlyArgAlaTyrAsnIleSerValPheSerValLysArgAsn
AGTAACAACAAGAATGACATCAGCAGGCCTGCCGTGCTGCTGGCCCGCACGCGACCCCGC
SerAsnAsnLysAsnAspIleSerArgProAlaValLeuLeuAlaArgThrArgProArg
CCTGTGGAAGGCTTCGAGGTCACCAATGTGACGGCTAGCACCATCTCAGTGCAGTGGGCC
ProValGluGlyPheGluValThrAsnValThrAlaSerThrIleSerValGlnTrpAla
CTGCACAGGATCCGCCATGCCACCGTCAGTGGGGTCCGTGTGTCCATCCGCCACCCTGAG
LeuHisArgIleArgHisAlaThrValSerGlyValArgValSerIleArgHisProGlu
GCCCTCAGGGACCAGGCCACCGATGTGGACAGGAGTGTGGACAGGTTCACCTTTAGGGCC
AlaLeuArgAspGlnAlaThrAspValAspArgSerValAspArgPheThrPheArgAla
CTGCTGCCTGGGAAGAGGTACACCATCCAGCTGACCACCCTCAGTGGGCTCAGGGGAGAG
LeuLeuProGlyLysArgTyrThrIleGlnLeuThrThrLeuSerGlyLeuArgGlyGlu
GAGCACCCCACAGAGAGCCTGGCCACCGCGCCGACGCACGTGTGGACCCGGCCCCTGCCT
GluHisProThrGluSerLeuAlaThrAlaProThrHisValTrpThrArgProLeuPro
CCAGCAAACCTGACCGCCGCCCGAGTCACTGCCACCTCTGCCCACGTGGTCTGGGATGCC
ProAlaAsnLeuThrAlaAlaArgValThrAlaThrSerAlaHisValValTrpAspAla
CCGACTCCAGGCAGCTTGCTGGAGGCTTATGTCATCAATGTGACCACCAGCCAGAGCACC
ProThrProGlySerLeuLeuGluAlaTyrValIleAsnValThrThrSerGlnSerThr
AAGAGCCGCTATGTCCCCAACGGGAAGCTGGCGTCCTACACGGTGCGCGACCTGCTGCCG
LysSerArgTyrValProAsnGlyLysLeuAlaSerTyrThrValArgAspLeuLeuPro
GGACGGCGGTACCAGCTCTCTGTGATAGCAGTGCAGAGCACGGAGCTCGGGCCGCATCAC
GlyArgArgTyrGlnLeuSerValIleAlaValGlnSerThrGluLeuGlyProGlnHis
AGCGAGCCCGCCCACCTCTACATCATCACCTCCCCCAGGGATGGCGCTGACAGACGCTGG
SerGluProAlaHisLeuTyrIleIleThrSerProArgAspGlyAlaAspArgArgTrp
CACCAGGGAGGACACCACCCTCGGGTGCTCAAGAACAGACCGCCCCCGGCGCGCCTGCCG
HisGlnGlyGlyHisHisProArgValLeuLysAsnArgProProProAlaArgLeuPro
GAGCTGCGCCTGCTCAATGACCACAGCGCCCCCGAGACCCCCACCCAGCCCCCCAGGTTC
GluLeuArgLeuLeuAsnAspHisSerAlaProGluThrProThrGlnProProArgPhe
TCGGAGCTTGTGGACGGCAGAGGAAGAGTGAGCGCCAGGTTCGGTGGCTCACCCAGCAAA
SerGluLeuValAspGlyArgGlyArgValSerAlaArgPheGlyGlySerProSerLys
GCAGCCACCGTGAGATCACAACCCACAGCCTCGGCGCAGCTCGAGAACATGGAGGAAGCC
AlaAlaThrValArgSerGlnProThrAlaSerAlaGlnLeuGluAsnMetGluGluAla
CCCAAGCGGGTCAGCCTGGCCCTCCAGCTCCCTGAACACGGCAGCAAGGACATCGGAAAC
ProLysArgValSerLeuAlaLeuGlnLeuProGluHisGlySerLysAspIleGlyAsn
GTCCCTGGCAACTGTTCAGAAAACCCCTGTCAGAACGGAGGCACTTGTGTGCCGGGCGCA
ValProGlyAsnCysSerGluAsnProCysGlnAsnGlyGlyThrCysValProGlyAla
GACGCCCACAGCTGTGACTGCGGGCCAGGGTTCAAAGGCAGACGCTGCGAGCTCGCCTGT
AspAlaHisSerCysAspCysGlyProGlyPheLysGlyArgArgCysGluLeuAlaCys
ATAAAGGTGTCCCGCCCCTGCACAAGGCTGTTCTCCGAGACAAAGGCCTTTCCAGTCTGG
IleLysValSerArgProCysThrArgLeuPheSerGluThrLysAlaPheProValTrp
GAGGGAGGCGTCTGTCACCACGTGTATAAAAGAGTCTACCGAGTTCACCAAGACATCTGC

FIG. 6B (CONTINUED, PART 3)

GluGlyGlyValCysHisHisValTyrLysArgValTyrArgValHisGlnAspIleCys
TTCAAAGAGAGCTGTGAAAGCACAAGCCTCAAGAAGACCCCAAACAGGAAACAAAGTAAG
PheLysGluSerCysGluSerThrSerLeuLysLysThrProAsnArgLysGlnSerLys
AGTCAGACACTGGAGAAATCTTAA
SerGlnThrLeuGluLysSer

FIG. 6C

GGATTTAAGACGTTCTTGTTACACTCCACCAACCT
CACGAGTTTCTAACACCCAGGAAGATGAGGTCTAAAAACTGGATGAAAAAGGACACCCTG
AGAAAAGGTCCTAGCTGGAGTCAGTCCCCTCTGTGACCTCTCTCCTCAGGCCTCTAGAGG
ACAGATGGCCAGGCCTGTGCACACACCAGCCCACCCTGAGAGACCCCTCTGGGACCAACC
ACCTGTGAGTCCTGCGATGCGTTTAAGCAGCCTGTGCCCTCACCCAAGCTGCAGTTCCTG
AAGGTGTAGTCTGTGTCTCTGCGGATGAGATGACAGCTCGCCATTCCCCGGAATCAGTGA
GGCTGTCAGTCAGCCACGCTTCTGCAGTATGCAGAAACCTGTTCTTAGACTCCAAAGCCA
GAGAAAGAATTCTCCCTTCGAGGCCCAACAAATTGAGAAGGAACTGTGATGGACCACTTC
CAAAACAGAGACGGGGGCAGGGGCTGAAGGGCAGAGACCAGGTGATGTCAGAAGGAAAGC
CGGGTTGCAGACACAGCCGCCCCTGCTCTGGTCCTCCAGCGTGTTTATGACGCTCGTGCA
GGTCGACGAGCCATCCTATGGACTAGTTAACACTAAGGTGGAGTTCAGACTTTTTTAGAC
AACGGCGCGACTGGCAGCCTTTCTCTATCAAGGGTCAGACGGTAAACGTTTTCAGCTTTG
CAGACCAGAGGTCCCTGTGGCTACAGTAGCGCAGACACAGCCACAGGCATGTCATTGAAT
GGCTGCGGCTATGTTCCAATAAAAACTTATTTACAATAACAGGTGGTGGCCAAATTGGCC
CATGGGCCTTATTTGGTGAACCCTGTTCTATGAGATCACCTAGGCTTCAGCCTTAAACAG
TGGAAGCCATCCCCTGAATGACAAGTCACAAGGGTATCAAAGAAAGACCCCTGAATTTTC
ATGGAAAAAGCTATTCAGACCCCTGCTTGGAAAGCTAAGGCACACTGCCACGAAGCAGCA
AGGACGCCTTACAAGTCTCAGTGCAACAGAGATGGACACCTGGGCTGGGCTGGACAATGT
TTAAGGTTCCTTTTAGTCCATGACTCAAGTGATACTGTTTTAGGCTATCAGGTAGTAAAC
ACGATCTTAGACATCCCCATCTTTGTAAGCAGAACAGTACGGCACTTCACCACATCTGCT
TCCCACCATGCTTCTAAGCAGCTGTCTTCCCCCTGCTAATGTTACAACCAAAGCAGCCAC
CCCACCTCCTCTCGTGTTGAGCCTCACGACCGCTGACCCAGCTGGAAAGCCAGCGCCCTG
CCGCGTCACCCTGACTCTGCTCAGAGCCAGCATTCCAGCCACAAAGAGGGCCTCCTTCCT
TTCCTCTTTCATAAAAATGTTTTTGAAGAGTTAGAGTATATTTAGGCTTTTATCTTT
ATTAAAATTTCATGTGCATGTGTA

FIG. 7 (PART 1)

SEQ ID NO: 57

GCCTCGTCCAT
AATGATGGCTGCATGGCCACTTCCGGCCCAAGAGGGATCCAAGAGGCAGCGCGGTCCGAT
CGGAGAGCACCCTTACCGTGGGCACCTGCACGAGCGGCCCAGGCTGTCAAATCAGTGACC
AGGATTTGTTTGCAACACCAGCGGGCCCCAAATATGAGGGTGTTAGTGTCTCAGGCTGTG
GTCTTCCAAGTGGCAGACCAGACCGCAGACTGGGGTAGCAGGCTTTTTCTGTAGAGGGCC
AGGTAGTGACTATTTTCAGCTTTTCAGGCCACAGGGTCTCTGCTGTTGTCACAAAAAAGC
AGCCGTAGACAGTAAGTACGTGAGTGTGCTCAGCCGTGCTCCCACAAACCCTGTTTCTGA
AACCAGGCTGGGGTCCACAGAGGATGGATGGCCACATCTGACCCAAGGCCTGTTTGTGTA
TGACCTGTGAACTAAGAATGTTCTTAATACTTTTAAAGGGCTGCAAAAACAAAAAGAACA
AAAAAGAATATGCAACAGAGACCACGTGTGGTCCACAGGGCCAGAAATATTTGCGATCTG
GCCCTTCCCAGAAAGTCTGCTGGCCCTTGGGCAGACCGCACCATTTGCAACAACCAAAAT
TCAGTAAAACTTCAATGTTTCTGGTCCTTAAGAGTCCTAAGGCCAGGGTGGCAGCTTCCA
GCCCAGCCCCAATACTCACTGGTCTTCTGCTGTCTCCCAGAGTTGGCGCTGGGGCTGGAC
AGCCACTGCCCAGGGGACGCCATTGGGCTCCAGCTTAGCCGGACCATCCTTGAACCAGGC
CCAGGCATCGGGGGCCCCGTGACTCGAGCACCCCGCAGAGCCAGTGGCTCACGTCAGGCA
CTGGACCGGAAG

SEQ ID NO: 58

GTGAACAACAACGGGATCATCTCCTTCCTGAAGGAGGTTTCTCAGTTC
ACCCCAGTGGCCTTCCCCATTGCCAAGGACCGCTGCGTGGTGGCAGCCTTCTGGGCAGAT
GTGAACGAACCGGCGTGCAGGCACGTGTACTACCGGGAGGCCACCGACCCAGCCATGCTG
CGCCGAGCCACGGAGGACGTCAGGCACTACTTCCCCGAGCTCCTGGACTTCAATGCCACC
TGGGTTTTTGTTGCCACCTGGTACCGAGTGACCTTCTTTGGAGGCAGTTCCTCATCCCCT

SEQ ID NO: 59

GTCAACACATTCCAGACTGTGCTCATCACAGACGGCAAGCTCTCCTTCACCATCTTCAAC
TATGAGTCCATCGTGTGGACCACAGGCACACACGCCAGCAGCGGGGGCAACGCCACTGGC
CTCGGGGGCATCGCAGCCCAG

SEQ ID NO: 60

GCTGGCTTCAACGCAGGCGATGGGCAGCGTTACTTCAGT
ATCCCCGGCTCGCGCACAGCAGACATGGCCGAGGTGGAGACCACCACCAACGTGGGTGTG
CCCGGGCGCTGGGCGTTCAGAATCGATGATGCCCAGGTGCGCGTGGGGGGCTGCGGCCAT
ACAA

SEQ ID NO: 61

CGTCCGTGTGCCTGGCCCTGCGCCCCTGCCTCAACGGCGGCAAGTGCATCGACGACTG
CGTCACGGGCAACCCCTCCTACACCTGCTCCTGCCTCTCGGGCTTCACGGGGCGGAGGTG
CCACCTGG

SEQ ID NO: 62

ACGTGAACGAATGTGCCTCCCAGCCCTGTCAGAATGGTGGGACCTGTACTCA
CGGCATCAACAGTTTCCGCTGCCAGTGCCCGGCTGGCTTTGGGGGACCCACCTGTGAGAC
AG

SEQ ID NO: 16

CCCAATCCCCCTGTGACACCAAAGAGTGTCAACATGGTGGCCAGTGCCAGGTGGAGAA
TGGCTCTGCGGTGTGTGTGTGCCAGGCCGGATACACCGGAGCAGCCTGCGAGATGG

SEQ ID NO: 17

ATGTGGACGACTGCAGCCCTGACCCCTGCCTGAATGGAGGCTCTTGTGTTGACCTAGT
GGGGAATTACACCTGCTTGTGTGCCGAGCCCTTCAAGGGACTTCGCTGTGAGACAG

FIG. 7 (CONTINUED, PART 2)

SEQ ID NO: 18

GAGA
CCATCCAGTGCCAGACGCCTGCCTCTCGGCCCCTTGCCACAATGGGGGCACCTGTGTGGA
TGCGGACCAGGGCTACGTGTGCGAGTGCCCCGAAGGCTTCATGGGCCTGGACTGCAGGGA
GA

SEQ ID NO: 19

GAGTCCCCGATGACTGTGAGTGCCGCAACGGAGGCAGATGCCTGGGCGCCAACACCAC
CCTCTGCCAGTGCCCCCTGGGATTCTTTGGGCTTCTCTGTGAATTTG

SEQ ID NO: 20

AAATCACAGCCAT
GCCCTGCAACATGAACACACAGTGCCCAGATGGGGGCTACTGCATGGAGCACGGCGGGAG
CTACCTCTGCGTCTGCCACACCGACCACAATGCCAGCCACT

SEQ ID NO: 21

CCCTGCCATCACCCTGCGA
CTCGGACCCCTGCTTCAACGGAGGCTCCTGCGATGCCCATGACGACTCCTACACCTGCGA
GTGCCCGCGCGGGTTCCACGGCAAGCACTGCGAGAAA

SEQ ID NO: 22

GCCCGGCCACACCTGTGCAGCTC
AGGGCCCTGCCGGAACGGGGGCACGTGCAAGGAGGCGGGCGGCGAGTACCACTGCAGCTG
CCCCTACCGCTTCACTGGGAGGCACTGTGAGATCG

SEQ ID NO: 23

GGAAGCCAGACTCGTGTGCCTCTGG
CCCCTGTCACAACGGCGGCACCTGCTTCCACTACATTGGCAAATACAAGTGTGACTGTCC
CCCAGGCTTCTCCGGGCGGCACTGCGAGATAGC

SEQ ID NO: 24

CCCCTCCCCCTGCTTCCGGAGCCCGTG
TGTGAATGGGGGCACCTGCGAGGACCGGGACACGGATTTCTTCTGCCACTGCCAAGCAGG
GTACATGGGACGCCGGTGCCAGGCAG

SEQ ID NO: 25

AGGTGGACTGCGGCCCCCCGGAGGAGGTGAAGCA
CGCCACACTGCGCTTCAACGGCACGCGGCTGGGCGCGGTGGCCCTGTATGCATGTGACCG
TGGCTACAGCCTGAGCGCCCCCAGCCGCATCCGGGTCTGCCAGCCACACGGTGTCTGGAG
TGAGCCTCCCCAGTGCCTTG

SEQ ID NO: 26

AAATCGATGAGTGCCGGTCTCAGCCGTGCCTGCATGGGGG
CTCTTGTCAGGACCGCGTTGCTGGGTACCTGTGCCTCTGCAGCACAGGCTATGAGGGCGC
CCACTGTGAGCTGG

SEQ ID NO: 27

AGAGGGATGAGTGCCGAGCTCACCCGTGCAGAAATGGAGGGTCCTG
CAGGAACCTCCCAGGGGCCTATGTCTGCCGGTGCCCTGCAGGCTTCGTTGGAGTCCACTG
TGAGACAG

FIG. 7 (CONTINUED, PART 3)

SEQ ID NO: 28

AGGTGGACGCCTGCGACTCCAGCCCCTGCCAGCATGGAGGCCGGTGTGAGAG
CGGCGGCGGGGCCTACCTGTGCGTCTGCCCAGAGAGCTTCTTCGGCTACCACTGCGAGAC
AG

SEQ ID NO: 29

TGAGTGACCCCTGCTTCTCCAGCCCCTGTGGGGGCCGTGGCTATTGCCTGGCCAGCAA
CGGCTCCCACAGCTGCACCTGCAAAGTGGGCTACACGGGCGAGGACTGCGCCAAAG

SEQ ID NO: 30

AGCT
CTTCCCACCGACGGCCCTCAAGATGGAGAGAGTGGAGGAGAGTGGGGTCTCTATCTCCTG
GAACCCGCCCAATGGTCCAGCCGCCAGGCAGATGCTTGATGGCTACGCGGTCACCTACGT
CTCCTCCGACGGCTCCTACCGCCGCACAGACTTTGTGGACAGGACCCGCTCCTCGCACCA
GCTCCAGGCCCTGGCGGCCGGCAGGGCCTACAACATCTCCGTCTTCTCAGTGAAGCGAAA
CAGTAACAACAAGAATGACATCAGCAGGCCTGCCGTGCTGCTGGCCCGCACGC

SEQ ID NO: 31

GACCCCG
CCCTGTGGAAGGCTTCGAGGTCACCAATGTGACGGCTAGCACCATCTCAGTGCAGTGGGC
CCTGCACAGGATCCGCCATGCCACCGTCAGTGGGGTCCGTGTGTCCATCCGCCACCCTGA
GGCCCTCAGGGACCAGGCCACCGATGTGGACAGGAGTGTGGACAGGTTCACCTTTAGG

SEQ ID NO: 32

GC
CCTGCTGCCTGGGAAGAGGTACACCATCCAGCTGACCACCCTCAGTGGGCTCAGGGGAGA
GGAGCACCCCACAGAGAGCCTGGCCACCGCGCCGACGCACGTGTGGACCC

SEQ ID NO: 33

GGCCCCTGCC
TCCAGCAAACCTGACCGCCGCCCGAGTCACTGCCACCTCTGCCCACGTGGTCTGGGATGC
CCCGACTCCAGGCAGCTTGCTGGAGGCTTATGTCATCAATGTGACCACCAGCCAGAGCAC
CAAGAGCCGCTATGTCCCCAACGGGAAGCTGGCGTCCTACACGGTGCGCGACCTGCTGCC
GGGACGGCGGTACCAGCTCTCTGTGATAGCAGTGCAGAGCACGGAGCTCGGGCCGCAGCA
CAGCGAGCCCGCCCACCTCTACATCATCACCT

SEQ ID NO: 34

CCCCCAGGGATGGCGCTGACAGACGCTG
GCACCAGGGAGGACACCACCCTCGGGTGCTCAAGAACAGACCGCCCCCGGCGCGCCTGCC
GGAGCTGCGCCTGCTCAATGACCACAGCGCCCCCGAGACCCCCACCCAGCCCCCCAG

SEQ ID NO: 35

GTT
CTCGGAGCTTGTGGACGGCAGAGGAAGAGTGAGCGCCAGGTTCGGTGGCTCACCCAGCAA
AGCAGCCACCGTGAGATCAC

SEQ ID NO: 36

AACCCACAGCCTCGGCGCAGCTCGAGAACATGGAGGAAGC
CCCCAAGCGGGTCAGCCTGGCCCTCCAGCTCCCTGAACACGGCAGCAAGGACATCGGAA

FIG. 7 (CONTINUED, PART 4)

SEQ ID NO: 37

A
CGTCCCTGGCAACTGTTCAGAAAACCCCTGTCAGAACGGAGGCACTTGTGTGCCGGGCGC
AGACGCCCACAGCTGTGACTGCGGGCCAGGGTTCAAAGGCAGACGCTGCGAGCTCG

SEQ ID NO: 38

CCTG
TATAAAGGTGTCCCGCCCCTGCACAAGGCTGTTCTCCGAGACAAAGGCCTTTCCAGTCTG
GGAGGGAGGCGTCTGTCACCACGTG

SEQ ID NO: 39

TATAAAAGAGTCTACCGAGTTCACCAAGACATCTG
CTTCAAAGAGAGCTGTGAAAGCACAAGCCTCAAGAAGACCCCAAACAG

SEQ ID NO: 40

GAAACAAAGTAA
GAGTCAGACACTGGAGAAATCTTAAG

SEQ ID NO: 41

GATTTAAGACGTTCTTGTTACACTCCACCAACCT
CACGAGTTTCTAACACCCAGGAAGATGAGGTCTAAAAACTGGATGAAAAAGGACACCCTG
AGAAAAGGTCCTAGCTGGAGTCAGTCCCCTCTGTGACCTCTCTCCTCAGGCCTCTAGAGG
ACAGATGGCCAGGCCTGTGCACACACCAGCCCACCCTGAGAGACCCCTCTGGGACCAACC
ACCTGTGAGTCCTGCGATGCGTTTAAGCAGCCTGTGCCCTCACCCAAGCTGCAGTTCCTG
AAGGTGTAGTCTGTGTCTCTGCGGATGAGATGACAGCTCGCCATTCCCCGGAATCAGTGA
GGCTGTCAGTCAGCCACGCTTCTGCAGTATGCAGAAACCTGTTCTTAGACTCCAAAGCCA
GAGAAAGAATTCTCCCTTCGAGGCCCAACAAATTGAGAAGGAACTGTGATGGACCACTTC
CAAAACAGAGACGGGGGCAGGGGCTGAAGGGCAGAGACCAGGTGATGTCAGAAGGAAAGC
CGGGTTGCAGACACAGCCGCCCCTGCTCTGGTCCTCCAGCGTGTTTATGACGCTCGTGCA
GGTCGACGAGCCATCCTATGGACTAGTTAACACTAAGGTGGAGTTCAGACTTTTTTAGAC
AACGGCGCGACTGGCAGCCTTTCTCTATCAAGGGTCAGACGGTAAACGTTTTCAGCTTTG
CAGACCAGAGGTCCCTGTGGCTACAGTAGCGCAGACACAGCCACAGGCATGTCATTGAAT
GGCTGCGGCTATGTTCCAATAAAAACTTATTTACAATAACAGGTGGTGGCCAAATTGGCC
CATGGGCCTTATTTGGTGAACCCTGTTCTATGAGATCACCTAGGCTTCAGCCTTAAACAG
TGGAAGCCATCCCCTGAATGACAAGTCACAAGGGTATCAAAGAAAGACCCCTGAATTTTC
ATGGAAAAAGCTATTCAGACCCCTGCTTGGAAAGCTAAGGCACACTGCCACGAAGCAGCA
AGGACGCCTTACAAGTCTCAGTGCAACAGAGATGGACACCTGGGCTGGGCTGGACAATGT
TTAAGGTTCCTTTTAGTCCATGACTCAAGTGATACTGTTTTAGGCTATCAGGTAGTAAAC
ACGATCTTAGACATCCCCATCTTTGTAAGCAGAACAGTACGGCACTTCACCACATCTGCT
TCCCACCATGCTTCTAAGCAGCTGTCTTCCCCCTGCTAATGTTACAACCAAAGCAGCCAC
CCCACCTCCTCTCGTGTTGAGCCTCACGACCGCTGACCCAGCTGGAAAGCCAGCGCCCTG
CCGCGTCACCCTGACTCTGCTCAGAGCCAGCATTCCAGCCACAAAGAGGGCCTCCTTCCT
TTCCTCTTTCATAAAAATGTTTTTTGAAGAGTTAGAGTATATTTTAGGCTTTTTATCTTT
ATTAAAATTTCATGTGCATGTGTA

SEQ ID NO: 10

FIG. 8A (PART 1)

CTTGATGGCTACGCGGTCACCTACGTCTCCTCCGACGGCTCCTACCGCCGCACAGACTTT
LeuAspGlyTyrAlaValThrTyrValSerSerAspGlySerTyrArgArgThrAspPhe
GTGGACAGGACCCGCTCCTCGCACCAGCTCCAGGCCCTGGCGGCCGGCAGGGCCTACAAC
ValAspArgThrArgSerSerHisGlnLeuGlnAlaLeuAlaAlaGlyArgAlaTyrAsn
ATCTCCGTCTTCTCAGTGAAGCGAAACAGTAACAACAAGAATGACATCAGCAGGCCTGCC
IleSerValPheSerValLysArgAsnSerAsnAsnLysAsnAspIleSerArgProAla
GTGCTGCTGGCCCGCACGCGACCCCGCCCTGTGGAAGGCTTCGAGGTCACCAATGTGACG
ValLeuLeuAlaArgThrArgProArgProValGluGlyPheGluValThrAsnValThr
GCTAGCACCATCTCAGTGCAGTGGGCCCTGCACAGGATCCGCCATGCCACCGTCAGTGGG
AlaSerThrIleSerValGlnTrpAlaLeuHisArgIleArgHisAlaThrValSerGly
GTCCGTGTGTCCATCCGCCACCCTGAGGCCCTCAGGGACCAGGCCACCGATGTGGACAGG
ValArgValSerIleArgHisProGluAlaLeuArgAspGlnAlaThrAspValAspArg
AGTGTGGACAGGTTCACCTTTAGGGCCCTGCTGCCTGGGAAGAGGTACACCATCCAGCTG
SerValAspArgPheThrPheArgAlaLeuLeuProGlyLysArgTyrThrIleGlnLeu
ACCACCCTCAGTGGGCTCAGGGGAGAGGAGCACCCCACAGAGAGCCTGGCCACCGCGCCG
ThrThrLeuSerGlyLeuArgGlyGluGluHisProThrGluSerLeuAlaThrAlaPro
ACGCACGTGTGGACCCGGCCCCTGCCTCCAGCAAACCTGACCGCCGCCCGAGTCACTGCC
ThrHisValTrpThrArgProLeuProProAlaAsnLeuThrAlaAlaArgValThrAla
ACCTCTGCCCACGTGGTCTGGGATGCCCCGACTCCAGGCAGCTTGCTGGAGGCTTATGTC
ThrSerAlaHisValValTrpAspAlaProThrProGlySerLeuLeuGluAlaTyrVal
ATCAATGTGACCACCAGCCAGAGCACCAAGAGCCGCTATGTCCCCAACGGGAAGCTGGCG
IleAsnValThrThrSerGlnSerThrLysSerArgTyrValProAsnGlyLysLeuAla
TCCTACACGGTGCGCGACCTGCTGCCGGGACGGCGGTACCAGCTCTCTGTGATAGCAGTG
SerTyrThrValArgAspLeuLeuProGlyArgArgTyrGlnLeuSerValIleAlaVal
CAGAGCACGGAGCTCGGGCCGCAGCACAGCGAGCCCGCCCACCTCTACATCATCACCTCC
GlnSerThrGluLeuGlyProGlnHisSerGluProAlaHisleuTyrIleIleThrSer
CCCAGGGATGGCGCTGACAGACGCTGGCACCAGGGAGGACACCACCCTCGGGTGCTCAAG
ProArgAspGlyAlaAspArgArgTrpHisGlnGlyGlyHisHisProArgValLeuLys
AACAGACCGCCCCCGGCGCGCCTGCCGGAGCTGCGCCTGCTCAATGACCACAGCGCCCCC
AsnArgProProProAlaArgLeuProGluLeuArgLeuLeuAsnAspHisSerAlaPro
GAGACCCCCACCCAGCCCCCCAGGTTCTCGGAGCTTGTGGACGGCAGAGGAAGAGTGAGC
GluThrProThrGlnProProArgPheSerGluLeuValAspGlyArgglyArgValSer
GCCAGGTTCGGTGGCTCACCCAGCAAAGCAGCCACCGTGAGATCACAACCCACAGCCTCG
AlaArgPheGlyGlySerProSerLysAlaAlaThrValArgSerGlnProThrAlaSer
GCGCAGCTCGAGAACATGGAGGAAGCCCCCAAGCGGGTCAGCCTGGCCCTCCAGCTCCCT
AlaGlnLeuGluAsnMetGluGluAlaProLysArgValSerLeuAlaLeuGlnLeuPro
GAACACGGCAGCAAGGACATCGGAAGTGAGTCAGCAGCGCTGGTGGGGACTTTGGACTG
GluHisGlySerLysAspIleGlySerGluSerAlaAlaLeuValGlyThrLeuGlyLeu
ACTGACTGCTCTCAGGGGCCTTAG
ThrAspCysSerGlnGlyPro

Fig. 8B (CONTINUED, PART 2)

```
                        AGGCTGCAGGCAGGAGGGACCACCCACGGTGAGGAA
TCAGGAGGCACAGAGCCTACCTGAGGGGAGGCTGAGCACCAGGCACCCCGGTGTGGGAAG
ATGGGGTGAAGCTACACCACCCAAGCAGTGGGACCCCACAGACGGGAACAGGCCAGGGGG
CAGGACCCACCCAAACCACCCAGAGTCTGAGCTAGAGAGACTGGCTTTGATGCTGCCTCC
CCTCCCCTCTCCTCCTTCGCCTCCACATGCAGCAGAGCCCACCCCAGCCCCTGCCTCTGG
GCCCCTCACCCCTCACTTCTCCAAAGAGGAGCAGGCGGAGTCAGGAGGGGAGAAGCAGAG
GGAGCAGCCACTGGGCGAGCCCCAGCTTGAGGACTAGCTGGGCCCTGTGGACACTCAGGT
TATGCAGGACCTGAACTGTCTCCTAGTCCGGGGCTCTGCCTCGTGAGGATCGAGGCCAGC
ACGTCCCTGCAGGGCACCAAGCATCTGCTGAGCACCTGCAGTAAGAGTTCCCAGACGCTC
ACGAGGCAGTTCCCCTTCGGGCAGCACCAATATATGTGTGTTCCTCAAAAAAAAAAA
```

FIG. 9 (PART 1)

SEQ ID NO: 11

```
Cys Leu Asn Gly Gly Ser Cys Val Asp Leu Val Gly Asn Tyr Ser Cys
 1               5                  10                  15
Ile Cys Val Glu Pro Phe Glu Gly Pro Gln Cys Glu Thr Gly Ser Tyr
            20                  25                  30
Val Val Pro Ser Pro Cys Leu Ser Asn Pro Cys Leu Asn Gly Gly Thr
        35                  40                  45
Cys Val Asp Ala Asp Gln Gly Tyr Val Cys Glu Cys Pro Glu Gly Phe
    50                  55                  60
Met Gly Leu Asp Cys Arg Glu Arg Ile Leu Asn Asp Cys Asp Cys Arg
65                  70                  75                  80
Asn Gly Gly Arg Cys Leu Gly Ala Asn Thr Thr Ile Cys Gln Cys Pro
                85                  90                  95
Pro Gly Ser Phe Gly Leu Leu Cys Glu Phe Glu Val Thr Ala Thr Pro
            100                 105                 110
Cys Asn Met Asn Thr Gln Cys Pro Asp Gly Gly Tyr Cys Met Glu Tyr
        115                 120                 125
Gly Gly Ser Tyr Leu Cys Val Cys His Thr Asp His Asn Leu Ser His
    130                 135                 140
Ser Leu Pro Ser Pro Cys Asp Ser Asp Pro Cys Phe Asn Gly Gly Ser
145                 150                 155
Cys Asp Ala His Glu Asp Ser Tyr Thr Cys Glu Cys Pro Arg Gly Phe
                165                 170                 175
His Gly Arg His Cys Glu Lys Ala Arg Pro His Leu Cys Ser Ser Gly
            180                 185                 190
Pro Cys Arg Asn Gly Gly Thr Tyr Lys Glu Thr Gly Asp Glu Tyr Arg
        195                 200                 205
Cys Thr Cys Pro Tyr Arg Phe Thr Gly Arg His Cys Glu Ile Gly Lys
    210                 215                 220
Pro Asp Ser Cys Ala Ser Gly Pro Cys His Asn Gly Gly Thr Cys Phe
225                 230                 235                 240
His Tyr Ile Gly Lys Tyr Lys Cys Asp Cys Pro Pro Gly Phe Ser Gly
                245                 250                 255
Arg His Cys Glu Ile Ala Pro Ser Pro Cys Phe Arg Ser Pro Cys Met
            260                 265                 270
Asn Gly Gly Ile Cys Glu Asp Leu Gly Thr Asp Phe Ser Cys His Cys
        275                 280                 285
Gln Pro Gly Tyr Thr Gly His Arg Cys Gln Ala Glu Val Asp Cys Gly
    290                 295                 300
Gln Pro Glu Glu Val Lys His Ala Thr Met Arg Leu Asn Gly Thr Arg
305                 310                 315                 320
Met Gly Ser Val Ala Leu Tyr Thr Cys Asp Pro Gly Phe Ser Leu Ser
                325                 330                 335
Val Leu Ser His Met Arg Val Cys Gln Pro Gln Gly Val Trp Ser Gln
            340                 345                 350
```

FIG. 9 (CONTINUED, PART 2)

```
Pro Pro Gln Cys Ile Glu Val Asp Glu Cys Gln Ser Gln Pro Tyr Leu
        355                 360                 365
His Lys Gly Ser Cys Gln Asp Leu Ile Ala Gly Tyr Gln Cys Leu Cys
    370                 375                 380
Ser Pro Gly Tyr Glu Gly Val His Cys Glu Leu Glu Thr Asp Glu Cys
385                 390                 395
Gln Ala Gln Pro Cys Arg Asn Gly Gly Ser Cys Arg Asp Leu Pro Gly
                405                 410                 415
Ala Phe Ile Cys Gln Cys Pro Glu Gly Phe Val Gly Thr His Tyr Glu
            420                 425                 430
Thr Glu Val Asp Ala Cys Ala Ser Ser Pro Cys Gln His Gly Gly Arg
        435                 440                 445
Cys Glu Asp Gly Gly Gly Ala Tyr Leu Cys Val Cys Pro Glu Gly Phe
    450                 455                 460
Phe Gly Tyr Asn Cys Glu Thr Val Ser Asn Pro Cys Phe Ser Ser Pro
465                 470                 475                 480
Cys Gly Gly Arg Gly Tyr Cys Leu Ala Ser Asn Gly Ser His Ser Cys
                485                 490                 495
Thr Cys Lys Val Gly Tyr Thr Gly Lys Asp Cys Thr Lys Glu Leu Leu
            500                 505                 510
Pro Pro Thr Ala Leu Arg Val Glu Arg Val Glu Glu Ser Gly Val Ser
        515                 520                 525
Ile Ser Trp Ser Pro Pro Glu Gly Thr Thr Ala Arg Gln Val Leu Asp
    530                 535                 540
Gly Tyr Ala Val Thr Tyr Ala Ser Ser Asp Gly Ser Ser Arg Arg Thr
545                 550                 555                 560
Asp Phe Val Asp Arg Ser Arg Ser Ser His Gln Leu Arg Ala Leu Ala
                565                 570                 575
Ala Gly Arg Ala Tyr Asn Ile Ser Val Phe Ser Val Lys Arg Asn Thr
            580                 585                 590
Asn Asn Lys Asn Asp Ile Ser Arg Pro Ala Ala Leu Leu Thr Arg Thr
        595                 600                 605
Arg Pro Arg Pro Ile Glu Asp Phe Glu Val Thr Asn Ile Ser Ala Asn
    610                 615                 620
Ala Ile Ser Val Gln Trp Ala Leu His Arg Ile Gln His Ala Thr Val
625                 630                 635                 640
Ser Arg Val Arg Val Ser Val Leu Tyr Pro Glu Asp Thr Val Val Gln
                645                 650                 655
Ser Thr Glu Val Asp Arg Ser Val Asp Arg Leu Thr Phe Gly Asp Leu
            660                 665                 670
Leu Pro Gly Arg Arg Tyr Ser Val Arg Leu Thr Thr Leu Ser Gly Pro
        675                 680                 685
Gly Gly Ala Glu Tyr Pro Thr Glu Ser Leu Ala Ser Ala Pro Leu Asn
    690                 695                 700
Val Trp Thr Arg Pro Leu Pro Pro Ala Asn Leu Thr Ala Ser Arg Val
705                 710                 715                 720
```

FIG. 9 (CONTINUED, PART 3)

```
Thr Ala Thr Ser Ala His Met Val Trp Asp Pro Pro Thr Pro Gly Ile
                725                 730                 735
Ser Leu Glu Ala Tyr Val Ile Asn Val Thr Thr Ser Gln Asn Thr Lys
            740                 745                 750
Ser Arg Tyr Ile Pro Asn Gly Lys Leu Val Ser Tyr Thr Val Arg Asp
        755                 760                 765
Leu Met Pro Gly Arg Arg Tyr Gln Leu Ser Val Thr Ala Val Gln Ser
    770                 775                 780
Thr Glu Gln Gly Gln Leu His Ser Glu Pro Ala His Leu Tyr Ile Ile
785                 790                 795                 800
Thr Ser Pro Arg Asp Gly Thr Asp Arg Arg Trp His Gln Gly Gly His
                805                 810                 815
His Ser Arg Met Leu Arg Asn Arg Pro Ala Pro Leu Arg Leu Pro Glu
            820                 825                 830
Leu Arg Leu Leu Asn Asp His Gly Ala Pro Glu Thr Pro Thr Gln Pro
        835                 840                 845
Pro Arg Phe Ser Glu Leu Val Asp Gly Arg Ala Arg Val Ser Ala Arg
    850                 855                 860
Phe Gly Gly Leu Pro Ser Arg Ala Val Thr Val Arg Ser Gln Pro Thr
865                 870                 875                 880
Thr Pro Val Pro Leu Lys Asn Thr Glu Ala Pro Glu Gln Ala Arg Leu
                885                 890                 895
Ala Leu Gln Leu Pro Lys Asn Asn Ser Lys Asp Thr Glu Ser Thr Pro
            900                 905                 910
Gly Ser Cys Ser Glu Asp Thr Cys Gln Asn Gly Gly Thr Cys Val Pro
        915                 920                 925
Gly Ala Asn Ala His Ser Cys Asp Cys Arg Pro Gly Phe Lys Gly Arg
    930                 935                 940
His Cys Glu Leu Ala Cys Glu Lys Val Pro Arg Pro Cys Thr Arg Leu
945                 950                 955                 960
Phe Ser Glu Thr Lys Ser Phe Pro Val Trp Glu Gly Asp Val Cys His
                965                 970                 975
His Val Tyr Lys Lys Val Tyr Lys Val His Gln Asp Val Cys Phe Lys
            980                 985                 990
Glu Arg Cys Gln Ser Thr Ser Leu Lys Lys Leu Lys Gln Glu Ser Asn
        995                1000                1005
```

Fig. 10 (PART 1)

SEQ ID NO: 12

```
Glu Asn Gly Ser Ala Val Cys Val Cys Gln Ala Gly Tyr Thr Gly Ala
 1               5                  10                  15
Ala Cys Glu Met Asp Val Asp Asp Cys Ser Pro Asp Pro Cys Leu Asn
            20                  25                  30
Gly Gly Ser Cys Val Asp Leu Val Gly Asn Tyr Thr Cys Leu Cys Ala
        35                  40                  45
Glu Pro Phe Lys Gly Leu Arg Cys Glu Thr Gly Asp His Pro Val Pro
    50                  55                  60
Asp Ala Cys Leu Ser Ala Pro Cys His Asn Gly Gly Thr Cys Val Asp
 65                  70                  75                  80
Ala Asp Gln Gly Tyr Val Cys Glu Cys Pro Glu Gly Phe Met Gly Leu
                85                  90                  95
Asp Cys Arg Glu Arg Val Pro Asp Asp Cys Glu Cys Arg Asn Gly Gly
            100                 105                 110
Arg Cys Leu Gly Ala Asn Thr Thr Leu Cys Gln Cys Pro Leu Gly Phe
        115                 120                 125
Phe Gly Leu Leu Cys Glu Phe Glu Ile Thr Ala Met Pro Cys Asn Met
    130                 135                 140
Asn Thr Gln Cys Pro Asp Gly Gly Tyr Cys Met Glu His Gly Gly Ser
145                 150                 155                 160
Tyr Leu Cys Val Cys His Thr Asp His Asn Ala Ser His Ser Leu Pro
                165                 170                 175
Ser Pro Cys Asp Ser Asp Pro Cys Phe Asn Gly Gly Ser Cys Asp Ala
            180                 185                 190
His Asp Asp Ser Tyr Thr Cys Glu Cys Pro Arg Gly Phe His Gly Lys
        195                 200                 205
His Cys Glu Lys Ala Arg Pro His Leu Cys Ser Ser Gly Pro Cys Arg
    210                 215                 220
Asn Gly Gly Thr Cys Lys Glu Ala Gly Gly Glu Tyr His Cys Ser Cys
225                 230                 235                 240
Pro Tyr Arg Phe Thr Gly Arg His Cys Glu Ile Gly Lys Pro Asp Ser
                245                 250                 255
Cys Ala Ser Gly Pro Cys His Asn Gly Gly Thr Cys Phe His Tyr Ile
            260                 265                 270
Gly Lys Tyr Lys Cys Asp Cys Pro Pro Gly Phe Ser Gly Arg His Cys
        275                 280                 285
Glu Ile Ala Pro Ser Pro Cys Phe Arg Ser Pro Cys Val Asn Gly Gly
    290                 295                 300
Thr Cys Glu Asp Arg Asp Thr Asp Phe Phe Cys His Cys Gln Ala Gly
305                 310                 315                 320
Tyr Met Gly Arg Arg Cys Gln Ala Glu Val Asp Cys Gly Pro Pro Glu
                325                 320                 335
Glu Val Lys His Ala Thr Leu Arg Phe Asn Gly Thr Arg Leu Gly Ala
            340                 345                 350
```

FIG. 10 (CONTINUED, PART 2)

```
Val Ala Leu Tyr Ala Cys Asp Arg Gly Tyr Ser Leu Ser Ala Pro Ser
        355                 360                 365
Arg Ile Arg Val Cys Gln Pro His Gly Val Trp Ser Glu Pro Pro Gln
    370                 375                 380
Cys Leu Glu Ile Asp Glu Cys Arg Ser Gln Pro Cys Leu His Gly Gly
385                 390                 395                 400
Ser Cys Gln Asp Arg Val Ala Gly Tyr Leu Cys Leu Cys Ser Thr Gly
                405                 410                 415
Tyr Glu Gly Ala His Cys Glu Leu Glu Arg Asp Glu Cys Arg Ala His
            420                 425                 430
Pro Cys Arg Asn Gly Gly Ser Cys Arg Asn Leu Pro Gly Ala Tyr Val
        435                 440                 445
Cys Arg Cys Pro Ala Gly Phe Val Gly Val His Cys Glu Thr Glu Val
    450                 455                 460
Asp Ala Cys Asp Ser Ser Pro Cys Gln His Gly Gly Arg Cys Glu Ser
465                 470                 475                 480
Gly Gly Gly Ala Tyr Leu Cys Val Cys Pro Glu Ser Phe Phe Gly Tyr
                485                 490                 495
His Cys Glu Thr Val Ser Asp Pro Cys Phe Ser Ser Pro Cys Gly Gly
            500                 505                 510
Arg Gly Tyr Cys Leu Ala Ser Asn Gly Ser His Ser Cys Thr Cys Lys
        515                 520                 525
Val Gly Tyr Thr Gly Glu Asp Cys Ala Lys Glu Leu Phe Pro Pro Thr
    530                 535                 540
Ala Leu Lys Met Glu Arg Val Glu Glu Ser Gly Val Ser Ile Ser Trp
545                 550                 555                 560
Asn Pro Pro Asn Gly Pro Ala Ala Arg Gln Met Leu Asp Gly Tyr Ala
                565                 570                 575
Val Thr Tyr Val Ser Ser Asp Gly Ser Tyr Arg Arg Thr Asp Phe Val
            580                 585                 590
Asp Arg Thr Arg Ser ser His Gln Leu Gln Ala Leu Ala Ala Gly Arg
        595                 600                 605
Ala Tyr Asn Ile Ser Val Phe Ser Val Lys Arg Asn Ser Asn Asn Lys
    610                 615                 620
Asn Asp Ile Ser Arg Pro Ala Val Leu Leu Ala Arg Thr Arg Pro Arg
625                 630                 635                 640
Pro Val Glu Gly Phe Glu Val Thr Asn Val Thr Ala Ser Thr Ile Ser
                645                 650                 655
Val Gln Trp Ala Leu His Arg Ile Arg His Ala Thr Val Ser Gly Val
            660                 665                 670
Arg Val Ser Ile Arg His Pro Glu Ala Leu Arg Asp Gln Ala Thr Asp
        675                 680                 685
Val Asp Arg Ser Val Asp Arg Phe Thr Phe Arg Ala Leu Leu Pro Gly
    690                 695                 700
Lys Arg Tyr Thr Ile Gln Leu Thr Thr Leu Ser Gly Leu Arg Gly Glu
705                 710                 715                 720
```

FIG. 10 (CONTINUED, PART 3)

```
Glu His Pro Thr Glu Ser Leu Ala Thr Ala Pro Thr His Val Trp Thr
                725                 730                 735
Arg Pro Leu Pro Pro Ala Asn Leu Thr Ala Ala Arg Val Thr Ala Thr
            740                 745                 750
Ser Ala His Val Val Trp Asp Ala Pro Thr Pro Gly Ser Leu Leu Glu
        755                 760                 765
Ala Tyr Val Ile Asn Val Thr Thr Ser Gln Ser Thr Lys Ser Arg Tyr
    770                 775                 780
Val Pro Asn Gly Lys Leu Ala Ser Tyr Thr Val Arg Asp Leu Leu Pro
785                 790                 795                 800
Gly Arg Arg Tyr Gln Leu Ser Val Ile Ala Val Gln Ser Thr Glu Leu
                805                 810                 815
Gly Pro Gln His Ser Glu Pro Ala His Leu Tyr Ile Ile Thr Ser Pro
            820                 825                 830
Arg Asp Gly Ala Asp Arg Arg Trp His Gln Gly Gly His His Pro Arg
        835                 840                 845
Val Leu Lys Asn Arg Pro Pro Pro Ala Arg Leu Pro Glu Leu Arg Leu
    850                 855                 860
Leu Asn Asp His Ser Ala Pro Glu Thr Pro Thr Gln Pro Pro Arg Phe
865                 870                 875                 880
Ser Glu Leu Val Asp Gly Arg Gly Arg Val Ser Ala Arg Phe Gly Gly
                885                 890                 895
Ser Pro Ser Lys Ala Ala Thr Val Arg Ser Gln Pro Thr Ala Ser Ala
            900                 905                 910
Gln Leu Glu Asn Met Glu Glu Ala Pro Lys Arg Val Ser Leu Ala Leu
        915                 920                 925
Gln Leu Pro Glu His Gly Ser Lys Asp Ile Gly Asn Val Pro Gly Asn
    930                 935                 940
Cys Ser Glu Asn Pro Cys Gln Asn Gly Gly Thr Cys Val Pro Gly Ala
945                 950                 955                 960
Asp Ala His Ser Cys Asp Cys Gly Pro Gly Phe Lys Gly Arg Arg Cys
                965                 970                 975
Glu Leu Ala Cys Ile Lys Val Ser Arg Pro Cys Thr Arg Leu Phe Ser
            980                 985                 990
Glu Thr Lys Ala Phe Pro Val Trp Glu Gly Gly Val Cys His His Val
        995                 1000                1005
Tyr Lys Arg Val Tyr Arg Val His Gln Asp Ile Cys Phe Lys Glu Ser
    1010                1015                1020
Cys Glu Ser Thr Ser Leu Lys Lys Thr Pro Asn Arg Lys Gln Ser Lys
1025                1030                1035                1040
Ser Gln Thr Leu Glu Lys Ser
                1045
```

FIG. 11 (PART 1)

SEQ ID NO: 13

```
Leu Asp Gly Tyr Ala Val Thr Tyr Val Ser Ser Asp Gly Ser Tyr Arg
 1               5                  10                  15
Arg Thr Asp Phe Val Asp Arg Thr Arg Ser Ser His Gln Leu Gln Ala
            20                  25                  30
Leu Ala Ala Gly Arg Ala Tyr Asn Ile Ser Val Phe Ser Val Lys Arg
        35                  40                  45
Asn Ser Asn Asn Lys Asn Asp Ile Ser Arg Pro Ala Val Leu Leu Ala
    50                  55                  60
Arg Thr Arg Pro Arg Pro Val Glu Gly Phe Glu Val Thr Asn Val Thr
 65                  70                  75                  80
Ala Ser Thr Ile Ser Val Gln Trp Ala Leu His Arg Ile Arg His Ala
                85                  90                  95
Thr Val Ser Gly Val Arg Val Ser Ile Arg His Pro Glu Ala Leu Arg
            100                 105                 110
Asp Gln Ala Thr Asp Val Asp Arg Ser Val Asp Arg Phe Thr Phe Arg
        115                 120                 125
Ala Leu Leu Pro Gly Lys Arg Tyr Thr Ile Gln Leu Thr Thr Leu Ser
    130                 135                 140
Gly Leu Arg Gly Glu Glu His Pro Thr Glu Ser Leu Ala Thr Ala Pro
145                 150                 155                 160
Thr His Val Trp Thr Arg Pro Leu Pro Pro Ala Asn Leu Thr Ala Ala
                165                 170                 175
Arg Val Thr Ala Thr Ser Ala His Val Val Trp Asp Ala Pro Thr Pro
            180                 185                 190
Gly Ser Leu Leu Glu Ala Tyr Val Ile Asn Val Thr Thr Ser Gln Ser
        195                 200                 205
Thr Lys Ser Arg Tyr Val Pro Asn Gly Lys Leu Ala Ser Tyr Thr Val
    210                 215                 200
Arg Asp Leu Leu Pro Gly Arg Arg Tyr Gln Leu Ser Val Ile Ala Val
225                 230                 235                 240
Gln Ser Thr Glu Leu Gly Pro Gln His Ser Glu Pro Ala His Leu Tyr
                245                 250                 255
Ile Ile Thr Ser Pro Arg Asp Gly Ala Asp Arg Arg Trp His Gln Gly
            260                 265                 270
Gly His His Pro Arg Val Leu Lys Asn Arg Pro Pro Pro Ala Arg Leu
        275                 280                 285
Pro Glu Leu Arg Leu Leu Asn Asp His Ser Ala Pro Glu Thr Pro Thr
    290                 295                 300
Gln Pro Pro Arg Phe Ser Glu Leu Val Asp Gly Arg Gly Arg Val Ser
305                 310                 315                 320
Ala Arg Phe Gly Gly Ser Pro Ser Lys Ala Ala Thr Val Arg Ser Gln
                325                 330                 335
Pro Thr Ala Ser Ala Gln Leu Glu Asn Met Glu Glu Ala Pro Lys Arg
            340                 345                 350
```

FIG. 11 (CONTINUED, PART 2)

```
Val Ser Leu Ala Leu Gln Leu Pro Glu His Gly Ser Lys Asp Ile Gly
        355                 360                 365
Ser Glu Ser Ala Ala Leu Val Gly Thr Leu Gly Leu Thr Asp Cys Ser
    370                 375                 380
Gln Gly Pro
385
```

FIG. 12A (PART 1)

SEQ ID NO: 14

```
                              AAGAGCTCCTCCCACCAACAGCCCTCAGGGTAGAA
                                 GluLeuLeuProProThrAlaLeuArgValGlu
AGGGTGGAGGAGAGTGGGGTCTCCATCTCCTGGAGCCCACCCGAGGGCACCACGGCCAGA
ArgValGluGluSerGlyValSerIleSerTrpSerProProGluGlyThrThrAlaArg
CAGGTGCTGGACGGCTATGCAGTCACCTATGCCTCCTCGGATGGATCGTCCAGGCGCACG
GlnValLeuAspGlyTyrAlaValThrTyrAlaSerSerAspGlySerSerArgArgThr
GACTTTGTGGACCGGAGCCGCTCCTCTCACCAGCTTCGGGCCCTGGCAGCCGGCCGTGCC
AspPheValAspArgSerArgSerSerHisGlnLeuArgAlaLeuAlaAlaGlyArgAla
TACAACATCTCTGTTTTCTCAGTCAAGAGAAACACTAACAACAAAAATGACATCAGCAGG
TyrAsnIleSerValPheSerValLysArgAsnThrAsnAsnLysAsnAspIleSerArg
CCTGCAGCCCTGCTCACCCGCACCCGACCCCGCCCTATTGAAGACTTCGAGGTCACCAAC
ProAlaAlaLeuLeuThrArgThrArgProArgProIleGluAspPheGluValThrAsn
ATTTCAGCCAATGCCATCTCAGTGCAGTGGGCTCTTCATAGGATCCAGCATGCCACTGTC
IleSerAlaAsnAlaIleSerValGlnTrpAlaLeuHisArgIleGlnHisAlaThrVal
AGCAGGGTTCGAGTGTCTGTCCTCTACCCTGAGGACACTGTGGTCCAGTCCACGGAGGTG
SerArgValArgValSerValLeuTyrProGluAspThrValValGlnSerThrGluVal
GACAGGAGTGTGGACCGCCTCACATTTGGGGACCTGCTGCCAGGGAGAAGATACAGTGTG
AspArgSerValAspArgLeuThrPheGlyAspLeuLeuProGlyArgArgTyrSerVal
CGGCTAACCACCCTCAGTGGGCCTGGAGGAGCTGAATATCCTACAGAGAGCCTGGCCTCA
ArgLeuThrThrLeuSerGlyProGlyGlyAlaGluTyrProThrGluSerLeuAlaSer
GCTCCGCTGAACGTGTGGACCCGGCCTTTGCCTCCAGCAAACCTGACTGCCTCTCGAGTC
AlaProLeuAsnValTrpThrArgProLeuProProAlaAsnLeuThrAlaSerArgVal
ACAGCGACCTCTGCCCATATGGTCTGGGACCCGCCCACTCCAGGCATCTCACTGGAGGCT
ThrAlaThrSerAlaHisMetValTrpAspProProThrProGlyIleSerLeuGluAla
TACGTCATCAATGTGACCACCAGTCAGAATACCAAGAGCCGCTACATCCCCAATGGGAAG
TyrValIleAsnValThrThrSerGlnAsnThrLysSerArgTyrIleProAsnGlyLys
CTGGTGTCCTATACGGTGCGTGATCTGATGCCAGGTCGGCGGTACCAGCTCTCGGTCACA
LeuValSerTyrThrValArgAspLeuMetProGlyArgArgTyrGlnLeuSerValThr
GCGGTGCAGAGCACAGAGCAGGGCCAGCTGCACAGTGAGCCTGCGCACCTCTACATCATC
AlaValGlnSerThrGluGlnGlyGlnLeuHisSerGluProAlaHisLeuTyrIleIle
ACCTCCCCCAGGGATGGCACCGACAGGCGCTGGCACCAGGGAGGACACCACTCACGGATG
ThrSerProArgAspGlyThrAspArgArgTrpHisGlnGlyGlyHisHisSerArgMet
CTCAGAAATAGGCCGGCCCCTTTGCGCCTGCCAGAACTGCGCCTCCTCAATGACCACGGT
LeuArgAsnArgProAlaProLeuArgLeuProGluLeuArgLeuLeuAsnAspHisGly
GCCCCTGAAACACCAACCCAGCCACCCAGGTTCTCAGAGCTTGTAGACGGAAGAGCAAGA
AlaProGluThrProThrGlnProProArgPheSerGluLeuValAspGlyArgAlaArg
GTGAGTGCCAGGTTTGGTGGATTGCCCAGCAGAGCAGTAACTGTGAGATCACAACCCACT
ValSerAlaArgPheGlyGlyLeuProSerArgAlaValThrValArgSerGlnProThr
ACGCCGGTGCCGCTCAAGAACACAGAGGCCCCTGAGCAGGCCCGTCTGGCCCTTCAGCTA
ThrProValProLeuLysAsnThrGluAlaProGluGlnAlaArgLeuAlaLeuGlnLeu
CCCAAGAACAACAGCAAGGACACAGAAAGTACCCCTGGCAGCTGTTCAGAAGACACCTGT
ProLysAsnAsnSerLysAspThrGluSerThrProGlySerCysSerGluAspThrCys
CAGAATGGAGGCACCTGTGTCCCAGGTGCCAATGCCCACAGCTGTGACTGCAGGCCTGGG
GlnAsnGlyGlyThrCysValProGlyAlaAsnAlaHisSerCysAspCysArgProGly
TTCAAAGGCAGACACTGTGAGCTTGCCTGTGAAAAAGTGCCCCGCCCCTGCACACGGCTG
PheLysGlyArgHisCysGluLeuAlaCysGluLysValProArgProCysThrArgLeu
TTCTCTGAGACCAAGTCATTTCCTGTCTGGGAAGGAGATGTCTGCCACCATGTGTATAAG
PheSerGluThrLysSerPheProValTrpGluGlyAspValCysHisHisValTyrLys
```

FIG. 12A (CONTINUED, PART 2)

AAAGTCTACAAAGTTCACCAGGACGTGTGTTTAAGGAGCGCTGCCAGAGCACAAGCCTC
LysValTyrLysValHisGlnAspValCysPheLysGluArgCysGlnSerThrSerLeu
AAAAAGCTCAAACAGGAATCAAATTAA
LysLysLeuLysGlnGluSerAsn

FIG. 12B

CAGTCAAACACTGAAGAAATCTTAAGGTACATTCTCCTTCATACCAAGATCTGTT
GAGAACTGGAGACACCATCATACCCAGCACCTTGGACAACTGATGGTGCAAACTTAGCAC
TGTGCTATTACAGACCCAACCAGGAAGGTTCCAGAATTCCCTGTCTATAGCCTCCCAATA
GACATAACCTGGTCTGGCCTTCCATATGAATCCACTTTCAGGTGGAAATGACTCTCTGGG
GGAGGGGCAAATGCAGACCAGTTACAATGAGGCACAAGAATCACCTGGCCCCTTCAGGAC
AGTGGGCCTGGGTGTTAGATGGATCAAGGATGCCAAACAATCCTGGGGGTGCTAGGAAGG
ACCTAAGGACATACCCTCAAGCCCTATGAATAGCATTCTACTGGTGGAAAAGGGCGGGAG
CCTTGTCATGTAACCTGCAGGTGATCCTAAATAGAGCCTCTCACTGGGAGAGATATCATG
GATCCTGGAATTCTAAGCACTAATAACCCTGAAGTGAAAGAAACTTTGCCTGCTTGATCC
AGCATGTCCCACCCCACCCTCCCCATACATAAACTGTGAGATGTCAAAGGGCATTGGAAA
ATTTTTTTCACAAGCCTGGGAAATACTGGGTTACACTACAGAGATCCCTGTATAGCCTGA
ACTCAGCCCCAACACTGACTTACTGATGGGACATCAATTGGAAACGAGAGACTGGCTGGC
CAGAGACATTTCACTCCTCTCCCTTGGAGGAGCCAGAACAGTACATCTGTGCAGTGGTGG
GAGAGAGGCAGATCTGGAAGCCTGCCACTCCAGGAGTGAATCACCTTTGTTCTACAGTGT
AGGACGTGAAGGAGAAATGTCACCCAAAGGCCTAAGAACAAAGAAGAGCAAAGCAGTTCT
GGGCGAAGGTCATCCGAAGAGAAAAGTGTCTACAGTAAAAGGCAGGGCATCAGGAGAGCG
GGCTCTCAGACAGGCCTAAGCAGGGCCTGTGCATCTTGACCATTTCAGATGTGAAGACTG
CAGGAAGAGCAGCTGACCAGACTCAAATCCTGTCTACTTAACAGCATCACCTTTTCACCT
CAGCCCCCAAAAATGCACACAACACCCTCCAACACATGTGAGCAACTTCATTCTGGCAAA
GATCAAAAATCCACAAATTATTTGGTTTTAAAATATTTACATGGCAGTAAGTCAGATGAA
ATATTAATGCAAAAAAAGAAATATTAATGCATCCTTTAAGAACTCACAGAAAACTCATTT
TTAGAAAAAAAAATGAGAATCCCTAGGTACTTATCACATAATGGCTTATAGAAAACCTAT
TCTCAAAGCAACACACACACACACACACACCCCATACGTACGTACATACATACATCTAAC
ACACACATGTGTGTGTATATATATATATATATATATATATATATATATATGACACACACA
AAGCAAAAATAATTATATCTTTTTAAAGATATATATTTTCTTTTAGGAAACAGTAATTAC
TGACAACGCTGCATTTGAAATACTCAAAAAGATACTACCGTTACAAAACTCCAGTTTCTC
AGGGACAGGTTTGGTATTGCCAGCTAAGAATCCCAAGGAGGAGACTGAGCTGCTTAAGTC
GGAGGGAGCAACAGTAATGGCCAAGTCGCCTGAGCCTCCTTCACAGTCACAGGATTCAGA
AAATGGATACATCAATGTGACTTCTCTAAAGGAGACATACCACACACAAGGGGACCGGAA
GCCAAAACTATGACCTCACGGGATCTGAAACAATACTAATCATGCCTACTAAGTCAGAGC
CTGGGTACAGAGGTGCAAACTGAGCTGGAGACGTCTCACAGAACACCCTGGACATCAACA
AGGAGTCTTCAAAATCGCTTTTTAAACAGTCATTAAAATTTTTC

FIG. 13 (PART 1)
SEQ ID NO: 44

```
ATCACCTGCGTTGAAACCTGCCCGGGGCTTTCATCTGCCAGTGCCCTGAAGGTTTTGTTG ...60
GAACCCACTGTGAAACAGGTAGGGTTCTTTCAGGAGGGTCCCACAGAACCAGGGCTGCTG
GGAGATCAGAGGGGAAGCCAGGAGCCATGCTGAACAGAGCCACGGAGGACATCAGGCGGT
ACTTTCCTGAGCTCCCGGACTTCTCTGCTACCTGGGTTTTTGTTGCCACCTGGTACCGTG
TGACCTTCTTCGGAGGCAGCAGCTCTTCCCCCGTCAACACATTCCAAACGGTGCTCATCA ..300
CTGACGGCCGGTTCTCCTTCACCATCTTCAACTATGAGTCCATCCAGTGGACTACGGGCA
CACACGCCAGCAGTGGTGGTGATGCTGATGGCTTGGGAGGCATTGCAGCCCAGGCAGGTT
TCAACGCAGGTGATGGGCACCGCTACTTCAACATCCCTGGGTCGCGCACAGCAGACATGG
CTGAGGTGGAGACCATCACCAACGTGGGCGTGCCCGGGCGCTGGGCGTTTAGAATCGATG
ATGCCCAGCCTCTGTGTGCCTAGTCCTGCGTCCGTGCCTCAATGGTGGCAAGTGCATCGA ..600
TGACTGTGTCACGGGCAATCCCTCCTACACCTGTTCCTGTCTCGCTGGCTTCACGGGGCG
TGGATGCCACCTGGATGTGAACGAGTGTGCTTCCCACCCATGTCAGAACGGTGGGACCTG
CACCCACGGTGTCAACAAGCTTCAGTTGCCAGCCGGCTTCCAGGGACCCACTTGTGAATC
AGCCCAGTCTCCGTGTGACAACAAAGAGTGTCAACATGGTGGCCAGTGCCAGGCAGAGAG
CAGCTCTGCAGTATGTGTGTGTCAGGCTGGATACACTGGGGCCACCTGTGAGACCGATGT ..900
GGATGAATGCAGCTCTGACCCATGCCTGAATGGAGGCTCTTGTGTTGACCTGGTTGGAAA
CTACAGCTGTATTTGTGTGGAGCCCTTTGAAGGACCTCAGTGCGAGACAGGAAGCTACGT
GGTGCCTTCGCCCTGCCTCTCCAACCCCTGCCTGAACGGGGGCACCTGTGTGGATGCTGA
CCAGGGATACGTGTGCGAATGCCCTGAAGGTTTCATGGGCTTGGACTGCAGAGAGAGAAT
TCTCAATGACTGTGATTGCCGGAATGGAGGCAGATGCCTGGGTGCCAACACCACCATCTG .1200
CCAGTGTCCTCCAGGCTCCTTTGGGCTCCTCTGTGAATTTGAAGTCACAGCCACGCCCTG
CAACATGAACACACAGTGTCCAGATGGAGGCTACTGCATGGAGTATGGCGGAAGCTACCT
ATGTGTCTGCCACACGGACCACAACATCAGCCATTCTCTGCCCTCGCCCTGCGACTCAGA
CCCATGCTTTAATGGAGGTTCCTGTGACGCCCACGAGGACTCCTACACGTGCGAGTGCCC
TCGTGGATTCCATGGCAGGCACTGCGAGAAAGCCCGGCCACACCTGTGCAGCTCAGGGCC .1500
CTGCCGGAATGGGGGCACATACAAGGAGACTGGTGACGAGTACCGCTGCACCTGCCCTTA
CCGGTTCACTGGGAGACACTGTGAGATTGGAAAGCCAGACTCCTGTGCCTCTGGCCCCTG
TCACAACGGTGGCACTTGTTTCCACTACATTGGCAAATACAAGTGTGACTGCCCTCCAGG
CTTCTCTGGTCGGCACTGTGAGATAGCCCCCTCCCCCTGCTTCCGGAGCCCATGTATGAA
TGGGGGTATCTGCGAGGATCTAGGAACAGATTTCTCCTGCCACTGCCAACCAGGATATAC .1800
AGGACACCGGTGTCAGGCAGAGGTGGACTGCGGTCAGCCTGAGGAGGTAAAACATGCTAC
CATGCGTCTCAATGGAACTCGCATGGGCTCGGTGGCCCTGTACACATGTGACCCCGGCTT
CAGCCTGAGCGTCCTCAGCCATATGCGTGTCTGTCAGCCACAAGGTGTCTGGAGCCAGCC
TCCCCAGTGCATTGAAGTAGATGAGTGCCAGTCTCAGCCATACCTGCATAAAGGCTCCTG
CCAGGACCTCATTGCTGGTTACCAGTGCCTCTGCAGCCCGGGGTACGAAGGAGTCCACTG .2100
TGAGCTAGAGACAGACGAGTGCCAAGCACAGCCCTGCAGAAATGGAGGCTCCTGCAGGGA
CCTCCCCGGGGCTTTCATCTGCCAGTGCCCTGAAGGTTTTGTTGGAACCCACTATGAAAC
AGAGGTGGATGCCTGTGCCTCCAGCCCCTGCCAGCACGGAGGCCGGTGTGAGGACGGTGG
TGGGGCCTACCTGTGCGTTTGTCCAGAGGGCTTCTTCGGCTACAACTGTGAGACAGTGAG
TAACCCCTGCTTCTCTAGCCCCTGTGGGGGCCGCGGCTACTGCTTGGCCAGCAACGGGTC .2400
CCACAGCTGTACCTGCAAAGTGGGCTACACAGGCAAGGACTGCACCAAAGAGCTCCTCCC
ACCAACAGCCCTCAGGGTAGAAAGGGTGGAGGAGAGTGGGGTCTCCATCTCCTGGAGCCC
ACCCGAGGGCACCACGGCCAGACAGGTGCTGGACGGCTATGCAGTCACCTATGCCTCCTC
GGATGGATCGTCCAGGCGCACGGACTTTGTGGACCGGAGCCGCTCCTCTCACCAGCTTCG
GGCCCTGGCAGCCGGCCGTGCCTACAACATCTCTGTTTTCTCAGTCAAGAGAAACACTAA .2700
CAACAAAAATGACATCAGCAGGCCTGCAGCCCTGCTCACCCGCACCCGACCCCGCCCTAT
TGAAGACTTCGAGGTCACCAACATTTCAGCCAATGCCATCTCAGTGCAGTGGGCTCTTCA
TAGGATCCAGCATGCCACTGTCAGCAGGGTTCGAGTGTCTGTCCTCTACCCTGAGGACAC
TGTGGTCCAGTCCACGGAGGTGGACAGGAGTGTGGACCGCCTCACATTTGGGGACCTGCT
GCCAGGGAGAAGATACAGTGTGCGGCTAACCACCCTCAGTGGGCCTGGAGGAGCTGAATA .3000
```

FIG. 13 (CONTINUED, PART 2)

```
TCCTACAGAGAGCCTGGCCTCAGCTCCGCTGAACGTGTGGACCCGGCCTTTGCCTCCAGC
AAACCTGACTGCCTCTCGAGTCACAGCGACCTCTGCCCATATGGTCTGGGACCCGCCCAC
TCCAGGCATCTCACTGGAGGCTTACGTCATCAATGTGACCACCAGTCAGAATACCAAGAG
CCGCTACATCCCCAATGGGAAGCTGGTGTCCTATACGGTGCGTGATCTGATGCCAGGTCG
GCGGTACCAGCTCTCGGTCACAGCGGTGCAGAGCACAGAGCAGGGCCAGCTGCACAGTGA .3300
GCCTGCGCACCTCTACATCATCACCTCCCCCAGGGATGGCACCGACAGGCGCTGGCACCA
GGGAGGACACCACTCACGGATGCTCAGAAATAGGCCGGCCCCTTTGCGCCTGCCAGAACT
GCGCCTCCTCAATGACCACGGTGCCCCTGAAACACCAACCCAGCCACCCAGGTTCTCAGA
GCTTGTAGACGGAAGAGCAAGAGTGAGTGCCAGGTTTGGTGGATTGCCCAGCAGAGCAGT
AACTGTGAGATCACAACCCACTACTCCGGTGCCGCTCAAGAACACAGAGGCCCCTGAGCA .3600
GGCCCGTCTGGCCCTTCAGCTACCCAAGAACAACAGCAAGGACACAGAAAGTACCCCTGG
CAGCTGTTCAGAAGACACCTGTCAGAATGGAGGCACCTGTGTCCCAGGTGCCAATGCCCA
CAGCTGTGACTGCAGGCCTGGGTTCAAAGGCAGACACTGTGAGCTTGCCTGTGAAAAAGT
GCCCCGCCCCTGCACACGGCTGTTCTCTGAGACCAAGTCATTTCCTGTCTGGGAAGGAGA
TGTCTGCCACCATGTGTATAAGAAAGTCTACAAAGTTCACCAGGACGTGTGTTTTAAGGA .3900
GCGCTGCCAGAGCACAAGCCTCAAAAAGCTCAAACAGGAATCAAAFFAACAGTCAAACAC
TGAAGAAATCTTAAGGTACATTCTCCTTCATACCAAGATCTGTTGAGAACTGGAGACACC
ATCATACCCAGCACCTTGGACAACTGATGGTGCAAACTTAGCACTGTGCTATTACAGACC
CAACCAGGAAGGTTCCAGAATTCCCTGTCTATAGCCTCCCAATAGACATAACCTGGTCTG
GCCTTCCATATGAATCCACTTTCAGGTGGAAATGACTCTCTGGGGGAGGGGCAAATGCAG .4200
ACCAGTTACAATGAGGCACAAGAATCACCTGGCCCCTTCAGGACAGTGGGCCTGGGTGTT
AGATGGATCAAGGATGCCAAACAATCCTGGGGGTGCTAGGAAGGACCTAAGGACATACCC
TCAAGCCCTATGAATAGCATTCTACTGGTGGAAAAGGGCGGGAGCCTTGTCATGTAACCT
GCAGGTGATCCTAAATAGAGCCTCTCACTGGGAGAGATATCATGGATCCTGGAATTCTAA
GCACTAATAACCCTGAAGTGAAAGAAACTTTGCCTGCTTGATCCAGCATGTCCCACCCCA .4500
CCCTCCCCATACATAAACTGTGAGATGTCAAAGGGCATTGGAAAATTTTTTTCACAAGCC
TGGGAAATACTGGGTTACACTACAGAGATCCCTGTATAGCCTGAACTCAGCCCCAACACT
GACTTACTGATGGGACATCAATTGGAAACGAGAGACTGGCTGGCCAGAGACATTTCACTC
CTCTCCCTTGGAGGAGCCAGAACAGTACATCTGTGCAGTGGTGGGAGAGAGGCAGATCTG
GAAGCCTGCCACTCCAGGAGTGAATCACCTTTGTTCTACAGTGTAGGACGTGAAGGAGAA .4800
ATGTCACCCAAAGGCCTAAGAACAAAGAAGAGCAAAGCAGTTCTGGGCGAAGGTCATCCG
AAGAGAAAAGTGTCTACAGTAAAAGGCAGGGCATCAGGAGAGCGGGCTCTCAGACAGGCC
TAAGCAGGGCCTGTGCATCTTGACCATTTCAGATGTGAAGACTGCAGGAAGAGCAGCTGA
CCAGACTCAAATCCTGTCTACTTAACAGCATCACCTTTTCACCTCAGCCCCCAAAAATGC
ACACAACACCCTCCAACACATGTGAGCAACTTCATTCTGGCAAAGATCAAAAATCCACAA .5100
ATTATTTGGTTTTAAAATATTTACATGGCAGTAAGTCAGATGAAATATTAATGCAAAAAA
AGAAATATTAATGCATCCTTTAAGAACTCACAGAAAACTCATTTTTAGAAAAAAAAATGA
GAATCCCTAGGTACTTATCACATAATGGCTTATAGAAAACCTATTCTCAAAGCAACACAC
ACACACACACACACCCCATACGTACGTACATACATACATCTAACACACACATGTGTGTGT
ATATATATATATATATATATATATATATATATATATGACACACACAAAGCAAAAATAATTAT .5400
ATCTTTTTAAAGATATATATTTTCTTTTAGGAAACAGTAATTACTGACAACGCTGCATTT
GAAATACTCAAAAAGATACTACCGTTACAAAACTCCAGTTTCTCAGGGACAGGTTTGGTA
TTGCCAGCTAAGAATCCCAAGGAGGAGACTGAGCTGCTTAAGTCGGAGGGAGCAACAGTA
ATGGCCAAGTCGCCTGAGCCTCCTTCACAGTCACAGGATTCAGAAAATGGATACATCAAT
GTGACTTCTCTAAAGGAGACATACCACACACAAGGGGACCGGAAGCCAAAACTATGACCT .5700
CACGGGATCTGAAACAATACTAATCATGCCTACTAAGTCAGAGCCTGGGTACAGAGGTGC
AAACTGAGCTGGAGACGTCTCACAGAACACCCTGGACATCAACAAGGAGTCTTCAAAATC
GCTTTTTAAACAGTCATTAAAATTTTTC .5848
```

FIG. 14 (PART 1)

SEQ ID NO: 45

GCCTCGTCCATAATGATGGCTGCATGGCCACTTCCGGCCCAAGAGGGATCCAAGAGGCAG ...60
CGCGGTCCGATCGGAGAGCACCCTTACCGTGGGCACCTGCACGAGCGGCCCAGGCTGTCA
AATCAGTGACCAGGATTTGTTTGCAACACCAGCGGGCCCCAAATATGAGGGTGTTAGTGT
CTCAGGCTGTGGTCTTCCAAGTGGCAGACCAGACCGCAGACTGGGGTAGCAGGCTTTTTC
TGTAGAGGGCCAGGTAGTGACTATTTTCAGCTTTTCAGGCCACAGGGTCTCTGCTGTTGT ..300
CACAAAAAAGCAGCCGTAGACAGTAAGTACGTGAGTGTGCTCAGCCGTGCTCCCACAAAC
CCTGTTTCTGAAACCAGGCTGGGGTCCACAGAGGATGGATGGCCACATCTGACCCAAGGC
CTGTTTGTGTATGACCTGTGAACTAAGAATGTTCTTAATACTTTTAAAGGGCTGCAAAAA
CAAAAAGAACAAAAAAGAATATGCAACAGAGACCACGTGTGGTCCACAGGGCCAGAAATA
TTTGCGATCTGGCCCTTCCCAGAAAGTCTGCTGGCCCTTGGGCAGACCGCACCATTTGCA ..600
ACAACCAAAATTCAGTAAAACTTCAATGTTTCTGGTCCTTAAGAGTCCTAAGGCCAGGGT
GGCAGCTTCCAGCCCAGCCCCAATACTCACTGGTCTTCTGCTGTCTCCCAGAGTTGGCGC
TGGGGCTGGACAGCCACTGCCCAGGGGACGCCATTGGGCTCCAGCTTAGCCGGACCATCC
TTGAACCAGGCCCAGGCATCGGGGGCCCCGTGACTCGAGCACCCCGCAGAGCCAGTGGCT
CACGTCAGGCACTGGACCGGAAGGTGAACAACAACGGGATCATCTCCTTCCTGAAGGAGG ..900
TTTCTCAGTTCACCCCAGTGGCCTTCCCCATTGCCAAGGACCGCTGCGTGGTGGCAGCCT
TCTGGGCAGATGTGAACAACCGGCGTGCAGGCGACGTGTACTACCGGGAGGCCACCGACC
CAGCCATGCTGCGCCGAGCCACGGAGGACGTCAGGCACTACTTCCCCGAGCTCCTGGACT
TCAATGCCACCTGGGTTTTTGTTGCCACCTGGTACCGAGTGACCTTCTTTGGAGGCAGTT
CCTCATCCCCTGTCAACACATTCCAGACTGTGCTCATCACAGACGGCAAGCTCTCCTTCA .1200
CCATCTTCAACTATGAGTCCATCGTGTGGACCACAGGCACACACGCCAGCAGCGGGGGCA
ACGCCACTGGCCTCGGGGGCATCGCAGCCCAGGCTGGCTTCAACGCAGGCGATGGGCAGC
GTTACTTCAGTATCCCCGGCTCGCGCACAGCAGACATGGCCGAGGTGGAGACCACCACCA
ACGTGGGTGTGCCCGGGCGCTGGGCGTTCAGAATCGATGATGCCCAGGTGCGCGTGGGGG
GCTGCGGCCATACAACGTCCGTGTGCCTGGCCCTGCGCCCCTGCCTCAACGGCGGCAAGT .1500
GCATCGACGACTGCGTCACGGGCAACCCCTCCTACACCTGCTCCTGCCTCTCGGGCTTCA
CGGGGCGGAGGTGCCACCTGGACGTGAACGAATGTGCCTCCCAGCCCTGTCAGAATGGTG
GGACCTGTACTCACGGCATCAACAGTTTCCGCTGCCAGTGCCCGGCTGGCTTTGGGGGAC
CCACCTGTGAGACAGCCCAATCCCCCTGTGACACCAAAGAGTGTCAACATGGTGGCCAGT
GCCAGGTGGAGAATGGCTCTGCGGTGTGTGTGTGCCAGGCCGGATACACCGGAGCAGCCT .1800
GCGAGATGGATGTGGACGACTGCAGCCCTGACCCCTGCCTGAATGGAGGCTCTTGTGTTG
ACCTAGTGGGGAATTACACCTGCTTGTGTGCCGAGCCCTTCAAGGGACTTCGCTGTGAGA
CAGGAGACCATCCAGTGCCAGACGCCTGCCTCTCGGCCCCTTGCCACAATGGGGGCACCT
GTGTGGATGCGGACCAGGGCTACGTGTGCGAGTGCCCCGAAGGCTTCATGGGCCTGGACT
GCAGGGAGAGAGTCCCCGATGACTGTGAGTGCCGCAACGGAGGCAGATGCCTGGGCGCCA .2100
ACACCACCCTCTGCCAGTGCCCCCTGGGATTCTTTGGGCTTCTCTGTGAATTTGAAATCA
CAGCCATGCCCTGCAACATGAACACACAGTGCCCAGATGGGGGCTACTGCATGGAGCACG
GCGGGAGCTACCTCTGCGTCTGCCACACCGACCACAATGCCAGCCACTCCCTGCCATCAC
CCTGCGACTCGGACCCCTGCTTCAACGGAGGCTCCTGCGATGCCCATGACGACTCCTACA
CCTGCGAGTGCCCGCGCGGGTTCCACGGCAAGCACTGCGAGAAAGCCCGGCCACACCTGT .2400
GCAGCTCAGGGCCCTGCCGGAACGGGGGCACGTGCAAGGAGGCGGGCGGCGAGTACCACT
GCAGCTGCCCCTACCGCTTCACTGGGAGGCACTGTGAGATCGGGAAGCCAGACTCGTGTG
CCTCTGGCCCCTGTCACAACGGCGGCACCTGCTTCCACTACATTGGCAAATACAAGTGTG
ACTGTCCCCCAGGCTTCTCCGGGCGGCACTGCGAGATAGCCCCCTCCCCCTGCTTCCGGA
GCCCGTGTGTGAATGGGGGCACCTGCGAGGACCGGGACACGGATTTCTTCTGCCACTGCC .2700
AAGCAGGGTACATGGGACGCCGGTGCCAGGCAGAGGTGGACTGCGGCCCCCCGGAGGAGG
TGAAGCACGCCACACTGCGCTTCAACGGCACGCGGCTGGGCGCGGTGGCCCTGTATGCAT
GTGACCGTGGCTACAGCCTGAGCGCCCCCAGCCGCATCCGGGTCTGCCAGCCACACGGTG
TCTGGAGTGAGCCTCCCCAGTGCCTTGAAATCGATGAGTGCCGGTCTCAGCCGTGCCTGC
ATGGGGGCTCTTGTCAGGACCGCGTTGCTGGGTACCTGTGCCTCTGCAGCACAGGCTATG .3000
AGGGCGCCCACTGTGAGCTGGAGAGGGATGAGTGCCGAGCTCACCCGTGCAGAAATGGAG
GGTCCTGCAGGAACCTCCCAGGGGCCTATGTCTGCCGGTGCCCTGCAGGCTTCGTTGGAG
TCCACTGTGAGACAGAGGTGGACGCCTGCGACTCCAGCCCCTGCCAGCATGGAGGCCGGT
GTGAGAGCGGCGGCGGGGCCTACCTGTGCGTCTGCCCAGAGAGCTTCTTCGGCTACCACT
GCGAGACAGTGAGTGACCCCTGCTTCTCCAGCCCCTGTGGGGGCCGTGGCTATTGCCTGG .3300
CCAGCAACGGCTCCCACAGCTGCACCTGCAAAGTGGGCTACACGGGCGAGGACTGCGCCA

FIG. 14 (CONTINUED, PART 2)

AAGAGCTCTTCCCACCGACGGCCCTCAAGATGGAGAGAGTGGAGGAGAGTGGGGTCTCTA
TCTCCTGGAACCCGCCCAATGGTCCAGCCGCCAGGCAGATGCTTGATGGCTACGCGGTCA
CCTACGTCTCCTCCGACGGCTCCTACCGCCGCACAGACTTTGTGGACAGGACCCGCTCCT
CGCACCAGCTCCAGGCCCTGGCGGCCGGCAGGGCCTACAACATCTCCGTCTTCTCAGTGA .3600
AGCGAAACAGTAACAACAAGAATGACATCAGCAGGCCTGCCGTGCTGCTGGCCCGCACGC
GACCCCGCCCTGTGGAAGGCTTCGAGGTCACCAATGTGACGGCTAGCACCATCTCAGTGC
AGTGGGCCCTGCACAGGATCCGCCATGCCACCGTCAGTGGGGTCCGTGTGTCCATCCGCC
ACCCTGAGGCCCTCAGGGACCAGGCCACCGATGTGGACAGGAGTGTGGACAGGTTCACCT
TTAGGGCCCTGCTGCCTGGGAAGAGGTACACCATCCAGCTGACCACCCTCAGTGGGCTCA .3900
GGGGAGAGGAGCACCCCACAGAGAGCCTGGCCACCGCGCCGACGCACGTGTGGACCCGGC
CCCTGCCTCCAGCAAACCTGACCGCCGCCCGAGTCACTGCCACCTCTGCCCACGTGGTCT
GGGATGCCCCGACTCCAGGCAGCTTGCTGGAGGCTTATGTCATCAATGTGACCACCAGCC
AGAGCACCAAGAGCCGCTATGTCCCCAACGGGAAGCTGGCGTCCTACACGGTGCGCGACC
TGCTGCCGGGACGGCGGTACCAGCTCTCTGTGATAGCAGTGCAGAGCACGGAGCTCGGGC .4200
CGCAGCACAGCGAGCCCGCCCACCTCTACATCATCACCTCCCCCAGGGATGGCGCTGACA
GACGCTGGCACCAGGGAGGACACCACCCTCGGGTGCTCAAGAACAGACCGCCCCCGGCGC
GCCTGCCGGAGCTGCGCCTGCTCAATGACCACAGCGCCCCCGAGACCCCCACCCAGCCCC
CCAGGTTCTCGGAGCTTGTGGACGGCAGAGGAAGAGTGAGCGCCAGGTTCGGTGGCTCAC
CCAGCAAAGCAGCCACCGTGAGATCACAACCCACAGCCTCGGCGCAGCTCGAGAACATGG .4500
AGGAAGCCCCCAAGCGGGTCAGCCTGGCCCTCCAGCTCCCTGAACACGGCAGCAAGGACA
TCGGAAACGTCCCTGGCAACTGTTCAGAAAACCCCTGTCAGAACGGAGGCACTTGTGTGC
CGGGCGCAGACGCCCACAGCTGTGACTGCGGGCCAGGGTTCAAAGGCAGACGCTGCGAGC
TCGCCTGTATAAAGGTGTCCCGCCCCTGCACAAGGCTGTTCTCCGAGACAAAGGCCTTTC
CAGTCTGGGAGGGAGGCGTCTGTCACCACGTGTATAAAAGAGTCTACCGAGTTCACCAAG .4800
ACATCTGCTTCAAAGAGAGCTGTGAAAGCACAAGCCTCAAGAAGACCCCAAACAGGAAAC
AAAGTAAGAGTCAGACACTGGAGAAATCTTAAGGATTTAAGACGTTCTTGTTACACTCCA
CCAACCTCACGAGTTTCTAACACCCAGGAAGATGAGGTCTAAAAACTGGATGAAAAAGGA
CACCCTGAGAAAAGGTCCTAGCTGGAGTCAGTCCCCTCTGTGACCTCTCTCCTCAGGCCT
CTAGAGGACAGATGGCCAGGCCTGTGCACACACCAGCCCACCCTGAGAGACCCCTCTGGG .5100
ACCAACCACCTGTGAGTCCTGCGATGCGTTTAAGCAGCCTGTGCCCTCACCCAAGCTGCA
GTTCCTGAAGGTGTAGTCTGTGTCTCTGCGGATGAGATGACAGCTCGCCATTCCCCGGAA
TCAGTGAGGCTGTCAGTCAGCCACGCTTCTGCAGTATGCAGAAACCTGTTCTTAGACTCC
AAAGCCAGAGAAAGAATTCTCCCTTCGAGGCCCAACAAATTGAGAAGGAACTGTGATGGA
CCACTTCCAAAACAGAGACGGGGGCAGGGGCTGAAGGGCAGAGACCAGGTGATGTCAGAA .5400
GGAAAGCCGGGTTGCAGACACAGCCGCCCCTGCTCTGGTCCTCCAGCGTGTTTATGACGC
TCGTGCAGGTCGACGAGCCATCCTATGGACTAGTTAACACTAAGGTGGAGTTCAGACTTT
TTTAGACAACGGCGCGACTGGCAGCCTTTCTCTATCAAGGGTCAGACGGTAAACGTTTTC
AGCTTTGCAGACCAGAGGTCCCTGTGGCTACAGTAGCGCAGACACAGCCACAGGCATGTC
ATTGAATGGCTGCGGCTATGTTCCAATAAAAACTTATTTACAATAACAGGTGGTGGCCAA .5700
ATTGGCCCATGGGCCTTATTTGGTGAACCCTGTTCTATGAGATCACCTAGGCTTCAGCCT
TAAACAGTGGAAGCCATCCCCTGAATGACAAGTCACAAGGGTATCAAAGAAAGACCCCTG
AATTTTCATGGAAAAAGCTATTCAGACCCCTGCTTGGAAAGCTAAGGCACACTGCCACGA
AGCAGCAAGGACGCCTTACAAGTCTCAGTGCAACAGAGATGGACACCTGGGCTGGGCTGG
ACAATGTTTAAGGTTCCTTTTAGTCCATGACTCAAGTGATACTGTTTTAGGCTATCAGGT .6000
AGTAAACACGATCTTAGACATCCCCATCTTTGTAAGCAGAACAGTACGGCACTTCACCAC
ATCTGCTTCCCACCATGCTTCTAAGCAGCTGTCTTCCCCCTGCTAATGTTACAACCAAAG
CAGCCACCCCACCTCCTCTCGTGTTGAGCCTCACGACCGCTGACCCAGCTGGAAAGCCAG
CGCCCTGCCGCGTCACCCTGACTCTGCTCAGAGCCAGCATTCCAGCCACAAAGAGGGCCT
CCTTCCTTTCCTCTTTCATAAAAATGTTTTTTGAAGAGTTAGAGTATATTTTAGGCTTTT .6300
TATCTTTATTAAAATTTCATGTGCATGTGTA .6331

SEQ ID NO: 47

ECQHGGQCQAESSSAVCVCQAGYTGATCETDVDECSSDPCLNGGSCVDLVGNYSCIC
VEPFEGPQCETGSYVVPSPCLSNPCLNGGTCVDADQGYVCECPEGFMGLDCRERILN
DCDCRNGGRCLGANTTICQCPPGSFGLLCEFEVTATPCNMNTQCPDGGYCMEYGGSY
LCVCHTDHNISHSLPSPCDSDPCFNGGSCDAHEDSYTCECPRGFHGRHCEKARPHLC
SSGPCRNGGTYKETGDEYRCTCPYRFTGRHCEIGKPDSCASGPCHNGGTCFHYIGKY
KCDCPPGFSGRHCEIAPSPCFRSPCMNGGICEDLGTDFSCHCQPGYTGHRCQAEVDC
GQPEEVKHATMRLNGTRMGSVALYTCDPGFSLSVLSHMRVCQPQGVWSQPPQCIEVD
ECQSQPYLHKGSCQDLIAGYQCLCSPGYEGVHCELETDECQAQPCRNGGSCRDLPGA
FICQCPEGFVGTHYETEVDACASSPCQHGGRCEDGGGAYLCVCPEGFFGYNCETVSN
PCFSSPCGGRGYCLASNGSHSCTCKVGYTGKDCTKELLPPTALRVERVEESGVSISW
SPPEGTTARQVLDGYAVTYASSDGSSRRTDFVDRSRSSHQLRALAAGRAYNISVFSV
KRNTNNKNDISRPAALLTRTRPRPIEDFEVTNISANAISVQWALHRIQHATVSRVRV
SVLYPEDTVVQSTEVDRSVDRLTFGDLLPGRRYSVRLTTLSGPGGAEYPTESLASAP
LNVWTRPLPPANLTASRVTATSAHMVWDPPTPGISLEAYVINVTTSQNTKSRYIPNG
KLVSYTVRDLMPGRRYQLSVTAVQSTEQGQLHSEPAHLYIITSPRDGTDRRWHQGGH
HSRMLRNRPAPLRLPELRLLNDHGAPETPTQPPRFSELVDGRARVSARFGGLPSRAV
TVRSQPTTPVPLKNTEAPEQARLALQLPKNNSKDTESTPGSCSEDTCQNGGTCVPGA
NAHSCDCRPGFKGRHCELACEKVPRPCTRLFSETKSFPVWEGDVCHHVYKKVYKVHQ
DVCFKERCQSTSLKKLKQESNQSNTEEI

*Fig. 15*

SEQ ID NO: 48

MQQRPRVVHRARNICDLALPRKSAGPWADRTICNNQNSVKLQCFWSLRVLRPGWQLPAQP...60
QYSLVFCCLPELALGLDSHCPGDAIGLQLSRTILEPGPGIGGPVTRAPRRASGSRQALDR
KVNNNGIISFLKEVSQFTPVAFPIAKDRCVVAAFWADVNNRRAGDVYYREATDPAMLRRA
TEDVRHYFPELLDFNATWVFVATWYRVTFFGGSSSSPVNTFQTVLITDGKLSFTIFNYES
IVWTTGTHASSGGNATGLGGIAAQAGFNAGDGQRYFSIPGSRTADMAEVETTTNVGVPGR..300
WAFRIDDAQVRVGGCGHTTSVCLALRPCLNGGKCIDDCVTGNPSYTCSCLSGFTGRRCHL
DVNECASQPCQNGGTCTHGINSFRCQCPAGFGGPTCETAQSPCDTKECQHGGQCQVENGS
AVCVCQAGYTGAACEMDVDDCSPDPCLNGGSCVDLVGNYTCLCAEPFKGLRCETGDHPVP
DACLSAPCHNGGTCVDADQGYVCECPEGFMGLDCRERVPDDCECRNGGRCLGANTTLCQC..600
PLGFFGLLCEFEITAMPCNMNTQCPDGGYCMEHGGSYLCVCHTDHNASHSLPSPCDSDPC
FNGGSCDAHDDSYTCECPRGFHGKHCEKARPHLCSSGPCRNGGTCKEAGGEYHCSCPYRF
TGRHCEIGKPDSCASGPCHNGGTCFHYIGKYKCDCPPGFSGRHCEIAPSPCFRSPCVNGG
TCEDRDTDFFCHCQAGYMGRRCQAEVDCGPPEEVKHATLRFNGTRLGAVALYACDRGYSL..900
SAPSRIRVCQPHGVWSEPPQCLEIDECRSQPCLHGGSCQDRVAGYLCLCSTGYEGAHCEL
ERDECRAHPCRNGGSCRNLPGAYVCRCPAGFVGVHCETEVDACDSSPCQHGGRCESGGGA
YLCVCPESFFGYHCETVSDPCFSSPCGGRGYCLASNGSHSCTCKVGYTGEDCAKELFPPT
ALKMERVEESGVSISWNPPNGPAARQMLDGYAVTYVSSDGSYRRTDFVDRTRSSHQLQAL.1200
AAGRAYNISVFSVKRNSNNKNDISRPAVLLARTRPRPVEGFEVTNVTASTISVQWALHRI
RHATVSGVRVSIRHPEALRDQATDVDRSVDRFTFRALLPGKRYTIQLTTLSGLRGEEHPT
ESLATAPTHVWTRPLPPANLTAARVTATSAHVVWDAPTPGSLLEAYVINVTTSQSTKSRY
VPNGKLASYTVRDLLPGRRYQLSVIAVQSTELGPQHSEPAHLYIITSPRDGADRRWHQGG.1500
HHPRVLKNRPPPARLPELRLLNDHSAPETPTQPPRFSELVDGRGRVSARFGGSPSKAATV
RSQPTASAQLENMEEAPKRVSLALQLPEHGSKDIGNVPGNCSENPCQNGGTCVPGADAHS
CDCGPGFKGRRCELACIKVSRPCTRLFSETKAFPVWEGGVCHHVYKRVYRVHQDICFKES
CESTSLKKTPNRKQSKSQTLEKS 1463

*Fig. 16*

Clone 52

Vector Only

Zucker Rat Brain, 10X

Increased c52 expression in the Lateral Hypothalamus of Obese Rat (In-situ Hybridization)

Expression of c52 mRNA in Nucleus of the Solitary Tract c52 expression at the level of Pyramidal decussation (Obese *zucker* rat-transverse section)

Dark-field,25X

Light-field,25X

Sense Riboprobe

Antisense Riboprobe

Antisense Riboprobe c52 expression at the level of Pyramidal decussation(Lean *zucker* rat-transverse section)

Sense riboprobe, 25X

Antisense riboprobe, 25X

C52 mRNA is localized to the Olfactory Bulb
(In-situ Hybridization with antisense probe)
Olfactory Bulb, 10X
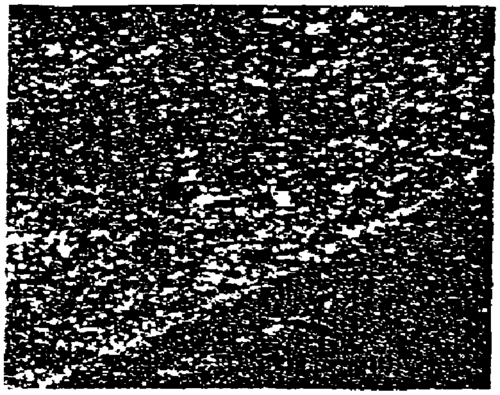
Olfactory Bulb, 25X
*Fig. 37*

Obese fa/fa rat, 25X

Lean fa/+ rat, 25X

Clone 52 increases Glut 4 and Glut 1 expressions and translocation of Glut 4 to the plasma membrane Clone 52-transfected L6 cells Immunodetection of c52 in glomerulus Pre-immune serum c52 Antiserum Immunostain of Endothelium with c52

Immunodetection of c52 in neurons

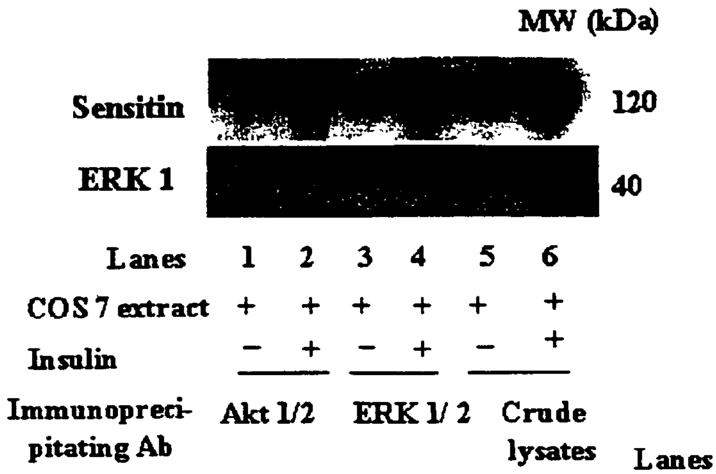
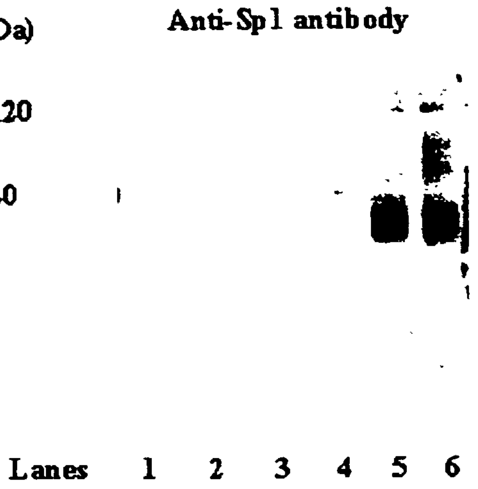
*Fig. 44A*

Sensitin

Vector

```
                        SEQUENCE LISTING

<160> NUMBER OF SEQ ID NOS: 63

<210> SEQ ID NO 1
<211> LENGTH: 27
<212> TYPE: DNA
<213> ORGANISM: Rattus norvegicus

<400> SEQUENCE: 1

aattcaaggg tatccaggaa agtctcc                                          27


<210> SEQ ID NO 2
<211> LENGTH: 952
<212> TYPE: DNA
<213> ORGANISM: Rattus norvegicus
<220> FEATURE:
<221> NAME/KEY: exon
<222> LOCATION: (1)..(363)
<220> FEATURE:
<221> NAME/KEY: 3'UTR
<222> LOCATION: (364)..(952)

<400> SEQUENCE: 2

ctt aga tca tgt ttc act aca tgc cct ttg acc tct cac cac ttc ctt        48
Leu Arg Ser Cys Phe Thr Thr Cys Pro Leu Thr Ser His His Phe Leu
1               5                   10                  15

ctg tcc att cct cat cca ggg cct ttg cct cca gca aac ctg act gcc        96
Leu Ser Ile Pro His Pro Gly Pro Leu Pro Pro Ala Asn Leu Thr Ala
            20                  25                  30

tct cga gtc aca gcg acc tct gcc cat atg gtc tgg gac ccg ccc act       144
Ser Arg Val Thr Ala Thr Ser Ala His Met Val Trp Asp Pro Pro Thr
        35                  40                  45

cca ggc atc tca ctg gag gct tac gtc atc aat gtg acc acc agt cag       192
Pro Gly Ile Ser Leu Glu Ala Tyr Val Ile Asn Val Thr Thr Ser Gln
    50                  55                  60

aat acc aag agc cgc tac atc ccc aat ggg aag ctg gtg tcc tat acg       240
Asn Thr Lys Ser Arg Tyr Ile Pro Asn Gly Lys Leu Val Ser Tyr Thr
65                  70                  75                  80

gtg cgt gat ctg atg cca ggt cgg cgg tac cag ctc tcg gtc aca gcg       288
Val Arg Asp Leu Met Pro Gly Arg Arg Tyr Gln Leu Ser Val Thr Ala
                85                  90                  95

gtg cag agc aca gag cag ggc cag ctg cac agt gag cct gcg cac ctc       336
Val Gln Ser Thr Glu Gln Gly Gln Leu His Ser Glu Pro Ala His Leu
            100                 105                 110
```

-continued

```
tac atc atc acc tgt gag tta gtt ccc tgacaggacg gcctgggatg           383
Tyr Ile Ile Thr Cys Glu Leu Val Pro
        115                 120

ctgttcaaac ccacggctgc tgtttgctgc tgttggggtg tgggatcctt gcccagaaga    443

ggcagcatag acaacttgca tgggccattc ctcggaacag agatgtaggc ataagggtga    503

ggaaggacag ttgacagcat gagcctcatc ttacactgtt ttaccagtcc aatcccagca    563

ggcttagcag caaatacagg acctcaccgt gaaagagcta ccaagcaggc agcaatgccg    623

aggcccaggc ctgacccaaa aggggccact gggcatgaac accagagggc ggggcaagag    683

actacaagta gctgggtagg gcaggaaggg taagaatgaa aagctggggt gtagacattc    743

aggtggccac attaacaacc tcactctatt cccaaggtga cagggcactc agctggagcc    803

caaaagtgtc ctgtgtgccc cttattacct tctcaaacct tacgtgaggt gctgtatgag    863

agagtttcag gagtgcaggg agcagaactc agcgagaaaa caagcagaag gtgcacaaga    923

aaacaagaca gcgggtcgac gcggccgcg                                      952


<210> SEQ ID NO 3
<211> LENGTH: 121
<212> TYPE: PRT
<213> ORGANISM: Rattus norvegicus

<400> SEQUENCE: 3

Leu Arg Ser Cys Phe Thr Thr Cys Pro Leu Thr Ser His His Phe Leu
1               5                   10                  15

Leu Ser Ile Pro His Pro Gly Pro Leu Pro Pro Ala Asn Leu Thr Ala
            20                  25                  30

Ser Arg Val Thr Ala Thr Ser Ala His Met Val Trp Asp Pro Pro Thr
        35                  40                  45

Pro Gly Ile Ser Leu Glu Ala Tyr Val Ile Asn Val Thr Thr Ser Gln
    50                  55                  60

Asn Thr Lys Ser Arg Tyr Ile Pro Asn Gly Lys Leu Val Ser Tyr Thr
65                  70                  75                  80

Val Arg Asp Leu Met Pro Gly Arg Arg Tyr Gln Leu Ser Val Thr Ala
                85                  90                  95

Val Gln Ser Thr Glu Gln Gly Gln Leu His Ser Glu Pro Ala His Leu
            100                 105                 110

Tyr Ile Ile Thr Cys Glu Leu Val Pro
        115                 120


<210> SEQ ID NO 4
<211> LENGTH: 168
<212> TYPE: DNA
<213> ORGANISM: Rattus norvegicus

<400> SEQUENCE: 4

tcgagtcaca gcgacctctg cccatatggt ctgggacccg cccactccag gcatctcact     60

ggaggcttac gtcatcaatg tgaccaccag tcagaatacc aagagccgct acatccccaa    120

tgggaagctg gtgtcccggt gcgtgatctg atgccaggtc ggcggtac                 168


<210> SEQ ID NO 5
<211> LENGTH: 4926
<212> TYPE: DNA
<213> ORGANISM: Rattus norvegicus
<220> FEATURE:
<221> NAME/KEY: exon
<222> LOCATION: (1)..(3024)
```

-continued

```
<220> FEATURE:
<221> NAME/KEY: 3'UTR
<222> LOCATION: (3025)..(4926)

<400> SEQUENCE: 5

tgc ctg aat gga ggc tct tgt gtt gac ctg gtt gga aac tac agc tgt        48
Cys Leu Asn Gly Gly Ser Cys Val Asp Leu Val Gly Asn Tyr Ser Cys
1               5                   10                  15

att tgt gtg gag ccc ttt gaa gga cct cag tgc gag aca gga agc tac        96
Ile Cys Val Glu Pro Phe Glu Gly Pro Gln Cys Glu Thr Gly Ser Tyr
            20                  25                  30

gtg gtg cct tcg ccc tgc ctc tcc aac ccc tgc ctg aac ggg ggc acc       144
Val Val Pro Ser Pro Cys Leu Ser Asn Pro Cys Leu Asn Gly Gly Thr
        35                  40                  45

tgt gtg gat gct gac cag gga tac gtg tgc gaa tgc cct gaa ggt ttc       192
Cys Val Asp Ala Asp Gln Gly Tyr Val Cys Glu Cys Pro Glu Gly Phe
    50                  55                  60

atg ggc ttg gac tgc aga gag aga att ctc aat gac tgt gat tgc cgg       240
Met Gly Leu Asp Cys Arg Glu Arg Ile Leu Asn Asp Cys Asp Cys Arg
65                  70                  75                  80

aat gga ggc aga tgc ctg ggt gcc aac acc acc atc tgc cag tgt cct       288
Asn Gly Gly Arg Cys Leu Gly Ala Asn Thr Thr Ile Cys Gln Cys Pro
                85                  90                  95

cca ggc tcc ttt ggg ctc ctc tgt gaa ttt gaa gtc aca gcc acg ccc       336
Pro Gly Ser Phe Gly Leu Leu Cys Glu Phe Glu Val Thr Ala Thr Pro
            100                 105                 110

tgc aac atg aac aca cag tgt cca gat gga ggc tac tgc atg gag tat       384
Cys Asn Met Asn Thr Gln Cys Pro Asp Gly Gly Tyr Cys Met Glu Tyr
        115                 120                 125

ggc gga agc tac cta tgt gtc tgc cac acg gac cac aac atc agc cat       432
Gly Gly Ser Tyr Leu Cys Val Cys His Thr Asp His Asn Ile Ser His
    130                 135                 140

tct ctg ccc tcg ccc tgc gac tca gac cca tgc ttt aat gga ggt tcc       480
Ser Leu Pro Ser Pro Cys Asp Ser Asp Pro Cys Phe Asn Gly Gly Ser
145                 150                 155                 160

tgt gac gcc cac gag gac tcc tac acg tgc gag tgc cct cgt gga ttc       528
Cys Asp Ala His Glu Asp Ser Tyr Thr Cys Glu Cys Pro Arg Gly Phe
                165                 170                 175

cat ggc agg cac tgc gag aaa gcc cgg cca cac ctg tgc agc tca ggg       576
His Gly Arg His Cys Glu Lys Ala Arg Pro His Leu Cys Ser Ser Gly
            180                 185                 190

ccc tgc cgg aat ggg ggc aca tac aag gag act ggt gac gag tac cgc       624
Pro Cys Arg Asn Gly Gly Thr Tyr Lys Glu Thr Gly Asp Glu Tyr Arg
        195                 200                 205

tgc acc tgc cct tac cgg ttc act ggg aga cac tgt gag att gga aag       672
Cys Thr Cys Pro Tyr Arg Phe Thr Gly Arg His Cys Glu Ile Gly Lys
    210                 215                 220

cca gac tcc tgt gcc tct ggc ccc tgt cac aac ggt ggc act tgt ttc       720
Pro Asp Ser Cys Ala Ser Gly Pro Cys His Asn Gly Gly Thr Cys Phe
225                 230                 235                 240

cac tac att ggc aaa tac aag tgt gac tgc cct cca ggc ttc tct ggt       768
His Tyr Ile Gly Lys Tyr Lys Cys Asp Cys Pro Pro Gly Phe Ser Gly
                245                 250                 255

cgg cac tgt gag ata gcc ccc tcc ccc tgc ttc cgg agc cca tgt atg       816
Arg His Cys Glu Ile Ala Pro Ser Pro Cys Phe Arg Ser Pro Cys Met
            260                 265                 270

aat ggg ggt atc tgc gag gat cta gga aca gat ttc tcc tgc cac tgc       864
Asn Gly Gly Ile Cys Glu Asp Leu Gly Thr Asp Phe Ser Cys His Cys
        275                 280                 285

caa cca gga tat aca gga cac cgg tgt cag gca gag gtg gac tgc ggt       912
```

-continued

```
Gln Pro Gly Tyr Thr Gly His Arg Cys Gln Ala Glu Val Asp Cys Gly
    290                 295                 300

cag cct gag gag gta aaa cat gct acc atg cgt ctc aat gga act cgc      960
Gln Pro Glu Glu Val Lys His Ala Thr Met Arg Leu Asn Gly Thr Arg
305                 310                 315                 320

atg ggc tcg gtg gcc ctg tac aca tgt gac ccc ggc ttc agc ctg agc     1008
Met Gly Ser Val Ala Leu Tyr Thr Cys Asp Pro Gly Phe Ser Leu Ser
                325                 330                 335

gtc ctc agc cat atg cgt gtc tgt cag cca caa ggt gtc tgg agc cag     1056
Val Leu Ser His Met Arg Val Cys Gln Pro Gln Gly Val Trp Ser Gln
            340                 345                 350

cct ccc cag tgc att gaa gta gat gag tgc cag tct cag cca tac ctg     1104
Pro Pro Gln Cys Ile Glu Val Asp Glu Cys Gln Ser Gln Pro Tyr Leu
        355                 360                 365

cat aaa ggc tcc tgc cag gac ctc att gct ggt tac cag tgc ctc tgc     1152
His Lys Gly Ser Cys Gln Asp Leu Ile Ala Gly Tyr Gln Cys Leu Cys
    370                 375                 380

agc ccg ggg tac gaa gga gtc cac tgt gag cta gag aca gac gag tgc     1200
Ser Pro Gly Tyr Glu Gly Val His Cys Glu Leu Glu Thr Asp Glu Cys
385                 390                 395                 400

caa gca cag ccc tgc aga aat gga ggc tcc tgc agg gac ctc ccc ggg     1248
Gln Ala Gln Pro Cys Arg Asn Gly Gly Ser Cys Arg Asp Leu Pro Gly
                405                 410                 415

gct ttc atc tgc cag tgc cct gaa ggt ttt gtt gga acc cac tat gaa     1296
Ala Phe Ile Cys Gln Cys Pro Glu Gly Phe Val Gly Thr His Tyr Glu
            420                 425                 430

aca gag gtg gat gcc tgt gcc tcc agc ccc tgc cag cac gga ggc cgg     1344
Thr Glu Val Asp Ala Cys Ala Ser Ser Pro Cys Gln His Gly Gly Arg
        435                 440                 445

tgt gag gac ggt ggt ggg gcc tac ctg tgc gtt tgt cca gag ggc ttc     1392
Cys Glu Asp Gly Gly Gly Ala Tyr Leu Cys Val Cys Pro Glu Gly Phe
    450                 455                 460

ttc ggc tac aac tgt gag aca gtg agt aac ccc tgc ttc tct agc ccc     1440
Phe Gly Tyr Asn Cys Glu Thr Val Ser Asn Pro Cys Phe Ser Ser Pro
465                 470                 475                 480

tgt ggg ggc cgc ggc tac tgc ttg gcc agc aac ggg tcc cac agc tgt     1488
Cys Gly Gly Arg Gly Tyr Cys Leu Ala Ser Asn Gly Ser His Ser Cys
                485                 490                 495

acc tgc aaa gtg ggc tac aca ggc aag gac tgc acc aaa gag ctc ctc     1536
Thr Cys Lys Val Gly Tyr Thr Gly Lys Asp Cys Thr Lys Glu Leu Leu
            500                 505                 510

cca cca aca gcc ctc agg gta gaa agg gtg gag gag agt ggg gtc tcc     1584
Pro Pro Thr Ala Leu Arg Val Glu Arg Val Glu Glu Ser Gly Val Ser
        515                 520                 525

atc tcc tgg agc cca ccc gag ggc acc acg gcc aga cag gtg ctg gac     1632
Ile Ser Trp Ser Pro Pro Glu Gly Thr Thr Ala Arg Gln Val Leu Asp
    530                 535                 540

ggc tat gca gtc acc tat gcc tcc tcg gat gga tcg tcc agg cgc acg     1680
Gly Tyr Ala Val Thr Tyr Ala Ser Ser Asp Gly Ser Ser Arg Arg Thr
545                 550                 555                 560

gac ttt gtg gac cgg agc cgc tcc tct cac cag ctt cgg gcc ctg gca     1728
Asp Phe Val Asp Arg Ser Arg Ser Ser His Gln Leu Arg Ala Leu Ala
                565                 570                 575

gcc ggc cgt gcc tac aac atc tct gtt ttc tca gtc aag aga aac act     1776
Ala Gly Arg Ala Tyr Asn Ile Ser Val Phe Ser Val Lys Arg Asn Thr
            580                 585                 590

aac aac aaa aat gac atc agc agg cct gca gcc ctg ctc acc cgc acc     1824
Asn Asn Lys Asn Asp Ile Ser Arg Pro Ala Ala Leu Leu Thr Arg Thr
        595                 600                 605
```

-continued

```
cga ccc cgc cct att gaa gac ttc gag gtc acc aac att tca gcc aat      1872
Arg Pro Arg Pro Ile Glu Asp Phe Glu Val Thr Asn Ile Ser Ala Asn
    610                 615                 620

gcc atc tca gtg cag tgg gct ctt cat agg atc cag cat gcc act gtc      1920
Ala Ile Ser Val Gln Trp Ala Leu His Arg Ile Gln His Ala Thr Val
625                 630                 635                 640

agc agg gtt cga gtg tct gtc ctc tac cct gag gac act gtg gtc cag      1968
Ser Arg Val Arg Val Ser Val Leu Tyr Pro Glu Asp Thr Val Val Gln
                645                 650                 655

tcc acg gag gtg gac agg agt gtg gac cgc ctc aca ttt ggg gac ctg      2016
Ser Thr Glu Val Asp Arg Ser Val Asp Arg Leu Thr Phe Gly Asp Leu
            660                 665                 670

ctg cca ggg aga aga tac agt gtg cgg cta acc acc ctc agt ggg cct      2064
Leu Pro Gly Arg Arg Tyr Ser Val Arg Leu Thr Thr Leu Ser Gly Pro
        675                 680                 685

gga gga gct gaa tat cct aca gag agc ctg gcc tca gct ccg ctg aac      2112
Gly Gly Ala Glu Tyr Pro Thr Glu Ser Leu Ala Ser Ala Pro Leu Asn
    690                 695                 700

gtg tgg acc cgg cct ttg cct cca gca aac ctg act gcc tct cga gtc      2160
Val Trp Thr Arg Pro Leu Pro Pro Ala Asn Leu Thr Ala Ser Arg Val
705                 710                 715                 720

aca gcg acc tct gcc cat atg gtc tgg gac ccg ccc act cca ggc atc      2208
Thr Ala Thr Ser Ala His Met Val Trp Asp Pro Pro Thr Pro Gly Ile
                725                 730                 735

tca ctg gag gct tac gtc atc aat gtg acc acc agt cag aat acc aag      2256
Ser Leu Glu Ala Tyr Val Ile Asn Val Thr Thr Ser Gln Asn Thr Lys
            740                 745                 750

agc cgc tac atc ccc aat ggg aag ctg gtg tcc tat acg gtg cgt gat      2304
Ser Arg Tyr Ile Pro Asn Gly Lys Leu Val Ser Tyr Thr Val Arg Asp
        755                 760                 765

ctg atg cca ggt cgg cgg tac cag ctc tcg gtc aca gcg gtg cag agc      2352
Leu Met Pro Gly Arg Arg Tyr Gln Leu Ser Val Thr Ala Val Gln Ser
    770                 775                 780

aca gag cag ggc cag ctg cac agt gag cct gcg cac ctc tac atc atc      2400
Thr Glu Gln Gly Gln Leu His Ser Glu Pro Ala His Leu Tyr Ile Ile
785                 790                 795                 800

acc tcc ccc agg gat ggc acc gac agg cgc tgg cac cag gga gga cac      2448
Thr Ser Pro Arg Asp Gly Thr Asp Arg Arg Trp His Gln Gly Gly His
                805                 810                 815

cac tca cgg atg ctc aga aat agg ccg gcc cct ttg cgc ctg cca gaa      2496
His Ser Arg Met Leu Arg Asn Arg Pro Ala Pro Leu Arg Leu Pro Glu
            820                 825                 830

ctg cgc ctc ctc aat gac cac ggt gcc cct gaa aca cca acc cag cca      2544
Leu Arg Leu Leu Asn Asp His Gly Ala Pro Glu Thr Pro Thr Gln Pro
        835                 840                 845

ccc agg ttc tca gag ctt gta gac gga aga gca aga gtg agt gcc agg      2592
Pro Arg Phe Ser Glu Leu Val Asp Gly Arg Ala Arg Val Ser Ala Arg
    850                 855                 860

ttt ggt gga ttg ccc agc aga gca gta act gtg aga tca caa ccc act      2640
Phe Gly Gly Leu Pro Ser Arg Ala Val Thr Val Arg Ser Gln Pro Thr
865                 870                 875                 880

act ccg gtg ccg ctc aag aac aca gag gcc cct gag cag gcc cgt ctg      2688
Thr Pro Val Pro Leu Lys Asn Thr Glu Ala Pro Glu Gln Ala Arg Leu
                885                 890                 895

gcc ctt cag cta ccc aag aac aac agc aag gac aca gaa agt acc cct      2736
Ala Leu Gln Leu Pro Lys Asn Asn Ser Lys Asp Thr Glu Ser Thr Pro
            900                 905                 910

ggc agc tgt tca gaa gac acc tgt cag aat gga ggc acc tgt gtc cca      2784
Gly Ser Cys Ser Glu Asp Thr Cys Gln Asn Gly Gly Thr Cys Val Pro
        915                 920                 925
```

-continued ggt gcc aat gcc cac agc tgt gac tgc agg cct ggg ttc aaa ggc aga 2832
Gly Ala Asn Ala His Ser Cys Asp Cys Arg Pro Gly Phe Lys Gly Arg
930 935 940 cac tgt gag ctt gcc tgt gaa aaa gtg ccc cgc ccc tgc aca cgg ctg 2880
His Cys Glu Leu Ala Cys Glu Lys Val Pro Arg Pro Cys Thr Arg Leu
945 950 955 960 ttc tct gag acc aag tca ttt cct gtc tgg gaa gga gat gtc tgc cac 2928
Phe Ser Glu Thr Lys Ser Phe Pro Val Trp Glu Gly Asp Val Cys His
965 970 975 cat gtg tat aag aaa gtc tac aaa gtt cac cag gac gtg tgt ttt aag 2976
His Val Tyr Lys Lys Val Tyr Lys Val His Gln Asp Val Cys Phe Lys
980 985 990 gag cgc tgc cag agc aca agc ctc aaa aag ctc aaa cag gaa tca aat 3024
Glu Arg Cys Gln Ser Thr Ser Leu Lys Lys Leu Lys Gln Glu Ser Asn
995 1000 1005 taacagtcaa acactgaaga aatcttaagg tacattctcc ttcataccaa gatctgttga 3084 gaactggaga caccatcata cccagcacct tggacaactg atggtgcaaa cttagcactg 3144 tgctattaca gacccaacca ggaaggttcc agaattccct gtctatagcc tcccaataga 3204 cataacctgg tctggccttc catatgaatc cactttcagg tggaaatgac tctctggggg 3264 aggggcaaat gcagaccagt tacaatgagg cacaagaatc acctggcccc ttcaggacag 3324 tgggcctggg tgttagatgg atcaaggatg ccaaacaatc ctgggggtgc taggaaggac 3384 ctaaggacat accctcaagc cctatgaata gcattctact ggtggaaaag ggcgggagcc 3444 ttgtcatgta acctgcaggt gatcctaaat agagcctctc actgggagag atatcatgga 3504 tcctggaatt ctaagcacta ataaccctga agtgaaagaa actttgcctg cttgatccag 3564 catgtcccac cccaccctcc ccatacataa actgtgagat gtcaaagggc attggaaaat 3624 ttttttcaca agcctgggaa atactgggtt acactacaga gatccctgta tagcctgaac 3684 tcagccccaa cactgactta ctgatgggac atcaattgga aacgagagac tggctggcca 3744 gagacatttc actcctctcc cttggaggag ccagaacagt acatctgtgc agtggtggga 3804 gagaggcaga tctggaagcc tgccactcca ggagtgaatc acctttgttc tacagtgtag 3864 gacgtgaagg agaaatgtca cccaaaggcc taagaacaaa gaagagcaaa gcagttctgg 3924 gcgaaggtca tccgaagaga aaagtgtcta cagtaaaagg cagggcatca ggagagcggg 3984 ctctcagaca ggcctaagca gggcctgtgc atcttgacca tttcagatgt gaagactgca 4044 ggaagagcag ctgaccagac tcaaatcctg tctacttaac agcatcacct tttcacctca 4104 gcccccaaaa atgcacacaa caccctccaa cacatgtgag caacttcatt ctggcaaaga 4164 tcaaaaatcc acaaattatt tggttttaaa atatttacat ggcagtaagt cagatgaaat 4224 attaatgcaa aaaaagaaat attaatgcat cctttaagaa ctcacagaaa actcattttt 4284 agaaaaaaaa atgagaatcc ctaggtactt atcacataat ggcttataga aaacctattc 4344 tcaaagcaac acacacacac acacacaccc catacgtacg tacatacata catctaacac 4404 acacatgtgt gtgtatatat atatatatat atatatatat atatatatga cacacacaaa 4464 gcaaaaataa ttatatcttt ttaaagatat atattttctt ttaggaaaca gtaattactg 4524 acaacgctgc atttgaaata ctcaaaaaga tactaccgtt acaaaactcc agtttctcag 4584 ggacaggttt ggtattgcca gctaagaatc ccaaggagga gactgagctg cttaagtcgg 4644 agggagcaac agtaatggcc aagtcgcctg agcctccttc acagtcacag gattcagaaa 4704 atggatacat caatgtgact tctctaaagg agacatacca cacacaaggg gaccggaagc 4764

-continued

```
caaaactatg acctcacggg atctgaaaca atactaatca tgcctactaa gtcagagcct   4824

gggtacagag gtgcaaactg agctggagac gtctcacaga acaccctgga catcaacaag   4884

gagtcttcaa aatcgctttt taaacagtca ttaaaatttt tc                      4926


<210> SEQ ID NO 6
<211> LENGTH: 4061
<212> TYPE: DNA
<213> ORGANISM: Rattus norvegicus
<220> FEATURE:
<221> NAME/KEY: exon
<222> LOCATION: (1)..(777)
<220> FEATURE:
<221> NAME/KEY: 3'UTR
<222> LOCATION: (778)..(4042)
<220> FEATURE:
<221> NAME/KEY: polyA_site
<222> LOCATION: (4043)..(4061)

<400> SEQUENCE: 6

aat acc aag agc cgc tac atc ccc aat ggg aag ctg gtg tcc tat acg       48
Asn Thr Lys Ser Arg Tyr Ile Pro Asn Gly Lys Leu Val Ser Tyr Thr
1               5                   10                  15

gtg cgt gat ctg atg cca ggt cgg cgg tac cag ctc tcg gtc aca gcg       96
Val Arg Asp Leu Met Pro Gly Arg Arg Tyr Gln Leu Ser Val Thr Ala
            20                  25                  30

gtg cag agc aca gag cag ggc cag ctg cac agt gag cct gcg cac ctc      144
Val Gln Ser Thr Glu Gln Gly Gln Leu His Ser Glu Pro Ala His Leu
        35                  40                  45

tac atc atc acc tcc ccc agg gat ggc acc gac agg cgc tgg cac cag      192
Tyr Ile Ile Thr Ser Pro Arg Asp Gly Thr Asp Arg Arg Trp His Gln
    50                  55                  60

gga gga cac cac tca cgg atg ctc aga aat agg ccg gcc cct ttg cgc      240
Gly Gly His His Ser Arg Met Leu Arg Asn Arg Pro Ala Pro Leu Arg
65                  70                  75                  80

ctg cca gaa ctg cgc ctc ctc aat gac cac ggt gcc cct gaa aca cca      288
Leu Pro Glu Leu Arg Leu Leu Asn Asp His Gly Ala Pro Glu Thr Pro
                85                  90                  95

acc cag cca ccc agg ttc tca gag ctt gta gac gga aga gca aga gtg      336
Thr Gln Pro Pro Arg Phe Ser Glu Leu Val Asp Gly Arg Ala Arg Val
            100                 105                 110

agt gcc agg ttt ggt gga ttg ccc agc aga gca gta act gtg aga tca      384
Ser Ala Arg Phe Gly Gly Leu Pro Ser Arg Ala Val Thr Val Arg Ser
        115                 120                 125

caa ccc act act ccg gtg ccg ctc aag aac aca gag gcc cct gag cag      432
Gln Pro Thr Thr Pro Val Pro Leu Lys Asn Thr Glu Ala Pro Glu Gln
    130                 135                 140

gcc cgt ctg gcc ctt cag cta ccc aag aac aac agc aag gac aca gaa      480
Ala Arg Leu Ala Leu Gln Leu Pro Lys Asn Asn Ser Lys Asp Thr Glu
145                 150                 155                 160

agt acc cct ggc agc tgt tca gaa gac acc tgt cag aat gga ggc acc      528
Ser Thr Pro Gly Ser Cys Ser Glu Asp Thr Cys Gln Asn Gly Gly Thr
                165                 170                 175

tgt gtc cca ggt gcc aat gcc cac agc tgt gac tgc agg cct ggg ttc      576
Cys Val Pro Gly Ala Asn Ala His Ser Cys Asp Cys Arg Pro Gly Phe
            180                 185                 190

aaa ggc aga cac tgt gag ctt gcc tgt gaa aaa gtg ccc cgc ccc tgc      624
Lys Gly Arg His Cys Glu Leu Ala Cys Glu Lys Val Pro Arg Pro Cys
        195                 200                 205

aca cgg ctg ttc tct gag acc aag tca ttt cct gtc tgg gaa gga gat      672
Thr Arg Leu Phe Ser Glu Thr Lys Ser Phe Pro Val Trp Glu Gly Asp
    210                 215                 220
```

-continued

```
gtc tgc cac cat gtg tat aag aaa gtc tac aaa gtt cac cag gac gtg      720
Val Cys His His Val Tyr Lys Lys Val Tyr Lys Val His Gln Asp Val
225                 230                 235                 240

tgt ttt aag gag cgc tgc cag agc aca agc ctc aaa aag ctc aaa cag      768
Cys Phe Lys Glu Arg Cys Gln Ser Thr Ser Leu Lys Lys Leu Lys Gln
                245                 250                 255

gaa tca aat taacagtcaa acactgaaga aatcttaagg tacattctcc              817
Glu Ser Asn

ttcataccaa gatctgttga gaactggaga caccatcata cccagcacct tggacaactg    877

atggtgcaaa cttagcactg tgctattaca gacccaacca ggaaggttcc agaattccct    937

gtctatagcc tcccaataga cataacctgg tctggccttc catatgaatc cactttcagg    997

tggaaatgac tctctggggg aggggcaaat gcagaccagt tacaatgtgg atcaaggatg   1057

ccaaacaatc ctgggggtgc taggaaggac ctaaggacat accctcaagc cctatgaata   1117

gcattctact ggtggaaaag ggcgggagcc ttgtcatgta acctgcaggt gatcctaaat   1177

agagcctctc actgggagag atatcatgga tcctggaatt ctaagcacta ataaccctga   1237

agtgaaagaa actttgcctg cttgatccag catgtcccac cccaccctcc ccatacataa   1297

actgtgagat gtcaaagggc attggaaaat ttttttcaca agcctgggaa atactgggtt   1357

acactacaga gatccctgta tagcctgaac tcagccccaa cactgactta ctgatgggac   1417

atcaattgga aacgagagac tggctggcca gagacatttc actcctctcc cttggaggag   1477

ccagaacagt acatctgtgc agtggtggga gagaggcaga tctggaagcc tgccactcca   1537

ggagtgaatc acctttgttc tacagtgtag gacgtgaagg agaaatgtca cccaaaggcc   1597

taagaacaaa gaagagcaaa gcagttctgg gcgaaggtca tccgaagaga aaagtgtcta   1657

cagtaaaagg cagggcatca ggagagcggg ctctcagaca ggcctaagca gggcctgtgc   1717

atcttgacca tttcagatgt gaagactgca ggaagagcag ctgaccagac tcaaatcctg   1777

tctacttaac agcatcacct tttacctcag cccccaaaaa tgcacacaac accctccaac   1837

acatgtgagc aacttcattc tggcaaagat caaaaatcca caaattattt ggttttaaaa   1897

tatttacatg gcagtaagtc agatgaaata ttaatgcaaa aaaagaaata ttaatgcatc   1957

ctttaagaac tcacagaaaa ctcattttta gaaaaaaaaa tgagaatccc taggtactta   2017

tcacataatg gcttatagaa aacctattct caaagcaaca cacacacaca cacacacaca   2077

cacacacaca tcacacacac cccttctctt tctgaagaaa ccagaattcg ccatccacag   2137

ctgccctgag aaaatgagca gtgccacccg cccctaagga aaggcagcag aggaccagca   2197

agcagcaaac ttaaagccgg aggctgatcg caagtgtcct aagaggtgcg tgtgtccctt   2257

ccatcccgcc ctgcatcaca gccagctgga attctggctc ctggggacaa tgcctgctgc   2317

ctccagagaa agactggata taaagaggag tgtgcctcag ttcactgtta ctccttttgt   2377

caaaaggacc ggcatgtgct ggtaattctg tccacacctc aaggatttcc aaaacccagg   2437

aaatgaggtt caaaacttaa acgccaagct cccagcagta ggcagtctcc ccgagatctc   2497

tgtcctccaa attctagaaa agagacagcc agacatgcac acccaaagga ctcctgccag   2557

ggaagcaaca atgcaccctg ctgcaaccca gggttgctgt ttccgcagtt ctggtcaatc   2617

cctctgtgga gagttacctg tgttaccagg ctctttgtga tgcttctgtg ctcagaaacc   2677

cacatccaga tcccagtgcc aagaaaaaga ctcagctttc acaagagatg caagagaggc   2737

tgtgcagaaa tagatgggct ctaccctgct cctcttctca tttatactga tgacctaaag   2797

aagtgctaat tctactatgg tggggcttag acacttggtc tacaactcag gggtggcagg   2857
```

-continued

```
gcaggcagat gctcaggcag gattttgggc tccgcaggta ggatgacttg tacctctggc   2917

acacacccaa ccctgctact gtactgccaa caccatcaca gatgtagata gcatagctgt   2977

gtcccaatga gactgcattt acaaaaacag gcagcaggcc atagctggca gctttataag   3037

atgatctaga cctcagcctt ccttctgcgg agaaaaccat cctgaatgac aagttggcat   3097

caagacatga aagacccctg aactttcata caagaaaagc gatcaagacc cctgctctga   3157

aacctgaggt aaacttacac ccagagcagg aagagctacc tgttcaaacc tgtgacacag   3217

ggcaggctgg ctccaggaga cagggtccaa ggcttcttgt aagctgtgcc ccaactagac   3277

agctgtggtt caccaaaaca aaaatatttt acacagcctc cgctttccat cccactccga   3337

acaaggctgt aaacagctgt cctctccctg cagtaacatc acaatcagaa aagccgacat   3397

accctgactc cttgctccag cctgagcaga gctgactaga gatccagcac caagaactac   3457

atcccaacca gagaggcctc ctgcccttca gaggtcataa aaacacagtt tgaagcataa   3517

ccttttaagt tttattctca ctaaaaactt ctgaacctat gttatcacat aattttttc   3577

tctttcaaaa actcactact gtaccttaga tactcgctag agtcctggag accgcataag   3637

ctacagcgtt agcagggagt tgcaagctca ggtggcatca ctgaagagca gatgggatct   3697

ttgtacttta ctactaacct cagggccctc accgccaggc cgatgctgcc acattcccat   3757

ttccagttgg agcctgtgtt tcaaacaaga gtcagcctgc tgactgctga gtgtggagtg   3817

gagaaagact cgctggtgct gaggaattag tgtatgacat tccacacatg cggtctctgc   3877

tttcttacat gcctttctta tgcagactaa ttaaatccct caaaacagtc actgtccact   3937

taagaaatgt cacagtgggg gttgggcatt tagctcagtg gtagagggct tgcctaggaa   3997

gcgcaaggcc ctgggttcag tccccagctc cgaaaaaaaa gaaccaaaaa aaaaaaaaaa   4057

aaaa                                                                4061


<210> SEQ ID NO 7
<211> LENGTH: 4524
<212> TYPE: DNA
<213> ORGANISM: Homo sapiens
<220> FEATURE:
<221> NAME/KEY: 5'UTR
<222> LOCATION: (1)..(58)
<220> FEATURE:
<221> NAME/KEY: exon
<222> LOCATION: (59)..(3082)
<220> FEATURE:
<221> NAME/KEY: 3'UTR
<222> LOCATION: (3083)..(4524)

<400> SEQUENCE: 7

ggagaacggc tctgcggtgt gtgtgtgcca ggccggatac accggagcag cctgcgag       58

atg gat gtg gac gac tgc agc cct gac ccc tgc ctg aat gga ggc tct      106
Met Asp Val Asp Asp Cys Ser Pro Asp Pro Cys Leu Asn Gly Gly Ser
1               5                   10                  15

tgt gtt gac cta gtg ggg aat tac acc tgc ttg tgt gcc gag ccc ttc      154
Cys Val Asp Leu Val Gly Asn Tyr Thr Cys Leu Cys Ala Glu Pro Phe
            20                  25                  30

aag gga ctt cgc tgt gag aca gga gac cat cca gtg cca gac gcc tgc      202
Lys Gly Leu Arg Cys Glu Thr Gly Asp His Pro Val Pro Asp Ala Cys
        35                  40                  45

ctc tcg gcc cct tgc cac aat ggg ggc acc tgt gtg gat gcg gac cag      250
Leu Ser Ala Pro Cys His Asn Gly Gly Thr Cys Val Asp Ala Asp Gln
    50                  55                  60

ggc tac gtg tgc gag tgc ccc gaa ggc ttc atg ggc ctg gac tgc agg      298
Gly Tyr Val Cys Glu Cys Pro Glu Gly Phe Met Gly Leu Asp Cys Arg
```

-continued

```
65                  70                  75                  80

gag aga gtc ccc gat gac tgt gag tgc cgc aac gga ggc aga tgc ctg      346
Glu Arg Val Pro Asp Asp Cys Glu Cys Arg Asn Gly Gly Arg Cys Leu
            85                  90                  95

ggc gcc aac acc acc ctc tgc cag tgc ccc ctg gga ttc ttt ggg ctt      394
Gly Ala Asn Thr Thr Leu Cys Gln Cys Pro Leu Gly Phe Phe Gly Leu
            100                 105                 110

ctc tgt gaa ttt gaa atc aca gcc atg ccc tgc aac atg aac aca cag      442
Leu Cys Glu Phe Glu Ile Thr Ala Met Pro Cys Asn Met Asn Thr Gln
        115                 120                 125

tgc cca gat ggg ggc tac tgc atg gag cac ggc ggg agc tac ctc tgc      490
Cys Pro Asp Gly Gly Tyr Cys Met Glu His Gly Gly Ser Tyr Leu Cys
    130                 135                 140

gtc tgc cac acc gac cac aat gcc agc cac tcc ctg cca tca ccc tgc      538
Val Cys His Thr Asp His Asn Ala Ser His Ser Leu Pro Ser Pro Cys
145                 150                 155                 160

aac tcg gac ccc tgc ttc aac gga ggc tcc tgc gat gcc cat gac gac      586
Asn Ser Asp Pro Cys Phe Asn Gly Gly Ser Cys Asp Ala His Asp Asp
            165                 170                 175

tcc tac acc tgc gag tgc ccg cgc ggg ttc cac ggc aag cac tgc gag      634
Ser Tyr Thr Cys Glu Cys Pro Arg Gly Phe His Gly Lys His Cys Glu
            180                 185                 190

aaa gcc cgg cca cac ctg tgc agc tca ggg ccc tgc cgg aac ggg ggc      682
Lys Ala Arg Pro His Leu Cys Ser Ser Gly Pro Cys Arg Asn Gly Gly
        195                 200                 205

acg tgc aag gag gcg ggc ggc gag tac cac tgc agc tgc ccc tac cgc      730
Thr Cys Lys Glu Ala Gly Gly Glu Tyr His Cys Ser Cys Pro Tyr Arg
    210                 215                 220

ttc act ggg agg cac tgt gag atc ggg aag cca gac tcg tgt gcc tct      778
Phe Thr Gly Arg His Cys Glu Ile Gly Lys Pro Asp Ser Cys Ala Ser
225                 230                 235                 240

ggc ccc tgt cac aac ggc ggc acc tgc ttc cac tac att ggc aaa tac      826
Gly Pro Cys His Asn Gly Gly Thr Cys Phe His Tyr Ile Gly Lys Tyr
            245                 250                 255

aag tgt gac tgt ccc cca ggc ttc tcc ggg cgg tac tgt gag ata gcc      874
Lys Cys Asp Cys Pro Pro Gly Phe Ser Gly Arg Tyr Cys Glu Ile Ala
            260                 265                 270

ccc tcc ccc tgc ttc cgg agc ccg tgt gtg aat ggg ggc acc tgc gag      922
Pro Ser Pro Cys Phe Arg Ser Pro Cys Val Asn Gly Gly Thr Cys Glu
        275                 280                 285

gac cgg gac acg gat ttc ttc tgc cac tgc caa gca ggg tac atg gga      970
Asp Arg Asp Thr Asp Phe Phe Cys His Cys Gln Ala Gly Tyr Met Gly
    290                 295                 300

cgc cgg tgc cag gca gag gtg gac tgc ggc ccc ccg gag gag gtg aag     1018
Arg Arg Cys Gln Ala Glu Val Asp Cys Gly Pro Pro Glu Glu Val Lys
305                 310                 315                 320

cac gcc aca ctg cgc ttc aac ggc acg cgg ctg ggc gcg gcg gcc ctg     1066
His Ala Thr Leu Arg Phe Asn Gly Thr Arg Leu Gly Ala Ala Ala Leu
            325                 330                 335

tat gca tgt gac cgt ggc tac agc ctg agc gcc ccc agc cgc atc cgg     1114
Tyr Ala Cys Asp Arg Gly Tyr Ser Leu Ser Ala Pro Ser Arg Ile Arg
            340                 345                 350

gtc tgc cag cca cac ggt gtc tgg agt gag cct ccc cag tgc ctt gaa     1162
Val Cys Gln Pro His Gly Val Trp Ser Glu Pro Pro Gln Cys Leu Glu
        355                 360                 365

atc gat gag tgc cgg tct cag ccg tgc ctg cat ggg ggc tct tgt cag     1210
Ile Asp Glu Cys Arg Ser Gln Pro Cys Leu His Gly Gly Ser Cys Gln
    370                 375                 380

gac cgc gtt gct ggg tac ctg tgc ctc tgc agc aca ggc tat gag ggc     1258
```

-continued

```
Asp Arg Val Ala Gly Tyr Leu Cys Leu Cys Ser Thr Gly Tyr Glu Gly
385                 390                 395                 400

gcc cac tgt gag ctg gag agg gat gag tgc cga gct cac ccg tgc aga      1306
Ala His Cys Glu Leu Glu Arg Asp Glu Cys Arg Ala His Pro Cys Arg
                405                 410                 415

aat gga ggg tcc tgc agg aac ctc cca ggg gcc tat gtc tgc cgg tgc      1354
Asn Gly Gly Ser Cys Arg Asn Leu Pro Gly Ala Tyr Val Cys Arg Cys
            420                 425                 430

cct gca ggc ttc gtt gga gtc cac tgt gag aca gag gtg gac gcc tgc      1402
Pro Ala Gly Phe Val Gly Val His Cys Glu Thr Glu Val Asp Ala Cys
        435                 440                 445

gac tcc agc ccc tgc cag cat gga ggc cgg tgt gag agc ggc ggt ggg      1450
Asp Ser Ser Pro Cys Gln His Gly Gly Arg Cys Glu Ser Gly Gly Gly
    450                 455                 460

gcc tac ctg tgc gtc tgc cca gag ggc ttc ttc ggc tac cac tgc gag      1498
Ala Tyr Leu Cys Val Cys Pro Glu Gly Phe Phe Gly Tyr His Cys Glu
465                 470                 475                 480

aca gtg agt gac ccc tgc ttc tcc agc ccc tgt ggg ggc cgt ggc tat      1546
Thr Val Ser Asp Pro Cys Phe Ser Ser Pro Cys Gly Gly Arg Gly Tyr
                485                 490                 495

tgc ctg gcc agc aac ggc tcc cac agc tgc acc tgc aaa gtg ggc tac      1594
Cys Leu Ala Ser Asn Gly Ser His Ser Cys Thr Cys Lys Val Gly Tyr
            500                 505                 510

acg ggc gag gac tgc gcc aaa gag ctc ttc cca ccg acg gcc ctc aag      1642
Thr Gly Glu Asp Cys Ala Lys Glu Leu Phe Pro Pro Thr Ala Leu Lys
        515                 520                 525

atg gag aga gtg gag gag agt ggg gtc tct atc tcc tgg aac ccg ccc      1690
Met Glu Arg Val Glu Glu Ser Gly Val Ser Ile Ser Trp Asn Pro Pro
    530                 535                 540

aat ggt cca gcc gcc agg cag atg ctt gat ggc tac gcg gtc acc tac      1738
Asn Gly Pro Ala Ala Arg Gln Met Leu Asp Gly Tyr Ala Val Thr Tyr
545                 550                 555                 560

gtc tcc tcc gac ggc tcc tac cgc cgc aca gac ttt gtg gac agg acc      1786
Val Ser Ser Asp Gly Ser Tyr Arg Arg Thr Asp Phe Val Asp Arg Thr
                565                 570                 575

cgc tcc tcg cac cag ctc cag gcc ctg gcg gcc ggc agg gcc tac aac      1834
Arg Ser Ser His Gln Leu Gln Ala Leu Ala Ala Gly Arg Ala Tyr Asn
            580                 585                 590

atc tcc gtc ttc tca gtg aag cga aac agt aac aac aag aat gac atc      1882
Ile Ser Val Phe Ser Val Lys Arg Asn Ser Asn Asn Lys Asn Asp Ile
        595                 600                 605

agc agg cct gcc gtg ctg ctg gcc cgc acg cga ccc cgc cct gtg gaa      1930
Ser Arg Pro Ala Val Leu Leu Ala Arg Thr Arg Pro Arg Pro Val Glu
    610                 615                 620

ggc ttc gag gtc acc aat gtg acg gct agc acc atc tca gtg cag tgg      1978
Gly Phe Glu Val Thr Asn Val Thr Ala Ser Thr Ile Ser Val Gln Trp
625                 630                 635                 640

gcc ctg cac agg atc cgc cat gcc acc gtc agt ggg gtc cgt gtg tcc      2026
Ala Leu His Arg Ile Arg His Ala Thr Val Ser Gly Val Arg Val Ser
                645                 650                 655

atc cgc cac cct gag gcc ctc agg gac cag gcc acc gat gtg gac agg      2074
Ile Arg His Pro Glu Ala Leu Arg Asp Gln Ala Thr Asp Val Asp Arg
            660                 665                 670

agt gtg gac agg ttc acc ttt agg gcc ctg ctg cct ggg aag agg tac      2122
Ser Val Asp Arg Phe Thr Phe Arg Ala Leu Leu Pro Gly Lys Arg Tyr
        675                 680                 685

acc atc cag ctg acc acc ctc agt ggg ctc agg gga gag gag cac ccc      2170
Thr Ile Gln Leu Thr Thr Leu Ser Gly Leu Arg Gly Glu Glu His Pro
    690                 695                 700
```

-continued

```
aca gag agc ctg gcc acc gcg ccg acg cac gtg tgg acc cgg ccc ctg     2218
Thr Glu Ser Leu Ala Thr Ala Pro Thr His Val Trp Thr Arg Pro Leu
705                 710                 715                 720

cct cca gca aac ctg acc gcc gcc cga gtc act gcc acc tct gcc cac     2266
Pro Pro Ala Asn Leu Thr Ala Ala Arg Val Thr Ala Thr Ser Ala His
                725                 730                 735

gtg gtc tgg gat gcc ccg act cca ggc agc ttg ctg gag gct tat gtc     2314
Val Val Trp Asp Ala Pro Thr Pro Gly Ser Leu Leu Glu Ala Tyr Val
            740                 745                 750

atc aat gtg acc acc agc cag agc acc aag agc cgc tat gtc ccc aac     2362
Ile Asn Val Thr Thr Ser Gln Ser Thr Lys Ser Arg Tyr Val Pro Asn
        755                 760                 765

ggg aag ctg gcg tcc tac acg gtg cgc gac ctg ctg ccg gga cgg cgg     2410
Gly Lys Leu Ala Ser Tyr Thr Val Arg Asp Leu Leu Pro Gly Arg Arg
    770                 775                 780

tac cag ctc tct gtg ata gca gtg cag agc acg gag ctc ggg ccg cag     2458
Tyr Gln Leu Ser Val Ile Ala Val Gln Ser Thr Glu Leu Gly Pro Gln
785                 790                 795                 800

cag cac cag gga gga cac cac cct cgg gtg ctc aag aac aga ccg ccc     2506
Gln His Gln Gly Gly His His Pro Arg Val Leu Lys Asn Arg Pro Pro
                805                 810                 815

ccg gcg cgc ctg ccg gag ctg cgc ctg ctc aat gac cac agc gcc ccc     2554
Pro Ala Arg Leu Pro Glu Leu Arg Leu Leu Asn Asp His Ser Ala Pro
            820                 825                 830

gag acc ccc acc cag ccc ccc agg ttc tcg gag ctt gtg gac ggc aga     2602
Glu Thr Pro Thr Gln Pro Pro Arg Phe Ser Glu Leu Val Asp Gly Arg
        835                 840                 845

gga aga gtg agc gcc agg ttc ggt ggc tca ccc agc aaa gca gcc acc     2650
Gly Arg Val Ser Ala Arg Phe Gly Gly Ser Pro Ser Lys Ala Ala Thr
    850                 855                 860

gtg aga tca caa ccc aca gcc tcg gcg cag ctc gag aac atg gag gaa     2698
Val Arg Ser Gln Pro Thr Ala Ser Ala Gln Leu Glu Asn Met Glu Glu
865                 870                 875                 880

gcc ccc aag cgg gtc agc ctg gcc ctc cag ctc cct gaa cac ggc agc     2746
Ala Pro Lys Arg Val Ser Leu Ala Leu Gln Leu Pro Glu His Gly Ser
                885                 890                 895

aag gac atc gga aac gtc cct ggc aac tgt tca gaa aac ccc tgt cag     2794
Lys Asp Ile Gly Asn Val Pro Gly Asn Cys Ser Glu Asn Pro Cys Gln
            900                 905                 910

aac gga ggc act tgt gtg ccg ggc gca gac gcc cac agc tgt gac tgc     2842
Asn Gly Gly Thr Cys Val Pro Gly Ala Asp Ala His Ser Cys Asp Cys
        915                 920                 925

ggg cca ggg ttc aaa ggc aga cgc tgc gag ctc gcc tgt ata aag gtg     2890
Gly Pro Gly Phe Lys Gly Arg Arg Cys Glu Leu Ala Cys Ile Lys Val
    930                 935                 940

tcc cgc ccc tgc aca agg ctg ttc tcc gag aca aag gcc ttt cca gtc     2938
Ser Arg Pro Cys Thr Arg Leu Phe Ser Glu Thr Lys Ala Phe Pro Val
945                 950                 955                 960

tgg gag gga ggc gtc tgt cac cac gtg tat aaa aga gtc tac cga gtt     2986
Trp Glu Gly Gly Val Cys His His Val Tyr Lys Arg Val Tyr Arg Val
                965                 970                 975

cac caa gac atc tgc ttc aaa gag agc tgt gaa agc aca agc ctc aag     3034
His Gln Asp Ile Cys Phe Lys Glu Ser Cys Glu Ser Thr Ser Leu Lys
            980                 985                 990

aag acc cca aac agg aaa caa agt  aag agt cag aca ctg  gag aaa tct   3082
Lys Thr Pro Asn Arg Lys Gln Ser  Lys Ser Gln Thr Leu  Glu Lys Ser
        995                 1000                1005

taaggattta agacgttctt gttacactcc accaacctca cgagtttcta acacccagga   3142

agatgaggtc taaaaactgg atgaaaaagg acaccctgag aaaaggtcct agctggagtc   3202
```

-continued

```
agtcccctct gtgacctctc tcctcaggcc tctagaggac agatggccag gcctgtgcac   3262

acaccagccc accctgagag acccctctgg gaccaaccac ctgtgagtcc tgcgatgcgt   3322

ttaagcagcc tgtgccctca cccaagctgc agttcctgaa ggtgtagtct gtgtctctgc   3382

ggatgagatg acagctcgcc attccccgga atcagtgagg ctgtcagtca gccacgcttc   3442

tgcagtatgc agaaacctgt tcttagactc caaagccaga gaaagaattc tcccttcgag   3502

gcccaacaaa ttgagaagga actgtgatgg accacttcca aaacagagac gggggcaggg   3562

gctgaagggc agagaccagg tgatgtcaga aggaaagccg ggttgcagac acagccgccc   3622

ctgctctggt cctccagcgt gtttatgacg ctcgtgcagg tcgacgagcc atcctatgga   3682

ctagttaaca ctaaggtgga gttcagactt ttttagacaa cggcgcgact ggcagccttt   3742

ctctatcaag ggtcagacgg taaacgtttt cagctttgca gaccagaggt ccctgtggct   3802

acagtagcgc agacacagcc acaggcatgt cattgaatgg ctgcggctat gttccaataa   3862

aaacttattt acaataacag gtggtggcca aattggccca tgggccttat ttggtgaacc   3922

ctgttctatg agatcaccta ggcttcagcc ttaaacagtg gaagccatcc cctgaatgac   3982

aagtcacaag ggtatcaaag aaagacccct gaattttcat ggaaaaagct attcagaccc   4042

ctgcttggaa agctaaggca cactgccacg aagcagcaag gacgccttac aagtctcagt   4102

gcaacagaga tggacacctg ggctgggctg gacaatgttt aaggttcctt ttagtccatg   4162

actcaagtga tactgtttta ggctatcagg tagtaaacac gatcttagac atccccatct   4222

ttgtaagcag aacagtacgg cacttcacca catctgcttc ccaccatgct tctaagcagc   4282

tgtcttcccc ctgctaatgt tacaaccaaa gcagccaccc cacctcctct cgtgttgagc   4342

ctcacgaccg ctgacccagc tggaaagcca gcgccctgcc gcgtcaccct gactctgctc   4402

agagccagca ttccagccac aaagagggcc tccttccttt cctctttcat aaaaatgttt   4462

tttgaagagt tagagtatat tttaggcttt ttatctttat taaaatttca tgtgcatgtg   4522

ta                                                                  4524


<210> SEQ ID NO 8
<211> LENGTH: 3027
<212> TYPE: DNA
<213> ORGANISM: Homo sapiens
<220> FEATURE:
<221> NAME/KEY: exon
<222> LOCATION: (1)..(3024)

<400> SEQUENCE: 8

tgc ctg aat gga ggc tct tgt gtt gac ctg gtt gga aac tac agc tgt       48
Cys Leu Asn Gly Gly Ser Cys Val Asp Leu Val Gly Asn Tyr Ser Cys
1               5                   10                  15

att tgt gtg gag ccc ttt gaa gga cct cag tgc gag aca gga agc tac       96
Ile Cys Val Glu Pro Phe Glu Gly Pro Gln Cys Glu Thr Gly Ser Tyr
            20                  25                  30

gtg gtg cct tcg ccc tgc ctc tcc aac ccc tgc ctg aac ggg ggc acc      144
Val Val Pro Ser Pro Cys Leu Ser Asn Pro Cys Leu Asn Gly Gly Thr
        35                  40                  45

tgt gtg gat gct gac cag gga tac gtg tgc gaa tgc cct gaa ggt ttc      192
Cys Val Asp Ala Asp Gln Gly Tyr Val Cys Glu Cys Pro Glu Gly Phe
    50                  55                  60

atg ggc ttg gac tgc aga gag aga att ctc aat gac tgt gat tgc cgg      240
Met Gly Leu Asp Cys Arg Glu Arg Ile Leu Asn Asp Cys Asp Cys Arg
65                  70                  75                  80

aat gga ggc aga tgc ctg ggt gcc aac acc acc atc tgc cag tgt cct      288
```

-continued

```
Asn Gly Gly Arg Cys Leu Gly Ala Asn Thr Thr Ile Cys Gln Cys Pro
                85                  90                  95

cca ggc tcc ttt ggg ctc ctc tgt gaa ttt gaa gtc aca gcc acg ccc      336
Pro Gly Ser Phe Gly Leu Leu Cys Glu Phe Glu Val Thr Ala Thr Pro
            100                 105                 110

tgc aac atg aac aca cag tgt cca gat gga ggc tac tgc atg gag tat      384
Cys Asn Met Asn Thr Gln Cys Pro Asp Gly Gly Tyr Cys Met Glu Tyr
        115                 120                 125

ggc gga agc tac cta tgt gtc tgc cac acg gac cac aac atc agc cat      432
Gly Gly Ser Tyr Leu Cys Val Cys His Thr Asp His Asn Ile Ser His
    130                 135                 140

tct ctg ccc tcg ccc tgc gac tca gac cca tgc ttt aat gga ggt tcc      480
Ser Leu Pro Ser Pro Cys Asp Ser Asp Pro Cys Phe Asn Gly Gly Ser
145                 150                 155                 160

tgt gac gcc cac gag gac tcc tac acg tgc gag tgc cct cgt gga ttc      528
Cys Asp Ala His Glu Asp Ser Tyr Thr Cys Glu Cys Pro Arg Gly Phe
                165                 170                 175

cat ggc agg cac tgc gag aaa gcc cgg cca cac ctg tgc agc tca ggg      576
His Gly Arg His Cys Glu Lys Ala Arg Pro His Leu Cys Ser Ser Gly
            180                 185                 190

ccc tgc cgg aat ggg ggc aca tac aag gag act ggt gac gag tac cgc      624
Pro Cys Arg Asn Gly Gly Thr Tyr Lys Glu Thr Gly Asp Glu Tyr Arg
        195                 200                 205

tgc acc tgc cct tac cgg ttc act ggg aga cac tgt gag att gga aag      672
Cys Thr Cys Pro Tyr Arg Phe Thr Gly Arg His Cys Glu Ile Gly Lys
    210                 215                 220

cca gac tcc tgt gcc tct ggc ccc tgt cac aac ggt ggc act tgt ttc      720
Pro Asp Ser Cys Ala Ser Gly Pro Cys His Asn Gly Gly Thr Cys Phe
225                 230                 235                 240

cac tac att ggc aaa tac aag tgt gac tgc cct cca ggc ttc tct ggt      768
His Tyr Ile Gly Lys Tyr Lys Cys Asp Cys Pro Pro Gly Phe Ser Gly
                245                 250                 255

cgg cac tgt gag ata gcc ccc tcc ccc tgc ttc cgg agc cca tgt atg      816
Arg His Cys Glu Ile Ala Pro Ser Pro Cys Phe Arg Ser Pro Cys Met
            260                 265                 270

aat ggg ggt atc tgc gag gat cta gga aca gat ttc tcc tgc cac tgc      864
Asn Gly Gly Ile Cys Glu Asp Leu Gly Thr Asp Phe Ser Cys His Cys
        275                 280                 285

caa cca gga tat aca gga cac cgg tgt cag gca gag gtg gac tgc ggt      912
Gln Pro Gly Tyr Thr Gly His Arg Cys Gln Ala Glu Val Asp Cys Gly
    290                 295                 300

cag cct gag gag gta aaa cat gct acc atg cgt ctc aat gga act cgc      960
Gln Pro Glu Glu Val Lys His Ala Thr Met Arg Leu Asn Gly Thr Arg
305                 310                 315                 320

atg ggc tcg gtg gcc ctg tac aca tgt gac ccc ggc ttc agc ctg agc     1008
Met Gly Ser Val Ala Leu Tyr Thr Cys Asp Pro Gly Phe Ser Leu Ser
                325                 330                 335

gtc ctc agc cat atg cgt gtc tgt cag cca caa ggt gtc tgg agc cag     1056
Val Leu Ser His Met Arg Val Cys Gln Pro Gln Gly Val Trp Ser Gln
            340                 345                 350

cct ccc cag tgc att gaa gta gat gag tgc cag tct cag cca tac ctg     1104
Pro Pro Gln Cys Ile Glu Val Asp Glu Cys Gln Ser Gln Pro Tyr Leu
        355                 360                 365

cat aaa ggc tcc tgc cag gac ctc att gct ggt tac cag tgc ctc tgc     1152
His Lys Gly Ser Cys Gln Asp Leu Ile Ala Gly Tyr Gln Cys Leu Cys
    370                 375                 380

agc ccg ggg tac gaa gga gtc cac tgt gag cta gag aca gac gag tgc     1200
Ser Pro Gly Tyr Glu Gly Val His Cys Glu Leu Glu Thr Asp Glu Cys
385                 390                 395                 400
```

-continued

```
caa gca cag ccc tgc aga aat gga ggc tcc tgc agg gac ctc ccc ggg      1248
Gln Ala Gln Pro Cys Arg Asn Gly Gly Ser Cys Arg Asp Leu Pro Gly
            405                 410                 415

gct ttc atc tgc cag tgc cct gaa ggt ttt gtt gga acc cac tat gaa      1296
Ala Phe Ile Cys Gln Cys Pro Glu Gly Phe Val Gly Thr His Tyr Glu
            420                 425                 430

aca gag gtg gat gcc tgt gcc tcc agc ccc tgc cag cac gga ggc cgg      1344
Thr Glu Val Asp Ala Cys Ala Ser Ser Pro Cys Gln His Gly Gly Arg
        435                 440                 445

tgt gag gac ggt ggt ggg gcc tac ctg tgc gtt tgt cca gag ggc ttc      1392
Cys Glu Asp Gly Gly Gly Ala Tyr Leu Cys Val Cys Pro Glu Gly Phe
    450                 455                 460

ttc ggc tac aac tgt gag aca gtg agt aac ccc tgc ttc tct agc ccc      1440
Phe Gly Tyr Asn Cys Glu Thr Val Ser Asn Pro Cys Phe Ser Ser Pro
465                 470                 475                 480

tgt ggg ggc cgc ggc tac tgc ttg gcc agc aac ggg tcc cac agc tgt      1488
Cys Gly Gly Arg Gly Tyr Cys Leu Ala Ser Asn Gly Ser His Ser Cys
                485                 490                 495

acc tgc aaa gtg ggc tac aca ggc aag gac tgc acc aaa gag ctc ctc      1536
Thr Cys Lys Val Gly Tyr Thr Gly Lys Asp Cys Thr Lys Glu Leu Leu
            500                 505                 510

cca cca aca gcc ctc agg gta gaa agg gtg gag gag agt ggg gtc tcc      1584
Pro Pro Thr Ala Leu Arg Val Glu Arg Val Glu Glu Ser Gly Val Ser
        515                 520                 525

atc tcc tgg agc cca ccc gag ggc acc acg gcc aga cag gtg ctg gac      1632
Ile Ser Trp Ser Pro Pro Glu Gly Thr Thr Ala Arg Gln Val Leu Asp
    530                 535                 540

ggc tat gca gtc acc tat gcc tcc tcg gat gga tcg tcc agg cgc acg      1680
Gly Tyr Ala Val Thr Tyr Ala Ser Ser Asp Gly Ser Ser Arg Arg Thr
545                 550                 555                 560

gac ttt gtg gac cgg agc cgc tcc tct cac cag ctt cgg gcc ctg gca      1728
Asp Phe Val Asp Arg Ser Arg Ser Ser His Gln Leu Arg Ala Leu Ala
                565                 570                 575

gcc ggc cgt gcc tac aac atc tct gtt ttc tca gtc aag aga aac act      1776
Ala Gly Arg Ala Tyr Asn Ile Ser Val Phe Ser Val Lys Arg Asn Thr
            580                 585                 590

aac aac aaa aat gac atc agc agg cct gca gcc ctg ctc acc cgc acc      1824
Asn Asn Lys Asn Asp Ile Ser Arg Pro Ala Ala Leu Leu Thr Arg Thr
        595                 600                 605

cga ccc cgc cct att gaa gac ttc gag gtc acc aac att tca gcc aat      1872
Arg Pro Arg Pro Ile Glu Asp Phe Glu Val Thr Asn Ile Ser Ala Asn
    610                 615                 620

gcc atc tca gtg cag tgg gct ctt cat agg atc cag cat gcc act gtc      1920
Ala Ile Ser Val Gln Trp Ala Leu His Arg Ile Gln His Ala Thr Val
625                 630                 635                 640

agc agg gtt cga gtg tct gtc ctc tac cct gag gac act gtg gtc cag      1968
Ser Arg Val Arg Val Ser Val Leu Tyr Pro Glu Asp Thr Val Val Gln
                645                 650                 655

tcc acg gag gtg gac agg agt gtg gac cgc ctc aca ttt ggg gac ctg      2016
Ser Thr Glu Val Asp Arg Ser Val Asp Arg Leu Thr Phe Gly Asp Leu
            660                 665                 670

ctg cca ggg aga aga tac agt gtg cgg cta acc acc ctc agt ggg cct      2064
Leu Pro Gly Arg Arg Tyr Ser Val Arg Leu Thr Thr Leu Ser Gly Pro
        675                 680                 685

gga gga gct gaa tat cct aca gag agc ctg gcc tca gct ccg ctg aac      2112
Gly Gly Ala Glu Tyr Pro Thr Glu Ser Leu Ala Ser Ala Pro Leu Asn
    690                 695                 700

gtg tgg acc cgg cct ttg cct cca gca aac ctg act gcc tct cga gtc      2160
Val Trp Thr Arg Pro Leu Pro Pro Ala Asn Leu Thr Ala Ser Arg Val
705                 710                 715                 720
```

-continued

```
aca gcg acc tct gcc cat atg gtc tgg gac ccg ccc act cca ggc atc     2208
Thr Ala Thr Ser Ala His Met Val Trp Asp Pro Pro Thr Pro Gly Ile
                725                 730                 735

tca ctg gag gct tac gtc atc aat gtg acc acc agt cag aat acc aag     2256
Ser Leu Glu Ala Tyr Val Ile Asn Val Thr Thr Ser Gln Asn Thr Lys
            740                 745                 750

agc cgc tac atc ccc aat ggg aag ctg gtg tcc tat acg gtg cgt gat     2304
Ser Arg Tyr Ile Pro Asn Gly Lys Leu Val Ser Tyr Thr Val Arg Asp
        755                 760                 765

ctg atg cca ggt cgg cgg tac cag ctc tcg gtc aca gcg gtg cag agc     2352
Leu Met Pro Gly Arg Arg Tyr Gln Leu Ser Val Thr Ala Val Gln Ser
    770                 775                 780

aca gag cag ggc cag ctg cac agt gag cct gcg cac ctc tac atc atc     2400
Thr Glu Gln Gly Gln Leu His Ser Glu Pro Ala His Leu Tyr Ile Ile
785                 790                 795                 800

acc tcc ccc agg gat ggc acc gac agg cgc tgg cac cag gga gga cac     2448
Thr Ser Pro Arg Asp Gly Thr Asp Arg Arg Trp His Gln Gly Gly His
                805                 810                 815

cac tca cgg atg ctc aga aat agg ccg gcc cct ttg cgc ctg cca gaa     2496
His Ser Arg Met Leu Arg Asn Arg Pro Ala Pro Leu Arg Leu Pro Glu
            820                 825                 830

ctg cgc ctc ctc aat gac cac ggt gcc cct gaa aca cca acc cag cca     2544
Leu Arg Leu Leu Asn Asp His Gly Ala Pro Glu Thr Pro Thr Gln Pro
        835                 840                 845

ccc agg ttc tca gag ctt gta gac gga aga gca aga gtg agt gcc agg     2592
Pro Arg Phe Ser Glu Leu Val Asp Gly Arg Ala Arg Val Ser Ala Arg
    850                 855                 860

ttt ggt gga ttg ccc agc aga gca gta act gtg aga tca caa ccc act     2640
Phe Gly Gly Leu Pro Ser Arg Ala Val Thr Val Arg Ser Gln Pro Thr
865                 870                 875                 880

act ccg gtg ccg ctc aag aac aca gag gcc cct gag cag gcc cgt ctg     2688
Thr Pro Val Pro Leu Lys Asn Thr Glu Ala Pro Glu Gln Ala Arg Leu
                885                 890                 895

gcc ctt cag cta ccc aag aac aac agc aag gac aca gaa agt acc cct     2736
Ala Leu Gln Leu Pro Lys Asn Asn Ser Lys Asp Thr Glu Ser Thr Pro
            900                 905                 910

ggc agc tgt tca gaa gac acc tgt cag aat gga ggc acc tgt gtc cca     2784
Gly Ser Cys Ser Glu Asp Thr Cys Gln Asn Gly Gly Thr Cys Val Pro
        915                 920                 925

ggt gcc aat gcc cac agc tgt gac tgc agg cct ggg ttc aaa ggc aga     2832
Gly Ala Asn Ala His Ser Cys Asp Cys Arg Pro Gly Phe Lys Gly Arg
    930                 935                 940

cac tgt gag ctt gcc tgt gaa aaa gtg ccc cgc ccc tgc aca cgg ctg     2880
His Cys Glu Leu Ala Cys Glu Lys Val Pro Arg Pro Cys Thr Arg Leu
945                 950                 955                 960

ttc tct gag acc aag tca ttt cct gtc tgg gaa gga gat gtc tgc cac     2928
Phe Ser Glu Thr Lys Ser Phe Pro Val Trp Glu Gly Asp Val Cys His
                965                 970                 975

cat gtg tat aag aaa gtc tac aaa gtt cac cag gac gtg tgt ttt aag     2976
His Val Tyr Lys Lys Val Tyr Lys Val His Gln Asp Val Cys Phe Lys
            980                 985                 990

gag cgc tgc cag agc aca agc ctc  aaa aag ctc aaa cag  gaa tca aat   3024
Glu Arg Cys Gln Ser Thr Ser Leu  Lys Lys Leu Lys Gln  Glu Ser Asn
        995                 1000                1005

taa                                                                 3027
```

<210> SEQ ID NO 9
<211> LENGTH: 3087
<212> TYPE: DNA

-continued

```
<213> ORGANISM: Homo sapiens
<220> FEATURE:
<221> NAME/KEY: exon
<222> LOCATION: (1)..(3084)

<400> SEQUENCE: 9

atg gat gtg gac gac tgc agc cct gac ccc tgc ctg aat gga ggc tct       48
Met Asp Val Asp Asp Cys Ser Pro Asp Pro Cys Leu Asn Gly Gly Ser
1               5                   10                  15

tgt gtt gac cta gtg ggg aat tac acc tgc ttg tgt gcc gag ccc ttc       96
Cys Val Asp Leu Val Gly Asn Tyr Thr Cys Leu Cys Ala Glu Pro Phe
            20                  25                  30

aag gga ctt cgc tgt gag aca gga gac cat cca gtg cca gac gcc tgc      144
Lys Gly Leu Arg Cys Glu Thr Gly Asp His Pro Val Pro Asp Ala Cys
        35                  40                  45

ctc tcg gcc cct tgc cac aat ggg ggc acc tgt gtg gat gcg gac tag      192
Leu Ser Ala Pro Cys His Asn Gly Gly Thr Cys Val Asp Ala Asp
    50                  55                  60

ggc tac gtg tgc gag tgc ccc gaa ggc ttc atg ggc ctg gac tgc agg      240
Gly Tyr Val Cys Glu Cys Pro Glu Gly Phe Met Gly Leu Asp Cys Arg
    65                  70                  75

gag aga gtc ccc gat gac tgt gag tgc cgc aac gga ggc aga tgc ctg      288
Glu Arg Val Pro Asp Asp Cys Glu Cys Arg Asn Gly Gly Arg Cys Leu
80                  85                  90                  95

ggc gcc aac acc acc ctc tgc cag tgc ccc ctg gga ttc ttt ggg ctt      336
Gly Ala Asn Thr Thr Leu Cys Gln Cys Pro Leu Gly Phe Phe Gly Leu
                100                 105                 110

ctc tgt gaa ttt gaa atc aca gcc atg ccc tgc aac atg aac aca cag      384
Leu Cys Glu Phe Glu Ile Thr Ala Met Pro Cys Asn Met Asn Thr Gln
            115                 120                 125

tgc cca gat ggg ggc tac tgc atg gag cac ggc ggg agc tac ctc tgc      432
Cys Pro Asp Gly Gly Tyr Cys Met Glu His Gly Gly Ser Tyr Leu Cys
        130                 135                 140

gtc tgc cac acc gac cac aat gcc agc cac tcc ctg cca tca ccc tgc      480
Val Cys His Thr Asp His Asn Ala Ser His Ser Leu Pro Ser Pro Cys
    145                 150                 155

aac tcg gac ccc tgc ttc aac gga ggc tcc tgc gat gcc cat gac gac      528
Asn Ser Asp Pro Cys Phe Asn Gly Gly Ser Cys Asp Ala His Asp Asp
160                 165                 170                 175

tcc tac acc tgc gag tgc ccg cgc ggg ttc cac ggc aag cac tgc gag      576
Ser Tyr Thr Cys Glu Cys Pro Arg Gly Phe His Gly Lys His Cys Glu
                180                 185                 190

aaa gcc cgg cca cac ctg tgc agc tca ggg ccc tgc cgg aac ggg ggc      624
Lys Ala Arg Pro His Leu Cys Ser Ser Gly Pro Cys Arg Asn Gly Gly
            195                 200                 205

acg tgc aag gag gcg ggc ggc gag tac cac tgc agc tgc ccc tac cgc      672
Thr Cys Lys Glu Ala Gly Gly Glu Tyr His Cys Ser Cys Pro Tyr Arg
        210                 215                 220

ttc act ggg agg cac tgt gag atc ggg aag cca gac tcg tgt gcc tct      720
Phe Thr Gly Arg His Cys Glu Ile Gly Lys Pro Asp Ser Cys Ala Ser
    225                 230                 235

ggc ccc tgt cac aac ggc ggc acc tgc ttc cac tac att ggc aaa tac      768
Gly Pro Cys His Asn Gly Gly Thr Cys Phe His Tyr Ile Gly Lys Tyr
240                 245                 250                 255

aag tgt gac tgt ccc cca ggc ttc tcc ggg cgg tac tgt gag ata gcc      816
Lys Cys Asp Cys Pro Pro Gly Phe Ser Gly Arg Tyr Cys Glu Ile Ala
                260                 265                 270

ccc tcc ccc tgc ttc cgg agc ccg tgt gtg aat ggg ggc acc tgc gag      864
Pro Ser Pro Cys Phe Arg Ser Pro Cys Val Asn Gly Gly Thr Cys Glu
            275                 280                 285
```

-continued

```
gac cgg gac acg gat ttc ttc tgc cac tgc caa gca ggg tac atg gga      912
Asp Arg Asp Thr Asp Phe Phe Cys His Cys Gln Ala Gly Tyr Met Gly
        290                 295                 300

cgc cgg tgc cag gca gag gtg gac tgc ggc ccc ccg gag gag gtg aag      960
Arg Arg Cys Gln Ala Glu Val Asp Cys Gly Pro Pro Glu Glu Val Lys
    305                 310                 315

cac gcc aca ctg cgc ttc aac ggc acg cgg ctg ggc gcg gcg gcc ctg     1008
His Ala Thr Leu Arg Phe Asn Gly Thr Arg Leu Gly Ala Ala Ala Leu
320                 325                 330                 335

tat gca tgt gac cgt ggc tac agc ctg agc gcc ccc agc cgc atc cgg     1056
Tyr Ala Cys Asp Arg Gly Tyr Ser Leu Ser Ala Pro Ser Arg Ile Arg
                340                 345                 350

gtc tgc cag cca cac ggt gtc tgg agt gag cct ccc cag tgc ctt gaa     1104
Val Cys Gln Pro His Gly Val Trp Ser Glu Pro Pro Gln Cys Leu Glu
            355                 360                 365

atc gat gag tgc cgg tct cag ccg tgc ctg cat ggg ggc tct tgt cag     1152
Ile Asp Glu Cys Arg Ser Gln Pro Cys Leu His Gly Gly Ser Cys Gln
        370                 375                 380

gac cgc gtt gct ggg tac ctg tgc ctc tgc agc aca ggc tat gag ggc     1200
Asp Arg Val Ala Gly Tyr Leu Cys Leu Cys Ser Thr Gly Tyr Glu Gly
    385                 390                 395

gcc cac tgt gag ctg gag agg gat gag tgc cga gct cac ccg tgc aga     1248
Ala His Cys Glu Leu Glu Arg Asp Glu Cys Arg Ala His Pro Cys Arg
400                 405                 410                 415

aat gga ggg tcc tgc agg aac ctc cca ggg gcc tat gtc tgc cgg tgc     1296
Asn Gly Gly Ser Cys Arg Asn Leu Pro Gly Ala Tyr Val Cys Arg Cys
                420                 425                 430

cct gca ggc ttc gtt gga gtc cac tgt gag aca gag gtg gac gcc tgc     1344
Pro Ala Gly Phe Val Gly Val His Cys Glu Thr Glu Val Asp Ala Cys
            435                 440                 445

gac tcc agc ccc tgc cag cat gga ggc cgg tgt gag agc ggc ggt ggg     1392
Asp Ser Ser Pro Cys Gln His Gly Gly Arg Cys Glu Ser Gly Gly Gly
        450                 455                 460

gcc tac ctg tgc gtc tgc cca gag ggc ttc ttc ggc tac cac tgc gag     1440
Ala Tyr Leu Cys Val Cys Pro Glu Gly Phe Phe Gly Tyr His Cys Glu
    465                 470                 475

aca gtg agt gac ccc tgc ttc tcc agc ccc tgt ggg ggc cgt ggc tat     1488
Thr Val Ser Asp Pro Cys Phe Ser Ser Pro Cys Gly Gly Arg Gly Tyr
480                 485                 490                 495

tgc ctg gcc agc aac ggc tcc cac agc tgc acc tgc aaa gtg ggc tac     1536
Cys Leu Ala Ser Asn Gly Ser His Ser Cys Thr Cys Lys Val Gly Tyr
                500                 505                 510

acg ggc gag gac tgc gcc aaa gag ctc ttc cca ccg acg gcc ctc aag     1584
Thr Gly Glu Asp Cys Ala Lys Glu Leu Phe Pro Pro Thr Ala Leu Lys
            515                 520                 525

atg gag aga gtg gag gag agt ggg gtc tct atc tcc tgg aac ccg ccc     1632
Met Glu Arg Val Glu Glu Ser Gly Val Ser Ile Ser Trp Asn Pro Pro
        530                 535                 540

aat ggt cca gcc gcc agg cag atg ctt gat ggc tac gcg gtc acc tac     1680
Asn Gly Pro Ala Ala Arg Gln Met Leu Asp Gly Tyr Ala Val Thr Tyr
    545                 550                 555

gtc tcc tcc gac ggc tcc tac cgc cgc aca gac ttt gtg gac agg acc     1728
Val Ser Ser Asp Gly Ser Tyr Arg Arg Thr Asp Phe Val Asp Arg Thr
560                 565                 570                 575

cgc tcc tcg cac cag ctc cag gcc ctg gcg gcc ggc agg gcc tac aac     1776
Arg Ser Ser His Gln Leu Gln Ala Leu Ala Ala Gly Arg Ala Tyr Asn
                580                 585                 590

atc tcc gtc ttc tca gtg aag cga aac agt aac aac aag aat gac atc     1824
Ile Ser Val Phe Ser Val Lys Arg Asn Ser Asn Asn Lys Asn Asp Ile
            595                 600                 605
```

-continued

```
agc agg cct gcc gtg ctg ctg gcc cgc acg cga ccc cgc cct gtg gaa     1872
Ser Arg Pro Ala Val Leu Leu Ala Arg Thr Arg Pro Arg Pro Val Glu
        610                 615                 620

ggc ttc gag gtc acc aat gtg acg gct agc acc atc tca gtg cag tgg     1920
Gly Phe Glu Val Thr Asn Val Thr Ala Ser Thr Ile Ser Val Gln Trp
    625                 630                 635

gcc ctg cac agg atc cgc cat gcc acc gtc agt ggg gtc cgt gtg tcc     1968
Ala Leu His Arg Ile Arg His Ala Thr Val Ser Gly Val Arg Val Ser
640                 645                 650                 655

atc cgc cac cct gag gcc ctc agg gac cag gcc acc gat gtg gac agg     2016
Ile Arg His Pro Glu Ala Leu Arg Asp Gln Ala Thr Asp Val Asp Arg
                660                 665                 670

agt gtg gac agg ttc acc ttt agg gcc ctg ctg cct ggg aag agg tac     2064
Ser Val Asp Arg Phe Thr Phe Arg Ala Leu Leu Pro Gly Lys Arg Tyr
            675                 680                 685

acc atc cag ctg acc acc ctc agt ggg ctc agg gga gag gag cac ccc     2112
Thr Ile Gln Leu Thr Thr Leu Ser Gly Leu Arg Gly Glu Glu His Pro
        690                 695                 700

aca gag agc ctg gcc acc gcg ccg acg cac gtg tgg acc cgg ccc ctg     2160
Thr Glu Ser Leu Ala Thr Ala Pro Thr His Val Trp Thr Arg Pro Leu
    705                 710                 715

cct cca gca aac ctg acc gcc gcc cga gtc act gcc acc tct gcc cac     2208
Pro Pro Ala Asn Leu Thr Ala Ala Arg Val Thr Ala Thr Ser Ala His
720                 725                 730                 735

gtg gtc tgg gat gcc ccg act cca ggc agc ttg ctg gag gct tat gtc     2256
Val Val Trp Asp Ala Pro Thr Pro Gly Ser Leu Leu Glu Ala Tyr Val
                740                 745                 750

atc aat gtg acc acc agc cag agc acc aag agc cgc tat gtc ccc aac     2304
Ile Asn Val Thr Thr Ser Gln Ser Thr Lys Ser Arg Tyr Val Pro Asn
            755                 760                 765

ggg aag ctg gcg tcc tac acg gtg cgc gac ctg ctg ccg gga cgg cgg     2352
Gly Lys Leu Ala Ser Tyr Thr Val Arg Asp Leu Leu Pro Gly Arg Arg
        770                 775                 780

tac cag ctc tct gtg ata gca gtg cag agc acg gag ctc ggg ccg cag     2400
Tyr Gln Leu Ser Val Ile Ala Val Gln Ser Thr Glu Leu Gly Pro Gln
    785                 790                 795

cac agc gag ccc gcc cac ctc tac atc atc acc tcc ccc agg gat ggc     2448
His Ser Glu Pro Ala His Leu Tyr Ile Ile Thr Ser Pro Arg Asp Gly
800                 805                 810                 815

gct gac aga cgc tgg cac cag gga gga cac cac cct cgg gtg ctc aag     2496
Ala Asp Arg Arg Trp His Gln Gly Gly His His Pro Arg Val Leu Lys
                820                 825                 830

aac aga ccg ccc ccg gcg cgc ctg ccg gag ctg cgc ctg ctc aat gac     2544
Asn Arg Pro Pro Pro Ala Arg Leu Pro Glu Leu Arg Leu Leu Asn Asp
            835                 840                 845

cac agc gcc ccc gag acc ccc acc cag ccc ccc agg ttc tcg gag ctt     2592
His Ser Ala Pro Glu Thr Pro Thr Gln Pro Pro Arg Phe Ser Glu Leu
        850                 855                 860

gtg gac ggc aga gga aga gtg agc gcc agg ttc ggt ggc tca ccc agc     2640
Val Asp Gly Arg Gly Arg Val Ser Ala Arg Phe Gly Gly Ser Pro Ser
    865                 870                 875

aaa gca gcc acc gtg aga tca caa ccc aca gcc tcg gcg cag ctc gag     2688
Lys Ala Ala Thr Val Arg Ser Gln Pro Thr Ala Ser Ala Gln Leu Glu
880                 885                 890                 895

aac atg gag gaa gcc ccc aag cgg gtc agc ctg gcc ctc cag ctc cct     2736
Asn Met Glu Glu Ala Pro Lys Arg Val Ser Leu Ala Leu Gln Leu Pro
                900                 905                 910

gaa cac ggc agc aag gac atc gga aac gtc cct ggc aac tgt tca gaa     2784
Glu His Gly Ser Lys Asp Ile Gly Asn Val Pro Gly Asn Cys Ser Glu
```

-continued

```
            915                 920                 925

aac ccc tgt cag aac gga ggc act tgt gtg ccg ggc gca gac gcc cac      2832
Asn Pro Cys Gln Asn Gly Gly Thr Cys Val Pro Gly Ala Asp Ala His
        930                 935                 940

agc tgt gac tgc ggg cca ggg ttc aaa ggc aga cgc tgc gag ctc gcc      2880
Ser Cys Asp Cys Gly Pro Gly Phe Lys Gly Arg Arg Cys Glu Leu Ala
    945                 950                 955

tgt ata aag gtg tcc cgc ccc tgc aca agg ctg ttc tcc gag aca aag      2928
Cys Ile Lys Val Ser Arg Pro Cys Thr Arg Leu Phe Ser Glu Thr Lys
960                 965                 970                 975

gcc ttt cca gtc tgg gag gga ggc gtc tgt cac cac gtg tat aaa aga      2976
Ala Phe Pro Val Trp Glu Gly Gly Val Cys His His Val Tyr Lys Arg
                980                 985                 990

gtc tac cga gtt cac caa gac atc tgc  ttc aaa gag agc tgt  gaa agc   3024
Val Tyr Arg Val His Gln Asp Ile Cys  Phe Lys Glu Ser Cys  Glu Ser
            995                 1000                 1005

aca agc ctc  aag aag acc cca aac  agg aaa caa agt aag  agt cag      3069
Thr Ser Leu  Lys Lys Thr Pro Asn  Arg Lys Gln Ser Lys  Ser Gln
        1010                 1015                 1020

aca ctg gag  aaa tct taa                                             3087
Thr Leu Glu  Lys Ser
        1025


<210> SEQ ID NO 10
<211> LENGTH: 1737
<212> TYPE: DNA
<213> ORGANISM: Homo sapiens
<220> FEATURE:
<221> NAME/KEY: exon
<222> LOCATION: (1)..(1161)
<220> FEATURE:
<221> NAME/KEY: 3'UTR
<222> LOCATION: (1162)..(1726)

<400> SEQUENCE: 10

ctt gat ggc tac gcg gtc acc tac gtc tcc tcc gac ggc tcc tac cgc        48
Leu Asp Gly Tyr Ala Val Thr Tyr Val Ser Ser Asp Gly Ser Tyr Arg
1               5                   10                  15

cgc aca gac ttt gtg gac agg acc cgc tcc tcg cac cag ctc cag gcc        96
Arg Thr Asp Phe Val Asp Arg Thr Arg Ser Ser His Gln Leu Gln Ala
            20                  25                  30

ctg gcg gcc ggc agg gcc tac aac atc tcc gtc ttc tca gtg aag cga       144
Leu Ala Ala Gly Arg Ala Tyr Asn Ile Ser Val Phe Ser Val Lys Arg
        35                  40                  45

aac agt aac aac aag aat gac atc agc agg cct gcc gtg ctg ctg gcc       192
Asn Ser Asn Asn Lys Asn Asp Ile Ser Arg Pro Ala Val Leu Leu Ala
    50                  55                  60

cgc acg cga ccc cgc cct gtg gaa ggc ttc gag gtc acc aat gtg acg       240
Arg Thr Arg Pro Arg Pro Val Glu Gly Phe Glu Val Thr Asn Val Thr
65                  70                  75                  80

gct agc acc atc tca gtg cag tgg gcc ctg cac agg atc cgc cat gcc       288
Ala Ser Thr Ile Ser Val Gln Trp Ala Leu His Arg Ile Arg His Ala
                85                  90                  95

acc gtc agt ggg gtc cgt gtg tcc atc cgc cac cct gag gcc ctc agg       336
Thr Val Ser Gly Val Arg Val Ser Ile Arg His Pro Glu Ala Leu Arg
            100                 105                 110

gac cag gcc acc gat gtg gac agg agt gtg gac agg ttc acc ttt agg       384
Asp Gln Ala Thr Asp Val Asp Arg Ser Val Asp Arg Phe Thr Phe Arg
        115                 120                 125

gcc ctg ctg cct ggg aag agg tac acc atc cag ctg acc acc ctc agt       432
Ala Leu Leu Pro Gly Lys Arg Tyr Thr Ile Gln Leu Thr Thr Leu Ser
    130                 135                 140
```

-continued

```
ggg ctc agg gga gag gag cac ccc aca gag agc ctg gcc acc gcg ccg      480
Gly Leu Arg Gly Glu Glu His Pro Thr Glu Ser Leu Ala Thr Ala Pro
145                 150                 155                 160

acg cac gtg tgg acc cgg ccc ctg cct cca gca aac ctg acc gcc gcc      528
Thr His Val Trp Thr Arg Pro Leu Pro Pro Ala Asn Leu Thr Ala Ala
                165                 170                 175

cga gtc act gcc acc tct gcc cac gtg gtc tgg gat gcc ccg act cca      576
Arg Val Thr Ala Thr Ser Ala His Val Val Trp Asp Ala Pro Thr Pro
            180                 185                 190

ggc agc ttg ctg gag gct tat gtc atc aat gtg acc acc agc cag agc      624
Gly Ser Leu Leu Glu Ala Tyr Val Ile Asn Val Thr Thr Ser Gln Ser
        195                 200                 205

acc aag agc cgc tat gtc ccc aac ggg aag ctg gcg tcc tac acg gtg      672
Thr Lys Ser Arg Tyr Val Pro Asn Gly Lys Leu Ala Ser Tyr Thr Val
    210                 215                 220

cgc gac ctg ctg ccg gga cgg cgg tac cag ctc tct gtg ata gca gtg      720
Arg Asp Leu Leu Pro Gly Arg Arg Tyr Gln Leu Ser Val Ile Ala Val
225                 230                 235                 240

cag agc acg gag ctc ggg ccg cag cac agc gag ccc gcc cac ctc tac      768
Gln Ser Thr Glu Leu Gly Pro Gln His Ser Glu Pro Ala His Leu Tyr
                245                 250                 255

atc atc acc tcc ccc agg gat ggc gct gac aga cgc tgg cac cag gga      816
Ile Ile Thr Ser Pro Arg Asp Gly Ala Asp Arg Arg Trp His Gln Gly
            260                 265                 270

gga cac cac cct cgg gtg ctc aag aac aga ccg ccc ccg gcg cgc ctg      864
Gly His His Pro Arg Val Leu Lys Asn Arg Pro Pro Pro Ala Arg Leu
        275                 280                 285

ccg gag ctg cgc ctg ctc aat gac cac agc gcc ccc gag acc ccc acc      912
Pro Glu Leu Arg Leu Leu Asn Asp His Ser Ala Pro Glu Thr Pro Thr
    290                 295                 300

cag ccc ccc agg ttc tcg gag ctt gtg gac ggc aga gga aga gtg agc      960
Gln Pro Pro Arg Phe Ser Glu Leu Val Asp Gly Arg Gly Arg Val Ser
305                 310                 315                 320

gcc agg ttc ggt ggc tca ccc agc aaa gca gcc acc gtg aga tca caa     1008
Ala Arg Phe Gly Gly Ser Pro Ser Lys Ala Ala Thr Val Arg Ser Gln
                325                 330                 335

ccc aca gcc tcg gcg cag ctc gag aac atg gag gaa gcc ccc aag cgg     1056
Pro Thr Ala Ser Ala Gln Leu Glu Asn Met Glu Glu Ala Pro Lys Arg
            340                 345                 350

gtc agc ctg gcc ctc cag ctc cct gaa cac ggc agc aag gac atc gga     1104
Val Ser Leu Ala Leu Gln Leu Pro Glu His Gly Ser Lys Asp Ile Gly
        355                 360                 365

agt gag tca gca gcg ctg gtg ggg act ttg gga ctg act gac tgc tct     1152
Ser Glu Ser Ala Ala Leu Val Gly Thr Leu Gly Leu Thr Asp Cys Ser
    370                 375                 380

cag ggg cct tagaggctgc aggcaggagg gaccacccac ggtgaggaat             1201
Gln Gly Pro
385

caggaggcac agagcctacc tgaggggagg ctgagcacca ggcaccccgg tgtgggaaga   1261

tggggtgaag ctacaccacc caagcagtgg gaccccacag acgggaacag gccagggggc   1321

aggacccacc caaaccaccc agagtctgag ctagagagac tggctttgat gctgcctccc   1381

ctcccctctc ctccttcgcc tccacatgca gcagagccca ccccagcccc tgcctctggg   1441

cccctcaccc ctcacttctc caaagaggag caggcggagt caggagggga gaagcagagg   1501

gagcagccac tgggcgagcc ccagcttgag gactagctgg gccctgtgga cactcaggtt   1561

atgcaggacc tgaactgtct cctagtccgg ggctctgcct cgtgaggatc gaggccagca   1621
```

-continued

```
cgtccctgca gggcaccaag catctgctga gcacctgcag taagagttcc cagacgctca   1681

cgaggcagtt ccccttcggg cagcaccaat atatgtgtgt tcctcaaaaa aaaaaa       1737


<210> SEQ ID NO 11
<211> LENGTH: 1008
<212> TYPE: PRT
<213> ORGANISM: Rattus norvegicus

<400> SEQUENCE: 11

Cys Leu Asn Gly Gly Ser Cys Val Asp Leu Val Gly Asn Tyr Ser Cys
1               5                   10                  15

Ile Cys Val Glu Pro Phe Glu Gly Pro Gln Cys Glu Thr Gly Ser Tyr
            20                  25                  30

Val Val Pro Ser Pro Cys Leu Ser Asn Pro Cys Leu Asn Gly Gly Thr
        35                  40                  45

Cys Val Asp Ala Asp Gln Gly Tyr Val Cys Glu Cys Pro Glu Gly Phe
    50                  55                  60

Met Gly Leu Asp Cys Arg Glu Arg Ile Leu Asn Asp Cys Asp Cys Arg
65                  70                  75                  80

Asn Gly Gly Arg Cys Leu Gly Ala Asn Thr Thr Ile Cys Gln Cys Pro
                85                  90                  95

Pro Gly Ser Phe Gly Leu Leu Cys Glu Phe Glu Val Thr Ala Thr Pro
            100                 105                 110

Cys Asn Met Asn Thr Gln Cys Pro Asp Gly Gly Tyr Cys Met Glu Tyr
        115                 120                 125

Gly Gly Ser Tyr Leu Cys Val Cys His Thr Asp His Asn Ile Ser His
    130                 135                 140

Ser Leu Pro Ser Pro Cys Asp Ser Asp Pro Cys Phe Asn Gly Gly Ser
145                 150                 155                 160

Cys Asp Ala His Glu Asp Ser Tyr Thr Cys Glu Cys Pro Arg Gly Phe
                165                 170                 175

His Gly Arg His Cys Glu Lys Ala Arg Pro His Leu Cys Ser Ser Gly
            180                 185                 190

Pro Cys Arg Asn Gly Gly Thr Tyr Lys Glu Thr Gly Asp Glu Tyr Arg
        195                 200                 205

Cys Thr Cys Pro Tyr Arg Phe Thr Gly Arg His Cys Glu Ile Gly Lys
    210                 215                 220

Pro Asp Ser Cys Ala Ser Gly Pro Cys His Asn Gly Gly Thr Cys Phe
225                 230                 235                 240

His Tyr Ile Gly Lys Tyr Lys Cys Asp Cys Pro Pro Gly Phe Ser Gly
                245                 250                 255

Arg His Cys Glu Ile Ala Pro Ser Pro Cys Phe Arg Ser Pro Cys Met
            260                 265                 270

Asn Gly Gly Ile Cys Glu Asp Leu Gly Thr Asp Phe Ser Cys His Cys
        275                 280                 285

Gln Pro Gly Tyr Thr Gly His Arg Cys Gln Ala Glu Val Asp Cys Gly
    290                 295                 300

Gln Pro Glu Glu Val Lys His Ala Thr Met Arg Leu Asn Gly Thr Arg
305                 310                 315                 320

Met Gly Ser Val Ala Leu Tyr Thr Cys Asp Pro Gly Phe Ser Leu Ser
                325                 330                 335

Val Leu Ser His Met Arg Val Cys Gln Pro Gln Gly Val Trp Ser Gln
            340                 345                 350

Pro Pro Gln Cys Ile Glu Val Asp Glu Cys Gln Ser Gln Pro Tyr Leu
```

-continued

```
        355                 360                 365

His Lys Gly Ser Cys Gln Asp Leu Ile Ala Gly Tyr Gln Cys Leu Cys
    370                 375                 380

Ser Pro Gly Tyr Glu Gly Val His Cys Glu Leu Glu Thr Asp Glu Cys
385                 390                 395                 400

Gln Ala Gln Pro Cys Arg Asn Gly Gly Ser Cys Arg Asp Leu Pro Gly
                405                 410                 415

Ala Phe Ile Cys Gln Cys Pro Glu Gly Phe Val Gly Thr His Tyr Glu
            420                 425                 430

Thr Glu Val Asp Ala Cys Ala Ser Ser Pro Cys Gln His Gly Gly Arg
        435                 440                 445

Cys Glu Asp Gly Gly Gly Ala Tyr Leu Cys Val Cys Pro Glu Gly Phe
    450                 455                 460

Phe Gly Tyr Asn Cys Glu Thr Val Ser Asn Pro Cys Phe Ser Ser Pro
465                 470                 475                 480

Cys Gly Gly Arg Gly Tyr Cys Leu Ala Ser Asn Gly Ser His Ser Cys
                485                 490                 495

Thr Cys Lys Val Gly Tyr Thr Gly Lys Asp Cys Thr Lys Glu Leu Leu
            500                 505                 510

Pro Pro Thr Ala Leu Arg Val Glu Arg Val Glu Glu Ser Gly Val Ser
        515                 520                 525

Ile Ser Trp Ser Pro Pro Glu Gly Thr Thr Ala Arg Gln Val Leu Asp
    530                 535                 540

Gly Tyr Ala Val Thr Tyr Ala Ser Ser Asp Gly Ser Ser Arg Arg Thr
545                 550                 555                 560

Asp Phe Val Asp Arg Ser Arg Ser Ser His Gln Leu Arg Ala Leu Ala
                565                 570                 575

Ala Gly Arg Ala Tyr Asn Ile Ser Val Phe Ser Val Lys Arg Asn Thr
            580                 585                 590

Asn Asn Lys Asn Asp Ile Ser Arg Pro Ala Ala Leu Leu Thr Arg Thr
        595                 600                 605

Arg Pro Arg Pro Ile Glu Asp Phe Glu Val Thr Asn Ile Ser Ala Asn
    610                 615                 620

Ala Ile Ser Val Gln Trp Ala Leu His Arg Ile Gln His Ala Thr Val
625                 630                 635                 640

Ser Arg Val Arg Val Ser Val Leu Tyr Pro Glu Asp Thr Val Val Gln
                645                 650                 655

Ser Thr Glu Val Asp Arg Ser Val Asp Arg Leu Thr Phe Gly Asp Leu
            660                 665                 670

Leu Pro Gly Arg Arg Tyr Ser Val Arg Leu Thr Thr Leu Ser Gly Pro
        675                 680                 685

Gly Gly Ala Glu Tyr Pro Thr Glu Ser Leu Ala Ser Ala Pro Leu Asn
    690                 695                 700

Val Trp Thr Arg Pro Leu Pro Pro Ala Asn Leu Thr Ala Ser Arg Val
705                 710                 715                 720

Thr Ala Thr Ser Ala His Met Val Trp Asp Pro Pro Thr Pro Gly Ile
                725                 730                 735

Ser Leu Glu Ala Tyr Val Ile Asn Val Thr Thr Ser Gln Asn Thr Lys
            740                 745                 750

Ser Arg Tyr Ile Pro Asn Gly Lys Leu Val Ser Tyr Thr Val Arg Asp
        755                 760                 765

Leu Met Pro Gly Arg Arg Tyr Gln Leu Ser Val Thr Ala Val Gln Ser
    770                 775                 780
```

-continued

Thr Glu Gln Gly Gln Leu His Ser Glu Pro Ala His Leu Tyr Ile Ile
785 790 795 800

Thr Ser Pro Arg Asp Gly Thr Asp Arg Arg Trp His Gln Gly Gly His
805 810 815

His Ser Arg Met Leu Arg Asn Arg Pro Ala Pro Leu Arg Leu Pro Glu
820 825 830

Leu Arg Leu Leu Asn Asp His Gly Ala Pro Glu Thr Pro Thr Gln Pro
835 840 845

Pro Arg Phe Ser Glu Leu Val Asp Gly Arg Ala Arg Val Ser Ala Arg
850 855 860

Phe Gly Gly Leu Pro Ser Arg Ala Val Thr Val Arg Ser Gln Pro Thr
865 870 875 880

Thr Pro Val Pro Leu Lys Asn Thr Glu Ala Pro Glu Gln Ala Arg Leu
885 890 895

Ala Leu Gln Leu Pro Lys Asn Asn Ser Lys Asp Thr Glu Ser Thr Pro
900 905 910

Gly Ser Cys Ser Glu Asp Thr Cys Gln Asn Gly Gly Thr Cys Val Pro
915 920 925

Gly Ala Asn Ala His Ser Cys Asp Cys Arg Pro Gly Phe Lys Gly Arg
930 935 940

His Cys Glu Leu Ala Cys Glu Lys Val Pro Arg Pro Cys Thr Arg Leu
945 950 955 960

Phe Ser Glu Thr Lys Ser Phe Pro Val Trp Glu Gly Asp Val Cys His
965 970 975

His Val Tyr Lys Lys Val Tyr Lys Val His Gln Asp Val Cys Phe Lys
980 985 990

Glu Arg Cys Gln Ser Thr Ser Leu Lys Lys Leu Lys Gln Glu Ser Asn
995 1000 1005

<210> SEQ ID NO 12
<211> LENGTH: 1047
<212> TYPE: PRT
<213> ORGANISM: Homo sapiens

<400> SEQUENCE: 12

Glu Asn Gly Ser Ala Val Cys Val Cys Gln Ala Gly Tyr Thr Gly Ala
1 5 10 15

Ala Cys Glu Met Asp Val Asp Asp Cys Ser Pro Asp Pro Cys Leu Asn
20 25 30

Gly Gly Ser Cys Val Asp Leu Val Gly Asn Tyr Thr Cys Leu Cys Ala
35 40 45

Glu Pro Phe Lys Gly Leu Arg Cys Glu Thr Gly Asp His Pro Val Pro
50 55 60

Asp Ala Cys Leu Ser Ala Pro Cys His Asn Gly Gly Thr Cys Val Asp
65 70 75 80

Ala Asp Gln Gly Tyr Val Cys Glu Cys Pro Glu Gly Phe Met Gly Leu
85 90 95

Asp Cys Arg Glu Arg Val Pro Asp Asp Cys Glu Cys Arg Asn Gly Gly
100 105 110

Arg Cys Leu Gly Ala Asn Thr Thr Leu Cys Gln Cys Pro Leu Gly Phe
115 120 125

Phe Gly Leu Leu Cys Glu Phe Glu Ile Thr Ala Met Pro Cys Asn Met
130 135 140

Asn Thr Gln Cys Pro Asp Gly Gly Tyr Cys Met Glu His Gly Gly Ser

-continued

```
145                 150                 155                 160

Tyr Leu Cys Val Cys His Thr Asp His Asn Ala Ser His Ser Leu Pro
                165                 170                 175

Ser Pro Cys Asp Ser Asp Pro Cys Phe Asn Gly Gly Ser Cys Asp Ala
            180                 185                 190

His Asp Asp Ser Tyr Thr Cys Glu Cys Pro Arg Gly Phe His Gly Lys
        195                 200                 205

His Cys Glu Lys Ala Arg Pro His Leu Cys Ser Ser Gly Pro Cys Arg
    210                 215                 220

Asn Gly Gly Thr Cys Lys Glu Ala Gly Gly Glu Tyr His Cys Ser Cys
225                 230                 235                 240

Pro Tyr Arg Phe Thr Gly Arg His Cys Glu Ile Gly Lys Pro Asp Ser
                245                 250                 255

Cys Ala Ser Gly Pro Cys His Asn Gly Gly Thr Cys Phe His Tyr Ile
            260                 265                 270

Gly Lys Tyr Lys Cys Asp Cys Pro Pro Gly Phe Ser Gly Arg His Cys
        275                 280                 285

Glu Ile Ala Pro Ser Pro Cys Phe Arg Ser Pro Cys Val Asn Gly Gly
    290                 295                 300

Thr Cys Glu Asp Arg Asp Thr Asp Phe Phe Cys His Cys Gln Ala Gly
305                 310                 315                 320

Tyr Met Gly Arg Arg Cys Gln Ala Glu Val Asp Cys Gly Pro Pro Glu
                325                 330                 335

Glu Val Lys His Ala Thr Leu Arg Phe Asn Gly Thr Arg Leu Gly Ala
            340                 345                 350

Val Ala Leu Tyr Ala Cys Asp Arg Gly Tyr Ser Leu Ser Ala Pro Ser
        355                 360                 365

Arg Ile Arg Val Cys Gln Pro His Gly Val Trp Ser Glu Pro Pro Gln
    370                 375                 380

Cys Leu Glu Ile Asp Glu Cys Arg Ser Gln Pro Cys Leu His Gly Gly
385                 390                 395                 400

Ser Cys Gln Asp Arg Val Ala Gly Tyr Leu Cys Leu Cys Ser Thr Gly
                405                 410                 415

Tyr Glu Gly Ala His Cys Glu Leu Glu Arg Asp Glu Cys Arg Ala His
            420                 425                 430

Pro Cys Arg Asn Gly Gly Ser Cys Arg Asn Leu Pro Gly Ala Tyr Val
        435                 440                 445

Cys Arg Cys Pro Ala Gly Phe Val Gly Val His Cys Glu Thr Glu Val
    450                 455                 460

Asp Ala Cys Asp Ser Ser Pro Cys Gln His Gly Gly Arg Cys Glu Ser
465                 470                 475                 480

Gly Gly Gly Ala Tyr Leu Cys Val Cys Pro Glu Ser Phe Phe Gly Tyr
                485                 490                 495

His Cys Glu Thr Val Ser Asp Pro Cys Phe Ser Ser Pro Cys Gly Gly
            500                 505                 510

Arg Gly Tyr Cys Leu Ala Ser Asn Gly Ser His Ser Cys Thr Cys Lys
        515                 520                 525

Val Gly Tyr Thr Gly Glu Asp Cys Ala Lys Glu Leu Phe Pro Pro Thr
    530                 535                 540

Ala Leu Lys Met Glu Arg Val Glu Glu Ser Gly Val Ser Ile Ser Trp
545                 550                 555                 560

Asn Pro Pro Asn Gly Pro Ala Ala Arg Gln Met Leu Asp Gly Tyr Ala
                565                 570                 575
```

-continued

```
Val Thr Tyr Val Ser Ser Asp Gly Ser Tyr Arg Arg Thr Asp Phe Val
            580                 585                 590

Asp Arg Thr Arg Ser Ser His Gln Leu Gln Ala Leu Ala Ala Gly Arg
        595                 600                 605

Ala Tyr Asn Ile Ser Val Phe Ser Val Lys Arg Asn Ser Asn Asn Lys
    610                 615                 620

Asn Asp Ile Ser Arg Pro Ala Val Leu Leu Ala Arg Thr Arg Pro Arg
625                 630                 635                 640

Pro Val Glu Gly Phe Glu Val Thr Asn Val Thr Ala Ser Thr Ile Ser
                645                 650                 655

Val Gln Trp Ala Leu His Arg Ile Arg His Ala Thr Val Ser Gly Val
            660                 665                 670

Arg Val Ser Ile Arg His Pro Glu Ala Leu Arg Asp Gln Ala Thr Asp
        675                 680                 685

Val Asp Arg Ser Val Asp Arg Phe Thr Phe Arg Ala Leu Leu Pro Gly
    690                 695                 700

Lys Arg Tyr Thr Ile Gln Leu Thr Thr Leu Ser Gly Leu Arg Gly Glu
705                 710                 715                 720

Glu His Pro Thr Glu Ser Leu Ala Thr Ala Pro Thr His Val Trp Thr
                725                 730                 735

Arg Pro Leu Pro Pro Ala Asn Leu Thr Ala Ala Arg Val Thr Ala Thr
            740                 745                 750

Ser Ala His Val Val Trp Asp Ala Pro Thr Pro Gly Ser Leu Leu Glu
        755                 760                 765

Ala Tyr Val Ile Asn Val Thr Thr Ser Gln Ser Thr Lys Ser Arg Tyr
    770                 775                 780

Val Pro Asn Gly Lys Leu Ala Ser Tyr Thr Val Arg Asp Leu Leu Pro
785                 790                 795                 800

Gly Arg Arg Tyr Gln Leu Ser Val Ile Ala Val Gln Ser Thr Glu Leu
                805                 810                 815

Gly Pro Gln His Ser Glu Pro Ala His Leu Tyr Ile Ile Thr Ser Pro
            820                 825                 830

Arg Asp Gly Ala Asp Arg Arg Trp His Gln Gly Gly His His Pro Arg
        835                 840                 845

Val Leu Lys Asn Arg Pro Pro Pro Ala Arg Leu Pro Glu Leu Arg Leu
    850                 855                 860

Leu Asn Asp His Ser Ala Pro Glu Thr Pro Thr Gln Pro Pro Arg Phe
865                 870                 875                 880

Ser Glu Leu Val Asp Gly Arg Gly Arg Val Ser Ala Arg Phe Gly Gly
                885                 890                 895

Ser Pro Ser Lys Ala Ala Thr Val Arg Ser Gln Pro Thr Ala Ser Ala
            900                 905                 910

Gln Leu Glu Asn Met Glu Glu Ala Pro Lys Arg Val Ser Leu Ala Leu
        915                 920                 925

Gln Leu Pro Glu His Gly Ser Lys Asp Ile Gly Asn Val Pro Gly Asn
    930                 935                 940

Cys Ser Glu Asn Pro Cys Gln Asn Gly Gly Thr Cys Val Pro Gly Ala
945                 950                 955                 960

Asp Ala His Ser Cys Asp Cys Gly Pro Gly Phe Lys Gly Arg Arg Cys
                965                 970                 975

Glu Leu Ala Cys Ile Lys Val Ser Arg Pro Cys Thr Arg Leu Phe Ser
            980                 985                 990
```

-continued

```
Glu Thr Lys Ala Phe Pro Val Trp  Glu Gly Gly Val Cys  His His Val
        995                 1000                 1005

Tyr Lys  Arg Val Tyr Arg Val  His Gln Asp Ile Cys  Phe Lys Glu
    1010                 1015                 1020

Ser Cys  Glu Ser Thr Ser Leu  Lys Lys Thr Pro Asn  Arg Lys Gln
    1025                 1030                 1035

Ser Lys  Ser Gln Thr Leu Glu  Lys Ser
    1040                 1045


<210> SEQ ID NO 13
<211> LENGTH: 387
<212> TYPE: PRT
<213> ORGANISM: Homo sapiens

<400> SEQUENCE: 13

Leu Asp Gly Tyr Ala Val Thr Tyr Val Ser Ser Asp Gly Ser Tyr Arg
1               5                   10                  15

Arg Thr Asp Phe Val Asp Arg Thr Arg Ser Ser His Gln Leu Gln Ala
            20                  25                  30

Leu Ala Ala Gly Arg Ala Tyr Asn Ile Ser Val Phe Ser Val Lys Arg
        35                  40                  45

Asn Ser Asn Asn Lys Asn Asp Ile Ser Arg Pro Ala Val Leu Leu Ala
    50                  55                  60

Arg Thr Arg Pro Arg Pro Val Glu Gly Phe Glu Val Thr Asn Val Thr
65                  70                  75                  80

Ala Ser Thr Ile Ser Val Gln Trp Ala Leu His Arg Ile Arg His Ala
                85                  90                  95

Thr Val Ser Gly Val Arg Val Ser Ile Arg His Pro Glu Ala Leu Arg
            100                 105                 110

Asp Gln Ala Thr Asp Val Asp Arg Ser Val Asp Arg Phe Thr Phe Arg
        115                 120                 125

Ala Leu Leu Pro Gly Lys Arg Tyr Thr Ile Gln Leu Thr Thr Leu Ser
    130                 135                 140

Gly Leu Arg Gly Glu Glu His Pro Thr Glu Ser Leu Ala Thr Ala Pro
145                 150                 155                 160

Thr His Val Trp Thr Arg Pro Leu Pro Pro Ala Asn Leu Thr Ala Ala
                165                 170                 175

Arg Val Thr Ala Thr Ser Ala His Val Val Trp Asp Ala Pro Thr Pro
            180                 185                 190

Gly Ser Leu Leu Glu Ala Tyr Val Ile Asn Val Thr Thr Ser Gln Ser
        195                 200                 205

Thr Lys Ser Arg Tyr Val Pro Asn Gly Lys Leu Ala Ser Tyr Thr Val
    210                 215                 220

Arg Asp Leu Leu Pro Gly Arg Arg Tyr Gln Leu Ser Val Ile Ala Val
225                 230                 235                 240

Gln Ser Thr Glu Leu Gly Pro Gln His Ser Glu Pro Ala His Leu Tyr
                245                 250                 255

Ile Ile Thr Ser Pro Arg Asp Gly Ala Asp Arg Arg Trp His Gln Gly
            260                 265                 270

Gly His His Pro Arg Val Leu Lys Asn Arg Pro Pro Pro Ala Arg Leu
        275                 280                 285

Pro Glu Leu Arg Leu Leu Asn Asp His Ser Ala Pro Glu Thr Pro Thr
    290                 295                 300

Gln Pro Pro Arg Phe Ser Glu Leu Val Asp Gly Arg Gly Arg Val Ser
305                 310                 315                 320
```

-continued

```
Ala Arg Phe Gly Gly Ser Pro Ser Lys Ala Ala Thr Val Arg Ser Gln
            325                 330                 335

Pro Thr Ala Ser Ala Gln Leu Glu Asn Met Glu Glu Ala Pro Lys Arg
        340                 345                 350

Val Ser Leu Ala Leu Gln Leu Pro Glu His Gly Ser Lys Asp Ile Gly
        355                 360                 365

Ser Glu Ser Ala Ala Leu Val Gly Thr Leu Gly Leu Thr Asp Cys Ser
    370                 375                 380

Gln Gly Pro
385


<210> SEQ ID NO 14
<211> LENGTH: 3401
<212> TYPE: DNA
<213> ORGANISM: Rattus norvegicus
<220> FEATURE:
<221> NAME/KEY: exon
<222> LOCATION: (3)..(1499)
<220> FEATURE:
<221> NAME/KEY: 3'UTR
<222> LOCATION: (1500)..(3401)

<400> SEQUENCE: 14

aa gag ctc ctc cca cca aca gcc ctc agg gta gaa agg gtg gag gag        47
   Glu Leu Leu Pro Pro Thr Ala Leu Arg Val Glu Arg Val Glu Glu
   1               5                   10                  15

agt ggg gtc tcc atc tcc tgg agc cca ccc gag ggc acc acg gcc aga       95
Ser Gly Val Ser Ile Ser Trp Ser Pro Pro Glu Gly Thr Thr Ala Arg
                20                  25                  30

cag gtg ctg gac ggc tat gca gtc acc tat gcc tcc tcg gat gga tcg      143
Gln Val Leu Asp Gly Tyr Ala Val Thr Tyr Ala Ser Ser Asp Gly Ser
            35                  40                  45

tcc agg cgc acg gac ttt gtg gac cgg agc cgc tcc tct cac cag ctt      191
Ser Arg Arg Thr Asp Phe Val Asp Arg Ser Arg Ser Ser His Gln Leu
        50                  55                  60

cgg gcc ctg gca gcc ggc cgt gcc tac aac atc tct gtt ttc tca gtc      239
Arg Ala Leu Ala Ala Gly Arg Ala Tyr Asn Ile Ser Val Phe Ser Val
    65                  70                  75

aag aga aac act aac aac aaa aat gac atc agc agg cct gca gcc ctg      287
Lys Arg Asn Thr Asn Asn Lys Asn Asp Ile Ser Arg Pro Ala Ala Leu
80                  85                  90                  95

ctc acc cgc acc cga ccc cgc cct att gaa gac ttc gag gtc acc aac      335
Leu Thr Arg Thr Arg Pro Arg Pro Ile Glu Asp Phe Glu Val Thr Asn
                100                 105                 110

att tca gcc aat gcc atc tca gtg cag tgg gct ctt cat agg atc cag      383
Ile Ser Ala Asn Ala Ile Ser Val Gln Trp Ala Leu His Arg Ile Gln
            115                 120                 125

cat gcc act gtc agc agg gtt cga gtg tct gtc ctc tac cct gag gac      431
His Ala Thr Val Ser Arg Val Arg Val Ser Val Leu Tyr Pro Glu Asp
        130                 135                 140

act gtg gtc cag tcc acg gag gtg gac agg agt gtg gac cgc ctc aca      479
Thr Val Val Gln Ser Thr Glu Val Asp Arg Ser Val Asp Arg Leu Thr
    145                 150                 155

ttt ggg gac ctg ctg cca ggg aga aga tac agt gtg cgg cta acc acc      527
Phe Gly Asp Leu Leu Pro Gly Arg Arg Tyr Ser Val Arg Leu Thr Thr
160                 165                 170                 175

ctc agt ggg cct gga gga gct gaa tat cct aca gag agc ctg gcc tca      575
Leu Ser Gly Pro Gly Gly Ala Glu Tyr Pro Thr Glu Ser Leu Ala Ser
                180                 185                 190

gct ccg ctg aac gtg tgg acc cgg cct ttg cct cca gca aac ctg act      623
```

-continued

```
Ala Pro Leu Asn Val Trp Thr Arg Pro Leu Pro Pro Ala Asn Leu Thr
            195                 200                 205

gcc tct cga gtc aca gcg acc tct gcc cat atg gtc tgg gac ccg ccc      671
Ala Ser Arg Val Thr Ala Thr Ser Ala His Met Val Trp Asp Pro Pro
        210                 215                 220

act cca ggc atc tca ctg gag gct tac gtc atc aat gtg acc acc agt      719
Thr Pro Gly Ile Ser Leu Glu Ala Tyr Val Ile Asn Val Thr Thr Ser
    225                 230                 235

cag aat acc aag agc cgc tac atc ccc aat ggg aag ctg gtg tcc tat      767
Gln Asn Thr Lys Ser Arg Tyr Ile Pro Asn Gly Lys Leu Val Ser Tyr
240                 245                 250                 255

acg gtg cgt gat ctg atg cca ggt cgg cgg tac cag ctc tcg gtc aca      815
Thr Val Arg Asp Leu Met Pro Gly Arg Arg Tyr Gln Leu Ser Val Thr
                260                 265                 270

gcg gtg cag agc aca gag cag ggc cag ctg cac agt gag cct gcg cac      863
Ala Val Gln Ser Thr Glu Gln Gly Gln Leu His Ser Glu Pro Ala His
            275                 280                 285

ctc tac atc atc acc tcc ccc agg gat ggc acc gac agg cgc tgg cac      911
Leu Tyr Ile Ile Thr Ser Pro Arg Asp Gly Thr Asp Arg Arg Trp His
        290                 295                 300

cag gga gga cac cac tca cgg atg ctc aga aat agg ccg gcc cct ttg      959
Gln Gly Gly His His Ser Arg Met Leu Arg Asn Arg Pro Ala Pro Leu
    305                 310                 315

cgc ctg cca gaa ctg cgc ctc ctc aat gac cac ggt gcc cct gaa aca     1007
Arg Leu Pro Glu Leu Arg Leu Leu Asn Asp His Gly Ala Pro Glu Thr
320                 325                 330                 335

cca acc cag cca ccc agg ttc tca gag ctt gta gac gga aga gca aga     1055
Pro Thr Gln Pro Pro Arg Phe Ser Glu Leu Val Asp Gly Arg Ala Arg
                340                 345                 350

gtg agt gcc agg ttt ggt gga ttg ccc agc aga gca gta act gtg aga     1103
Val Ser Ala Arg Phe Gly Gly Leu Pro Ser Arg Ala Val Thr Val Arg
            355                 360                 365

tca caa ccc act act ccg gtg ccg ctc aag aac aca gag gcc cct gag     1151
Ser Gln Pro Thr Thr Pro Val Pro Leu Lys Asn Thr Glu Ala Pro Glu
        370                 375                 380

cag gcc cgt ctg gcc ctt cag cta ccc aag aac aac agc aag gac aca     1199
Gln Ala Arg Leu Ala Leu Gln Leu Pro Lys Asn Asn Ser Lys Asp Thr
    385                 390                 395

gaa agt acc cct ggc agc tgt tca gaa gac acc tgt cag aat gga ggc     1247
Glu Ser Thr Pro Gly Ser Cys Ser Glu Asp Thr Cys Gln Asn Gly Gly
400                 405                 410                 415

acc tgt gtc cca ggt gcc aat gcc cac agc tgt gac tgc agg cct ggg     1295
Thr Cys Val Pro Gly Ala Asn Ala His Ser Cys Asp Cys Arg Pro Gly
                420                 425                 430

ttc aaa ggc aga cac tgt gag ctt gcc tgt gaa aaa gtg ccc cgc ccc     1343
Phe Lys Gly Arg His Cys Glu Leu Ala Cys Glu Lys Val Pro Arg Pro
            435                 440                 445

tgc aca cgg ctg ttc tct gag acc aag tca ttt cct gtc tgg gaa gga     1391
Cys Thr Arg Leu Phe Ser Glu Thr Lys Ser Phe Pro Val Trp Glu Gly
        450                 455                 460

gat gtc tgc cac cat gtg tat aag aaa gtc tac aaa gtt cac cag gac     1439
Asp Val Cys His His Val Tyr Lys Lys Val Tyr Lys Val His Gln Asp
    465                 470                 475

gtg tgt ttt aag gag cgc tgc cag agc aca agc ctc aaa aag ctc aaa     1487
Val Cys Phe Lys Glu Arg Cys Gln Ser Thr Ser Leu Lys Lys Leu Lys
480                 485                 490                 495

cag gaa tca aat taacagtcaa acactgaaga aatcttaagg tacattctcc         1539
Gln Glu Ser Asn

ttcataccaa gatctgttga gaactggaga caccatcata cccagcacct tggacaactg   1599
```

-continued

```
atggtgcaaa cttagcactg tgctattaca gacccaacca ggaaggttcc agaattccct   1659

gtctatagcc tcccaataga cataacctgg tctggccttc catatgaatc cactttcagg   1719

tggaaatgac tctctggggg aggggcaaat gcagaccagt tacaatgagg cacaagaatc   1779

acctggcccc ttcaggacag tgggcctggg tgttagatgg atcaaggatg ccaaacaatc   1839

ctgggggtgc taggaaggac ctaaggacat accctcaagc cctatgaata gcattctact   1899

ggtggaaaag ggcgggagcc ttgtcatgta acctgcaggt gatcctaaat agagcctctc   1959

actgggagag atatcatgga tcctggaatt ctaagcacta ataaccctga agtgaaagaa   2019

actttgcctg cttgatccag catgtcccac cccaccctcc ccatacataa actgtgagat   2079

gtcaaagggc attggaaaat ttttttcaca agcctgggaa atactgggtt acactacaga   2139

gatccctgta tagcctgaac tcagccccaa cactgactta ctgatgggac atcaattgga   2199

aacgagagac tggctggcca gagacatttc actcctctcc cttggaggag ccagaacagt   2259

acatctgtgc agtggtggga gagaggcaga tctggaagcc tgccactcca ggagtgaatc   2319

acctttgttc tacagtgtag gacgtgaagg agaaatgtca cccaaaggcc taagaacaaa   2379

gaagagcaaa gcagttctgg gcgaaggtca tccgaagaga aaagtgtcta cagtaaaagg   2439

cagggcatca ggagagcggg ctctcagaca ggcctaagca gggcctgtgc atcttgacca   2499

tttcagatgt gaagactgca ggaagagcag ctgaccagac tcaaatcctg tctacttaac   2559

agcatcacct tttcacctca gcccccaaaa atgcacacaa caccctccaa cacatgtgag   2619

caacttcatt ctggcaaaga tcaaaaatcc acaaattatt tggttttaaa atatttacat   2679

ggcagtaagt cagatgaaat attaatgcaa aaaaagaaat attaatgcat cctttaagaa   2739

ctcacagaaa actcattttt agaaaaaaaa atgagaatcc ctaggtactt atcacataat   2799

ggcttataga aaacctattc tcaaagcaac acacacacac acacacaccc catacgtacg   2859

tacatacata catctaacac acacatgtgt gtgtatatat atatatatat atatatatat   2919

atatatatga cacacacaaa gcaaaaataa ttatatcttt ttaaagatat atattttctt   2979

ttaggaaaca gtaattactg acaacgctgc atttgaaata ctcaaaaaga tactaccgtt   3039

acaaaactcc agtttctcag ggacaggttt ggtattgcca gctaagaatc ccaaggagga   3099

gactgagctg cttaagtcgg agggagcaac agtaatggcc aagtcgcctg agcctccttc   3159

acagtcacag gattcagaaa atggatacat caatgtgact tctctaaagg agacatacca   3219

cacacaaggg gaccggaagc caaaactatg acctcacggg atctgaaaca atactaatca   3279

tgcctactaa gtcagagcct gggtacagag gtgcaaactg agctggagac gtctcacaga   3339

acaccctgga catcaacaag gagtcttcaa aatcgctttt taaacagtca ttaaaatttt   3399

tc                                                                  3401
```

<210> SEQ ID NO 15
<211> LENGTH: 16
<212> TYPE: PRT
<213> ORGANISM: Rattus norvegicus

<400> SEQUENCE: 15

```
Cys Thr Ser Gln Asn Thr Lys Ser Arg Tyr Ile Pro Asn Gly Lys Leu
1               5                   10                  15
```

<210> SEQ ID NO 16
<211> LENGTH: 114
<212> TYPE: DNA
<213> ORGANISM: Homo sapiens -continued

<400> SEQUENCE: 16
cccaatcccc ctgtgacacc aaagagtgtc aacatggtgg ccagtgccag gtggagaatg 60
gctctgcggt gtgtgtgtgc caggccggat acaccggagc agcctgcgag atgg 114

<210> SEQ ID NO 17
<211> LENGTH: 115
<212> TYPE: DNA
<213> ORGANISM: Homo sapiens

<400> SEQUENCE: 17
atgtggacga ctgcagccct gacccctgcc tgaatggagg ctcttgtgtt gacctagtgg 60
ggaattacac ctgcttgtgt gccgagccct tcaagggact tcgctgtgag acagg 115

<210> SEQ ID NO 18
<211> LENGTH: 125
<212> TYPE: DNA
<213> ORGANISM: Homo sapiens

<400> SEQUENCE: 18
agaccatcca gtgccagacg cctgcctctc ggccccttgc cacaatgggg gcacctgtgt 60
ggatgcggac cagggctacg tgtgcgagtg ccccgaaggc ttcatgggcc tggactgcag 120
ggaga 125

<210> SEQ ID NO 19
<211> LENGTH: 105
<212> TYPE: DNA
<213> ORGANISM: Homo sapiens

<400> SEQUENCE: 19
gagtccccga tgactgtgag tgccgcaacg gaggcagatg cctgggcgcc aacaccaccc 60
tctgccagtg ccccctggga ttctttgggc ttctctgtga atttg 105

<210> SEQ ID NO 20
<211> LENGTH: 114
<212> TYPE: DNA
<213> ORGANISM: Homo sapiens

<400> SEQUENCE: 20
aaatcacagc catgccctgc aacatgaaca cacagtgccc agatggggc tactgcatgg 60 agcacggcgg gagctacctc tgcgtctgcc acaccgacca caatgccagc cact 114

<210> SEQ ID NO 21
<211> LENGTH: 116
<212> TYPE: DNA
<213> ORGANISM: Homo sapiens

<400> SEQUENCE: 21
ccctgccatc accctgcgac tcggacccct gcttcaacgg aggctcctgc gatgcccatg 60
acgactccta cacctgcgag tgcccgcgcg ggttccacgg caagcactgc gagaaa 116

<210> SEQ ID NO 22
<211> LENGTH: 118
<212> TYPE: DNA
<213> ORGANISM: Homo sapiens

<400> SEQUENCE: 22
gcccggccac acctgtgcag ctcagggccc tgccggaacg gggcacgtg caaggaggcg 60

-continued ggcggcgagt accactgcag ctgcccctac cgcttcactg ggaggcactg tgagatcg 118

<210> SEQ ID NO 23
<211> LENGTH: 118
<212> TYPE: DNA
<213> ORGANISM: Homo sapiens

<400> SEQUENCE: 23
ggaagccaga ctcgtgtgcc tctggcccct gtcacaacgg cggcacctgc ttccactaca 60
ttggcaaata caagtgtgac tgtcccccag gcttctccgg gcggcactgc gagatagc 118

<210> SEQ ID NO 24
<211> LENGTH: 113
<212> TYPE: DNA
<213> ORGANISM: Homo sapiens

<400> SEQUENCE: 24
cccctccccc tgcttccgga gcccgtgtgt gaatgggggc acctgcgagg accgggacac 60
ggatttcttc tgccactgcc aagcagggta catgggacgc cggtgccagg cag 113

<210> SEQ ID NO 25
<211> LENGTH: 174
<212> TYPE: DNA
<213> ORGANISM: Homo sapiens

<400> SEQUENCE: 25
aggtggactg cggccccccg gaggaggtga agcacgccac actgcgcttc aacggcacgc 60
ggctgggcgc ggtggccctg tatgcatgtg accgtggcta cagcctgagc gcccccagcc 120
gcatccgggt ctgccagcca cacggtgtct ggagtgagcc tccccagtgc cttg 174

<210> SEQ ID NO 26
<211> LENGTH: 114
<212> TYPE: DNA
<213> ORGANISM: Homo sapiens

<400> SEQUENCE: 26
aaatcgatga gtgccggtct cagccgtgcc tgcatggggg ctcttgtcag gaccgcgttg 60
ctgggtacct gtgcctctgc agcacaggct atgagggcgc ccactgtgag ctgg 114

<210> SEQ ID NO 27
<211> LENGTH: 114
<212> TYPE: DNA
<213> ORGANISM: Homo sapiens

<400> SEQUENCE: 27
agagggatga gtgccgagct cacccgtgca gaaatggagg gtcctgcagg aacctcccag 60
gggcctatgt ctgccggtgc cctgcaggct tcgttggagt ccactgtgag acag 114

<210> SEQ ID NO 28
<211> LENGTH: 114
<212> TYPE: DNA
<213> ORGANISM: Homo sapiens

<400> SEQUENCE: 28
aggtggacgc ctgcgactcc agcccctgcc agcatggagg ccggtgtgag agcggcggcg 60
gggcctacct gtgcgtctgc ccagagagct tcttcggcta ccactgcgag acag 114

<210> SEQ ID NO 29
<211> LENGTH: 114

-continued

<212> TYPE: DNA
<213> ORGANISM: Homo sapiens

<400> SEQUENCE: 29
tgagtgaccc ctgcttctcc agcccctgtg ggggccgtgg ctattgcctg gccagcaacg 60
gctcccacag ctgcacctgc aaagtgggct acacgggcga ggactgcgcc aaag 114

<210> SEQ ID NO 30
<211> LENGTH: 297
<212> TYPE: DNA
<213> ORGANISM: Homo sapiens

<400> SEQUENCE: 30
agctcttccc accgacggcc ctcaagatgg agagagtgga ggagagtggg gtctctatct 60
cctggaaccc gcccaatggt ccagccgcca ggcagatgct tgatggctac gcggtcacct 120
acgtctcctc cgacggctcc taccgccgca cagactttgt ggacaggacc cgctcctcgc 180
accagctcca ggccctggcg gccggcaggg cctacaacat ctccgtcttc tcagtgaagc 240
gaaacagtaa caacaagaat gacatcagca ggcctgccgt gctgctggcc cgcacgc 297

<210> SEQ ID NO 31
<211> LENGTH: 185
<212> TYPE: DNA
<213> ORGANISM: Homo sapiens

<400> SEQUENCE: 31
gaccccgccc tgtggaaggc ttcgaggtca ccaatgtgac ggctagcacc atctcagtgc 60
agtgggccct gcacaggatc cgccatgcca ccgtcagtgg ggtccgtgtg tccatccgcc 120
accctgaggc cctcagggac caggccaccg atgtggacag gagtgtggac aggttcacct 180
ttagg 185

<210> SEQ ID NO 32
<211> LENGTH: 112
<212> TYPE: DNA
<213> ORGANISM: Homo sapiens

<400> SEQUENCE: 32
gccctgctgc ctgggaagag gtacaccatc cagctgacca ccctcagtgg gctcagggga 60
gaggagcacc ccacagagag cctggccacc gcgccgacgc acgtgtggac cc 112

<210> SEQ ID NO 33
<211> LENGTH: 282
<212> TYPE: DNA
<213> ORGANISM: Homo sapiens

<400> SEQUENCE: 33
ggcccctgcc tccagcaaac ctgaccgccg cccgagtcac tgccacctct gcccacgtgg 60
tctgggatgc cccgactcca ggcagcttgc tggaggctta tgtcatcaat gtgaccacca 120
gccagagcac caagagccgc tatgtcccca acgggaagct ggcgtcctac acggtgcgcg 180
acctgctgcc gggacggcgg taccagctct ctgtgatagc agtgcagagc acggagctcg 240
ggccgcagca cagcgagccc gcccacctct acatcatcac ct 282

<210> SEQ ID NO 34
<211> LENGTH: 145
<212> TYPE: DNA
<213> ORGANISM: Homo sapiens -continued

<400> SEQUENCE: 34
cccccaggga tggcgctgac agacgctggc accagggagg acaccaccct cgggtgctca 60
agaacagacc gcccccggcg cgcctgccgg agctgcgcct gctcaatgac cacagcgccc 120
ccgagacccc cacccagccc cccag 145

<210> SEQ ID NO 35
<211> LENGTH: 83
<212> TYPE: DNA
<213> ORGANISM: Homo sapiens

<400> SEQUENCE: 35
gttctcggag cttgtggacg gcagaggaag agtgagcgcc aggttcggtg gctcacccag 60
caaagcagcc accgtgagat cac 83

<210> SEQ ID NO 36
<211> LENGTH: 99
<212> TYPE: DNA
<213> ORGANISM: Homo sapiens

<400> SEQUENCE: 36
aacccacagc ctcggcgcag ctcgagaaca tggaggaagc ccccaagcgg gtcagcctgg 60
ccctccagct ccctgaacac ggcagcaagg acatcggaa 99

<210> SEQ ID NO 37
<211> LENGTH: 117
<212> TYPE: DNA
<213> ORGANISM: Homo sapiens

<400> SEQUENCE: 37
acgtccctgg caactgttca gaaaacccct gtcagaacgg aggcacttgt gtgccgggcg 60
cagacgccca cagctgtgac tgcgggccag ggttcaaagg cagacgctgc gagctcg 117

<210> SEQ ID NO 38
<211> LENGTH: 89
<212> TYPE: DNA
<213> ORGANISM: Homo sapiens

<400> SEQUENCE: 38
cctgtataaa ggtgtcccgc ccctgcacaa ggctgttctc cgagacaaag gcctttccag 60
tctgggaggg aggcgtctgt caccacgtg 89

<210> SEQ ID NO 39
<211> LENGTH: 83
<212> TYPE: DNA
<213> ORGANISM: Homo sapiens

<400> SEQUENCE: 39
tataaaagag tctaccgagt tcaccaagac atctgcttca aagagagctg tgaaagcaca 60
agcctcaaga agaccccaaa cag 83

<210> SEQ ID NO 40
<211> LENGTH: 38
<212> TYPE: DNA
<213> ORGANISM: Homo sapiens

<400> SEQUENCE: 40
gaaacaaagt aagagtcaga cactggagaa atcttaag 38

-continued

<210> SEQ ID NO 41
<211> LENGTH: 1438
<212> TYPE: DNA
<213> ORGANISM: Homo sapiens

<400> SEQUENCE: 41
gatttaagac gttcttgtta cactccacca acctcacgag tttctaacac ccaggaagat 60
gaggtctaaa aactggatga aaaaggacac cctgagaaaa ggtcctagct ggagtcagtc 120
ccctctgtga cctctctcct caggcctcta gaggacagat ggccaggcct gtgcacacac 180
cagcccaccc tgagagaccc ctctgggacc aaccacctgt gagtcctgcg atgcgtttaa 240
gcagcctgtg ccctcaccca agctgcagtt cctgaaggtg tagtctgtgt ctctgcggat 300
gagatgacag ctcgccattc cccggaatca gtgaggctgt cagtcagcca cgcttctgca 360
gtatgcagaa acctgttctt agactccaaa gccagagaaa gaattctccc ttcgaggccc 420
aacaaattga gaaggaactg tgatggacca cttccaaaac agagacgggg gcaggggctg 480
aagggcagag accaggtgat gtcagaagga aagccgggtt gcagacacag ccgcccctgc 540
tctggtcctc cagcgtgttt atgacgctcg tgcaggtcga cgagccatcc tatggactag 600
ttaacactaa ggtggagttc agactttttt agacaacggc gcgactggca gcctttctct 660
atcaagggtc agacggtaaa cgttttcagc tttgcagacc agaggtccct gtggctacag 720
tagcgcagac acagccacag gcatgtcatt gaatggctgc ggctatgttc caataaaaac 780
ttatttacaa taacaggtgg tggccaaatt ggcccatggg ccttatttgg tgaaccctgt 840
tctatgagat cacctaggct tcagccttaa acagtggaag ccatcccctg aatgacaagt 900
cacaagggta tcaaagaaag acccctgaat tttcatggaa aaagctattc agacccctgc 960
ttggaaagct aaggcacact gccacgaagc agcaaggacg ccttacaagt ctcagtgcaa 1020
cagagatgga cacctgggct gggctggaca atgtttaagg ttccttttag tccatgactc 1080
aagtgatact gttttaggct atcaggtagt aaacacgatc ttagacatcc ccatctttgt 1140
aagcagaaca gtacggcact tcaccacatc tgcttcccac catgcttcta agcagctgtc 1200
ttccccctgc taatgttaca accaaagcag ccaccccacc tcctctcgtg ttgagcctca 1260
cgaccgctga cccagctgga aagccagcgc cctgccgcgt caccctgact ctgctcagag 1320
ccagcattcc agccacaaag agggcctcct tcctttcctc tttcataaaa atgtttttg 1380 aagagttaga gtatatttta ggctttttat ctttattaaa atttcatgtg catgtgta 1438

<210> SEQ ID NO 42
<211> LENGTH: 25
<212> TYPE: DNA
<213> ORGANISM: Rattus norvegicus

<400> SEQUENCE: 42
ctaactcaca ggtgatgatg tagag 25

<210> SEQ ID NO 43
<211> LENGTH: 25
<212> TYPE: DNA
<213> ORGANISM: Rattus norvegicus

<400> SEQUENCE: 43
ctctacatca tcacctgtga gttag 25

<210> SEQ ID NO 44
<211> LENGTH: 5848
<212> TYPE: DNA

-continued

<213> ORGANISM: Rattus norgevicus

<400> SEQUENCE: 44
atcacctgcg ttgaaacctg cccggggctt tcatctgcca gtgccctgaa ggttttgttg 60
gaacccactg tgaaacaggt agggttcttt caggagggtc ccacagaacc agggctgctg 120
ggagatcaga ggggaagcca ggagccatgc tgaacagagc cacggaggac atcaggcggt 180
actttcctga gctcccggac ttctctgcta cctgggtttt tgttgccacc tggtaccgtg 240
tgaccttctt cggaggcagc agctcttccc ccgtcaacac attccaaacg gtgctcatca 300
ctgacggccg gttctccttc accatcttca actatgagtc catccagtgg actacgggca 360
cacacgccag cagtggtggt gatgctgatg gcttgggagg cattgcagcc caggcaggtt 420
tcaacgcagg tgatgggcac cgctacttca acatccctgg gtcgcgcaca gcagacatgg 480
ctgaggtgga gaccatcacc aacgtgggcg tgcccgggcg ctgggcgttt agaatcgatg 540
atgcccagcc tctgtgtgcc tagtcctgcg tccgtgcctc aatggtggca agtgcatcga 600
tgactgtgtc acgggcaatc cctcctacac ctgttcctgt ctcgctggct tcacggggcg 660
tggatgccac ctggatgtga acgagtgtgc ttcccaccca tgtcagaacg gtgggacctg 720
cacccacggt gtcaacaagc ttcagttgcc agccggcttc cagggaccca cttgtgaatc 780
agcccagtct ccgtgtgaca acaaagagtg tcaacatggt ggccagtgcc aggcagagag 840
cagctctgca gtatgtgtgt gtcaggctgg atacactggg gccacctgtg agaccgatgt 900
ggatgaatgc agctctgacc catgcctgaa tggaggctct tgtgttgacc tggttggaaa 960
ctacagctgt atttgtgtgg agccctttga aggacctcag tgcgagacag gaagctacgt 1020
ggtgccttcg ccctgcctct ccaacccctg cctgaacggg ggcacctgtg tggatgctga 1080
ccagggatac gtgtgcgaat gccctgaagg tttcatgggc ttggactgca gagagagaat 1140
tctcaatgac tgtgattgcc ggaatggagg cagatgcctg ggtgccaaca ccaccatctg 1200
ccagtgtcct ccaggctcct ttgggctcct ctgtgaattt gaagtcacag ccacgccctg 1260
caacatgaac acacagtgtc cagatggagg ctactgcatg gagtatggcg gaagctacct 1320
atgtgtctgc cacacggacc acaacatcag ccattctctg ccctcgccct gcgactcaga 1380
cccatgcttt aatggaggtt cctgtgacgc ccacgaggac tcctacacgt gcgagtgccc 1440
tcgtggattc catggcaggc actgcgagaa agcccggcca cacctgtgca gctcagggcc 1500
ctgccggaat gggggcacat acaaggagac tggtgacgag taccgctgca cctgccctta 1560
ccggttcact gggagacact gtgagattgg aaagccagac tcctgtgcct ctggcccctg 1620
tcacaacggt ggcacttgtt tccactacat tggcaaatac aagtgtgact gccctccagg 1680
cttctctggt cggcactgtg agatagcccc ctccccctgc ttccggagcc catgtatgaa 1740
tgggggtatc tgcgaggatc taggaacaga tttctcctgc cactgccaac caggatatac 1800
aggacaccgg tgtcaggcag aggtggactg cggtcagcct gaggaggtaa aacatgctac 1860
catgcgtctc aatggaactc gcatgggctc ggtggccctg tacacatgtg accccggctt 1920
cagcctgagc gtcctcagcc atatgcgtgt ctgtcagcca caaggtgtct ggagccagcc 1980
tccccagtgc attgaagtag atgagtgcca gtctcagcca tacctgcata aaggctcctg 2040
ccaggacctc attgctggtt accagtgcct ctgcagcccg ggtacgaag gagtccactg 2100
tgagctagag acagacgagt gccaagcaca gccctgcaga aatggaggct cctgcaggga 2160
cctccccggg gctttcatct gccagtgccc tgaaggtttt gttggaaccc actatgaaac 2220
agaggtggat gcctgtgcct ccagcccctg ccagcacgga ggccggtgtg aggacggtgg 2280

-continued

```
tggggcctac ctgtgcgttt gtccagaggg cttcttcggc tacaactgtg agacagtgag   2340
taacccctgc ttctctagcc cctgtggggg ccgcggctac tgcttggcca gcaacgggtc   2400
ccacagctgt acctgcaaag tgggctacac aggcaaggac tgcaccaaag agctcctccc   2460
accaacagcc ctcagggtag aaagggtgga ggagagtggg gtctccatct cctggagccc   2520
acccgagggc accacggcca gacaggtgct ggacggctat gcagtcacct atgcctcctc   2580
ggatggatcg tccaggcgca cggactttgt ggaccggagc cgctcctctc accagcttcg   2640
ggccctggca gccggccgtg cctacaacat ctctgttttc tcagtcaaga gaaacactaa   2700
caacaaaaat gacatcagca ggcctgcagc cctgctcacc cgcacccgac cccgccctat   2760
tgaagacttc gaggtcacca acatttcagc caatgccatc tcagtgcagt gggctcttca   2820
taggatccag catgccactg tcagcagggt tcgagtgtct gtcctctacc ctgaggacac   2880
tgtggtccag tccacggagg tggacaggag tgtggaccgc ctcacatttg gggacctgct   2940
gccagggaga agatacagtg tgcggctaac caccctcagt gggcctggag gagctgaata   3000
tcctacagag agcctggcct cagctccgct gaacgtgtgg acccggcctt tgcctccagc   3060
aaacctgact gcctctcgag tcacagcgac ctctgcccat atggtctggg acccgcccac   3120
tccaggcatc tcactggagg cttacgtcat caatgtgacc accagtcaga ataccaagag   3180
ccgctacatc cccaatggga agctggtgtc ctatacggtg cgtgatctga tgccaggtcg   3240
gcggtaccag ctctcggtca cagcggtgca gagcacagag cagggccagc tgcacagtga   3300
gcctgcgcac ctctacatca tcacctcccc cagggatggc accgacaggc gctggcacca   3360
gggaggacac cactcacgga tgctcagaaa taggccggcc cctttgcgcc tgccagaact   3420
gcgcctcctc aatgaccacg gtgcccctga aacaccaacc cagccaccca ggttctcaga   3480
gcttgtagac ggaagagcaa gagtgagtgc caggtttggt ggattgccca gcagagcagt   3540
aactgtgaga tcacaaccca ctactccggt gccgctcaag aacacagagg cccctgagca   3600
ggcccgtctg gcccttcagc tacccaagaa caacagcaag gacacagaaa gtacccctgg   3660
cagctgttca gaagacacct gtcagaatgg aggcacctgt gtcccaggtg ccaatgccca   3720
cagctgtgac tgcaggcctg ggttcaaagg cagacactgt gagcttgcct gtgaaaaagt   3780
gccccgcccc tgcacacggc tgttctctga gaccaagtca tttcctgtct gggaaggaga   3840
tgtctgccac catgtgtata agaaagtcta caaagttcac caggacgtgt gttttaagga   3900
gcgctgccag agcacaagcc tcaaaaagct caaacaggaa tcaaattaac agtcaaacac   3960
tgaagaaatc ttaaggtaca ttctccttca taccaagatc tgttgagaac tggagacacc   4020
atcataccca gcaccttgga caactgatgg tgcaaactta gcactgtgct attacagacc   4080
caaccaggaa ggttccagaa ttccctgtct atagcctccc aatagacata acctggtctg   4140
gccttccata tgaatccact ttcaggtgga aatgactctc tgggggaggg gcaaatgcag   4200
accagttaca atgaggcaca agaatcacct ggccccttca ggacagtggg cctgggtgtt   4260
agatggatca aggatgccaa acaatcctgg gggtgctagg aaggacctaa ggacataccc   4320
tcaagcccta tgaatagcat tctactggtg gaaaagggcg ggagccttgt catgtaacct   4380
gcaggtgatc ctaaatagag cctctcactg ggagagatat catggatcct ggaattctaa   4440
gcactaataa ccctgaagtg aaagaaactt tgcctgcttg atccagcatg tcccacccca   4500
ccctccccat acataaactg tgagatgtca aagggcattg gaaaattttt ttcacaagcc   4560
tgggaaatac tgggttacac tacagagatc cctgtatagc ctgaactcag ccccaacact   4620
```

-continued

```
gacttactga tgggacatca attggaaacg agagactggc tggccagaga catttcactc   4680
ctctcccttg gaggagccag aacagtacat ctgtgcagtg gtgggagaga ggcagatctg   4740
gaagcctgcc actccaggag tgaatcacct ttgttctaca gtgtaggacg tgaaggagaa   4800
atgtcaccca aaggcctaag aacaaagaag agcaaagcag ttctgggcga aggtcatccg   4860
aagagaaaag tgtctacagt aaaaggcagg gcatcaggag agcgggctct cagacaggcc   4920
taagcagggc ctgtgcatct tgaccatttc agatgtgaag actgcaggaa gagcagctga   4980
ccagactcaa atcctgtcta cttaacagca tcaccttttc acctcagccc ccaaaaatgc   5040
acacaacacc ctccaacaca tgtgagcaac ttcattctgg caaagatcaa aaatccacaa   5100
attatttggt tttaaaatat ttacatggca gtaagtcaga tgaaatatta atgcaaaaaa   5160
agaaatatta atgcatcctt taagaactca cagaaaactc atttttagaa aaaaaaatga   5220
gaatccctag gtacttatca cataatggct tatagaaaac ctattctcaa agcaacacac   5280
acacacacac acaccccata cgtacgtaca tacatacatc taacacacac atgtgtgtgt   5340
atatatatat atatatatat atatatatat atatgacaca cacaaagcaa aaataattat   5400
atctttttaa agatatatat tttcttttag gaaacagtaa ttactgacaa cgctgcattt   5460
gaaatactca aaaagatact accgttacaa aactccagtt tctcagggac aggtttggta   5520
ttgccagcta agaatcccaa ggaggagact gagctgctta agtcggaggg agcaacagta   5580
atggccaagt cgcctgagcc tccttcacag tcacaggatt cagaaaatgg atacatcaat   5640
gtgacttctc taaaggagac ataccacaca caaggggacc ggaagccaaa actatgacct   5700
cacgggatct gaaacaatac taatcatgcc tactaagtca gagcctgggt acagaggtgc   5760
aaactgagct ggagacgtct cacagaacac cctggacatc aacaaggagt cttcaaaatc   5820
gctttttaaa cagtcattaa aatttttc                                      5848
```

<210> SEQ ID NO 45
<211> LENGTH: 6331
<212> TYPE: DNA
<213> ORGANISM: Homo sapiens

<400> SEQUENCE: 45

```
gcctcgtcca taatgatggc tgcatggcca cttccggccc aagagggatc caagaggcag     60
cgcggtccga tcggagagca cccttaccgt gggcacctgc acgagcggcc caggctgtca    120
aatcagtgac caggatttgt ttgcaacacc agcgggcccc aaatatgagg gtgttagtgt    180
ctcaggctgt ggtcttccaa gtggcagacc agaccgcaga ctggggtagc aggctttttc    240
tgtagagggc caggtagtga ctattttcag cttttcaggc cacagggtct ctgctgttgt    300
cacaaaaaag cagccgtaga cagtaagtac gtgagtgtgc tcagccgtgc tcccacaaac    360
cctgtttctg aaaccaggct ggggtccaca gaggatggat ggccacatct gacccaaggc    420
ctgtttgtgt atgacctgtg aactaagaat gttcttaata cttttaaagg gctgcaaaaa    480
caaaaagaac aaaaaagaat atgcaacaga gaccacgtgt ggtccacagg gccagaaata    540
tttgcgatct ggcccttccc agaaagtctg ctggcccttg ggcagaccgc accatttgca    600
acaaccaaaa ttcagtaaaa cttcaatgtt tctggtcctt aagagtccta aggccagggt    660
ggcagcttcc agcccagccc caatactcac tggtcttctg ctgtctccca gagttggcgc    720
tggggctgga cagccactgc ccaggggacg ccattgggct ccagcttagc cggaccatcc    780
ttgaaccagg cccaggcatc gggggccccg tgactcgagc accccgcaga gccagtggct    840
cacgtcaggc actggaccgg aaggtgaaca acaacgggat catctccttc ctgaaggagg    900
```

-continued

```
tttctcagtt caccccagtg gccttcccca ttgccaagga ccgctgcgtg gtggcagcct    960
tctgggcaga tgtgaacaac cggcgtgcag gcgacgtgta ctaccgggag gccaccgacc   1020
cagccatgct gcgccgagcc acggaggacg tcaggcacta cttccccgag ctcctggact   1080
tcaatgccac ctgggttttt gttgccacct ggtaccgagt gaccttcttt ggaggcagtt   1140
cctcatcccc tgtcaacaca ttccagactg tgctcatcac agacggcaag ctctccttca   1200
ccatcttcaa ctatgagtcc atcgtgtgga ccacaggcac acacgccagc agcgggggca   1260
acgccactgg cctcgggggc atcgcagccc aggctggctt caacgcaggc gatgggcagc   1320
gttacttcag tatccccggc tcgcgcacag cagacatggc cgaggtggag accaccacca   1380
acgtgggtgt gcccgggcgc tggcgttca gaatcgatga tgcccaggtg cgcgtggggg   1440
gctgcggcca tacaacgtcc gtgtgcctgg ccctgcgccc ctgcctcaac ggcggcaagt   1500
gcatcgacga ctgcgtcacg ggcaacccct cctacacctg ctcctgcctc tcgggcttca   1560
cggggcggag gtgccacctg gacgtgaacg aatgtgcctc ccagccctgt cagaatggtg   1620
ggacctgtac tcacggcatc aacagtttcc gctgccagtg cccggctggc tttgggggac   1680
ccacctgtga gacagcccaa tcccccctgtg acaccaaaga gtgtcaacat ggtggccagt   1740
gccaggtgga gaatggctct gcggtgtgtg tgtgccaggc cggatacacc ggagcagcct   1800
gcgagatgga tgtggacgac tgcagccctg acccctgcct gaatggaggc tcttgtgttg   1860
acctagtggg gaattacacc tgcttgtgtg ccgagccctt caagggactt cgctgtgaga   1920
caggagacca tccagtgcca gacgcctgcc tctcggcccc ttgccacaat gggggcacct   1980
gtgtggatgc ggaccagggc tacgtgtgcg agtgccccga aggcttcatg ggcctggact   2040
gcagggagag agtccccgat gactgtgagt gccgcaacgg aggcagatgc ctgggcgcca   2100
acaccaccct ctgccagtgc cccctgggat tctttgggct tctctgtgaa tttgaaatca   2160
cagccatgcc ctgcaacatg aacacacagt gcccagatgg gggctactgc atggagcacg   2220
gcgggagcta cctctgcgtc tgccacaccg accacaatgc cagccactcc ctgccatcac   2280
cctgcgactc ggacccctgc ttcaacggag gctcctgcga tgcccatgac gactcctaca   2340
cctgcgagtg cccgcgcggg ttccacggca agcactgcga gaaagcccgg ccacacctgt   2400
gcagctcagg gccctgccgg aacgggggca cgtgcaagga ggcgggcggc gagtaccact   2460
gcagctgccc ctaccgcttc actgggaggc actgtgagat cgggaagcca gactcgtgtg   2520
cctctggccc ctgtcacaac ggcggcacct gcttccacta cattggcaaa tacaagtgtg   2580
actgtccccc aggcttctcc gggcggcact gcgagatagc cccctccccc tgcttccgga   2640
gcccgtgtgt gaatgggggc acctgcgagg accgggacac ggatttcttc tgccactgcc   2700
aagcagggta catgggacgc cggtgccagg cagaggtgga ctgcggcccc ccggaggagg   2760
tgaagcacgc cacactgcgc ttcaacggca cgcggctggg cgcggtggcc ctgtatgcat   2820
gtgaccgtgg ctacagcctg agcgccccca gccgcatccg ggtctgccag ccacacggtg   2880
tctggagtga gcctccccag tgccttgaaa tcgatgagtg ccggtctcag ccgtgcctgc   2940
atgggggctc ttgtcaggac cgcgttgctg ggtacctgtg cctctgcagc acaggctatg   3000
agggcgccca ctgtgagctg gagagggatg agtgccgagc tcacccgtgc agaaatggag   3060
ggtcctgcag gaacctccca ggggcctatg tctgccggtg ccctgcaggc ttcgttggag   3120
tccactgtga gacagaggtg gacgcctgcg actccagccc ctgccagcat ggaggccggt   3180
gtgagagcgg cggcggggcc tacctgtgcg tctgcccaga gagcttcttc ggctaccact   3240
```

-continued

```
gcgagacagt gagtgacccc tgcttctcca gcccctgtgg gggccgtggc tattgcctgg   3300
ccagcaacgg ctcccacagc tgcacctgca aagtgggcta cacgggcgag gactgcgcca   3360
aagagctctt cccaccgacg gccctcaaga tggagagagt ggaggagagt ggggtctcta   3420
tctcctggaa cccgcccaat ggtccagccg ccaggcagat gcttgatggc tacgcggtca   3480
cctacgtctc ctccgacggc tcctaccgcc gcacagactt tgtggacagg acccgctcct   3540
cgcaccagct ccaggccctg gcggccggca gggcctacaa catctccgtc ttctcagtga   3600
agcgaaacag taacaacaag aatgacatca gcaggcctgc cgtgctgctg gcccgcacgc   3660
gaccccgccc tgtggaaggc ttcgaggtca ccaatgtgac ggctagcacc atctcagtgc   3720
agtgggccct gcacaggatc cgccatgcca ccgtcagtgg ggtccgtgtg tccatccgcc   3780
accctgaggc cctcagggac caggccaccg atgtggacag gagtgtggac aggttcacct   3840
ttagggccct gctgcctggg aagaggtaca ccatccagct gaccaccctc agtgggctca   3900
ggggagagga gcaccccaca gagagcctgg ccaccgcgcc gacgcacgtg tggacccggc   3960
ccctgcctcc agcaaacctg accgccgccc gagtcactgc cacctctgcc cacgtggtct   4020
gggatgcccc gactccaggc agcttgctgg aggcttatgt catcaatgtg accaccagcc   4080
agagcaccaa gagccgctat gtccccaacg ggaagctggc gtcctacacg gtgcgcgacc   4140
tgctgccggg acggcggtac cagctctctg tgatagcagt gcagagcacg gagctcgggc   4200
cgcagcacag cgagcccgcc cacctctaca tcatcacctc ccccagggat ggcgctgaca   4260
gacgctggca ccagggagga caccaccctc gggtgctcaa gaacagaccg cccccggcgc   4320
gcctgccgga gctgcgcctg ctcaatgacc acagcgcccc cgagaccccc acccagcccc   4380
ccaggttctc ggagcttgtg gacggcagag gaagagtgag cgccaggttc ggtggctcac   4440
ccagcaaagc agccaccgtg agatcacaac ccacagcctc ggcgcagctc gagaacatgg   4500
aggaagcccc caagcgggtc agcctggccc tccagctccc tgaacacggc agcaaggaca   4560
tcggaaacgt ccctggcaac tgttcagaaa acccctgtca gaacggaggc acttgtgtgc   4620
cgggcgcaga cgcccacagc tgtgactgcg ggccagggtt caaaggcaga cgctgcgagc   4680
tcgcctgtat aaaggtgtcc cgcccctgca caaggctgtt ctccgagaca aaggcctttc   4740
cagtctggga gggaggcgtc tgtcaccacg tgtataaaag agtctaccga gttcaccaag   4800
acatctgctt caaagagagc tgtgaaagca caagcctcaa gaagacccca aacaggaaac   4860
aaagtaagag tcagacactg gagaaatctt aaggatttaa gacgttcttg ttacactcca   4920
ccaacctcac gagtttctaa cacccaggaa gatgaggtct aaaaactgga tgaaaaagga   4980
caccctgaga aaaggtccta gctggagtca gtcccctctg tgacctctct cctcaggcct   5040
ctagaggaca gatggccagg cctgtgcaca caccagccca ccctgagaga cccctctggg   5100
accaaccacc tgtgagtcct gcgatgcgtt taagcagcct gtgccctcac ccaagctgca   5160
gttcctgaag gtgtagtctg tgtctctgcg gatgagatga cagctcgcca ttccccggaa   5220
tcagtgaggc tgtcagtcag ccacgcttct gcagtatgca gaaacctgtt cttagactcc   5280
aaagccagag aaagaattct cccttcgagg cccaacaaat tgagaaggaa ctgtgatgga   5340
ccacttccaa aacagagacg gggcagggg ctgaagggca gagaccaggt gatgtcagaa   5400
ggaaagccgg gttgcagaca cagccgcccc tgctctggtc ctccagcgtg tttatgacgc   5460
tcgtgcaggt cgacgagcca tcctatggac tagttaacac taaggtggag ttcagacttt   5520
tttagacaac ggcgcgactg gcagcctttc tctatcaagg gtcagacggt aaacgttttc   5580
agctttgcag accagaggtc cctgtggcta cagtagcgca gacacagcca caggcatgtc   5640
```

```
attgaatggc tgcggctatg ttccaataaa aacttattta caataacagg tggtggccaa   5700

attggcccat gggccttatt tggtgaaccc tgttctatga gatcacctag gcttcagcct   5760

taaacagtgg aagccatccc ctgaatgaca agtcacaagg gtatcaaaga aagacccctg   5820

aattttcatg gaaaaagcta ttcagacccc tgcttggaaa gctaaggcac actgccacga   5880

agcagcaagg acgccttaca agtctcagtg caacagagat ggacacctgg gctgggctgg   5940

acaatgttta aggttccttt tagtccatga ctcaagtgat actgttttag gctatcaggt   6000

agtaaacacg atcttagaca tccccatctt tgtaagcaga acagtacggc acttcaccac   6060

atctgcttcc caccatgctt ctaagcagct gtcttccccc tgctaatgtt acaaccaaag   6120

cagccacccc acctcctctc gtgttgagcc tcacgaccgc tgacccagct ggaaagccag   6180

cgccctgccg cgtcaccctg actctgctca gagccagcat tccagccaca aagagggcct   6240

ccttcctttc ctctttcata aaaatgtttt ttgaagagtt agagtatatt ttaggctttt   6300

tatctttatt aaaatttcat gtgcatgtgt a                                   6331
```

<210> SEQ ID NO 46
<211> LENGTH: 15
<212> TYPE: PRT
<213> ORGANISM: Rattus norvegicus

<400> SEQUENCE: 46

```
Cys Arg Asn Gly Gly Thr Tyr Lys Glu Thr Gly Asp Glu Tyr Arg
1               5                   10                  15
```

<210> SEQ ID NO 47
<211> LENGTH: 1054
<212> TYPE: PRT
<213> ORGANISM: Rattus norvegicus

<400> SEQUENCE: 47

```
Glu Cys Gln His Gly Gly Gln Cys Gln Ala Glu Ser Ser Ser Ala Val
1               5                   10                  15

Cys Val Cys Gln Ala Gly Tyr Thr Gly Ala Thr Cys Glu Thr Asp Val
            20                  25                  30

Asp Glu Cys Ser Ser Asp Pro Cys Leu Asn Gly Gly Ser Cys Val Asp
        35                  40                  45

Leu Val Gly Asn Tyr Ser Cys Ile Cys Val Glu Pro Phe Glu Gly Pro
    50                  55                  60

Gln Cys Glu Thr Gly Ser Tyr Val Val Pro Ser Pro Cys Leu Ser Asn
65                  70                  75                  80

Pro Cys Leu Asn Gly Gly Thr Cys Val Asp Ala Asp Gln Gly Tyr Val
                85                  90                  95

Cys Glu Cys Pro Glu Gly Phe Met Gly Leu Asp Cys Arg Glu Arg Ile
            100                 105                 110

Leu Asn Asp Cys Asp Cys Arg Asn Gly Gly Arg Cys Leu Gly Ala Asn
        115                 120                 125

Thr Thr Ile Cys Gln Cys Pro Pro Gly Ser Phe Gly Leu Leu Cys Glu
    130                 135                 140

Phe Glu Val Thr Ala Thr Pro Cys Asn Met Asn Thr Gln Cys Pro Asp
145                 150                 155                 160

Gly Gly Tyr Cys Met Glu Tyr Gly Gly Ser Tyr Leu Cys Val Cys His
                165                 170                 175

Thr Asp His Asn Ile Ser His Ser Leu Pro Ser Pro Cys Asp Ser Asp
            180                 185                 190
```

-continued

```
Pro Cys Phe Asn Gly Gly Ser Cys Asp Ala His Glu Asp Ser Tyr Thr
        195                 200                 205

Cys Glu Cys Pro Arg Gly Phe His Gly Arg His Cys Glu Lys Ala Arg
    210                 215                 220

Pro His Leu Cys Ser Ser Gly Pro Cys Arg Asn Gly Gly Thr Tyr Lys
225                 230                 235                 240

Glu Thr Gly Asp Glu Tyr Arg Cys Thr Cys Pro Tyr Arg Phe Thr Gly
                245                 250                 255

Arg His Cys Glu Ile Gly Lys Pro Asp Ser Cys Ala Ser Gly Pro Cys
            260                 265                 270

His Asn Gly Gly Thr Cys Phe His Tyr Ile Gly Lys Tyr Lys Cys Asp
        275                 280                 285

Cys Pro Pro Gly Phe Ser Gly Arg His Cys Glu Ile Ala Pro Ser Pro
    290                 295                 300

Cys Phe Arg Ser Pro Cys Met Asn Gly Gly Ile Cys Glu Asp Leu Gly
305                 310                 315                 320

Thr Asp Phe Ser Cys His Cys Gln Pro Gly Tyr Thr Gly His Arg Cys
                325                 330                 335

Gln Ala Glu Val Asp Cys Gly Gln Pro Glu Glu Val Lys His Ala Thr
            340                 345                 350

Met Arg Leu Asn Gly Thr Arg Met Gly Ser Val Ala Leu Tyr Thr Cys
        355                 360                 365

Asp Pro Gly Phe Ser Leu Ser Val Leu Ser His Met Arg Val Cys Gln
    370                 375                 380

Pro Gln Gly Val Trp Ser Gln Pro Pro Gln Cys Ile Glu Val Asp Glu
385                 390                 395                 400

Cys Gln Ser Gln Pro Tyr Leu His Lys Gly Ser Cys Gln Asp Leu Ile
                405                 410                 415

Ala Gly Tyr Gln Cys Leu Cys Ser Pro Gly Tyr Glu Gly Val His Cys
            420                 425                 430

Glu Leu Glu Thr Asp Glu Cys Gln Ala Gln Pro Cys Arg Asn Gly Gly
        435                 440                 445

Ser Cys Arg Asp Leu Pro Gly Ala Phe Ile Cys Gln Cys Pro Glu Gly
    450                 455                 460

Phe Val Gly Thr His Tyr Glu Thr Glu Val Asp Ala Cys Ala Ser Ser
465                 470                 475                 480

Pro Cys Gln His Gly Gly Arg Cys Glu Asp Gly Gly Gly Ala Tyr Leu
                485                 490                 495

Cys Val Cys Pro Glu Gly Phe Phe Gly Tyr Asn Cys Glu Thr Val Ser
            500                 505                 510

Asn Pro Cys Phe Ser Ser Pro Cys Gly Gly Arg Gly Tyr Cys Leu Ala
        515                 520                 525

Ser Asn Gly Ser His Ser Cys Thr Cys Lys Val Gly Tyr Thr Gly Lys
    530                 535                 540

Asp Cys Thr Lys Glu Leu Leu Pro Pro Thr Ala Leu Arg Val Glu Arg
545                 550                 555                 560

Val Glu Glu Ser Gly Val Ser Ile Ser Trp Ser Pro Pro Glu Gly Thr
                565                 570                 575

Thr Ala Arg Gln Val Leu Asp Gly Tyr Ala Val Thr Tyr Ala Ser Ser
            580                 585                 590

Asp Gly Ser Ser Arg Arg Thr Asp Phe Val Asp Arg Ser Arg Ser Ser
        595                 600                 605
```

-continued

```
His Gln Leu Arg Ala Leu Ala Ala Gly Arg Ala Tyr Asn Ile Ser Val
    610                 615                 620

Phe Ser Val Lys Arg Asn Thr Asn Asn Lys Asn Asp Ile Ser Arg Pro
625                 630                 635                 640

Ala Ala Leu Leu Thr Arg Thr Arg Pro Arg Pro Ile Glu Asp Phe Glu
                645                 650                 655

Val Thr Asn Ile Ser Ala Asn Ala Ile Ser Val Gln Trp Ala Leu His
            660                 665                 670

Arg Ile Gln His Ala Thr Val Ser Arg Val Arg Val Ser Val Leu Tyr
        675                 680                 685

Pro Glu Asp Thr Val Val Gln Ser Thr Glu Val Asp Arg Ser Val Asp
    690                 695                 700

Arg Leu Thr Phe Gly Asp Leu Leu Pro Gly Arg Arg Tyr Ser Val Arg
705                 710                 715                 720

Leu Thr Thr Leu Ser Gly Pro Gly Gly Ala Glu Tyr Pro Thr Glu Ser
                725                 730                 735

Leu Ala Ser Ala Pro Leu Asn Val Trp Thr Arg Pro Leu Pro Pro Ala
            740                 745                 750

Asn Leu Thr Ala Ser Arg Val Thr Ala Thr Ser Ala His Met Val Trp
        755                 760                 765

Asp Pro Pro Thr Pro Gly Ile Ser Leu Glu Ala Tyr Val Ile Asn Val
    770                 775                 780

Thr Thr Ser Gln Asn Thr Lys Ser Arg Tyr Ile Pro Asn Gly Lys Leu
785                 790                 795                 800

Val Ser Tyr Thr Val Arg Asp Leu Met Pro Gly Arg Arg Tyr Gln Leu
                805                 810                 815

Ser Val Thr Ala Val Gln Ser Thr Glu Gln Gly Gln Leu His Ser Glu
            820                 825                 830

Pro Ala His Leu Tyr Ile Ile Thr Ser Pro Arg Asp Gly Thr Asp Arg
        835                 840                 845

Arg Trp His Gln Gly Gly His His Ser Arg Met Leu Arg Asn Arg Pro
    850                 855                 860

Ala Pro Leu Arg Leu Pro Glu Leu Arg Leu Leu Asn Asp His Gly Ala
865                 870                 875                 880

Pro Glu Thr Pro Thr Gln Pro Pro Arg Phe Ser Glu Leu Val Asp Gly
                885                 890                 895

Arg Ala Arg Val Ser Ala Arg Phe Gly Gly Leu Pro Ser Arg Ala Val
            900                 905                 910

Thr Val Arg Ser Gln Pro Thr Thr Pro Val Pro Leu Lys Asn Thr Glu
        915                 920                 925

Ala Pro Glu Gln Ala Arg Leu Ala Leu Gln Leu Pro Lys Asn Asn Ser
    930                 935                 940

Lys Asp Thr Glu Ser Thr Pro Gly Ser Cys Ser Glu Asp Thr Cys Gln
945                 950                 955                 960

Asn Gly Gly Thr Cys Val Pro Gly Ala Asn Ala His Ser Cys Asp Cys
                965                 970                 975

Arg Pro Gly Phe Lys Gly Arg His Cys Glu Leu Ala Cys Glu Lys Val
            980                 985                 990

Pro Arg Pro Cys Thr Arg Leu Phe  Ser Glu Thr Lys Ser  Phe Pro Val
        995                 1000                 1005

Trp Glu  Gly Asp Val Cys His  His Val Tyr Lys Lys  Val Tyr Lys
    1010                 1015                 1020

Val His  Gln Asp Val Cys Phe  Lys Glu Arg Cys Gln  Ser Thr Ser
```

-continued

```
    1025                1030                1035

Leu Lys  Lys Leu Lys Gln Glu  Ser Asn Gln Ser Asn  Thr Glu Glu
    1040                1045                1050

Ile


<210> SEQ ID NO 48
<211> LENGTH: 1463
<212> TYPE: PRT
<213> ORGANISM: Homo sapiens

<400> SEQUENCE: 48

Met Gln Gln Arg Pro Arg Val Val His Arg Ala Arg Asn Ile Cys Asp
1               5                   10                  15

Leu Ala Leu Pro Arg Lys Ser Ala Gly Pro Trp Ala Asp Arg Thr Ile
            20                  25                  30

Cys Asn Asn Gln Asn Ser Val Lys Leu Gln Cys Phe Trp Ser Leu Arg
        35                  40                  45

Val Leu Arg Pro Gly Trp Gln Leu Pro Ala Gln Pro Gln Tyr Ser Leu
    50                  55                  60

Val Phe Cys Cys Leu Pro Glu Leu Ala Leu Gly Leu Asp Ser His Cys
65                  70                  75                  80

Pro Gly Asp Ala Ile Gly Leu Gln Leu Ser Arg Thr Ile Leu Glu Pro
                85                  90                  95

Gly Pro Gly Ile Gly Gly Pro Val Thr Arg Ala Pro Arg Arg Ala Ser
            100                 105                 110

Gly Ser Arg Gln Ala Leu Asp Arg Lys Val Asn Asn Asn Gly Ile Ile
        115                 120                 125

Ser Phe Leu Lys Glu Val Ser Gln Phe Thr Pro Val Ala Phe Pro Ile
    130                 135                 140

Ala Lys Asp Arg Cys Val Val Ala Ala Phe Trp Ala Asp Val Asn Asn
145                 150                 155                 160

Arg Arg Ala Gly Asp Val Tyr Tyr Arg Glu Ala Thr Asp Pro Ala Met
                165                 170                 175

Leu Arg Arg Ala Thr Glu Asp Val Arg His Tyr Phe Pro Glu Leu Leu
            180                 185                 190

Asp Phe Asn Ala Thr Trp Val Phe Val Ala Thr Trp Tyr Arg Val Thr
        195                 200                 205

Phe Phe Gly Gly Ser Ser Ser Ser Pro Val Asn Thr Phe Gln Thr Val
    210                 215                 220

Leu Ile Thr Asp Gly Lys Leu Ser Phe Thr Ile Phe Asn Tyr Glu Ser
225                 230                 235                 240

Ile Val Trp Thr Thr Gly Thr His Ala Ser Ser Gly Gly Asn Ala Thr
                245                 250                 255

Gly Leu Gly Gly Ile Ala Ala Gln Ala Gly Phe Asn Ala Gly Asp Gly
            260                 265                 270

Gln Arg Tyr Phe Ser Ile Pro Gly Ser Arg Thr Ala Asp Met Ala Glu
        275                 280                 285

Val Glu Thr Thr Thr Asn Val Gly Val Pro Gly Arg Trp Ala Phe Arg
    290                 295                 300

Ile Asp Asp Ala Gln Val Arg Val Gly Gly Cys Gly His Thr Thr Ser
305                 310                 315                 320

Val Cys Leu Ala Leu Arg Pro Cys Leu Asn Gly Gly Lys Cys Ile Asp
                325                 330                 335

Asp Cys Val Thr Gly Asn Pro Ser Tyr Thr Cys Ser Cys Leu Ser Gly
```

-continued

```
            340                 345                 350

Phe Thr Gly Arg Arg Cys His Leu Asp Val Asn Glu Cys Ala Ser Gln
        355                 360                 365

Pro Cys Gln Asn Gly Gly Thr Cys Thr His Gly Ile Asn Ser Phe Arg
    370                 375                 380

Cys Gln Cys Pro Ala Gly Phe Gly Gly Pro Thr Cys Glu Thr Ala Gln
385                 390                 395                 400

Ser Pro Cys Asp Thr Lys Glu Cys Gln His Gly Gly Gln Cys Gln Val
                405                 410                 415

Glu Asn Gly Ser Ala Val Cys Val Cys Gln Ala Gly Tyr Thr Gly Ala
            420                 425                 430

Ala Cys Glu Met Asp Val Asp Asp Cys Ser Pro Asp Pro Cys Leu Asn
        435                 440                 445

Gly Gly Ser Cys Val Asp Leu Val Gly Asn Tyr Thr Cys Leu Cys Ala
    450                 455                 460

Glu Pro Phe Lys Gly Leu Arg Cys Glu Thr Gly Asp His Pro Val Pro
465                 470                 475                 480

Asp Ala Cys Leu Ser Ala Pro Cys His Asn Gly Gly Thr Cys Val Asp
                485                 490                 495

Ala Asp Gln Gly Tyr Val Cys Glu Cys Pro Glu Gly Phe Met Gly Leu
            500                 505                 510

Asp Cys Arg Glu Arg Val Pro Asp Asp Cys Glu Cys Arg Asn Gly Gly
        515                 520                 525

Arg Cys Leu Gly Ala Asn Thr Thr Leu Cys Gln Cys Pro Leu Gly Phe
    530                 535                 540

Phe Gly Leu Leu Cys Glu Phe Glu Ile Thr Ala Met Pro Cys Asn Met
545                 550                 555                 560

Asn Thr Gln Cys Pro Asp Gly Gly Tyr Cys Met Glu His Gly Gly Ser
                565                 570                 575

Tyr Leu Cys Val Cys His Thr Asp His Asn Ala Ser His Ser Leu Pro
            580                 585                 590

Ser Pro Cys Asp Ser Asp Pro Cys Phe Asn Gly Gly Ser Cys Asp Ala
        595                 600                 605

His Asp Asp Ser Tyr Thr Cys Glu Cys Pro Arg Gly Phe His Gly Lys
    610                 615                 620

His Cys Glu Lys Ala Arg Pro His Leu Cys Ser Ser Gly Pro Cys Arg
625                 630                 635                 640

Asn Gly Gly Thr Cys Lys Glu Ala Gly Gly Glu Tyr His Cys Ser Cys
                645                 650                 655

Pro Tyr Arg Phe Thr Gly Arg His Cys Glu Ile Gly Lys Pro Asp Ser
            660                 665                 670

Cys Ala Ser Gly Pro Cys His Asn Gly Gly Thr Cys Phe His Tyr Ile
        675                 680                 685

Gly Lys Tyr Lys Cys Asp Cys Pro Pro Gly Phe Ser Gly Arg His Cys
    690                 695                 700

Glu Ile Ala Pro Ser Pro Cys Phe Arg Ser Pro Cys Val Asn Gly Gly
705                 710                 715                 720

Thr Cys Glu Asp Arg Asp Thr Asp Phe Phe Cys His Cys Gln Ala Gly
                725                 730                 735

Tyr Met Gly Arg Arg Cys Gln Ala Glu Val Asp Cys Gly Pro Pro Glu
            740                 745                 750

Glu Val Lys His Ala Thr Leu Arg Phe Asn Gly Thr Arg Leu Gly Ala
        755                 760                 765
```

-continued

```
Val Ala Leu Tyr Ala Cys Asp Arg Gly Tyr Ser Leu Ser Ala Pro Ser
    770                 775                 780

Arg Ile Arg Val Cys Gln Pro His Gly Val Trp Ser Glu Pro Pro Gln
785                 790                 795                 800

Cys Leu Glu Ile Asp Glu Cys Arg Ser Gln Pro Cys Leu His Gly Gly
                805                 810                 815

Ser Cys Gln Asp Arg Val Ala Gly Tyr Leu Cys Leu Cys Ser Thr Gly
            820                 825                 830

Tyr Glu Gly Ala His Cys Glu Leu Glu Arg Asp Glu Cys Arg Ala His
        835                 840                 845

Pro Cys Arg Asn Gly Gly Ser Cys Arg Asn Leu Pro Gly Ala Tyr Val
    850                 855                 860

Cys Arg Cys Pro Ala Gly Phe Val Gly Val His Cys Glu Thr Glu Val
865                 870                 875                 880

Asp Ala Cys Asp Ser Ser Pro Cys Gln His Gly Gly Arg Cys Glu Ser
                885                 890                 895

Gly Gly Gly Ala Tyr Leu Cys Val Cys Pro Glu Ser Phe Phe Gly Tyr
            900                 905                 910

His Cys Glu Thr Val Ser Asp Pro Cys Phe Ser Ser Pro Cys Gly Gly
        915                 920                 925

Arg Gly Tyr Cys Leu Ala Ser Asn Gly Ser His Ser Cys Thr Cys Lys
    930                 935                 940

Val Gly Tyr Thr Gly Glu Asp Cys Ala Lys Glu Leu Phe Pro Pro Thr
945                 950                 955                 960

Ala Leu Lys Met Glu Arg Val Glu Glu Ser Gly Val Ser Ile Ser Trp
                965                 970                 975

Asn Pro Pro Asn Gly Pro Ala Ala Arg Gln Met Leu Asp Gly Tyr Ala
            980                 985                 990

Val Thr Tyr Val Ser Ser Asp Gly  Ser Tyr Arg Arg Thr  Asp Phe Val
        995                 1000                1005

Asp Arg  Thr Arg Ser Ser His  Gln Leu Gln Ala Leu  Ala Ala Gly
    1010                1015                1020

Arg Ala  Tyr Asn Ile Ser Val  Phe Ser Val Lys Arg  Asn Ser Asn
    1025                1030                1035

Asn Lys  Asn Asp Ile Ser Arg  Pro Ala Val Leu Leu  Ala Arg Thr
    1040                1045                1050

Arg Pro  Arg Pro Val Glu Gly  Phe Glu Val Thr Asn  Val Thr Ala
    1055                1060                1065

Ser Thr  Ile Ser Val Gln Trp  Ala Leu His Arg Ile  Arg His Ala
    1070                1075                1080

Thr Val  Ser Gly Val Arg Val  Ser Ile Arg His Pro  Glu Ala Leu
    1085                1090                1095

Arg Asp  Gln Ala Thr Asp Val  Asp Arg Ser Val Asp  Arg Phe Thr
    1100                1105                1110

Phe Arg  Ala Leu Leu Pro Gly  Lys Arg Tyr Thr Ile  Gln Leu Thr
    1115                1120                1125

Thr Leu  Ser Gly Leu Arg Gly  Glu Glu His Pro Thr  Glu Ser Leu
    1130                1135                1140

Ala Thr  Ala Pro Thr His Val  Trp Thr Arg Pro Leu  Pro Pro Ala
    1145                1150                1155

Asn Leu  Thr Ala Ala Arg Val  Thr Ala Thr Ser Ala  His Val Val
    1160                1165                1170
```

-continued

```
Trp Asp  Ala Pro Thr Pro Gly  Ser Leu Leu Glu Ala  Tyr Val Ile
    1175                 1180                 1185

Asn Val  Thr Thr Ser Gln Ser  Thr Lys Ser Arg Tyr  Val Pro Asn
    1190                 1195                 1200

Gly Lys  Leu Ala Ser Tyr Thr  Val Arg Asp Leu Leu  Pro Gly Arg
    1205                 1210                 1215

Arg Tyr  Gln Leu Ser Val Ile  Ala Val Gln Ser Thr  Glu Leu Gly
    1220                 1225                 1230

Pro Gln  His Ser Glu Pro Ala  His Leu Tyr Ile Ile  Thr Ser Pro
    1235                 1240                 1245

Arg Asp  Gly Ala Asp Arg Arg  Trp His Gln Gly Gly  His His Pro
    1250                 1255                 1260

Arg Val  Leu Lys Asn Arg Pro  Pro Pro Ala Arg Leu  Pro Glu Leu
    1265                 1270                 1275

Arg Leu  Leu Asn Asp His Ser  Ala Pro Glu Thr Pro  Thr Gln Pro
    1280                 1285                 1290

Pro Arg  Phe Ser Glu Leu Val  Asp Gly Arg Gly Arg  Val Ser Ala
    1295                 1300                 1305

Arg Phe  Gly Gly Ser Pro Ser  Lys Ala Ala Thr Val  Arg Ser Gln
    1310                 1315                 1320

Pro Thr  Ala Ser Ala Gln Leu  Glu Asn Met Glu Glu  Ala Pro Lys
    1325                 1330                 1335

Arg Val  Ser Leu Ala Leu Gln  Leu Pro Glu His Gly  Ser Lys Asp
    1340                 1345                 1350

Ile Gly  Asn Val Pro Gly Asn  Cys Ser Glu Asn Pro  Cys Gln Asn
    1355                 1360                 1365

Gly Gly  Thr Cys Val Pro Gly  Ala Asp Ala His Ser  Cys Asp Cys
    1370                 1375                 1380

Gly Pro  Gly Phe Lys Gly Arg  Arg Cys Glu Leu Ala  Cys Ile Lys
    1385                 1390                 1395

Val Ser  Arg Pro Cys Thr Arg  Leu Phe Ser Glu Thr  Lys Ala Phe
    1400                 1405                 1410

Pro Val  Trp Glu Gly Gly Val  Cys His His Val Tyr  Lys Arg Val
    1415                 1420                 1425

Tyr Arg  Val His Gln Asp Ile  Cys Phe Lys Glu Ser  Cys Glu Ser
    1430                 1435                 1440

Thr Ser  Leu Lys Lys Thr Pro  Asn Arg Lys Gln Ser  Lys Ser Gln
    1445                 1450                 1455

Thr Leu  Glu Lys Ser
    1460
```

<210> SEQ ID NO 49
<211> LENGTH: 37
<212> TYPE: DNA
<213> ORGANISM: Artificial
<220> FEATURE:
<223> OTHER INFORMATION: Glyceradehyde-6-phosphate dehydrogenase IRE

<400> SEQUENCE: 49
aagttcccca actttcccgc ctctcagcct ttgaaag 37

<210> SEQ ID NO 50
<211> LENGTH: 15
<212> TYPE: DNA
<213> ORGANISM: Artificial
<220> FEATURE:
<223> OTHER INFORMATION: IGFBP-1 IRE -continued

<400> SEQUENCE: 50
gtttgttttg ctagt 15

<210> SEQ ID NO 51
<211> LENGTH: 24
<212> TYPE: DNA
<213> ORGANISM: Artificial
<220> FEATURE:
<223> OTHER INFORMATION: IGF-1 IRE

<400> SEQUENCE: 51
gcctcattat tcctgcccac caat 24

<210> SEQ ID NO 52
<211> LENGTH: 30
<212> TYPE: DNA
<213> ORGANISM: Artificial
<220> FEATURE:
<223> OTHER INFORMATION: Amylase IRE

<400> SEQUENCE: 52
tattttgcgt gagagtttct aaaagtccat 30

<210> SEQ ID NO 53
<211> LENGTH: 15
<212> TYPE: DNA
<213> ORGANISM: Artificial
<220> FEATURE:
<223> OTHER INFORMATION: Phosphoenolpyruvate carboxykinase IRE

<400> SEQUENCE: 53
tggtgttttg acaac 15

<210> SEQ ID NO 54
<211> LENGTH: 25
<212> TYPE: DNA
<213> ORGANISM: Artificial
<220> FEATURE:
<223> OTHER INFORMATION: TAT IRE

<400> SEQUENCE: 54
gactagaaca aacaagtcct gcgta 25

<210> SEQ ID NO 55
<211> LENGTH: 22
<212> TYPE: DNA
<213> ORGANISM: Artificial
<220> FEATURE:
<223> OTHER INFORMATION: Prolactin IRE

<400> SEQUENCE: 55
atctatttcc gtcattaaga ta 22

<210> SEQ ID NO 56
<211> LENGTH: 20
<212> TYPE: DNA
<213> ORGANISM: Artificial
<220> FEATURE:
<223> OTHER INFORMATION: NFkappaB IRE

<400> SEQUENCE: 56
gggactttcc gggactttcc 20

<210> SEQ ID NO 57

-continued

<211> LENGTH: 863
<212> TYPE: DNA
<213> ORGANISM: Homo sapiens

<400> SEQUENCE: 57
gcctcgtcca taatgatggc tgcatggcca cttccggccc aagagggatc caagaggcag 60
cgcggtccga tcggagagca cccttaccgt gggcacctgc acgagcggcc caggctgtca 120
aatcagtgac caggatttgt ttgcaacacc agcgggcccc aaatatgagg gtgttagtgt 180
ctcaggctgt ggtcttccaa gtggcagacc agaccgcaga ctggggtagc aggctttttc 240
tgtagagggc caggtagtga ctattttcag cttttcaggc cacagggtct ctgctgttgt 300
cacaaaaaag cagccgtaga cagtaagtac gtgagtgtgc tcagccgtgc tcccacaaac 360
cctgtttctg aaaccaggct ggggtccaca gaggatggat ggccacatct gacccaaggc 420
ctgtttgtgt atgacctgtg aactaagaat gttcttaata cttttaaagg gctgcaaaaa 480
caaaaagaac aaaaaagaat atgcaacaga gaccacgtgt ggtccacagg gccagaaata 540
tttgcgatct ggcccttccc agaaagtctg ctggcccttg ggcagaccgc accatttgca 600
acaaccaaaa ttcagtaaaa cttcaatgtt tctggtcctt aagagtccta aggccagggt 660
ggcagcttcc agcccagccc caatactcac tggtcttctg ctgtctccca gagttggcgc 720
tggggctgga cagccactgc ccaggggacg ccattgggct ccagcttagc cggaccatcc 780
ttgaaccagg cccaggcatc gggggccccg tgactcgagc accccgcaga gccagtggct 840
cacgtcaggc actggaccgg aag 863

<210> SEQ ID NO 58
<211> LENGTH: 179
<212> TYPE: DNA
<213> ORGANISM: Homo sapiens

<400> SEQUENCE: 58
gtgaacaaca acgggatcat ctccttcctg aaggaggttt ctcagttcac cccagtggcc 60
ttccccattg ccaaggaccg ctgcgtggtg gcagccttct gggcagatgt gaacaaccgg 120
cgtgcaggcg acgtgtacta ccgggaggcc accgacccag ccatgctgcg ccgagccac 179

<210> SEQ ID NO 59
<211> LENGTH: 109
<212> TYPE: DNA
<213> ORGANISM: Homo sapiens

<400> SEQUENCE: 59
ggaggacgtc aggcactact tccccgagct cctggacttc aatgccacct gggtttttgt 60
tgccacctgg taccgagtga ccttctttgg aggcagttcc tcatcccct 109

<210> SEQ ID NO 60
<211> LENGTH: 141
<212> TYPE: DNA
<213> ORGANISM: Homo sapiens

<400> SEQUENCE: 60
gtcaacacat tccagactgt gctcatcaca gacggcaagc tctccttcac catcttcaac 60
tatgagtcca tcgtgtggac cacaggcaca cacgccagca gcgggggcaa cgccactggc 120
ctcgggggca tcgcagccca g 141

<210> SEQ ID NO 61
<211> LENGTH: 163

-continued

```
<212> TYPE: DNA
<213> ORGANISM: Homo sapiens

<400> SEQUENCE: 61

gctggcttca acgcaggcga tgggcagcgt tacttcagta tccccggctc gcgcacagca     60

gacatggccg aggtggagac caccaccaac gtgggtgtgc ccgggcgctg ggcgttcaga    120

atcgatgatg cccaggtgcg cgtggggggc tgcggccata caa                      163


<210> SEQ ID NO 62
<211> LENGTH: 126
<212> TYPE: DNA
<213> ORGANISM: Homo sapiens

<400> SEQUENCE: 62

cgtccgtgtg cctggccctg cgcccctgcc tcaacggcgg caagtgcatc gacgactgcg     60

tcacgggcaa cccctcctac acctgctcct gcctctcggg cttcacgggg cggaggtgcc    120

acctgg                                                               126


<210> SEQ ID NO 63
<211> LENGTH: 30
<212> TYPE: DNA
<213> ORGANISM: Rattus norvegicus

<400> SEQUENCE: 63

aattcaaggg tatccaggaa agtctccttc                                      30
```

INSULIN-RESPONSIVE DNA BINDING PROTEIN-1 AND METHODS TO REGULATE INSULIN-RESPONSIVE GENES

REFERENCE TO RELATED APPLICATION

This application is a Continuation-in-Part of, and claims priority from, U.S. patent application Ser. No.: 09/703,559 filed Nov. 1, 2000, now abandoned and also claims priority from U.S. Provisional Applications Ser. Nos.: 60/336,585 filed Dec. 4, 2001 and 60/390,000 filed Jun. 18, 2002.

ACKNOWLEDGMENT OF FEDERAL RESEARCH SUPPORT

This invention was made, at least in part, with funding from the National Institutes of Health (Grants NO. K08 DK02215 and RO1 DK52965). Accordingly, the United States Government has certain rights in this invention.

FIELD OF THE INVENTION

The present invention relates generally to an Insulin-Responsive Sequence DNA Binding Protein (IRSBP) gene, specifically IRDBP-1, of mammals, and to corresponding IRDBP-1 proteins and coding sequences thereof. More specifically, the invention relates to a nucleotide sequence encoding an IRDBP-1 protein, to methods and compositions that employ this coding sequence and protein, to the use of therapeutic agents that mimic or facilitate the action of IRDBP-1, and to nucleotide sequences useful in diagnostic methods and treatment of diabetes, obesity, insulin resistance syndrome and other pathological ailments.

BACKGROUND

It is estimated that there are more than 6.5 million people in the U.S. diagnosed as having diabetes mellitus. Of those diagnosed, more than 90% have Type II diabetes mellitus. Although β-cell dysfunction is detectable in all diabetic patients whose pancreas exhibits an inability to produce sufficient insulin to maintain glucose levels in the normal range, the rapid increase in the prevalence of diabetes over the past several decades is apparently more likely to be due to insulin resistance (diminished insulin action on target tissues). The current epidemic of Type II diabetes in the United States is usually attributed to the aging of the population, the increased prevalence of obesity and sedentary activity, and the enrichment of the population with ethnic groups that may have a genetically predisposed inability of the pancreas to meet the challenge of increased insulin resistance or pancreatic dysfunction. The high incidence of diabetes represents a significant economic burden, such that approximately $92 billion in health care expenditures in 1992 were diverted to the treatment of diabetes.

Insulin resistance is a key factor in the pathogenesis of Type II diabetes, and can precede by decades abnormal insulin secretion and the onset of clinical diabetes. Resistance to insulin action involves all major target tissues, i.e., skeletal muscle, liver and fat. Although insulin resistance appears to involve defects in insulin signaling at the post-receptor level, the mechanism of insulin resistance remains poorly understood.

The action of insulin is initiated by binding to cell surface receptors. Autophosphorylation and activation of the intrinsic tyrosine kinase of the insulin receptor β-subunit leads to phosphorylation of several proximal interacting proteins, including insulin receptor substrate-1 (IRS-1), IRS-2, and Shc. IRS-1 interacts with several proteins that contain Src homology 2 (SH2) domains, including the p85 subunits of PI3'-kinase, GRB-2, Syp and Nck. Activation of these proteins and the subsequent cascade activation of other intracellular signaling molecules, such as $p21^{ras}$, raf-1, MAP kinases, and S6 kinase, account for many of insulin's pleiotropic effects. Each of these cytoplasmic substrates and the activating regulatory loop involved represents a potential linkage to the development of insulin resistance.

The substantial number of signaling circuits involved, including interacting, bypassing and overlapping pathways, the involvement of numerous serine/threonine kinases and phosphatases, and still uncharacterized links, characterize the complexity of the signaling from the insulin signal at the cell surface receptor to targets within the cell. One approach to the study of insulin interactions with cells is to select a physiological action of insulin and then trace back toward the receptor, an approach known as the target backward approach. This target backward approach has yielded information concerning the mechanism of insulin regulation by focusing on the genetic regulation of the insulin-regulated gene insulin-like growth factor binding protein-3 (IGFBP-3).

Genetic factors also contribute to the development of non-insulin dependent Type II diabetes mellitus (NIDDM). The concordance rate for NIDDM in identical twins approaches 100%, while the risk to other siblings of a diabetic proband is between 30 and 40%. Despite considerable investigative efforts, the genetic heterogeneity of diabetes and the contribution of environmental factors in the development of the phenotype make the identification of specific diabetes-related genes difficult. Methods used in the study of the genetics of NIDDM include association of case control studies, positional searches, parametric linkage, and molecular screening using single-strand conformation polymorphism analysis. In addition, cloned genes, including genes important for both insulin secretion and insulin action, have been examined for sequence abnormalities. Specific mutations associated with insulin resistance and the development of diabetes have been identified for the α- and β-subunits of the insulin receptor. Rad (Ras-associated with diabetes), and the glucokinase gene implicated in MODY (maturity onset diabetes of the young), as well as HNF-1 and HNF-4. Such mutations, however, appear to account for less than 5% of patients with Type II diabetes.

A series of adapter proteins or substrates link the receptor tyrosine kinases to gene transcription, and determine the response to insulin in a given cell or tissue. Each of the proteins in the signaling cascade is a potential candidate for an acquired or genetic defect contributing to insulin resistance. Thus, characterization of the insulin-responsive binding proteins (IRBPs) that may bind to gene transcriptional regulatory sequences essential for insulin-regulated expression of target genes, and delineation of the pattern of signal transduction to the IRBPs constitutes an important strategy to identify genes important in mediating insulin resistance.

Insulin-like growth factors I and II (IGF-I and -II) are proteins that have insulin-like metabolic and trophic effects and mediate some of the peripheral actions of growth hormone. IGFs also have a role in wound healing by stimulating fibroblasts to produce collagen and induce hematopoiesis through an erythropoietin-like activity. Studies have also shown that certain cancer cells, such as from breast and kidney, produce IGFs. IGF production in cancer cells auto-regulates cell proliferation and the production of a vascular system required for growth of the tumor mass. IGFs have also been implicated in diabetic retinopathy by stimulating endothelial and fibroblast proliferation.

The actions of IGFs are modulated by a family of six IGF-binding proteins (IGFBPs) that have different tissue distribution and production sites. One binding protein, IGFBP-1, has a molecular weight of approximately 30-40 kd in the human and the rat. Most of the circulating plasma IGF-I and IGF-II, however, are associated with IGFBP-3 and an acid-labile subunit thereof that serve as reservoirs for IGFs. Diabetes mellitus in humans and animal models is associated with decreased levels of serum IGFBP-3. Hepatic expression of IGFBP-3 is correlated with circulating IGFBP-3 levels in streptozotocin-diabetic and BB/W rats. Thus, hepatic expression of IGFBP-3 appears to determine systemic IGFBP-3 levels; and the study of the mechanisms by which insulin stimulates hepatic synthesis of IGFBP-3 is critical for understanding the regulation of systemic IGFBP-3.

Most evidence indicates that IGFBP-3 is inhibitory to IGF action. Furthermore, IGFBP-3 can: (a) mediate the growth inhibitory actions of transforming growth factor-β (TGF-β), retinoic acid, anti-estrogens and fibroblast growth factor, (b) mediate the induction of apoptosis by the tumor suppressor gene p53, and (c) travel to the cell nucleus, potentially directly regulating the transcription of critical growth inhibitory genes independent of IGF-I.

The levels of IGFBP-3 in serum and liver mRNA are highest during puberty and adult life. Unlike other IGFBPs, IGFBP-3 levels increase in the presence of anabolic hormones such as insulin and growth hormone. Dependence on growth hormone (GH) has been inferred from the deceased levels of IGFBP-3 in hypopituitary subjects and GH-deficient children and increased levels in acromegalic patients. Additionally, IGFBP-3 production is inhibited at the level of gene expression by glucocorticoids.

The mechanisms by which IGFBP-3 is regulated are complex. IGFBP-3 may undergo post-translational processing to yield various proteolytically cleaved, phosphorylated, and glycosylated products. These processes have been shown to alter the binding of IGFBP-3 to the acid-labile subunit, cell surfaces and to affect the affinity of IGFBP-3 for IGFs. IGFBP-3 can also associate with the cell surface and extracellular matrix; dissociation of cell-associated IGFBP-3 is one mechanism by which IGF-1 promotes release of IGFBP-3 into conditioned medium by fibroblasts and breast cancer cells.

Insulin increases IGFBP-3 expression by stimulating the rate of gene transcription rather than by stabilization of mRNA transcripts. This enhancement is mediated through a cis-regulatory insulin-responsive element (IRE) localized to the −1150 to −1124 bp region of the gene encoding IGFBP-3. The IGFBP-3 IRE comprises the nucleotide dyad ACC(A/G)A which has a strong resemblance to the recognition sequence of ETS-related transcription factors, namely AGGAA, which is within the IRE of both the prolactin and somatostatin genes. The 10-bp core sequence of the IGFBP-3 IRE that is most critical for insulin responses (base positions −1148 to −1139) had no significant consensus sequence similarity to previously identified transcription factor binding sites. What was not known, however, was any protein or other factor that would mediate a cellular response to insulin and which directly binds to such insulin-response elements like the IRE of IGFBP-3.

SUMMARY OF THE INVENTION

Briefly described, the present invention relates to a novel protein called Insulin-Responsive DNA Binding Protein-1 (IRDBP-1) and nucleotide sequences that encode it. IRDBP-1 is capable of binding to nucleic acid regions associated with genes that respond when cells are exposed to insulin or insulin-like factors. IRDBP-1 regulates genes important in mediating the insulin response in humans and animals and in regulating pathological conditions such as diabetes, obesity, insulin-resistant syndrome and cell proliferative disorders.

One aspect of the present invention relates to isolated or non-naturally occurring nucleic acid molecules that encode at least a portion of a human or animal IRDBP-1 protein or a variant thereof. The present invention provides isolated molecules that can hybridize to nucleic acid sequences of the genome of a human or animal and which encode an IRDBP-1 protein or variants thereof.

The present invention further provides nucleic acids that are fragments or derivatives of cDNA molecules comprising at least in part a region of the IRDBP-1 coding region and/or an untranslated region of the cDNA, wherein the fragments may be used as probes specific for hybridizing to, and detecting, nucleic acid molecules that encode at least in part a region of the IRDBP-1 protein.

Also within the scope of the present invention are recombinant cells, tissues and animals containing non-naturally occurring recombinant nucleic acid molecules encoding IRDBP-1, including expression vectors for the expression of IRDBP-1, antibodies to the IRDBP-1 proteins, assays utilizing the IRDBP-1 polypeptide, and methods relating to all of the foregoing. Also within the scope of the present invention is the development of therapeutic and diagnostic agents that mimic, facilitate or inhibit the action of IRDBP-1, and/or are based on relationships to the structure and action of IRDBP-1.

The invention further provides non-naturally occurring recombinant nucleic acid molecules encoding IRDBP-1 that can be delivered to a cell or an organism. The recombinant nucleic acid may comprise IRDBP-1-related sequences, functional derivatives thereof, and a vector or a promoter effective to initiate transcription in a host cell. The recombinant nucleic acid molecule can alternatively contain transcription regulatory sequences functional in a particular cell, a sequence complementary to a mRNA sequence encoding an IRDBP-1 polypeptide and transcriptional control sequences functional in that cell.

The present invention still further provides oligopeptides having amino acid sequences derived from the amino acid sequence of a human or animal IRDBP-1 protein that may be used to induce the formation of polyclonal or monoclonal antibodies that specifically bind to at least one region of the IRDBP-1 protein from human or animal. The antibodies may be used for, but are not limited to, the detection and assay of IRDBP-1 in biological samples, or the purification of the IRDBP-1 protein. Diagnostic kits for the detection of IRDBP-1 in biological samples are also within the scope of the present invention.

The invention also provides a recombinant cell or tissue containing non-naturally occurring recombinant nucleic acid molecules coding for an IRDBP-1 polypeptide or a portion thereof. In such cells, the IRDBP-1 coding sequence may be expressed under the control of its genomic regulatory elements, or may be under the control of exogenous regulatory elements including an exogenous promoter. The present invention further provides for the production of animals that have modified nucleic acids encoding at least a portion of the IRDBP-1 protein, or have the IRDBP-1 gene inactivated. The present invention further provides for methods of gene therapy and pharmaceutical compositions including anti-sense and sense nucleic acids that will modulate, in the human or animal, the activity of the IRDBP-1 gene or the IRDBP-1 protein encoded therein.

The invention features methods for identifying mammalian cells containing an IRDBP-1 polypeptide, or a related sequence. Such methods comprise identifying the IRDBP-1 polypeptide in mammalian cells using techniques that are routine and standard in the art, for example, PCR amplification, and Northern, Western, Southern and Southwestern blotting using oligonucleotides and derivatives thereof, or antibodies specific to the IRDBP-1 protein.

The present invention also relates to methods of detecting and treating proliferating cells, and the cells of humans or animals having diabetic disorders. The present invention further relates to methods of activating or inhibiting the expression of the gene in humans or animals that encode an IRDBP-1 protein, wherein the proliferation of cells may be modified. The present invention further contemplates that modulation of the activity of the IRDBP-1 protein or the expression thereof may be used to relieve the symptomatic effects of diabetes, particularly type II diabetes.

Additional objects and aspects of the present invention will become more apparent upon review of the detailed description set forth below when taken in conjunction with the accompanying figures, which are briefly described as follows.

BRIEF DESCRIPTION OF THE FIGURES

FIG. 1 shows the nucleotide sequence of the rat clone 52 cDNA SEQ ID NO: 2 with the translated protein sequence SEQ ID NO: 3 therefrom depicted in FIG. 2.

FIG. 2 shows the protein sequence of the rat clone 52 SEQ ID NO: 3 translated from the cDNA nucleic acid sequence SEQ ID NO: 2 depicted in FIG. 1.

FIG. 3 shows the nucleotide sequence of a nucleic acid probe SEQ ID NO: 4 derived from the rat clone 52 cDNA SEQ ID NO: 2 depicted in FIG. 1 that was subcloned into a transcription plasmid vector, transcribed and used as a riboprobe.

FIGS. 4A-4B show the nucleotide sequence of the rat cDNA SEQ ID NO: 5 encoding a rat IRDBP-1 protein having the translated protein sequence SEQ ID NO: 11 as depicted in FIG. 9, wherein FIG. 4A shows the rat IRDBP-1 coding region (SEQ ID NO: 8) with the corresponding 3-letter amino acid designation listed below its respective nucleotide triplet, and FIG. 4B shows the untranslated region that is 3' of the coding region in FIG. 4A.

FIGS. 5A-5B show the nucleotide sequence of a truncated rat cDNA SEQ ID NO: 6 wherein FIG. 5A is a partial region of a rat IRDBP-1 coding region with the corresponding 3-letter amino acid designation listed below its respective nucleotide triplet, and FIG. 5B is the untranslated region that is 3' of the coding region in FIG. 5A.

FIGS. 6A-6C show the nucleotide sequence of the human cDNA SEQ ID NO: 7 encoding a human IRDBP-1 protein having the translated protein sequence SEQ ID NO: 12 as shown in FIG. 10, wherein FIG. 6A shows a region 5' to the coding region, FIG. 6B is the coding region SEQ ID NO: 9, with the corresponding 3-letter amino acid designation listed below each respective nucleotide triplet, and FIG. 6C is the untranslated region that is 3' of the coding region shown in FIG. 6B.

FIG. 7 shows the exons SEQ ID NOS: 57-62 and 16-41 that comprise SEQ ID NO: 7.

FIGS. 8A-8B show the nucleotide sequence SEQ ID NO: 10 of a truncated variant human cDNA, wherein FIG. 8A is a partial region of a human variant IRDBP-1 coding region with the corresponding 3-letter amino acid designation listed below its respective nucleotide triplet, and FIG. 8B is the untranslated region that is 3' of the coding region in FIG. 8A.

FIG. 9 shows the amino acid sequence SEQ ID NO: 11 of the rat IRDBP-1 protein translated from the coding region of the rat IRDBP-1 cDNA, the sequence (SEQ ID NO: 8) of which is depicted in FIG. 4A.

FIG. 10 shows the amino acid sequence SEQ ID NO: 12 of the human IRDBP-1 protein translated from the coding region (SEQ ID NO: 9) of the human IRDBP-1 cDNA SEQ ID NO: 7 depicted in FIG. 6B.

FIG. 11 shows the amino acid sequence SEQ ID NO: 13 of the variant human IRDBP-1 protein translated from the coding region of the human IRDBP-1 cDNA, the sequence SEQ ID NO: 10 of which is depicted in FIG. 8A.

FIGS. 12A-12B show the nucleotide sequence of the truncated rat cDNA SEQ ID NO: 14, wherein FIG. 12A is a partial region of the rat IRDBP-1 coding region with the corresponding 3-letter amino acid designation listed below its respective nucleotide triplet, and FIG. 12B is the untranslated region that is 3' of the coding region in FIG. 12A.

FIG. 13 shows the nucleotide sequence of the rat IRDBP-1-encoding DNA SEQ ID NO: 44.

FIG. 14 shows the nucleotide sequence of the human IRDBP-1-encoding DNA SEQ ID NO: 45.

FIG. 15 shows the amino acid sequence of the rat IRDBP-1 SEQ ID NO: 47.

FIG. 16 shows the amino acid sequence of the human IRDBP-1 SEQ ID NO: 48.

FIG. 37 illustrates IRDBP-1 expression in the olfactory bulb.

FIG. 44A illustrates a Western blot analysis showing IRDBP-1 in COS 7 cell extracts and co-immunoprecipitation of IRDBP-1 with both anti-Akt 1 (lanes 1, 2) and anti-Erk2 (lanes 3, 4) that is increased with the addition of insulin.

DETAILED DESCRIPTION OF THE PREFERRED EMBODIMENTS

Figure 17A:
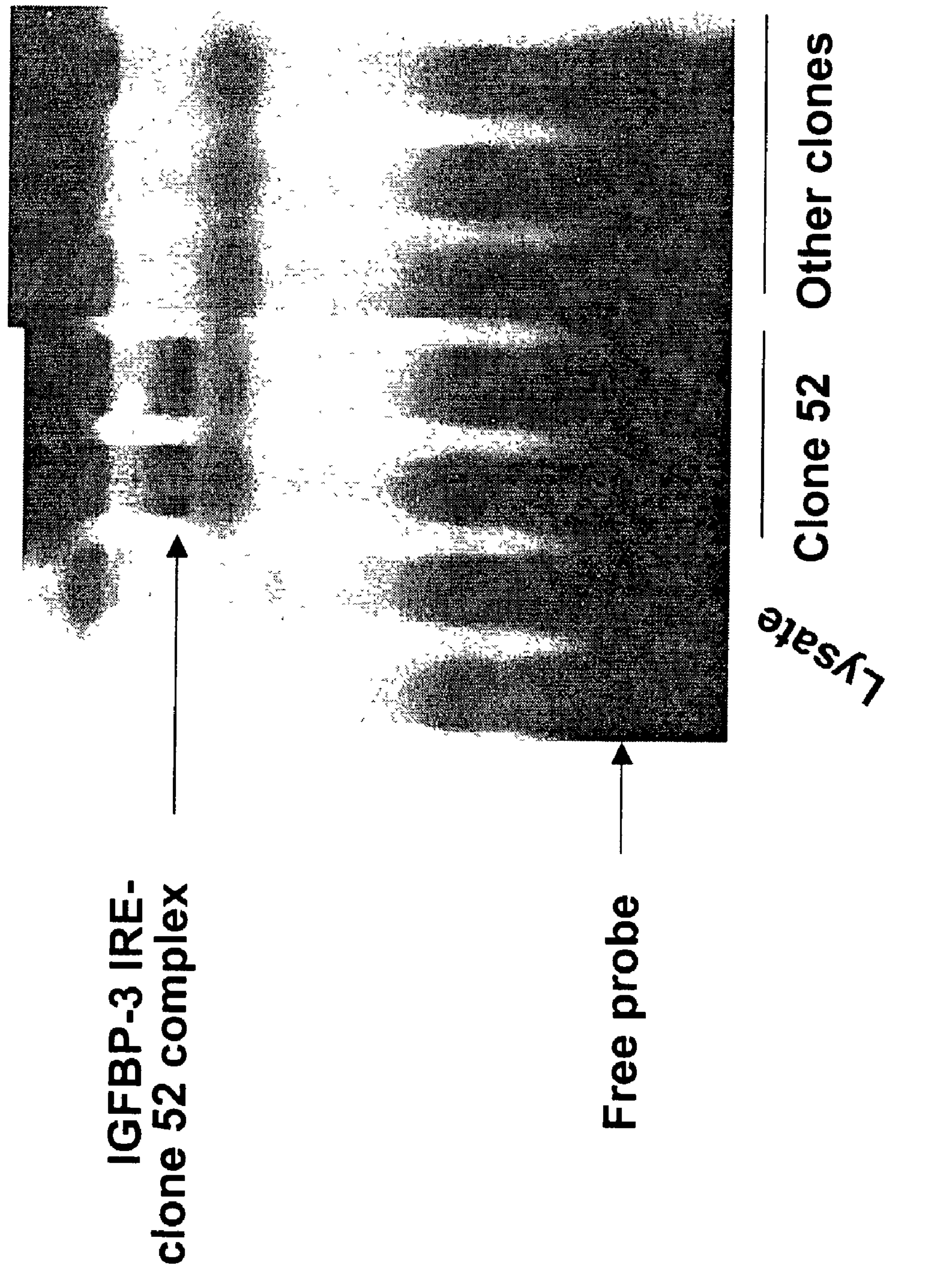
FIG. 17A illustrates gel mobility shift of the −1150/−1117 bp IRE fragment of IGFBP-3 (SEQ ID NO: 1) by polypeptides derived from cDNA clones isolated using the yeast one-hybrid system.

Reference now will be made in detail to the presently preferred embodiments of the invention, one or more examples of which are illustrated in the accompanying drawings. Each example is provided by way of explanation of the invention, not limitation of the invention. In fact, it will be apparent to those skilled in the art that various modifications, combination, additions, deletions and variations can be made in the present invention without departing from the scope or spirit of the invention. For instance, features illustrated or described as part of one embodiment can be used in another embodiment to yield a still further embodiment. It is intended that the present invention covers such modifications, combinations, additions, deletions and variations as come within the scope of the appended claims and their equivalents.

Definitions

This description uses gene nomenclature accepted by the Cucurbit Genetics Cooperative as it appears in the *Cucurbit Genetics Cooperative Report* 18:85 (1995); herein incorporated by reference in its entirety. Using this gene nomenclature, genes are symbolized by italicized Roman letters. If a mutant gene is recessive to the normal type, then the symbol and name of the mutant gene appear in italicized lower case letters.

For convenience, certain terms employed in the specification, examples, and appended claims are collected here.

The term "animal" is used herein to include all vertebrate animals, including humans. It also includes an individual animal in all stages of development, including embryonic and fetal stages. A "transgenic animal" is any animal containing one or more cells bearing genetic information altered or received, directly or indirectly, by deliberate genetic manipulation at a subcellular level, such as by targeted recombination or microinjection or by infection with recombinant virus. The term "transgenic animal" is not intended to encompass classical cross-breeding or in vitro fertilization, but rather is meant to encompass animals in which one or more cells are altered by, or receive, a recombinant nucleic acid molecule. This recombinant nucleic acid molecule may be specifically targeted to a defined genetic locus, may be randomly integrated within a chromosome, or it may be extrachromosomally replicating nucleic acid. The term "germ cell line transgenic animal" refers to a transgenic animal in which the genetic alteration or genetic information was introduced into a germ line cell, thereby conferring the ability to transfer the genetic information to offspring. If such offspring in fact possess some or all of that alteration or genetic information, they are transgenic animals as well.

The term "mammalian" as used herein refers to any species, subspecies or race of organism of the taxonomic class mammalia, such as, but not limited to, such organisms as mice, rats, rabbits, sheep, cattle, and primates, including humans.

As used herein, the term "IRDBP-1" refers to an Insulin-Responsive DNA Binding Protein-1 capable of binding to at least one insulin responsive element associated with a gene or genes, and by so doing may regulate the expression of an insulin-responsive gene. The term "IRDBP-1" is also intended to apply to proteins, peptides or polypeptides capable of binding to at least one insulin-responsive element of eukaryotic organisms, including fungi or animals.

The term "nucleic acid" as used herein refers to any natural and synthetic linear and sequential arrays of nucleotides and nucleosides, for example cDNA, genomic DNA, mRNA, RNA, oligonucleotides, oligonucleosides and derivatives thereof. For ease of discussion, such nucleic acids may be collectively referred to herein as "constructs," "plasmids," or "vectors." Representative examples of the nucleic acids of the present invention include bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, and the like, vectors derived from bacteriophage nucleic acid, and synthetic oligonucleotides like chemically synthesized DNA or RNA. The term "nucleic acid" further includes modified or derivatised nucleotides and nucleosides such as, but not limited to, halogenated nucleotides such as, but not only, 5-bromouracil, and derivatised nucleotides such as biotin-labeled nucleotides.

The term "isolated nucleic acid" as used herein refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, i.e., a gene encoding a fusion protein, and (e) a recombinant nucleotide sequence that is part of a hybrid sequence that is not naturally occurring. Isolated nucleic acid molecules of the present invention can include, for example, natural allelic variants as well as nucleic acid molecules modified by nucleotide deletions, insertions, inversions, or substitutions such that the resulting nucleic acid molecule still essentially encodes an IRDBP-1 protein or a variant thereof of the present invention.

By the use of the term "enriched" in reference to nucleic acid it is meant that the specific DNA or RNA sequence constitutes a significantly higher fraction of the total DNA or RNA present in the cells or solution of interest than in normal or diseased cells or in the cells from which the sequence was taken. Enriched does not imply that there are no other DNA or RNA sequences present, just that the relative amount of the sequence of interest has been significantly increased. The other DNA may, for example, be derived from a yeast or bacterial genome, or a cloning vector, such as a plasmid or a viral vector. The term significant as used herein is used to indicate that the level of increase is useful to the person making such an increase.

It is advantageous for some purposes that a nucleotide sequence is in purified form. The term "purified" in reference to nucleic acid represents that the sequence has increased purity relative to the natural environment.

As used herein the terms "polypeptide" and "protein" refer to a polymer of amino acids of three or more amino acids in a serial array, linked through peptide bonds. The term "polypeptide" includes proteins, protein fragments, protein analogues, oligopeptides and the like. The term "polypeptide" contemplates polypeptides as defined above that are encoded by nucleic acids, produced through recombinant technology, isolated from an appropriate source such as a mammal, or are synthesized. The term "polypeptide" further contemplates polypeptides as defined above that include chemically modified amino acids or amino acids covalently or noncovalently linked to labeling ligands.

The term "fragment" as used herein refers to a nucleic acid that is an isolated portion of the subject nucleic acid and may be constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art. The term "fragment" as used herein may also refer to an isolated portion of a polypeptide, wherein the portion of the polypeptide is cleaved from a naturally occurring polypeptide by proteolytic cleavage by at least one protease, or is a portion of the naturally occurring polypeptide synthesized by chemical methods well known to one of skill in the art.

The term "modulates" as used herein refers to the ability of a compound to alter the function of an IRE binding protein. A modulator preferably increases the binding or activating potential of an IRDBP-1. A modulator can alternatively decrease the binding or activating potential of IRDBP-1 polypeptide or fragments thereof. The terms "regulating" and "modulating" as used herein also refer to increasing or decraesing any parameter such as, but not limited to, the intracelular level of gene expression, the intracellular level of mRNA or polypeptide, the proliferationof a cell or the metabolic rate or uptake of glucose and the like.

The term "gene" or "genes" as used herein refers to nucleic acid sequences (including both RNA or DNA) that encode genetic information for the synthesis of a whole RNA, a whole protein, or any portion of such whole RNA or whole protein. Genes that are not naturally part of a particular organism's genome are referred to as "foreign genes", "heterologous genes" or "exogenous genes" and genes that are naturally a part of a particular organism's genome are referred to as "endogenous genes". The term "gene product" refers to RNAs or proteins that are encoded by the gene. "Foreign gene products" are RNA or proteins encoded by "foreign genes" and "endogenous gene products" are RNA or proteins encoded by endogenous genes. "Heterologous gene products" are RNAs or proteins encoded by "foreign, heterologous or exogenous genes" and which, therefore, are not naturally expressed in the cell.

The term "expressed" or "expression" as used herein refers to the transcription from a gene to give an RNA nucleic acid molecule at least complementary in part to a region of one of the two nucleic acid strands of the gene. The term "expressed" or "expression" as used herein may also refer to the translation from said RNA nucleic acid molecule to give a protein or polypeptide or a portion thereof.

As used herein, the term "locus" or "loci" refers to the site of a gene on a chromosome. Pairs of genes control hereditary traits, each in the same position on a pair of chromosomes. These gene pairs, or alleles, may both be dominant or both be recessive in expression of that trait. In either case, the individual is said to be homozygous for the trait controlled by that gene pair. If the gene pair (alleles) consists of one dominant and one recessive trait, the individual is heterozygous for the trait controlled by the gene pair. Natural variation in genes or nucleic acid molecules caused by, for example, recombination events or resulting from mutation, gives rise to allelic variants with similar, but not identical, nucleotide sequences. Such allelic variants typically encode proteins with similar activity to that of the protein encoded by the gene to which they are compared, because natural selection typically selects against variations that alter function. Allelic variants can also comprise alterations in the untranslated regions of the gene as, for example, in the 3' or 5' untranslated regions or can involve alternate splicing of a nascent transcript, resulting in alternative exons being positioned adjacently.

As used herein "genomic sequence" refers to the total DNA as found in the genome of an organism, and may include non-coding regions like introns, enhancers, promoters and the like.

The term "transcription regulatory sequences" as used herein refers to nucleotide sequences that are associated with a gene nucleic acid sequence and which regulate the transcriptional expression of the gene. The "transcription regulatory sequences" may be isolated and incorporated into a vector nucleic acid to enable regulated transcription in appropriate cells of portions of the vector DNA. The "transcription regulatory sequence" may precede, but is not limited to, the region of a nucleic acid sequence that is in the region 5' of the end of a protein coding sequence that may be transcribed into mRNA. Transcriptional regulatory sequences may also be located within a protein coding region, in regions of a gene that are identified as "intron" regions, or may be in regions of nucleic acid sequence that are in the region of nucleic acid.

The term "coding region" as used herein refers to a continuous linear arrangement of nucleotides which may be translated into a protein. A full length coding region is translated into a full length protein; that is, a complete protein as would be translated in its natural state absent any post-translational modifications. A full length coding region may also include any leader protein sequence or any other region of the protein that may be excised naturally from the translated protein.

The term "complementary" as used herein refers to two nucleic acid molecules that can form specific interactions with one another. In the specific interactions, an adenine base within one strand of a nucleic acid can form two hydrogen bonds with thymine within a second nucleic acid strand when the two nucleic acid strands are in opposing polarities. Also in the specific interactions, a guanine base within one strand of a nucleic acid can form three hydrogen bonds with cytosine within a second nucleic acid strand when the two nucleic acid strands are in opposing polarities. Complementary nucleic acids as referred to herein, may further. comprise modified bases wherein a modified adenine may form hydrogen bonds with a thymine or modified thymine, and a modified cytosine may form hydrogen bonds with a guanine or a modified guanine.

The term "probe" as used herein, when referring to a nucleic acid, refers to a nucleotide sequence that can be used to hybridize with and thereby identify the presence of a complementary sequence, or a complementary sequence differing from the probe sequence but not to a degree that prevents hybridization under the hybridization stringency conditions used. The probe may be modified with labels such as, but not only, radioactive groups, biotin, or any other label that is well known in the art.

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. The term "substantially similar" in the context of the present invention refers to sequences that are detectable under at least medium stringency conditions and typically remain hybridized under high-stringency conditions, there being at least 75% similarity between the hybridizing sequences For example, the first nucleic acid may be a test sample or probe, and the second nucleic acid may be the sense or antisense strand of a IRDBP-1 gene or a fragment thereof. The first nucleic acid may be a target nucleic acid derived from the genome, or RNA transcript therefrom, of a first species and the second nucleic acid may be isolated from a second animal species. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° Celsius in aqueous solution, followed by washing with 1×SSC at 65° Celsius. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al (1989) Molecular Cloning: A Laboratory Manual 2nd ed. Cold Spring Harbor Press, the contents of which are herein incorporated by reference in their entirety.

Typically, stringent conditions will be those in which the salt concentration is less than about 1.5 M Na ion, typically about 0.01 to 1.0 M Na ion concentration (or other salts) from about pH 7.0 to about pH 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1× to 2×SSC at 50 to 55° Celsius. Exemplary medium stringency conditions include hybridization in 40 to 45% formamide, 1 M NaCl, 1% SDS at 37° Celsius, and a wash in 0.5× to 1×SSC at 55 to 60° Celsius. Exemplary high stringency conditions include hybridization in 50% formamide, 1 M NaCl, 1% SDS at 37° Celsius, and a wash in 0.1×SSC at 60 to 65° Celsius.

The term "unique" nucleic acid region as used herein refers to a sequence present in a nucleic acid that is not present in any other nucleic acid sequence. The term "conserved nucleic acid region" as referred to herein is a nucleotide sequence present in two or more nucleic acid sequences, to which a particular nucleic acid sequence can hybridize under low, medium or high stringency conditions. The greater the degree of conservation between the conserved regions of two or more nucleic acid sequences, the higher the hybridization stringency that will allow hybridization between the conserved region and a particular nucleic acid sequence.

The terms "percent sequence identity" or "percent sequence similarity" as used herein refer to the degree of sequence identity between two nucleic acid sequences or two amino acid sequences as determined using the algorithm of Karlin & Attschul (1990) Proc. Natl. Acad. Sci. 87: 2264-2268, modified as in Karlin & Attschul (1993) Proc. Natl. Acad. Sci. 90: 5873-5877. Such an algorithm is incorporated into the NBLAST and XBLAST programs of Attschul et al. (1990) T. Mol. Biol. Q15: 403-410. BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Attschul et al. (1997) Nuc. Acids Res. 25: 3389-3402. When utilizing BLAST and Gapped BLAST programs, the default parameters of the respective programs (e.g. XBLAST and NBLAST) are used.

Other algorithms, programs and default settings may also be suitable such as, but not only, the GCG-Sequence Analysis Package of the U.K. Human Genome Mapping Project Resource Centre that includes programs for nucleotide or amino acid sequence comparisons.

The term "sense strand" as used herein refers to a single stranded DNA molecule from a genomic DNA that may be transcribed into RNA and translated into the natural polypeptide product of the gene. The term "antisense strand" is used herein to mean the single strand DNA molecule of a genomic DNA that is complementary with the sense strand of the gene.

The term "antisense DNA" as used herein refers to a gene sequence DNA that has a nucleotide sequence complementary to the "sense strand" of a gene when read in reverse orientation, i.e., DNA read into RNA in a 3' to 5' direction rather than in the 5' to 3' direction. The term "antisense RNA" is used to mean an RNA nucleotide sequence (for example that encoded by an antisense DNA or synthesized complementary with the antisense DNA). Antisense RNA is capable of hybridizing under stringent conditions with an antisense DNA. The antisense RNA of the invention is useful for regulating expression of a "target gene" either at the transcriptional or translational level. For example, transcription of the subject nucleic acids may produce antisense transcripts that are capable of inhibiting transcription by inhibiting initiation of transcription or by competing for limiting transcription factors; or, the antisense transcripts may inhibit transport of the "target RNA", or, the antisense transcripts may inhibit translation of "target RNA".

The term "antisense therapy" as used herein refers to the administration or in situ generation of oligonucleotide probes or their derivatives that specifically hybridize (e.g. bind) under cellular conditions, with the cellular mRNA and/or genomic DNA encoding a IRDBP-1 protein so as to inhibit expression of that protein, e.g. by inhibiting transcription and/or translation. The binding may be by conventional base pair complementation, or, for example, in the case of binding to DNA duplexes, through specific interactions in the major groove of the double helix. In general, "antisense" therapy refers to the range of techniques generally employed in the art, and includes any therapy that relies on specific binding to oligonucleotide sequences.

The terms "vector" and "nucleic acid vector" as used herein refers to a natural or synthetic single or double stranded plasmid or viral nucleic acid molecule that can be transfected or transformed into cells and replicate independently of, or within, the host cell genome. A circular double stranded plasmid can be linearized by treatment with an appropriate restriction enzyme based on the nucleotide sequence of the plasmid vector. A nucleic acid can be inserted into a vector by cutting the vector with restriction enzymes and ligating the pieces together. The nucleic acid molecule can be RNA or DNA.

The term "expression vector" as used herein refers to a nucleic acid vector that may further include at least one regulatory sequence operably linked to the nucleotide sequence coding for the IRDBP-1 protein. Regulatory sequences are well recognized in the art and may be selected to ensure good expression of the linked nucleotide sequence without undue experimentation by those skilled in the art. As used herein, the term "regulatory sequences" includes promoters, enhancers, and other elements that may control expression. Standard molecular biology textbooks such as Sambrook et al. eds "Molecular Cloning: A Laboratory Manual" 2nd ed. Cold Spring Harbor Press (1989) may be consulted to design suitable expression vectors, promoters, and other expression control elements. It should be recognized, however, that the choice of a suitable expression vector depends upon multiple factors including the choice of the host cell to be transformed and/or the type of protein to be expressed.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques, such as treating the cells with high concentrations of salt such as, but not only a calcium or magnesium salt, an electric field, detergent, or liposome mediated transfection, to render the host cell competent for the uptake of the nucleic acid molecules.

The term "recombinant nucleic acid" as used herein refers to combinations of at least two nucleic acid sequences that are not naturally found in a eukaryotic or prokaryotic cell. The nucleic acid sequences may include, but are not limited to nucleic acid vectors, gene expression regulatory elements, origins of replication, sequences that when expressed confer antibiotic resistance, and protein-encoding sequences. The term "recombinant polypeptide" it is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

The term "recombinant cell" refers to a cell that has a new combination of nucleic acid segments that are not covalently linked to each other in nature. A new combination of nucleic acid segments can be introduced into an organism using a wide array of nucleic acid manipulation techniques available to those skilled in the art. A recombinant cell can be a single eukaryotic cell, or a single prokaryotic cell, or a mammalian cell. The recombinant cell can harbor a vector that is extragenomic. An extragenomic nucleic acid vector does not insert into the cell's genome. A recombinant cell can further harbor a vector or a portion thereof that is intragenomic. The term intragenomic defines a nucleic acid construct incorporated within the recombinant cell's genome.

The term "antibody" as used herein refers to polyclonal and monoclonal antibodies and fragments thereof, and immunologic binding equivalents thereof that are capable of selectively binding to the IRDBP-1 polypeptides and fragments thereof, including epitopes thereof, or to polynucleotide sequences from the IRDBP-1 region, particularly from the IRDBP-1 locus or a portion thereof. The term "antibody" also refers to a homogeneous molecular entity, or a mixture such as a serum product made up of a plurality of different molecular entities, and may further comprise any modified or derivatised variant thereof that retains the ability to specifically bind to IRDBP-1-related polypeptides.

Described herein are methods for the production of antibodies capable of specifically recognizing one or more differentially expressed or pathway gene epitopes. Such antibodies may include, but are not limited to polyclonal antibodies, monoclonal antibodies (mAbs), humanized or chimeric antibodies, single chain antibodies, Fab fragments, $F(ab')_2$ fragments, fragments produced by a FAb expression library, anti-idiotypic (anti-Id) antibodies, and epitope-binding fragments of any of the above. Such antibodies may be used, for example, in the detection of a fingerprint, target, or pathway gene in a biological sample, or, alternatively, as a method for the inhibition of normal or abnormal target gene activity. Thus, such antibodies may be utilized as part of body weight disorder treatment methods, and/or may be used as part of diagnostic techniques whereby patients may be tested for abnormal levels of fingerprint, target, or pathway gene proteins, or for the presence of abnormal forms of the such proteins.

For the production of antibodies to a differentially expressed or pathway gene, various host animals may be immunized by injection with a differentially expressed or pathway gene protein, or a portion thereof. Such host animals may include but are not limited to rabbits, mice, and rats, to name but a few. Various adjuvants may be used to increase the immunologic response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Polyclonal antibodies are heterogeneous populations of antibody molecules derived from the sera of animals immunized with an antigen, such as a target gene product, or an antigenic functional derivative thereof. For the production of polyclonal antibodies, host animals such as those described above, may be immunized by injection with differentially expressed or pathway gene product supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to the hybridoma technique of Kohler &

Milstein (1975) Nature 256: 495-497; and U.S. Pat. No. 4,376,110), the human B-cell hybridoma technique (Kosbor et al. (1983) Immunology Today 4: 72; Cole et al. (1983) Proc. Natl. Acad. Sci. 80: 2026-2030), and the EBV-hybridoma technique (Cole et al. (1985) Monoclonal Antibodies And Cancer Therapy Alan R. Liss, Inc. pp. 77-96). Briefly, spleen cells are harvested from an immunized mouse and fused with immortalizing cells (i.e., myeloma cells) to yield antibody-producing hybridomas. Hybridomas can be screened immunochemically for production of monoclonal antibodies specifically reactive with the IRDBP-1 protein.

Protocols for producing, isolating and purifying conventional and monoclonal antibodies may be analogous to those described in Cassone et al. (1988) J. Med. Microbiol. 27: 233-238; Hancock & Evan Production and Characterization of Antibodies against Synthetic Peptides pp23-33 in Immunochemical Protocols ed. M. M. Manson, (1992) (Humana Press, Totowa, N.J.); Goding, J. W., Monoclonal Antibodies: Principles and Practice, 2d ed., (1986) (Academic Press Ltd., London) and Lam & Mutharia, "Antigen-Antibody Reactions," pp104-132 in Methods for General and Molecular Bacteriology, ed. P. Gerhardt, (1994) (ASM Press, Washington, D.C.) the contents of which are incorporated herein by reference in their entirety. Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al. (1984) Proc. Natl. Acad. Sci. 81: 6851-6855; Neuberger et al. (1984) Nature 312: 604-608; Takeda et al. (1985) Nature 314: 452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies such as, but not only U.S. Pat. No. 4,946,778; Bird (1988) Science 242: 423-426; Huston et al. (1988) Proc. Natl. Acad. Sci. 85: 5879-5883; and Ward et al. (1989) Nature 334: 544-546 can be adapted to produce differentially expressed or pathway gene-single chain antibodies. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al. (1989) Science 246: 1275-1281) to allow rapid and easy identification of monoclonal Fab fragments with the desired specificity.

The term "pharmaceutical compositions" as used herein refers to compositions comprising agents that will modulate the physiological activity of the IRDBP-1 gene product or the regulation of the expression of the IRDBP-1 gene. Such compositions can be administered in dosages and by techniques well known to those skilled in the medical or veterinary arts, taking into consideration such factors as the age, sex, weight, species and condition of the particular patient, and the route of administration. The route of administration can be percutaneous, via mucosal administration (e.g., oral, nasal, anal, vaginal) or via a parenteral route (intradermal, intramuscular, subcutaneous, intravenous, or intraperitoneal). Pharmaceutical compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Pharmaceutical compositions may be administered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remmington's Pharmaceutical Science," 17th edition, 1985 may be consulted to prepare suitable preparations, without undue experimentation. The effective dosage and route of administration are determined by the therapeutic range and nature of the compound, and by known factors, such as the age, weight, and condition of the host, as well as $LD_{50}$ and other screening procedures that are known and do not require undue experimentation. Dosages can generally range from a few hundred milligrams to a few grams.

As used herein, a "transgenic animal" is any animal, preferably a non-human mammal, in which one or more of the cells' of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals of the present invention, the transgene causes cells to express a recombinant form of the subject IRDBP-1 protein, e.g. either agonistic or antagonistic forms, or in which the endogenous IRDBP-1 gene has been disrupted. However, transgenic animals in which the recombinant IRDBP-1 gene is silent are also contemplated, as for example, the FLP or CRE recombinase dependent constructs described below. The "non-human animals" of the invention include vertebrates such as rodents, non-human primates, sheep, dog, cow, birds, amphibians, reptiles, etc. Preferred non-human animals are selected from the rodent family including rat and mouse, most preferably mouse. The term "chimeric animal" is used herein to refer to animals in which the recombinant gene is found, or in which the recombinant is expressed in some but not all cells of the animal. The term "tissue-specific chimeric animal" indicates that the recombinant IRDBP-1 gene is present and/or expressed in some tissues but not others.

As used herein, the term "transgene" means a nucleic acid sequence (encoding, e.g., a IRDBP-1 polypeptide) that is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As used herein, an "IRDBP-1 nucleic acid molecule" includes nucleic acid sequences related to a natural IRDBP-1 gene and may include all or some regions such as regulatory regions that control production of an RNA nucleic acid encoding the IRDBP-1 protein or production of the IRDBP-1 protein encoded by the gene (such as, but not limited to, transcription, translation or post-translation regulatory sequences) as well as the coding region itself, and any introns or non-translated coding regions or fragments thereof.

In the present context, an IRDBP-1 variant is an IRDBP-1 polypeptide that differs from an exemplified sequence in that one or more amino acids have been changed, added or deleted. An IRDBP-1 variant retains its useful function, i.e., for example, ability to bind IREs, activate or suppress insulin-regulating genes.

As used herein, the term "epitope" refers to a part of the protein that can specifically bind to an antibody by fitting into the antigen-binding site of the antibody.

The term "thiazolidinedione" as used herein refers to "insulin sensitizers" that can bind to peroxisome proliferator-activated receptors such as, but not limited to, PPARγ) resulting in increased glucose production. Exemplary thiazolidinediones include, but are not limited to, troglitazone, rosiglitazone and pioglitazone.

The terms "cancer" and "tumor" as used herein refer to a pathological condition of uncontrolled replication of a transformed cell. A cancer or tumor may be of any tissue such as, but not limited to, heart, breast, kidney, colon, intestinal and the like.

The techniques used to isolate and characterize the nucleic acids and proteins of the present invention are well known to those of skill in the art and standard molecular biology and biochemical manuals may be consulted to select suitable protocols without undue experimentation. See, for example, Sambrook et al (1989) Molecular Cloning: A Laboratory Manual 2nd ed. Cold Spring Harbor Press, the content of which is herein incorporated by reference in its entirety.

Abbreviations

Abbreviations used in the present specification include the following: aa, amino acid(s); bp, base pair(s); cDNA, DNA complementary to RNA; IRDBP-1, insulin responsive DNA-binding protein-1; IGF, insulin-like growth factor; IGFBP, IGF-binding protein; IRE, insulin response element; PEPCK, phosphoenol pryuvate carboxykinase; GAPDH, glyceraldehyde-3-phosphate dehydrogenase enzyme; nt, nucleotide(s); SSC, sodium chloride-sodium citrate; DMSO, dimethyl sulfoxide.

Rat and Human IRDBP-1 Nucleic Acids

One aspect of the present invention provides isolated nucleic acids, derivatives and variants thereof that encode human or rat IRDBP-1 proteins, derivatives or variants thereof. IRDBP-1 protein or functionally active derivatives or fragments thereof are particularly useful as direct or indirect modulators of gene expression wherein the genes so modulated comprise an IRE and are capable of responding to fluctuations in insulin levels. The present invention further provides an isolated nucleic acid encoding a fragment of a rat IRDBP-1 protein isolated based on the ability of the expressed protein product thereof to bind to the nucleic acid Insulin Responsive Element (IRE) associated with the rat IGFBP-3 and which has the nucleotide sequence 5'-AATTCAAGGGTATCCAGGAAAGTCTCC-3' (SEQ ID NO: 1). As used herein, IREs are regulatory nucleic acid sequences of insulin-regulated genes that are necessary to enable an insulin-dependent response. The nucleotide sequence of SEQ ID NO: 1 is localized between the −1150 and the −1124 bp positions of the promoter region of the IGFBP-3 encoding gene of the rat.

A rat liver cDNA library using the yeast one-hybrid system was screened using concatemerized IREs of rat IGFBP-3, using methods described by Wang & Reed (1993) Nature 364: 121-126, incorporated herein by reference in its entirety, and discussed in Example 1 below. The cDNA library screening provided a novel 952-bp cDNA (clone 52) encoding a portion of the Insulin-Responsive DNA Binding Protein-1 (IRDBP-1) that was identified and sequenced (SEQ ID NO: 2) (GenBank Accession No. AF439714), as illustrated in FIG. 1. The nucleic acid sequence of clone 52 (SEQ ID NO: 2) encodes a polypeptide having the amino acid sequence of SEQ ID NO: 3, as shown in FIG. 2, capable of binding to the IRE region of the rat IGFBP-3 (SEQ ID NO: 1), as described in Example 1 and 4.

A clone 52-thioredoxin (Trx) fusion protein also binds to the rat IGFBP-3 IRE SEQ ID NO: 1. The amino acid sequence SEQ ID NO: 3 deduced from the nucleotide sequence (SEQ ID NO: 2) of clone 52 comprises a homeodomain motif typical of transcription factors. Binding by the polypeptide SEQ ID NO: 3 to the IRE of IGFBP-3 (SEQ ID NO: 1) could be competed away by IGFBP-3 IRE nucleic acids but not by nucleic acids of sequences unrelated to the IRE, as shown in Example 1. The interaction between the IRDBP-1-related polypeptide (SEQ ID NO: 3) and the IGFBP-3 IRE nucleic acid (SEQ ID NO: 1) was specific.

The IRDBP-1 polypeptide fragment (SEQ ID NO: 3) encoded by clone 52 also interacts with IREs associated with other insulin-responsive genes besides IGFBP-3, as shown in Examples 4 and 7 below. The polypeptide interacts with the IREs from insulin-responsive genes encoding IGF-1, IGFBP-1, phosphoenol pyruvate carboxykinase (PEPCK), amylase, and glyceraldehyde-3-phosphate dehydrogenase (GAPDH).

IGFBP-1 is a hepatic acute phase reactant protein that coordinates the level of IGF-1 in response to changes in insulin levels (Lee et al. (1993)). Amylase is important for intestinal hydrolysis of carbohydrates. GAPDH catalyzes the conversion of glyceraldehyde-3-phosphate to 1,3-diphosphoglycerate, a rate-limiting step in adipose tissue glycolysis. While not being bound by any theory, the naturally occurring IRDBP-1 protein is likely a transcription factor that coordinates the responses of several genes to insulin. The IRDBP-1 polypeptide (SEQ ID NO: 3) of clone 52 can regulate critical genes in target tissues implicated in insulin resistance and insulin secretion. While not wishing to be held to any one theory, it is believed that th enaturally occurring IRDBP-1 polypeptide modulates the pleiotropic actions of insulin in the normal metabolism and storage of ingested carbohydrate and other fuels, in the modulation of intermediary metabolism, and in normal cellular growth and differentiation.

Ribonuclease protection assays (discussed in Example 3) using an antisense RNA probe obtained by transcribing a Kpn1-Xho1 fragment of clone 52 and having the nucleic acid sequence SEQ ID NO: 4, as shown in FIG. 3, showed that at least one gene, encoding at least one nucleic acid with sequence similarity to a region of the clone 52 cDNA sequence SEQ ID NO: 2 is expressed in at least liver, kidney, brain, small intestine, muscle, and fat pads.

The abundance of a rat RNA transcript capable of hybridizing to the probe having a nucleic acid sequence of the clone 52 (SEQ ID NO: 4) was increased with the addition of physiological concentrations of insulin ($10^{-9}$ M) in cell culture. It was also decreased in the livers of diabetic rats, as described in Example 8.

Another aspect of the present invention provides for the use of the isolated cDNA clone 52 (SEQ ID NO: 2) as a probe to screen rat and human cDNA libraries to obtain isolated nucleic acids capable of hybridizing with clone 52, as discussed in Example 5. Nucleic acid regions extending the cDNA sequences in the 5' direction from the isolated human and rat partial cDNA clones were obtained by primer extension reactions such as 5' RACE, and then sequenced.

The present invention further provides rat cDNA clones that hybridize to the clone 52 probe, and were identified and sequenced as SEQ ID NOS: 5, 6, 14 (GenBank Accession Nos: AF 439715, AF439716, and AF439719, respectively) and SEQ ID NO: 44 and shown in FIGS. 4A-4B, 5A-5B, 12A-12B, and 13, respectively. A first rat IRDBP-1 cDNA clone (SEQ ID NO 5; shown in FIGS. 4A and 4B) comprises about 4998 bp, and includes at least one open reading frame (ORF) (SEQ ID NO: 8) as in FIG. 4A and which encodes a rat ISRBP-1 protein (SEQ ID NO: 11; FIG. 4). The nucleotides at positions 68-349 of clone 52 (SEQ ID NO: 2) correspond to the nucleotide positions 2123-2404 of SEQ ID NO: 5 as shown in FIGS. 4A-4B. A second rat cDNA clone (SEQ ID NO: 6, shown in FIGS. 5A and 5B) is a partial cDNA comprising a partial open-reading frame (ORF) (FIG. 5A) having sequence similarity to a region of SEQ ID NO: 5 (FIG. 4A), and a 3' untranslated region (FIG. 5B) longer than that of SEQ ID NO: 5 (shown in FIG. 5B). Nucleic acid SEQ ID NO: 44 and the protein sequence encoded therein (SEQ ID NO: 47) are shown in FIGS. 6 and 15, respectively.

The present invention also provides for the human cDNA clones having the nucleic acid sequences SEQ ID NO: 7 as shown in FIGS. 6A-6C, SEQ ID NO: 10 as shown in FIGS. 8A and 8B) that were also identified by hybridization with a probe comprising the clone 52 nucleic acid sequence (SEQ ID NO: 2) during the screening of a human cDNA library, and SEQ ID NO: 45 (shown in FIG. 45) generated by 5' RACE extension of the isolated clone SEQ ID NO: 7.

It is contemplated that any nucleic acid of the present invention can comprise one or more regulatory regions, full-length or partial coding regions such as, but not limited to, the fragments SEQ ID NOS: 16-41 (FIG. 7) derived from the IRDBP-1 gene, or any combinations thereof. It is contemplated to be within the scope of the present invention for a probe to be derived from any of SEQ ID NOS: 2, 5-10, 14, 16-41 and 44-45 or a variant or truncated variant thereof. The minimal size of a nucleic acid molecule of the present invention is a size sufficient to allow the formation of a stable hybridization product with the complementary sequence of another nucleic acid molecule under selected stringency conditions.

Embodiments of the present invention may, therefore, include, but are not limited to, nucleic acid molecules such as: a) an IRDBP-1 cDNA molecule derived from the rat and comprising the protein coding region (SEQ ID NO: 8, shown in FIG. 4A) of SEQ ID NO: 5 or the coding region of SEQ ID NO: 44, and a 3' non-coding, or untranslated, region of SEQ ID NOS: 5 or 44; b) an IRDBP-1 cDNA molecule derived from the rat nucleic acid SEQ ID NOS: 5 or 44 and comprising the isolated coding region (SEQ ID NO: 8), or a substantial region thereof; or nucleic acid molecules representing degenerate variants, derivatives, modified sequences and truncated variants such as, but not limited to, SEQ ID NO: 6 shown in FIGS. 5A and 5B, thereof; c) an IRDBP-1-encoding cDNA molecule derived from the human comprising the protein coding region and a 5' and/or 3' non-coding regions of the sequence SEQ ID NO: 7 (GenBank Accession No. AF439717) as shown in FIG. 6A, or SEQ ID NO: 45 shown in FIG. 14; d) a nucleic acid molecule derived from the human IRDBP-1 cDNA sequence SEQ ID NO: 7 and comprising the human IRDBP-1 coding region alone (SEQ ID NO: 9), as depicted in FIG. 6B, or the coding region of SEQ ID NO: 45; and/or nucleic acid molecules representing degenerate variants, derivatives, alternatively spliced variants and modified variants thereof. A variant may be, but is not limited to, the sequence SEQ ID NO: 10 (GenBank Accession No. AF439718) as shown in FIGS. 8A and 8B. Such nucleic acid molecules can include nucleotides in addition to those included in SEQ ID NOS: 2, 5-10, 14, and 44-45 such as, but not limited to, a full-length gene, a full-length coding region, or a nucleic acid molecule encoding a fusion protein. BLASTN algorithm searching of the Genbank database using the human IRDBP-1 nucleic acid sequence SEQ ID NO: 7 or 45 as the search target found that there was almost 100% identity with regions of the human genomic DNA sequence GenBank Accession No. AC005237 from the human chromosome 1p31.31.3-32.2 and at least one human gene encoding the IRDBP-1 transcribed nucleic acid and protein derived therefrom is comprised of at least 26 exons as shown in Table 1, Example 5. The present invention, therefore, is intended also to provide isolated nucleic acids comprising at least one exon, or a fragment, variant or derivative thereof, capable of hybridizing with at least one region of the sequences SEQ ID NOS: 2, 5-10, 14, and 44-45 under low, medium or high stringency conditions, wherein the hybridization is specific for an IRDBP-1-encoding nucleic acid, or a fragment, variant or derivative thereof.

One aspect of the invention therefore also provides nucleic acids that hybridize under selected high, medium or low stringency conditions to a nucleic acid that encodes a peptide having all of, a derivative of, or a portion of an amino acid sequence derived from the nucleic acid sequences SEQ ID NOS: 2, 5-10, 14, and 44-45. Appropriate stringency conditions which promote DNA hybridization, for example, 6×SSC at about 45° C., followed by a wash of 2×SSC at 50° C., are well known to those skilled in the art or can be found, for example, in Current Protocols in Molecular Biology, John Wiley & Sons, N.Y. (1989), 6.3.1-6.3.6. For example, the salt concentration in the wash step can be selected from a low stringency of about 2×SSC at 50° C. to a high stringency of about 0.2×SSC at 50° C. In addition, the temperature in the wash step can be increased from low stringency conditions at room temperature, about 22° C., to high stringency conditions at about 65° C.

Isolated nucleic acids that differ in sequence from the nucleotide sequences represented in SEQ ID NOS: 2, 5-10, 13, and 44-45 due to degeneracy in the genetic code are also within the scope of the invention. Such nucleic acids can encode functionally equivalent peptides (i.e., a polypeptide having a biological activity of a IRDBP-1 protein). Isolated nucleic acid sequence variants may also encode non-functional polypeptides, the sequences of which are substantially similar, but not identical, to those of functional variants of IRDBP-1. These isolated nucleic acids may be used to generate variant animals with inactive or functionally modified IRDBP-1 polypeptides or fragments, variants or derivatives thereof.

For example, a number of amino acids are designated by more than one triplet. Codons that specify the same amino acid, or synonyms (for example, CAU and CAC are synonyms for histidine) may result in "silent" mutations which do not affect the amino acid sequence of the subject protein.

However, it is expected that DNA sequence polymorphisms that do lead to changes in the amino acid sequences of the present IRDBP-1 protein of the present invention will exist from one human or animal subject to the next of the same species. One skilled in the art will appreciate that these variations in one or more nucleotides (up to about 3-4% of the nucleotides) of the nucleic acids encoding peptides having an activity of, for example, an IRDBP-1 protein may exist among individuals due to natural allelic variation. Any and all such nucleotide variations and resulting amino acid polymorphisms are within the scope of this invention. Nucleic acid variants having sequence differences of about 3-4% may be readily detectable under high or medium stringency hybridization conditions using, for example, any of SEQ ID NOS: 2, 5-10, 13 or 44-45 or fragments thereof, such as SEQ ID NO: 4, as the probe.

Fragments of a nucleic acid encoding an active portion of one of the subject IRDBP-1 proteins are also within the scope of the invention. As used herein, a fragment of the nucleic acid encoding an active portion of a IRDBP-1 protein refers to a nucleotide sequence having fewer nucleotides than the nucleotide sequence encoding the entire amino acid sequence of the protein but which encodes a peptide that possesses agonistic or antagonistic activity relative to a naturally occurring form of the protein.

Nucleic acid fragments within the scope of the invention also include those capable of hybridizing under high or low stringency conditions with nucleic acids from other species for use in screening protocols to detect IRDBP-1 homologs. Comparison of the nucleic acid sequences of rat and human IRDBP-1 show that oligonucleotide primers can be generated that are suitable for detecting and isolating IRDBP-1 clones in other eukaryotes. For example, the cDNA clone 52 (SEQ ID NO: 2) could be used to detect IRDBP-1 homologs in other vertebrate species, such as, but not only, human, mice, rats, chickens. Thus SEQ ID NO: 2 was used to identify a hybridizing human IRDBP-1-encoding cDNA SEQ ID NO: 7 under medium stringency hybridization conditions.

One embodiment of the present invention, therefore, provides a nucleic acid comprising a nucleic acid sequence substantially similar to the clone 52 cDNA sequence (SEQ ID NO: 2) encoding at least a region of a rat IRDBP-1 protein (SEQ ID NO: 3) as shown in FIGS. 1 and 2 respectively, or any variants thereof. The nucleic acid molecules of the present invention can include an isolated deletion mutation corresponding to the IRDBP-1 phenotype, a natural IRDBP-1 gene, an IRDBP-1 cDNA molecule, a degenerate variant, a truncated form thereof, a homolog thereof or any other modified versions.

In another embodiment of the present invention, a nucleic acid is provided comprising a nucleic acid sequence substantially similar to the cDNA sequence for a rat IRDBP-1 (SEQ ID NO: 5) as shown in FIGS. 4A and 4B, or any variant thereof. The nucleic acid molecules of the present invention can include an isolated deletion mutation corresponding to the IRDBP-1 phenotype, a natural IRDBP-1 gene, an IRDBP-1 cDNA molecule, a degenerate variant thereof, a truncated variant thereof or a homolog thereof or any other variant thereof, including a human IRDBP-1-encoding nucleic acid having at least 75% sequence similarity to SEQ ID NOS: 2 or 5.

In yet another embodiment of the present invention, a nucleic acid is provided comprising a nucleic acid sequence substantially similar to the cDNA sequence for a rat IRDBP-1 (SEQ ID NO: 6) shown in FIGS. 5A and 5B comprising a variant of SEQ ID NO: 5.

In yet another embodiment of the present invention, an isolated nucleic acid is provided that comprises the nucleic acid sequence corresponding to a human IRDBP-1 sequence SEQ ID NO: 7 as shown in FIGS. 6A-6C.

In another embodiment of the present invention, an isolated nucleic acid is provided that comprises the nucleic acid sequence corresponding to a variant human IRDBP-1 (SEQ ID NO: 10) as shown in FIGS. 8A and 8B.

In still another embodiment of the present invention, a mammalian IRDBP-1 gene or nucleic acid molecule can be allelic variants of SEQ ID NOS: 2, 5-10 and 44-45. An allelic variant is a gene that occurs essentially at the same locus or loci in the mammalian genome as the genes comprising SEQ ID NOS: 5-10, 14 and 44-45, but which has similar, but not identical, sequences to that of SEQ ID NO: 5-10 and 44-45.

In one embodiment of the present invention, an isolated nucleic acid molecule of the present invention includes a nucleic acid that is at least about 75%, preferably at least about 80%, more preferably at least about 85%, even more preferably at least about 90%, and even more preferably at least about 95% identical to a rat-derived IRDBP-1-encoding nucleic acid molecule as depicted in SEQ ID NO: 5 or 44, and/or a variant thereof, such as, but not limited to, SEQ ID NOS: 6 and 14 or the human IRDBP-1 nucleic acids SEQ ID NOS: 7, 10 and 45.

In another embodiment of the present invention, an isolated nucleic acid molecule of the present invention includes a nucleic acid that is at least about 75%, preferably at least about 80%, more preferably at least about 85%, even more preferably. at least about 90%, and even more preferably at least about 95% identical to a human-derived nucleic acid molecule as depicted in SEQ ID NOS: 7 and 45, and/or a variant thereof, such as, but not limited to, SEQ ID NO: 10.

The nucleic acid sequences of a IRDBP-1 nucleic acid molecules (SEQ ID NOS: 2, 5-10, 14 and 44-45) of the present invention allow one skilled in the art to, for example, (a) make copies of those nucleic acid molecules by procedures such as, but not limited to, insertion into a cell for replication by the cell, by chemical synthesis or by procedures such as PCR or LCR, (b) obtain nucleic acid molecules which include at least a portion of such nucleic acid molecules, including full-length genes, full-length coding regions, regulatory control sequences, truncated coding regions and the like, (c) obtain IRDBP-1 nucleic acid homologs in other mammalian species such as the dog, cat, cow, pig or primates other than human and, (d) to obtain isolated nucleic acids capable of hybridizing to a mammalian IRDBP-1 nucleic acid and be used to detect the presence of IRDBP-1 nucleic acid sequences by complementation between the probe and the target nucleic acid.

Such nucleic acid homologs can be obtained in a variety of ways including by screening appropriate expression libraries with antibodies of the present invention; using traditional cloning techniques employing oligonucleotide probes made according to the present invention to screen appropriate libraries; amplifying appropriate libraries or DNA using oligonucleotide primers of the present invention in a polymerase chain reaction or other amplification method; and screening public and/or private databases containing genetic sequences using nucleic acid molecules of the present invention to identify targets. Examples of preferred libraries to screen, or from which to amplify nucleic acid molecules, include but are not limited to mammalian BAC libraries, genomic DNA libraries, and cDNA libraries. Similarly, preferred sequence databases useful for screening to identify sequences in other species homologous to IRDBP-1 include, but are not limited to, Gen- Bank and the mammalian Gene Index database of The Institute of Genomics Research (TIGR).

IRDBP-1 Polypeptides

Another aspect of the present invention is to provide protein sequences that comprise a mammalian IRDBP-1 protein, and derivatives and fragments thereof. One embodiment of the present invention, therefore, comprises a protein sequence (SEQ ID NO: 3, as shown in FIG. 2) encoded by the rat cDNA clone 52 nucleic acid sequence SEQ ID NO: 2.

In another embodiment of the present invention, a rat IRDBP-1 protein is provided having an amino acid sequence (SEQ ID NO: 11, illustrated in FIG. 9) derived from the coding region SEQ ID NO: 8, as in FIG. 4A, of the rat cDNA clone IRDBP-1 SEQ ID NO: 5.

In still yet another embodiment of the present invention, a rat IRDBP-1 protein sequence SEQ ID NO: 47, illustrated in FIG. 15 is provided that is encoded by the coding region of human nucleic acid sequence SEQ ID NO: 44 (FIG. 13).

In yet another embodiment of the present invention, a human IRDBP-1 protein sequence (SEQ ID NO: 12, illustrated in FIG. 10) is provided that is encoded by a coding region SEQ ID NO: 9 of the human nucleic acid sequence SEQ ID NO: 7, as shown in FIG. 6B.

In still yet another embodiment of the present invention, a human IRDBP-1 protein sequence SEQ ID NO: 48, illustrated in FIG. 16 is provided that is encoded by the coding region of human nucleic acid sequence SEQ ID NO: 45 (FIG. 14).

In still other embodiments of the present invention, peptide fragments of a human or animal IRDBP-1 protein are provided, wherein the fragments may be immunogenic peptides, capable of inducing an immune response when administered to an animal, and which will be recognized and bound by an antibody or not immunogenic when administered to an animal.

In one embodiment of the present invention, the peptide fragment is an epitope essentially within the carboxy-region of the rat IRDBP-1 protein SEQ ID NO: 3 (as in FIG. 2) and has the amino acid sequence: AcetylatedCys-Thr-Ser-Gln-Asn-Thr-Lys-Ser-Arg-Ty-Iso-Pro-Asn-Gly-Lys-Leu (SEQ ID NO: 15) at amino acid positions 62-76 of the rat IRDBP-1 amino acid sequence SEQ ID NO: 3 shown in FIG. 2.

In another embodiment, the epitope is substantially within the N-region of the IRDBP-1 protein between amino acid positions 233-247 of SEQ ID NO: 44 and having the sequence AcetylatedCys-Arg-Asn-Gly-Gly-Thr-Tyr-Lys-Glu-Thr-Gly-Asp-Glu-Tyr-Arg (SEQ ID NO: 46).

It is further contemplated to be within the scope of the present invention for proteins having substantial similarity to the rat or human protein amino acid sequences SEQ ID NOS: 11, 12, 47 and 48 wherein the proteins retain the capacity to bind to the IGFBP-3 IRE SEQ ID NO: 1. Isolated peptides and polypeptides of the present invention may also include any protein fragments thereof, a protein analogue, or any immunologic fragments thereof.

In another embodiment of the present invention, an IRDBP-1 nucleic acid molecule of the present invention encodes a protein having an amino acid sequence that is at least about 75%, preferably at least about 80%, more preferably at least about 85%, even more preferably at least about 90%, and more preferably still at least about 95% identical to a rat IRDBP-1 protein whose amino acid sequence is disclosed in SEQ ID NO: 11 or 47, as well as allelic variants of an IRDBP-1 nucleic acid molecule encoding a protein having these sequences, including nucleic acid molecules that have been modified to accommodate codon usage properties of the cells in which such nucleic acid molecules are to be expressed.

In an embodiment of the present invention, an IRDBP-1 nucleic acid molecule of the present invention encodes a protein having an amino acid sequence that is at least about 75%, preferably at least about 80%, more preferably at least about 85%, even more preferably at least about 90%, and more preferably still at least about 95% identical to a human IRDBP-1 protein whose amino acid sequence is disclosed in SEQ ID NO: 12 and 48, as well as allelic variants of an IRDBP-1 nucleic acid molecule encoding a protein having these sequences, including nucleic acid molecules that have been modified to accommodate codon usage properties of the cells in which such nucleic acid molecules are to be expressed.

Isolated peptidyl portions of the subject IRDBP-1 proteins within the scope of the present invention can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, one of the subject IRDBP-1 proteins may be arbitrarily divided into fragments of desired length with no overlap of the fragments, or preferably divided into overlapping fragments of a desired length. The fragments can be produced recombinantly or by chemical synthesis and tested to identify those peptidyl fragments which can function as either agonists or antagonists of, for example, IRDBP-1 binding to nucleic acids. Other fragments such as, for example, SEQ ID NOS: 15 and 46 are especially useful for the generation of antibodies specific for the IRDBP-1 protein or selected regions thereof. In an illustrative embodiment, peptidyl portions of IRDBP-1 can tested for nucleic acid-binding activity, as well as preventing inhibitory ability, by expression as, for example, thioredoxin fusion proteins each of which contains a discrete fragment of the IRDBP-1 protein (see, for example, U.S. Pat. Nos. 5,270,181 and 5,292,646; and PCT publication WO94/02502) incorporated herein by reference in their entireties.

Furthermore, it is also possible to modify the structure of an IRDBP-1 polypeptide for such purposes as enhancing therapeutic or prophylactic efficacy, or stability (e.g., shelf life ex vivo and resistance to proteolytic degradation in vivo). Such modified peptides are considered functional equivalents of peptides having an activity of, or which antagonize, a IRDBP-1 protein as defined herein. A modified polypeptide can be produced in which the amino acid sequence has been altered, such as by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed, Ed. by L. Stryer, WH Freeman and Co.: 1981). Whether a change in the amino acid sequence of a peptide results in a functional IRDBP-1 homolog can be readily determined by assessing the ability of the variant peptide to, for instance, mediate ubiquitination in a fashion similar to the wild-type IRDBP-1. Peptides in which more than one replacement has taken place can readily be tested in the same manner.

In one embodiment of the present invention, therefore, a host cell is transformed with a nucleic acid comprising the sequences SEQ ID NOS: 5-10, 14 or 44-45, or variants thereof. The transformed cell may, but not necessarily, express the transformed nucleic acid to yield rat (SEQ ID NOS: 3, 11, and 47) or human (SEQ ID NOS: 12-13 and 48) IRDBP-1 polypeptides respectively, or any fragment or derivative thereof. A recombinant expression vector suitable for transformation of a host cell means that the recombinant expression vector contains a nucleic acid molecule, or an oligonucleotide fragment thereof, of the present invention coupled to a regulatory sequence selected on the basis of the host cell used for expression. For example, the nucleic acid sequence coding for the IRDBP-1 protein of the present invention may be operatively linked to a regulatory sequence selected to direct expression of the desired protein in an appropriate host cell.

The protein of the present invention may be produced in purified form by any known conventional techniques. For example, rat or human cells may be homogenized and centrifuged. The supernatant is then subjected to sequential ammonium sulfate precipitation and heat treatment. The fraction containing the protein of the present invention is subjected to gel filtration in an appropriately sized dextran or polyacrylamide column to separate the proteins. If necessary, the protein fraction may be further purified by HPLC.

The present invention provides novel compositions comprising nucleotide sequences encoding IRDBP-1 fragments. Also provided are recombinant proteins produced using the novel coding sequences, and methods of using the recombinant proteins.

Recombinant Nucleic Acids Including IRDBP-1-related Sequences and Insertion into Vectors and Mammalian Cells The DNA nucleic acid molecules of the present invention can be incorporated into cells using conventional recombinant DNA technology. Such techniques are especially useful, for example, for producing IRDBP-1 polypeptides in cells, or to regulate the expression of the naturally occurring IRDBP-1 gene in the recipient cells. The DNA molecule may be inserted into an expression system to which the DNA molecule is heterologous (i.e. not normally present). Alternatively, as described more fully below, the DNA molecule may be introduced into cells which normally contain the DNA molecule, as, for example, to correct a deficiency or defect in IRDBP-1 expression, or where over-expression of the IRDBP-1 protein is desired.

For expression in heterologous systems, the heterologous DNA molecule can be inserted into the expression system or vector in proper sense orientation and correct reading frame. The vector contains the necessary elements for the transcription and translation of the inserted protein-coding sequences.

U.S. Pat. No. 4,237,224 to Cohen & Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, such as vaccinia virus or adenovirus. Recombinant viruses can be generated by transfection of plasmids into cells infected with virus. Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, PGEX, pET series (see Studier, F. W. et. al. (1990) "Use of T7 RNA Polymerase to Direct Expression of Cloned Genes" Gene Expression Technology, vol. 185, which is hereby incorporated by reference) and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al. Molecular Cloning: A Laboratory Manual, Cold Springs Laboratory, Cold Springs Harbor, N.Y. (1982), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation). Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals that differ from those of eukaryotes. Efficient translation of mRNA in prokaryotes requires a ribosome binding site called the Shine-Dalgarno (SD) sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts & Lauer (1979) Methods in Enzymology 68: 473, which is hereby incorporated by reference in its entirety.

Promoters vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promotor, trp promotor, recA promotor, ribosomal RNA promotor, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgamo (SD) sequence about 7-9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule of the present invention has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like.

Recombinant expression vectors can be designed for the expression of the encoded proteins in prokaryotic or eukaryotic cells. The prokaryotic expression system may comprise the host bacterial species *E. coli, B. subtilis* or any other host cell known to one of skill in the art. Useful vectors may comprise constitutive or inducible promoters to direct expression of either fusion or non-fusion proteins. With fusion vectors, a number of amino acids are usually added to the expressed target gene sequence such as, but not limited to, a protein sequence for thioredoxin. A proteolytic cleavage site may further be introduced at a site between the target recombinant protein and the fusion sequence. Additionally, a region of amino acids such as a polymeric histidine region may be introduced to allow binding to the fusion protein by metallic ions such as nickel bonded to a solid support, and thereby allow purification of the fusion protein. Once the fusion protein has been purified, the cleavage site allows the target recombinant protein to be separated from the fusion sequence. Enzymes suitable for use in cleaving the proteolytic cleavage site includes, but are not limited to, Factor Xa and thrombin. Fusion expression vectors that may be useful in the present invention include pGex (Amrad Corp., Melbourne, Australia), pRIT5 (Pharmacia, Piscataway, N.J.) and pMAL (New England Biolabs, Beverly, Mass.), that fuse glutathione S-transferase, protein A, or maltose E binding protein, respectively, to the target recombinant protein.

Expression of unfused foreign genes in *E. coli* may be accomplished with recombinant vectors including, but not limited to, the *E. coli* expression vector pUR278 as described in Ruther et aL (1983) *E.M.B.O.J.* 2: 1791, incorporated herein by reference in its entirety. Using the pUR278 vector, the nucleotide sequence coding for the IRDBP-1 gene product may be ligated in frame with the lacV coding region to produce a fusion protein.

Expression of a foreign gene can also be obtained using eukaryotic vectors such as mammalian, yeast or insect cells. The use of eukaryotic vectors permits partial or complete post-translational modification such as, but not only, glycosylation and/or the formation of the relevant inter- or intrachain disulfide bonds. Examples of vectors useful for expression in the yeast *Saccharomyces cerevisiae* include pYepSecl as in Baldari et al., (1987), *E.M.B.O.J,* 6: 229-234 and pYES2 (Invitrogen Corp., San Diego, Calif.), incorporated herein by reference in their entirety.

Baculovirus vectors are also available for the expression of proteins in cultured insect cells (F9 cells). The use of recombinant Baculovirus vectors can be, or is, analogous to the methods disclosed in Richardson C. D. ed., (1995), "Baculovirus Expression Protocol" Humana Press Inc.; Smith et al. (1983) Mol. Cell. Biol. 3: 2156-2165; Pennock et al. (1984) Mol. Cell. Biol. 4: 399-406 and incorporated herein by reference in their entirety.

Other vectors useful for expressing the IRDBP-1 protein, or an epitope of a IRDBP-1 protein, include viral vectors. Methods for making a viral recombinant vector useful for expressing the IRDBP-1 protein are analogous to the methods disclosed in U.S. Pat. Nos. 4,603,112; 4,769,330; 5,174,993; 5,505,941; 5,338,683; 5,494,807; 4,722,848; Paoletti, E. (1996) Proc. Natl. Acad. Sci. 93: 11349-11353; Moss (1996) Proc. Natl. Acad. Sci. 93: 11341-11348; Roizman (1996) Proc. Natl. Acad. Sci. 93: 11307-11302; Frolov et al. (1996) Proc. Natl. Acad. Sci. 93: 11371-11377; Grunhaus et al. (1993) Seminars in Virology 3: 237-252 and U.S. Pat. Nos. 5,591,639; 5,589,466; and 5,580,859 relating to DNA expression vectors, inter alia; the contents of which are incorporated herein by reference in their entireties.

One embodiment of the present invention, therefore, is a recombinant viral vector comprising an adenovirus vector capable of expressing in a suitable host cell a polypeptide encoded by at least a region of the nucleic acids SEQ ID NO: 44. The expressed polypeptide is capable of binding to an IRE, wherein the binding can be modulated by insulin, as described in Example 20.

In one embodiment of this aspect of the present invention, the recombinant adenoviral vector (or other suitable vector) may express the IRDBP-1 nucleic acid as an antisense nucleic acid that is not translated but, by hybridizing to a region of the IRDB-1 gene or a transcript thereof, can modulate the level of IRDBP-1 activity in a cell.

Probes, Primers and Sense/Antisense Oligonucleotides Specific for IRDBP-1

Another aspect of the present invention pertains to the use of an isolated nucleic acid molecule for constructing nucleotide probes and primers useful for a variety of functions. For example, synthetic oligonucleotide probes are useful for detecting complementary nucleotide sequences in biological materials such as cells, cell extracts or tissues (as well as in an in situ hybridization technique). Isolated nucleic acids synthesized according to the present invention can determine whether a cell expresses an mRNA transcript encoding the IRDBP-1 protein. The present invention also contemplates the use of antisense nucleic acid molecules, which are designed to be complementary to a coding strand of a nucleic acid (i.e., complementary to an mRNA sequence) or, alternatively, complimentary to a 5' or 3' untranslated region of the mRNA. Another use of synthetic nucleotides is as primers (DNA or RNA) for a polymerase chain reaction (PCR), ligase chain reaction (LCR), or the like.

Synthesized nucleotides can be produced in variable lengths—the number of bases synthesized will depend upon a variety of factors, including the desired use for the probes or primers. Additionally, sense or anti-sense nucleic acids or oligonucleotides can be chemically synthesized using modified nucleotides to increase the biological stability of the molecule or of the binding complex formed between the anti-sense and sense nucleic acids. For example, acridine substituted nucleotides can be synthesized. Protocols for designing isolated nucleotides, nucleotide probes, and/or nucleotide primers are well-known to those of ordinary skill, and can be purchased commercially from a variety of sources (e.g., Sigma Genosys, The Woodlands, Tex. or The Great American Gene Co., Ramona, Calif.).

Nucleotides constructed in accordance with the present invention can be labeled to provide a signal as a means of detection. For example, radioactive elements such as $^{32}P$, $^{3}H$, and $^{35}S$ or the like provide sufficient half-life to be useful as radioactive labels. Other materials useful for labeling synthetic nucleotides include fluorescent compounds, enzymes and chemiluminescent moieties. Methods useful in selecting appropriate labels and binding protocols for binding the labels to the synthetic nucleotides are well known to those of skill in the art. Standard immunology manuals such as *Promega: Protocol and Applications Guide,* 2nd Edition, 1991 (Promega Corp., Madison, Wis.; the content of which is incorporated herein in its entirety) may be consulted to select an appropriate labeling protocol without undue experimentation.

IRDBP-1 Specific Antibodies

It is further contemplated to be within the scope of the present invention to produce and use antibodies specifically reactive with an IRDBP-1 protein or a region thereof. The antibody may be monoclonal or polyclonal and may be produced by conventional methodology using the IRDBP-1 protein, or an immunologic fragment thereof, as an immunogen. For example, a mammal (i.e., a mouse, rabbit, horse, sheep, or goat) may be immunized with a IRDBP-1 protein of the present invention, an immunogenic fragment thereof, or an IRDBP-1 fusion protein or fragment thereof, using an immunization protocol conducive to producing antibodies reactive with the IRDBP-1 protein or a fragment thereof. Following completion of the immunization steps, antiserum reactive with the jointed protein may be collected and, if desired, polyclonal anti-IRDBP-1 antibodies isolated.

One embodiment of the present invention, therefore, is a fragment of an amino acid sequence of the rat IRDBP-1 protein of SEQ ID NOS: 3, 11 or 47, or human IRDBP-1 protein (SEQ ID NOS: 12, 13 or 48) that may be synthesized and used as an immunogen to produce an anti-IRDBP-1 polyclonal antibody. Exemplary sequences of the immunogenic peptide synthesized are: AcetylatedCys-Thr-Ser-Gln-Asn-Thr-Lys-Ser-Arg-Tyr-Ile-Pro-Asn-Gly-Lys-Leu (SEQ ID NO: 15) at amino acid positions 786-800 of the rat IRDBP-1 amino acid sequence SEQ ID NO: 47 and AcetylatedCys-Arg-Asn-Gly-Gly-Thr-Tyr-Lys-Glu-Thr-Gly-Asp-Glu-Tyr-Arg (SEQ ID NO: 46). The polyclonal antibody raised against the peptide SEQ ID NO: 15 was specific for the carboxy region rat IRDBP-1 protein and cross-reacted with the human IRDBP-1 protein. The polyclonal antibody raised against the peptide SEQ ID NO: 46 is specific for the N-region of the rat or human IRDBP-1.

Antibodies that specifically bind, for example, IRDBP-1 epitopes can also be used in immunohistochemical staining of tissue samples in order to evaluate the abundance and pattern of expression of IRDBP-1. Anti-IRDBP-1 antibodies can be used diagnostically in immuno-precipitation and immunoblotting to detect and evaluate IRDBP-1 levels in tissue or bodily fluid as part of a clinical testing procedure. For instance, such measurements can be useful in predictive valuations of the onset or progression of diabetes or cell proliferation disorders. Likewise, the ability to monitor IRDBP-1 levels in an individual can allow determination of the efficacy of a given treatment regimen for an individual afflicted with such a disorder. The level of IRDBP-1 can be measured in cells isolated from bodily fluid, such as in samples of cerebral spinal fluid or blood, or can be measured in tissue, such as produced by biopsy. Diagnostic assays using anti-IRDBP-1 antibodies can include, for example, immunoassays designed to aid in early diagnosis of a diabetic, neoplastic or hyperplastic disorder, e.g. the presence of insulin-responsive negative cells in the sample, e.g. to detect cells in which a lesion of the IRDBP-1 gene has occurred.

Another application of anti-IRDBP-1 antibodies is in the immunological screening of cDNA libraries constructed in expression vectors, such as λgt11, λgt18-23, λZAP, and λORF8. Messenger libraries of this type, having coding sequences inserted in the correct reading frame and orientation, can produce fusion proteins. For instance, λgt11 will produce fusion proteins whose amino termini consist of .beta.-galactosidase amino acid sequences and whose carboxy termini consist of a foreign polypeptide. Antigenic epitopes of IRDBP-1 can then be detected with antibodies, as, for example, reacting nitrocellulose filters lifted from infected plates with anti-IRDBP-1 antibodies. Phage, scored by this assay, can then be isolated from the infected plate. Thus, the presence of IRDBP-1 homologs can be detected and cloned from other human sources, i.e. to identified other closely homologous human isoforms, as well as to identify IRDBP-1 homologs in other mammals.

It is further contemplated to be within the scope of the present invention for an assay to detect natural serum antibodies specific for the IRDBP-1 protein. These antibodies may be induced as a result of the release of IRDBP-1 or fragments thereof, during the onset of deterioration and destruction of the cells of the islets of Langerhan. The detection of the antibodies will provide a diagnostic indication of the onset of diabetes, cancer and the progressive loss of pancreatic activity.

IRDBP-1-specific Oligonucleotide Probes

Moreover, the nucleotide sequence determined from the cloning of subject IRDBP-1 from a human or animal cell line will further allow for the generation of probes designed for use in identifying IRDBP-1 homologs in other animal cell-types, particularly cells associated with the onset and maintenance of diabetes and obesity, cancer or other transformed or immortalized cells, as well as IRDBP-1 homologs from other non-human mammals.

In addition the present invention contemplates nucleotide probes can be generated from a cloned nucleic acid sequence of the IRDBP-1 protein, which allow for histological screening of intact tissue and tissue samples for the presence of IRDBP-1 mRNA. Similar to the diagnostic uses of anti-IRDBP-1 antibodies, the use of probes directed to IDBP-1 mRNA, or to genomic IRDBP-1 sequences, can be used for both predictive and therapeutic evaluation of allelic mutations which might be manifest in, for example, diabetes or other metabolic disorders directly or indirectly attributed to a failure of the cells to respond or over-respond to insulin as well as neoplastic or hyperplastic disorders such as, but not limited to, unwanted cell growth. Used in conjunction with anti-IRDBP-1 antibody immunoassays, the nucleotide probes can help facilitate the determination of the molecular basis for a disorder or ailment that may involve some abnormality associated with expression (or lack thereof) of an IRDBP-1 protein and perturbation of insulin regulation of a gene expression or activity. For instance, nucleic acid molecules complementary to an IRDBP-1 coding sequence can be used to determine if cells contain IRDBP-1 coding sequences using Southern hybridization analysis. Nucleic acid molecules can also be used to determine the level of expression of IRDBP-1 mRNA in cells using Northern analysis as discussed in Example 8.

In a diagnostic embodiment of the present invention, therefore the nucleotide sequence of the isolated DNA molecule of the present invention may be used as a probe in nucleic acid hybridization assays for the detection of the IRDBP-1 gene in various patient, body fluids. The nucleotide sequence of the present invention may be used in any nucleic acid hybridization assay system known in the art, including, but not limited to, Southern blots (Southern, E. M. (1975) J. Mol. Biol. 98: 508; Northern blots (Thomas et al. (1980) Proc. Natl. Acad. Sci. 77: 5201-05); Colony blots (Grunstein et al, (1975) Proc. Natl. Acad. Sci. 72: 3961-65, which are hereby incorporated by reference). Alternatively, the isolated DNA molecule of the present invention can be used in a gene amplification detection procedure such as a polymerase chain reaction (Erlich et al. (1991) "Recent Advances in the Polymerase Chain Reaction" Science 252: 1643-51, which is hereby incorporated by reference) or in restriction fragment length polymorphism (RFLP) diagnostic techniques, as described in Watson et al., (2d ed. 1992), Recombinant DNA, Scientific American Books, 519-522, 545-547, which is hereby incorporated by reference.

Specifically, for example, the DNA molecules of the invention can be used in prenatal or postnatal diagnosis of the human diseases associated with defects in response to variation in the level of insulin. A probe for the DNA encoding IRDBP-1 can be designed using the DNA molecule of the invention, and used to probe the DNA obtained from amniotic fluid or chorionic tissue and amplified by PCR, LCR or any other known amplification technique for the presence of the IRDBP-1 gene or a variant thereof, as noted above. Similar procedures can be used in postnatal diagnostic work, as, for example, to diagnose the source of an IRDBP-1 deficiency in a person who is diabetic.

For example, the present method provides a method for determining if a subject is at risk for a disorder characterized by unwanted insulin non-responsiveness or cell proliferation. In preferred embodiments, the subject method can be generally characterized as comprising: detecting in a tissue of a subject (e.g. a human patient), the presence or absence of a genetic lesion characterized by at least one of (i) a mutation of a gene encoding IRDBP-1 or (ii) the mis-expression of the IRDBP-1 gene. To illustrate, such genetic lesions can be detected by ascertaining the existence of at least one of (i) a deletion of one or more nucleotides from the IRDBP-1 gene, (ii) an addition of one or more nucleotides to the IRDBP-1 gene, (iii) a substitution of one or more nucleotides of the IRDBP-1 gene, (iv) a gross chromosomal rearrangement of the IRDBP-1 gene, (v) a gross alteration in the level of a messenger RNA transcript of the IRDBP-1 gene, (vi) the presence of a non-wild type splicing pattern of a messenger RNA transcript of the IRDBP-1 gene, and (vii) a non-wild type level of the IRDBP-1 protein. In one aspect of the invention there is provided a probe/primer comprising an oligonucleotide containing a region of nucleotide sequence which is capable of hybridizing to a sense or antisense sequence derived from nay of the rat or human IRDBP-1 sequences SEQ ID NOS: 2, 5-10, 14 or 44-45, or naturally occurring mutants thereof, or 5' or 3' flanking sequences or intronic sequences naturally associated with the IRDBP-1 gene. The probe is exposed to nucleic acid of a tissue sample; and the hybridization of the probe to the sample nucleic acid is detected. In certain embodiments, detection of the lesion comprises utilizing the probe/primer in, for example, a polymerase chain reaction (PCR) (see, e.g., U.S. Pat. Nos. 4,683,195 and 4,683,202), or, alternatively, in a ligation chain reaction (LCR) (see, e.g., Landegran et al. (1988) Science 241: 1077-1080; and Nakazawa et al. (1994) Proc. Natl. Acad. Sci. 91: 360-364), the later of which can be particularly useful for detecting even point mutations in the IRDBP-1 gene and which are incorporated herein in their entirety. Alternatively, or additionally, the level of IRDBP-1 protein can be detected in an immunoassay.

IRDBP-1 and its Role in the Onset and Maintenance of Obesity

IRDBP-1 can also be used for the treatment of obesity and complications associated with obesity. The organ systems and the specific diseases associated with obesity include the following: (1) cardiovascular system: hypertension, congestive heart failure, cor pulmonale, varicose veins, pulmonary embolism, coronary heart disease; (2) Endocrine: insulin resistance, glucose intolerance, type II diabetes mellitus, dyslipidemia, polycystic ovary syndrome, infertility, amenorrhea; (3) Musculoskeletal: immobility, degenerative arthritis, low back pain; (4) Integument: venous stasis of legs, cellulitis, intertrigo, carbuncles; (5) Respiratory system: dyspnea and fatigue, obstructive sleep apnea, hypoventilation (pickwickian) syndrome; (6) Gastrointestinal: gastroesophageal reflux disease, hepatic steatosis, nonalcoholic steatohepatitis, cholelithiasis, hernias, colon cancer; (7) Psychosocial: work disability, depression; (8) Genitourinary: urinary stress incontinence, hypogonadism, breast and uterine cancer; (9) Neurologic: stroke, meralgia paresthetica, idiopathic interacranial hypertension. Any of the above conditions, when associated with obesity, could be used as indications for the effective use of IRDBP-1 agonists or antagonists.

Using in-situ hybridization to localize IRDBP-1 mRNA in the brain, IRDBP-1 expression was detected in the areas of the brain known to be involved in ingestive, autonomic and neuroendocrine functions of feeding and satiety, as described in the Examples 10-12 below. Regulation of body weight requires a balance among energy intake, expenditure, and storage. The brain appears to define the set point around which body weight is regulated. The levels of IRDBP-1 mRNA in the lateral hypothalamus and the nucleus of the solitary tract are differentially regulated in obese as compared to lean Zucker rats, showing a significant interactive role of IRDBP-1 in modulating body weight.

Gene Therapy Modulation of IRDBP-1 Activity

The IRDBP-1 polypeptides of the invention can be used in therapeutic applications. Since IRDBP-1 increases the transcription of IGFBP-3, IRDBP-1 can be used to treat diseases (e.g., diabetes) associated with low levels of IGFBP-3. Further, many diseases are associated with an excess of circulating IGF-1 or IGF-II, for example, some cancers and type II diabetes. IRDBP-1 can be used in patients with low levels of IGFBP-3 or high levels of IGF. Introduction of the gene encoding IRDBP-1 (or a functional derivative) into cells using either retroviral vectors or liposomes results in increased production of IGFBP-3. Many methods of delivering expressible coding sequences to cells are known in the art.

A useful application of the DNA molecules of the present invention is the possibility of increasing the amount of IRDBP-1 protein present in a mammal by gene transfer (so-called "gene therapy"). Of course, in most instances, this gene would be transferred into the animal host along with promoters, inducers, and the like (which are well known and recognized techniques in the field of genetic engineering, as noted supra) to allow the cell to initiate and continue production of the genetic product protein. The DNA molecule of the present invention can be transferred into the extra-chromosomal or genomic DNA of the host.

Methods for gene therapy are described in U.S. Pat. No. 5,399,346, issued to Anderson et al. and U.S. Pat. No. 5,766,899, issued to Kuo et al. describes methods for gene delivery into liver cells. The use of amphipathic compounds to deliver DNA is described in U.S. Pat. No. 5,744,335 issued to Wolf et al. and which are incorporated herein in their entirety.

It is further contemplated to be within the scope of the present invention for IRDBP-1-expression vectors to be used as a part, of a gene therapy protocol to reconstitute IRDBP-1 function in a cell in which IRDBP-1 is mis-expressed, or alternatively, to provide an antagonist of the naturally-occurring IRDBP-1 or an antisense construct. For instance, expression constructs of the subject IRDBP-1-proteins may be administered in any biologically effective carrier, e.g. any formulation or composition capable of effectively transfecting cells in vivo with a recombinant IRDBP-1-gene. Approaches include insertion of the subject gene in viral vectors including recombinant retroviruses, adenovirus, adeno-associated virus, and herpes simplex virus-1, or recombinant bacterial or eukaryotic plasmids. Viral vectors can be used to transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically.

A preferred approach for in vivo introduction of nucleic acid encoding one of the subject proteins into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") that produce only replication-defective retroviruses has increased the utility of retroviruses for gene therapy, and defective retroviruses are well characterized for use in gene transfer for gene therapy purposes (for a review see Miller, A. D. (1990) Blood 76: 271). Thus, recombinant retrovirus can be constructed in which part of the retroviral coding sequence (gag, pol, env) has been replaced by nucleic acid encoding an IRDBP-1 proteins, thereby rendering the retrovirus replication defective. The replication defective retrovirus is then packaged into virions that can be used to infect a target cell through the use of a helper virus by standard techniques. Protocols for producing recombinant retroviruses and for infecting cells in vitro or in vivo with such viruses can be found in Current Protocols in Molecular Biology, Ausubel et al. (1989) (eds.) Greene Publishing Associates, Sections 9.10-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include psiCrip, psiCre, psi2 and psiAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. (1985) Science 230: 1395-1398; Danos & Mulligan (1988) Proc. Natl. Acad. Sci. 85: 6460-6464; Wilson et al. (1988) Proc. Natl. Acad. Sci. 85: 3014-3018; Armentano et al. (1990) Proc. Natl. Acad. Sci. 87: 6141-6145; Huber et al. (1991) Proc. Natl. Acad. Sci. 88: 8039-8043; Ferry et al. (1991) Proc. Natl. Acad. Sci. 88: 8377-8381; Chowdhury et al. (1991) Science 254: 1802-1805; van Beusechem et al. (1992) Proc. Natl. Acad. Sci. 89: 7640-7644; Kay et al. (1992) Human Gene Therapy 3: 641-647; Dai et al. (1992) Proc. Natl. Acad. Sci. 89: 10892-10895; Hwu et al. (1993) J. Immunol. 150: 4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573), and which are incorporated herein in their entireties.

Furthermore, it has also been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al. (1989) Proc. Natl. Acad. Sci. 86: 9079-9083; Julan et al. (1992) J. Gen. Virol. 73: 3251-3255; and Goud et al. (1983) Virology 163: 251-254); or coupling cell surface ligands to the viral env proteins (Neda et al. (1991) J. Biol. Chem. 266: 14143-14146), and which are incorporated herein in their entireties. Coupling can be in the form of the chemical cross-linking with a protein or other variety (e.g.

lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector into an amphotropic vector. Moreover, use of retroviral gene delivery can be further enhanced by the use of tissue- or cell-specific transcriptional regulatory sequences that control expression of the IRDBP-1-gene of the retroviral vector.

Another viral gene delivery system useful in the present invention utilizes adenovirus-derived vectors. The genome of an adenovirus can be manipulated such that it encodes a gene product of interest, but is inactivated in terms of its ability to replicate in a normal lytic viral life cycle (see, for example, Berkner et al. (1988) BioTechniques 6: 616; Rosenfeld et al. (1991) Science 252: 43 1434; and Rosenfeld et al. (1992) Cell 68: 143-155), and which are incorporated herein in their entirety. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al. (1992) cited supra), endothelial cells (LeMarchand et al. (1992) Proc. Natl. Acad. Sci. 89: 6482-6486), hepatocytes (Herz & Gerard (1993) Proc. Natl. Acad. Sci. 90: 2812-2816) and muscle cells (Quantin et al. (1992) Proc. Natl. Acad. Sci. 89: 2581-2584), and which are incorporated herein in their entireties. Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. supra; Haj-Ahmand & Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) Cell 16:683; Berkner et al., supra; and Graham et al. in Methods in Molecular Biology, E. J. Murray, (1991) Ed. (Humana, Clifton, N.J.) vol. 7. pp. 109-127), and which are incorporated herein in their entirety. Expression of the inserted IRDBP-1-gene can be under control of, for example, the E1A promoter, the major late promoter (MLP) and associated leader sequences, the E3 promoter, or exogenously added promoter sequences.

Yet another viral vector system useful for delivery of, for example, the subject IRDBP-1-gene, is the adeno-associated virus (AAV): Adeno-associated virus is a naturally occurring defective virus that requires another virus, such as an adenovirus or a herpes virus, as a helper virus for efficient replication and a productive life cycle. (For a review see Muzyczka et al. (1992) Curr. Topics in Micro. and Immunol. 158: 97-129). It is also one of the few viruses that may integrate its DNA into non-dividing cells, and exhibits a high frequency of stable integration (see for example Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into cells. A variety of nucleic acids have been introduced into different cell types using AAV vectors (see for example Hermonat et al. (1984) Proc. Natl. Acad. Sci. 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790), and which are incorporated herein in their entirety.

Other viral vector systems that may have application in gene therapy have been derived from such as, but not limited to, herpes virus, vaccinia virus, and several RNA viruses. In particular, herpes virus vectors may provide a unique strategy for persistence of the recombinant IRDBP-1 gene in cells of the central nervous system.

In addition to viral transfer methods, such as those illustrated above, non-viral methods can also be employed to cause expression of an IRDBP-1-protein, or an IRDBP-1 antisense molecule, in the tissue of an animal. Most non-viral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject IRDBP-1 gene by the targeted cell. Exemplary gene delivery systems of this type include liposomal derived systems, poly-lysine conjugates, and artificial viral envelopes.

In a representative embodiment, a gene encoding one of the subject IRDBP-1 proteins can be entrapped in liposomes bearing positive charges on their surface (e.g., lipofectins) and (optionally) which are tagged with antibodies against cell surface antigens of the target tissue (Mizuno et al. (1992) NO Shinkei Geka 20:547-551; PCT publication WO91/06309; Japanese patent application 1047381; and European patent publication EP-A-43075), and which are incorporated herein in their entireties. For example, lipofection of papillomavirus infected epithelial cells can be carried out using liposomes tagged with monoclonal antibodies against, for example, squamous cells.

In similar fashion, the gene delivery system comprises an antibody or cell surface ligand that is cross-linked with a gene binding agent such as polylysine (see, for example, PCT publications WO93/04701, WO92/22635, WO92/20316, WO92/19749, and WO92/06180), and which are incorporated herein in their entireties. For example, an IRDBP-1 gene construct encoding an antagonistic form of the protein, e.g. a dominant negative mutant, can be used to transfect HPV-infected squamous cells in vivo using a soluble polynucleotide carrier comprising an HPV viral coat protein conjugated to a polycation, e.g. poly-lysine (see U.S. Pat. No. 5,166,320). It will also be appreciated that effective delivery of the subject nucleic acid constructs via receptor-mediated endocytosis can be improved using agents which enhance escape of gene from the endosomal structures. For instance, whole adenovirus or fusogenic peptides of the influenza HA gene product can be used as part of the delivery system to induce efficient disruption of DNA-containing endosomes (Mulligan et al. (1993) Science 260-926; Wagner et al. (1992) Proc. Natl. Acad. Sci. 89:7934; and Christiano et al. (1993) Proc. Natl. Acad. Sci. 90:2122), and which are incorporated herein in their entirety.

In clinical settings, the gene delivery systems can be introduced into a patient by any of a number of methods, each of which is familiar in the art. For instance, a pharmaceutical preparation of the gene delivery system can be introduced systemically, e.g. by intravenous injection, and specific transduction of the gene into the target cells relies predominantly on the specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) Proc. Natl. Acad. Sci. 91: 3054-3057), both of which references are incorporated herein in their entireties.

Moreover, the phamnaceutical preparation can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral packages, the pharmaceutical preparation can comprise one or more cells which produce the gene delivery system. In the case of the latter, methods of introducing the viral packaging cells may be provided by, for example, rechargeable or biodegradable devices. The generation of such implants is generally known in the art. See, for example, Concise Encyclopedia of Medical & Dental Materials, ed. by David Williams (MIT Press: Cambridge, Mass., 1990); Sabel et al. U.S. Pat. No. 4,883,666; Aebischer et al. U.S. Pat. No. 4,892,538; Aebischer et al. U.S. Pat. No. 5,106,627; Lim U.S. Pat. No. 4,391,909; Sefton U.S. Pat. No. 4,353,888; and Aebischer et al. (1991) Biomaterials 12:50-55), and which are incorporated herein in their entireties.

Further, IRDBP-1 encoding sequences of the invention are useful in increasing production of recombinant IGFBP-3 for treatment of the aforementioned diseases, including GH deficiencies and complications caused by increased unbound IGF, can be accomplished by administration of recombinant IGFBP-3 (for example, produced in cell culture) via pharmaceutical compositions. Production of IGFBP-3 from recombinant cells can be increased by transfecting such cells with an IRDBP-1 encoding sequence either under the control of its own or a heterologous promoter.

IRDBP-1 polypeptides of the present invention are also useful in the treatment of growth hormone disorders, especially those where IGFBP-3 levels are below normal. IRDBP-1 is formulated into a pharmaceutical composition for parenteral administration, and a therapeutical dose is administered, with the result of raising IGFBP-3 and IRDBP-1 levels in the treated patient.

The presence of micro-satellite DNA downstream of the IRDBP-1 coding sequence is also further noted. Expression of the IRDBP-1 coding sequence is greater in the presence than absence of this micro-satellite DNA. Probes and/or primers for analysis of this region may allow the identification of genetic diseases associated with aberrant IRDBP-1 expression.

Antisense/Sense Nucleic Acid Modulation of IRDBP-1 Gene Expression

Another aspect of the invention relates to the use of the isolated nucleic acid in "antisense" therapy. An antisense construct of the present invention can be delivered, for example, as an expression plasmid which, when transcribed in the cell, produces RNA which is complementary to at least a unique portion of the cellular mRNA which encodes a IRDBP-1-protein, e.g. the rat or human IRI)BP-1 nucleic acid sequences represented in SEQ ID NOS: 2, 5-10, 14, and 44-45, as described in Example 21. Alternatively, the antisense construct can be an oligonucleotide probe which is generated ex vivo and which, when introduced into the cell causes inhibition of expression by hybridizing with the mRNA and/or genomic sequences encoding one of the subject IRDBP-1 proteins. Such oligonucleotide probes are preferably modified oligonucleotides that are resistant to endogenous nucleases, e.g. exonucleases and/or endonucleases, and are therefore stable in vivo. Exemplary nucleic acid molecules for use as antisense oligonucleotides are phosphoramidate, phosphorothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der Krol et al. (1988) Biotechniques 6: 958-976; and Stein et al. (1988) Cancer Res. 48: 2659-2668 and which are incorporated herein in their entirety.

Accordingly, the modified oligomers of the invention are useful in therapeutic, diagnostic, and research contexts. Inhibition of cell proliferation may result, but this condition may be desirable where, for example, proliferation may lead to a pathological condition such as, but not limited to a blockage of a blood vessel after angioplasty, or proliferation of endothelial cells for angiogenesis in tumor formation. An increase in cell regulation may result, but this condition may be desirable where, for example, a deterioration or deficiency in the number of cells results in a pathological condition such as, but not limited to, a progressive decrease in neural cells, or muscular atrophy. In therapeutic applications, the oligomers are utilized in a manner appropriate for antisense therapy in general. For such therapy, the oligomers of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind. Such diagnostic tests are described in further detail below.

Transgenic Animals

Another aspect of the present invention concerns transgenic animals, such as, but not limited to animal models for diabetes, obesity, mood disorders, developmental and, proliferative diseases, that are comprised of cells (of that animal)

which contain a transgene of the present invention and which preferably (though optionally) express the subject IRDBP-1 in one or more cells in the animal. In embodiments of the present invention, therefore, the expression of the transgene is restricted to specific subsets of cells, tissues or developmental stages utilizing, for example, cis-acting sequences that control expression in the desired pattern. In the present invention, such mosaic expression of the subject IRDBP-1 proteins can be essential for many forms of lineage analysis and can additionally provide a means to assess the effects of IRDBP-1 mutations or overexpression that might grossly alter development in small patches of tissue within an otherwise normal embryo. Toward this end, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques that allow for the expression of transgenes can be regulated via site-specific genetic manipulation in vivo are well known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject receptor. For example, excision of a target sequence that interferes with the expression of the receptor can be designed to activate expression of that protein. This interference with expression of the subject protein can result from a variety of mechanisms, such as spatial separation of the IRDBP-1 gene from the promoter element or an internal stop codon. Moreover, the transgene can be made wherein the coding sequence of the IRDBP-1 gene is flanked by recombinase recognition sequences and is initially transfected into cells in a 3' to 5' orientation with respect to the promoter element. In such an instance, inversion of the target sequence will reorient the subject IRDBP-1 gene by placing the 5' end of the coding sequence in an orientation with respect to the promoter element that allow for promoter driven transcriptional activation.

In an illustrative embodiment, either the cre/loxP recombinase system of bacteriophage P1 (Lakso et al. (1992) Proc. Natl. Acad. Sci. 89:6232-6236; Orban et al. (1992) Proc. Natl. Acad. Sci. 89:6861-6865) or the FLP recombinase system of *Saccharomyces cerevisiae* (O'Gorman et al. (1991) Science 251:1351-1355; PCT publication WO 92/15694), and which are incorporated herein in their entireties, can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) J. Biol. Chem. 259:1509-1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation of expression of the recombinant UBC9 gene can be regulated via regulation of recombinase expression.

Use of the these recombinase system to regulate expression of, for example, a dominant negative IRDBP-1 gene, or an antisense gene, requires the construction of a transgenic animal containing transgenes encoding both the Cre recombinase and the subject gene. Animals containing both the Cre recombinase and the IRDBP-1 genes can be provided through the construction of "double" transgenic animals. A convenient method for providing such animals is to mate two transgenic animals each containing a transgene, e.g., one harboring the IRDBP-1 gene, and the other harboring the recombinase gene.

One advantage derived from initially constructing transgenic animals containing a IRDBP-1 transgene in a recombinase-mediated expressible format derives from the likelihood that the subject IRDBP-1 protein, whether antagonistic or agonistic, will be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues, or in a developmentally restricted pattern. Thus, the creation of a founder population in which, for example, an antagonistic IRDBP-1 transgene is silent will allow the study of progeny from that founder in which disruption of IRDBP-1-mediated insulin responsiveness in a particular tissue or at certain developmental stages could result in, for example, a lethal phenotype.

Similar conditional transgenes can be provided using prokaryotic promoter sequences which require prokaryotic proteins to be simultaneous expressed in order to facilitate expression of the transgene. Operators present in prokaryotic cells have been extensively characterized in vivo and in vitro and can be readily manipulated to place them in any position upstream from or within a gene by standard techniques. Such operators comprise promoter regions and regions which specifically bind proteins such as activators and repressors. One example is the operator region of the lexA gene of *E. coli* to which the LexA polypeptide binds. Other exemplary prokaryotic regulatory sequences and the corresponding trans-activating prokaryotic proteins are given in U.S. Pat. No. 4,833,080. Thus, as described above for the recombinase-mediated activation, silent transgenic animals can be created which harbor the subject transgene under transcriptional control of a prokaryotic sequence that is not appreciably activated by eukaryotic proteins. Breeding of this transgenic animal with another animal that is transgenic for the corresponding prokaryotic trans-activator, can permit activation of the IRDBP-1 transgene. Moreover, expression of the conditional transgenes can be induced by gene therapy-like methods (such as described above) wherein a gene encoding the trans-activating protein, e.g. a recombinase or a prokaryotic protein, is delivered to the tissue and caused to be expressed, such as in a cell-type specific manner. By this method, the IRDBP-1 transgene could remain silent into adulthood until "turned on" by the introduction of the trans-activator.

Additionally, inducible promoters can be employed, such as the tet operator and the metallothionein promoter which can be induced by treatment with tetracycline and zinc ions, respectively (Gossen et al. (1992) Proc. Natl. Acad. Sci. 89:5547-5551; and Walden et al. (1987) Gene 61:317-327), and which are incorporated herein in their entirety.

Methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert recombinase target sequences flanking portions of an endogenous IRDBP-1 gene, such that tissue specific and/or temporal control of inactivation of an IRDBP-1 allele can be controlled as above. Furthermore, the present invention, by making available purified and recombinant forms of the subject IRDBP-1 proteins, will allow the development of assays which can be used to screen for drugs which either agonize or antagonize the function of IRDBP-1 in vivo.

Screening for IRDBP-1 Agonists/Antagonists

Assays for the measurement of IRDBP-1 can be generated in many different forms, and include assays based on cell-free systems, e.g. purified proteins or cell lysates, as well as cell-based assays which utilize intact cells. Such agents can be used, for example, in the treatment of diabetic or feeding disorders, proliferative and/or differentiative disorders, and to modulate cellular metabolism.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target. Accordingly, potential inhibitors of IRDBP-1 function can be detected in a cell-free assay generated by constitution of a functional IRDBP-1/target nucleic acid sequence in a cell lysate.

Another aspect of the present invention concerns three-dimensional molecular models of the subject IRDBP-1 proteins, and their use as templates for the design of agents able to inhibit at least one biological activity of the IRDBP-1 protein. An integral step to designing inhibitors of the subject IRDBP-1 involves construction of computer graphics models of the IRDBP-1 that can be used to design pharmacophores by rational drug design. For instance, for an inhibitor to interact optimally with the subject protein, it will generally be desirable that it have a shape which is at least partly complimentary to that of a particular binding site of the protein, as for example those portions of the human IRDBP-1 that are involved in recognition of a particular region of a nucleic acid sequence. Additionally, other factors, including electrostatic interactions, hydrogen bonding, hydrophobic interactions, desolvation effects, and cooperative motions of ligand and enzyme, all influence the binding effect and should be taken into account in attempts to design bioactive inhibitors.

A computer-generated molecular model of the subject protein can be created by homology modeling, and then calculate the structure of the protein and velocities of each atom at a simulation temperature. Computer programs for performing energy minimization routines are commonly used to generate molecular models. For example, both the CHARMM (Brooks et al. (1983) J. Comput. Chem. 4:187-217) and AMBER (Weiner et al (1981) J. Comput. Chem. 106: 765) algorithms handle all of the molecular system setup, force field calculation, and analysis (see also, Eisenfield et al. (1991) Am. J. Physiol. 261:C376-386; Lybrand (1991) J Pharm. Belg. 46:49-54; Froimowitz (1990) Biotechniques 8:640-644; Burbam et al. (1990) Proteins 7:99-111; Pedersen (1985) Environ Health Perspect. 61:185-190; and Kini et al. (1991) J. Biomol. Struct. Dyn. 9:475488), and which are incorporated herein in their entirety.

Moreover, a number of programs are presently available for virtual design of IRDBP-1 protein inhibitors. For instance, the increasing availability of biomacromolecule structures of potential pharmacophoric molecules that have been solved crystallographically has prompted the development of a variety of direct computational methods for molecular design, in which the steric and electronic properties of substrate binding sites are used to guide the design of potential inhibitors (Cohen et al. (1990) J. Med. Cam. 33: 883-894; Kuntz et al. (1982) J. Mol. Biol. 161: 269-288; Desjarlais (1988) J. Med. Cam. 31: 722-729; Bartlett et al. (1989) Spec. Publ., Roy. Soc. Chem. 78: 182-196; Goodford et al. (1985) J. Med. Cam. 28: 849-857; Desjarlais et al. J. Med. Cam. 29: 2149-2153), and which are incorporated herein in their entireties. Most algorithms of this type provide a method for finding a wide assortment of chemical structures that are complementary to the shape of a binding site of the subject protein. Each of a set of small molecules from a particular data-base, such as the Cambridge Crystallographic Data Bank (CCDB) (Allen et al. (1973) J. Chem. Doc. 13: 119), is individually docked to a nucleic acid or other ligand binding site of the IRDBP-1 protein in a number of geometrically permissible orientations with use of a docking algorithm. In an illustrative embodiment, a set of computer algorithms called DOCK, can be used to characterize the shape of invaginations and grooves that form the active sites and recognition surfaces of the subject protein (Kuntz et al. (1982) J. Mol. Biol. 161: 269-288). The program can also search a database of small molecules for templates whose shapes are complementary to particular binding sites of the protein (Desjarlais et al. (1988) J. Med. Chem. 31: 722-729). These templates normally require modification to achieve good chemical and electrostatic interactions (Desjarlais et al. (1989) ACS Symp. Ser. 413: 60-69). However, the program has been shown to position accurately known cofactors for inhibitors based on shape constraints alone.

Other exemplary virtual drug design programs include GRID (Goodford (1985, J. Med. Chem. 28:849-857); Boobbyer et al. (1989) J. Med. Chem. 32:1083-1094), CLIX Lawrence et al. (1992) Proteins 12:31-41), GROW (Moon et al. (1991) Proteins 11:314-328), the multiple copy simultaneous search method (MCSS) (described by Miranker et al. (1991) Proteins 11: 29-34), and NEWLEAD (Tschinke et al. (1993) J. Med. Chem. 36: 3863,3870), which are incorporated herein in their entireties.

The present invention is further illustrated by the following examples, which are provided by way of illustration and should not be construed as limiting. The contents of all references, published patents and patents cited throughout the present application are hereby incorporated by reference in their entirety.

EXAMPLE 1

Cloning of cDNAs Encoding IRSBP

An isolated nucleic acid with the IRE associated with the IGFBP-3 gene and comprising the nucleotide sequence SEQ ID NO: 1 was multimerized as follows. Two antiparallel oligonucleotides, one representing the sense strand of SEQ ID NO: 1, and the other its antisense complement were annealed. The resulting double-stranded DNA was phosphorylated with T4 polynucleotide kinase, concatemerized with T4 DNA ligase at 22° C. for 5 minutes, and electrophoretically fractionated on a polyacrylamide gel. A fragment containing three contiguous copies of the annealed oligonucleotides was inserted into the pHISi reporter vector (Clontech, Palo Alto, Calif.), and transformed into the yeast *Saccharomyces cerevisiae* strainYM4271 (Clontech, Palo Alto, Calif.).

Southern blotting confirmed the integration of the multimerized IRE nucleic acid sequence into the yeast genome. Southern blotting was carried out using prehybridization and hybridization buffers containing 1% w/v BSA, 1 mM EDTA. 0.5 M $NaHPO_4$, pH 7.2, and 7% w/v SDS. Hybridization was done with the radiolabeled multimerized IRE of IGFBP-3 with $^{32}P$ as the radiolabel. The radioactive probe was added at a concentration of 1-2×$10^6$ cpm/ml. After hybridization, blots were washed twice with 2×SSC, 0.1% SDS for 30 mins., followed by a 30 min. wash with 0.1×SSC, 0.1% SDS at 50° C., and autoradiography. The procedure was as described in Ausubel et al. (1993) incorporated herein by reference in its entirety A rat liver cDNA library was screened using a yeast one-hybrid system, as described by Chong et al., (1995) Cell 80: 949-957 and Li & Herskowitz, (1993) Science 1252: 1870-1873, incorporated herein by reference in their entireties. The yeast one-hybrid system is an in vivo genetic assay that uses growth selection based on reconstruction and activation of the nutritional reporter gene HIS3. A nucleic acid fragment comprising three contiguous repeats of the IGFBP-3 IRE (SEQ ID NO: 1) was inserted in the region 5' upstream of a HIS3 reporter under the control of a GAL4-responsive promoter. The construct was transformed into yeast cells.

Yeast containing the IRE target nucleic acid sequence SEQ ID NO: 1 were transformed with DNA purified from an activation domain (AD) library that contained fusions between a target-independent activation domain (GAL4 AD) and cDNA derived from a normal rat liver. Colonies of yeast were selected on $His^-Leu^-$ plates and their plasmid contents were isolated. Positive clones were confirmed by retransformation of the cDNA into yeast containing a Lac Z reporter gene with tandem repeats of the IRE target nucleic acid, and tested for transcriptional activation of the GAL4 promoter.

Seventy-nine clones were found which grew on $His^-Leu^-$ plates containing 15 mM 3-amino-1,2,4-triazole (Sigma Chemical Co., St. Louis, Mo.). The plasmids from those clones were isolated and transformed into *E. coli*. The isolated cDNAs were sequenced using automated sequencing. The sequences were identified by an NCBI BLAST search for similarity to sequences reported in GenBank.

Two of the clones contained cDNAs encoding the known transcription factors NFkB p65 and HBP1. Eleven out of seventy-nine clones contained novel sequences that were selected for further characterization.

Figure 17B:
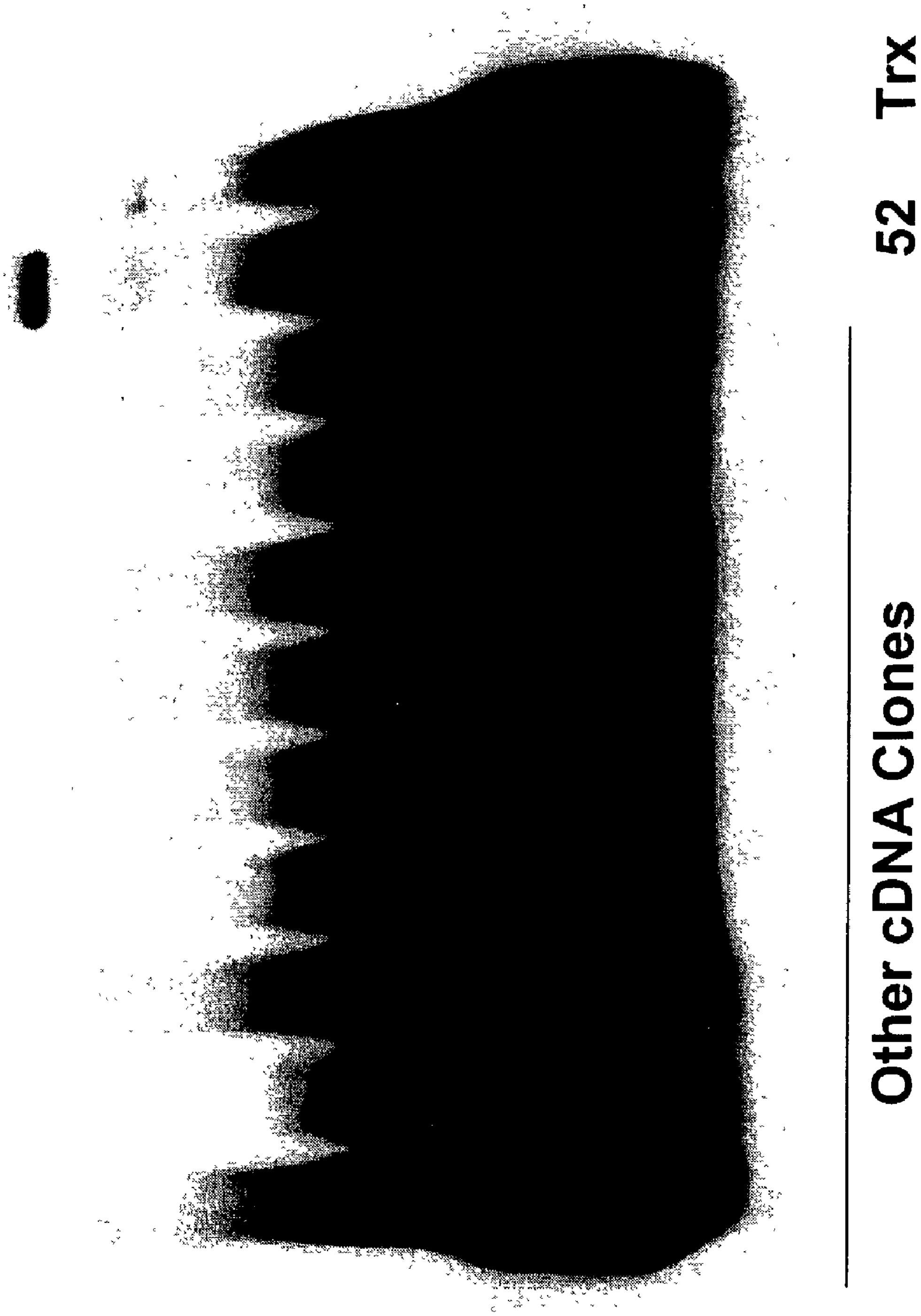
FIG. 17B illustrates gel mobility shift analysis of the −1150/−1117 IRE fragment of IGFBP-3 (SEQ ID NO: 1) by cDNAs expressed as thioredoxin fusion proteins.

Gel Shift Mobility Assays cDNAs from the 11 novel clones were subcloned into the plasmid pSPUTK (Stratagene). The coding regions of the cDNA clones were translated into protein using coupled transcriptional in vitro translation as described by Hook et al. (1996) Peptide Research 9: 183-187 and incorporated herein in its entirety. After translation, the proteins were tested for their ability to bind to the IRE element of IGFBP-3 (SEQ ID NO: 1) by gel mobility shift analysis (FIGS. 17A and 17B).

Gel mobility shift assays were done essentially as described in Villafuerte et al, (1997) J. Biol. Chem. 272: 5024-5030, incorporated herein by reference in its entirety. $^{32}P$-ATP-labeled oligonucleotides corresponding to nucleotide positions −1150 to −1117 bp-fragment (SEQ ID NO: 1) of the rat IGFBP-3 gene were incubated with the proteins derived from the cDNA clones at concentrations of approximately 20 ng protein per lane in 25 μl of binding buffer containing 10 mM Tris, pH 7.6, 50 mM KCl, 1 mM EDTA, 0.5 mM dithiothreitol, 0.2% Nonidet P-40, 20 μg of bovine serum albumin, 36 μg of salmon sperm DNA, and 10% glycerol at 25° C. for 20 mins. Incubations were carried out with or without unlabeled competitor DNA. Protein-DNA complexes were separated from free probe on 6% polyacrylamide gels in 0.25.×TBE at 12 V/cm for 2-3 hours, and visualized by autoradiography.

One clone of the eleven, clone 52 contained a 952 bp cDNA insert (SEQ ID NO: 2, shown in FIG. 1) that encoded a polypeptide (SEQ ID NO: 3, shown in FIG. 2) that formed a DNA-protein complex. The clone 52 nucleic acid sequence (SEQ ID NO: 2) comprises 952 bp of sequence capable of hybridizing to a second IRDBP-1 nucleic acid sequences SEQ ID NOS: 5, 14 and 44 shown in FIGS. 4A-4B, and 12A-12B and 6 respectively, and to a region of the human genomic sequence having the GenBank Accession number AC005237.

Figure 18:
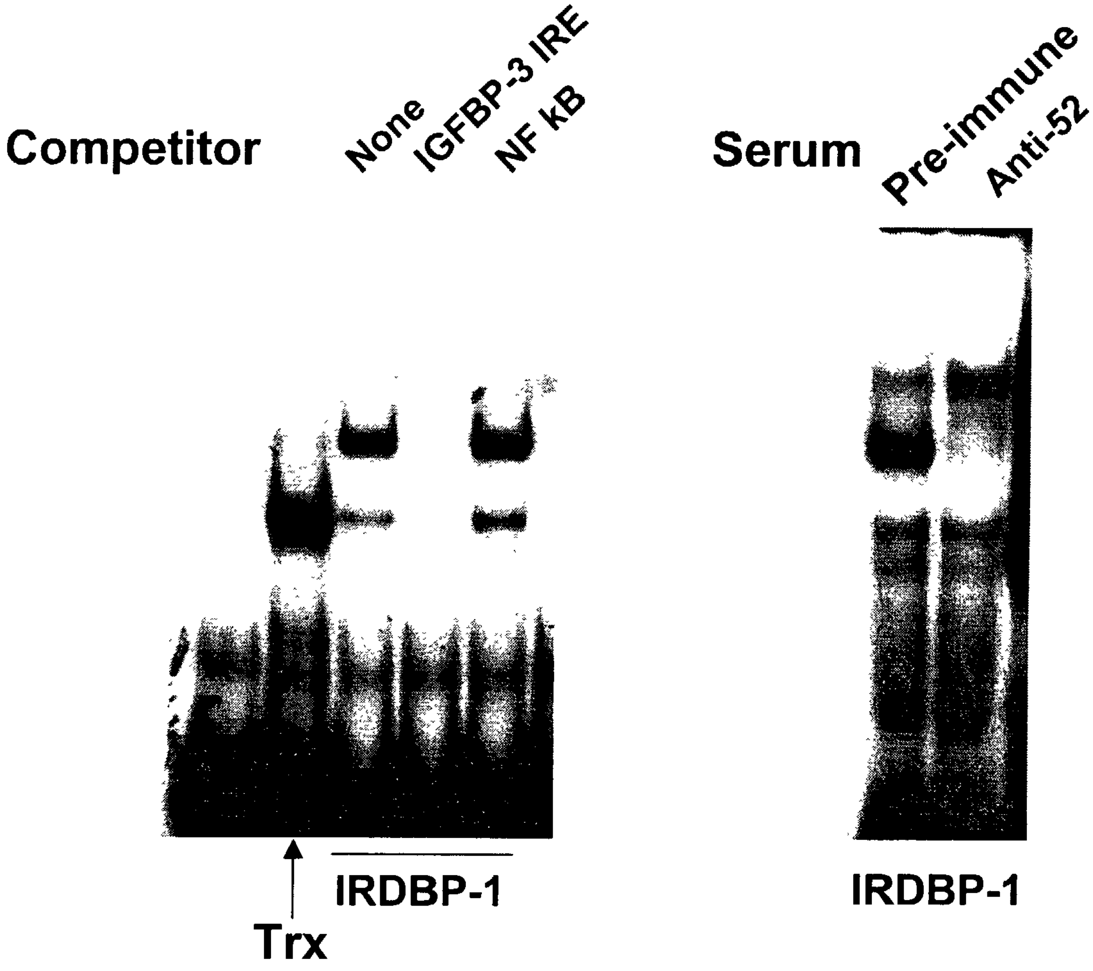
FIG. 18 illustrates a competition-binding assay of the polypeptide encoded by clone 52 binding to the −1150/−1117 bp IRE fragment of IGFBP-3 (SEQ ID NO: 1).
Figure 19:
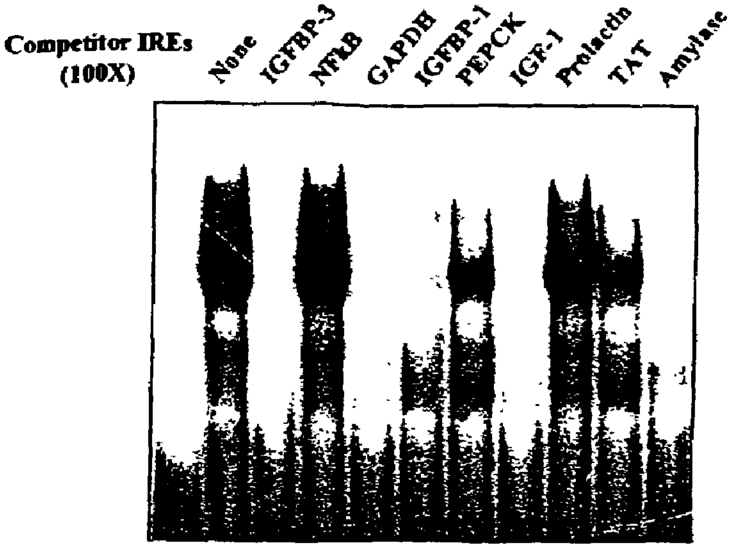
FIG. 19 illustrates IREs derived from other genes competing with the IRE of IGFBP-3 (SEQ ID NO: 1) for binding to the protein product of clone 52.

The specificity of binding was established by using 25 pmoles of labeled or unlabeled IGFBP-3 IRE (SEQ ID NO: 1) as shown in FIG. 18. Excesses of unlabeled IGFBP-3 IRE and NFκB were incubated with about 20 ng protein per lane. The double-stranded DNA competitors were added at molar concentrations between about 10-fold and about 100-fold greater than labeled oligonucleotides, or 2.5 pmole, 12.5 pmole and 25 pmole, and electrophoresed on a 6% polyacrylamide gel.

cDNA coding sequences were also expressed as thioredoxin (Trx) fusion proteins in *E. coli*. The clone 52 cDNA (SEQ ID NO: 2) was subcloned in-frame into a prokaryotic expression vector (pET-32a from Novagen, Madison, Wis.), transformed into the AD494(DE3) strain of *E. coli*, and grown in culture until $OD_{600}$0.6. IPTG (isopropyl-β-thiogalactopyranoside) was added to a final concentration of 1 mM three hours before harvest. The thioredoxin-clone 52 fusion protein was purified by affinity chromatography on immobilized His-bound metal chelation resin (Novagen), and used in a gel-shift assays, as shown in FIGS. 17A, 17B and 18. The fusion proteins were tested in additional gel mobility shift experiments with the IGFBP-3 IRE nucleic acid (SEQ ID NO: 1) as describe above. While not wishing to be bound by any particular theory, the IRE of IGFBP-3 (SEQ ID NO: 1) includes an AGGAAAGTCTCCTTpalindrome, and the leucine zipper encourages dimerization, and gel shift bands seen in FIGS. 17A-18 reflect binding of IRDBP-1 to the IGFBP-3 IRE as a homodimer and monomer, respectively. Competiton assays demonstrate that IREs associated with other insulin-responsive genes compete with the IRE of IGFBP-3 (SEQ ID NO: 1) for binding to IRDBP-1, as shown in FIG. 19.

EXAMPLE 2

Sequencing of cDNA Clones

Single-strand sequencing of cDNA clones use an Applied Biosystems Automated DNA Sequencer and a PCR-based fluorescent dideoxy method, according to the recommendations of the manufacturer. The partial rat IRDBP-1 cDNA clone 52 (SEQ ID NO: 2) is shown in FIG. 1. The longest open-reading frame amino acid sequence derived from SEQ ID NO: 2 is SEQ ID NO: 3, as shown in FIG. 2.

EXAMPLE 3

Expression of Clone 52 mRNAs Using Northern Blot Analysis

Figure 20:
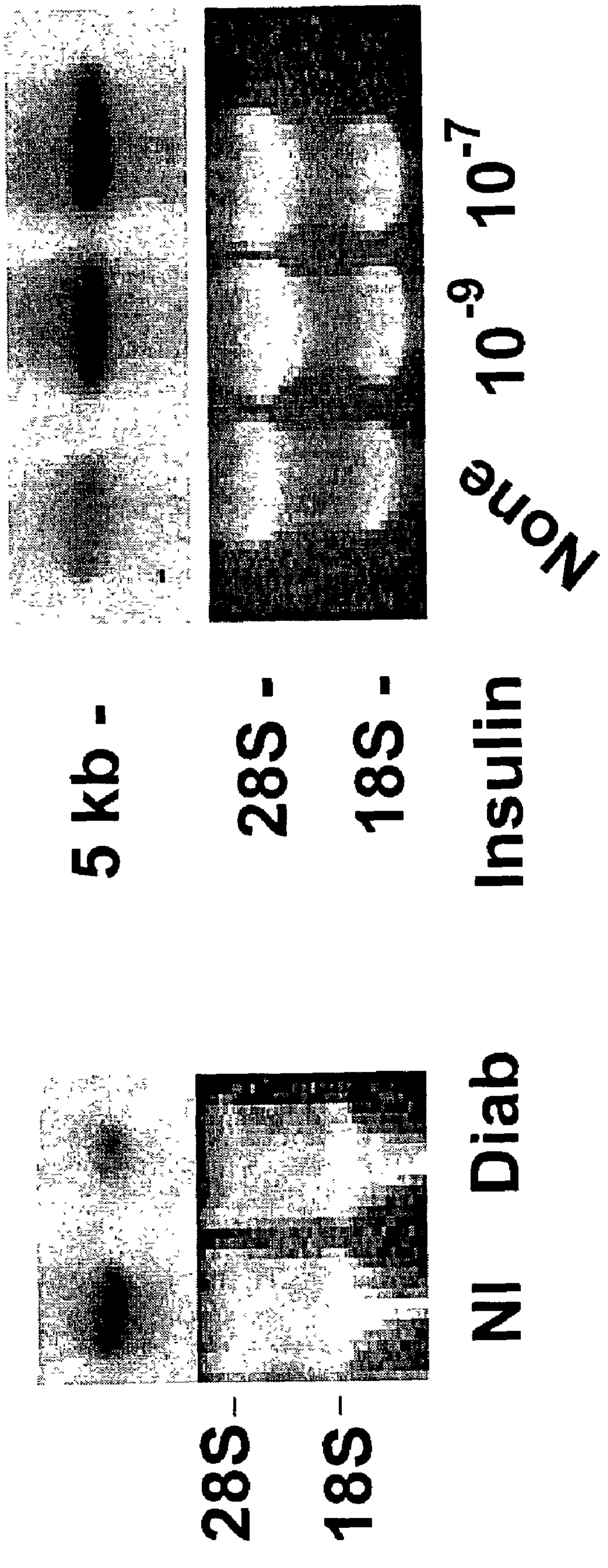
FIG. 20 illustrates the expression of IRDBP-1 in the liver and other tissues. A Northern blot of RNAs from hepatic nonparenchymal cells (50 μg/lane) treated with or without insulin for 24 hours (left panel) and from normal and streptozotocin-diabetic rat livers (right panel) were probed with the 3.4 kb IRDBP-1 probe.

Total RNA was isolated from cultured hepatic non-parenchymal cells using a Tri-Reagent Kit (Molecular Research Center, Cincinnati, Ohio) according to the manufacturer's protocol. Clone 52 cDNA (SEQ ID NO: 2) containing the 952 bp cDNA nucleic acid obtained from the yeast one-hybrid screen as described in Example 1, was random primer labeled with [$^{32}$P] dCTP and used as a probe to hybridize with RNA electrophoresed on 1.2% formaldehyde-agarose gel using protocols described by Ausubel et al. (1993) and incorporated herein by reference in its entirety, as shown in FIG. 20.

Northern analysis showed that hepatic cells expressed an mRNA species of at least 5.0 kb in length. Densitometric analysis of IRDBP-1 expression normalized to β-actin expression showed that IRDBP-1 expression levels were highest in the brain and muscle, followed by liver, small intestine, kidney, subcutaneous fat, and spleen, as shown in FIG. 21B. Tissue distribution in adipose tissues is shown in FIG. 21C. IRDBP-1 is, therefore, distributed to target tissues known to be critical for the peripheral and central actions of insulin, and IRDBP-1 expression is responsive to the insulin/diabetes status of the RNA source.

The membrane was hybridized with a radiolabelled human IRDBP-1 probe. IRDBP-1 is highly expressed in the jejenum, ascending colon, descending colon, transverse colon, cecum and rectum. A multiple tissue Northern blot from Clontech Laboratories, Inc (Palo Alto, Calif.) contained 2 μg of polyadenylayed RNA per lane isolated from various human tissues. The RNA was analyzed on a formaldehyde-agarose gel, and transferred to anylon membrane. The mRNA was expressed as two transcripts of about 9 kb and 6 kb. While not wishing to be bound by any one theory, this result may indicate alternative splicing or differential adenylation. The high expression of the IRDBP-1 in the gastro-intestinal tract shows its importance in the physiologic functioning of this system.

Use of a 250 bp β-actin and a 170 bp IRDBP-1 probe for ribonuclease protection studies demonstrated expression of IRDBP-1 in multiple organs (FIG. 21 A). The RNase Protection assay utilized a Kpnl/Xhol fragment of the 3.4 kb IRDBP-1 cDNA that was inserted into pGEM 7Z and transcribed in vitro to produce a 170 nt antisense probe. The assays were carried out using a Hybspeed RPA kit (Ambion, Austin, Tex.) according to the manufacturer's protocol.

EXAMPLE 4

Interactions with Other Insulin-response Binding Proteins

Figure 23:
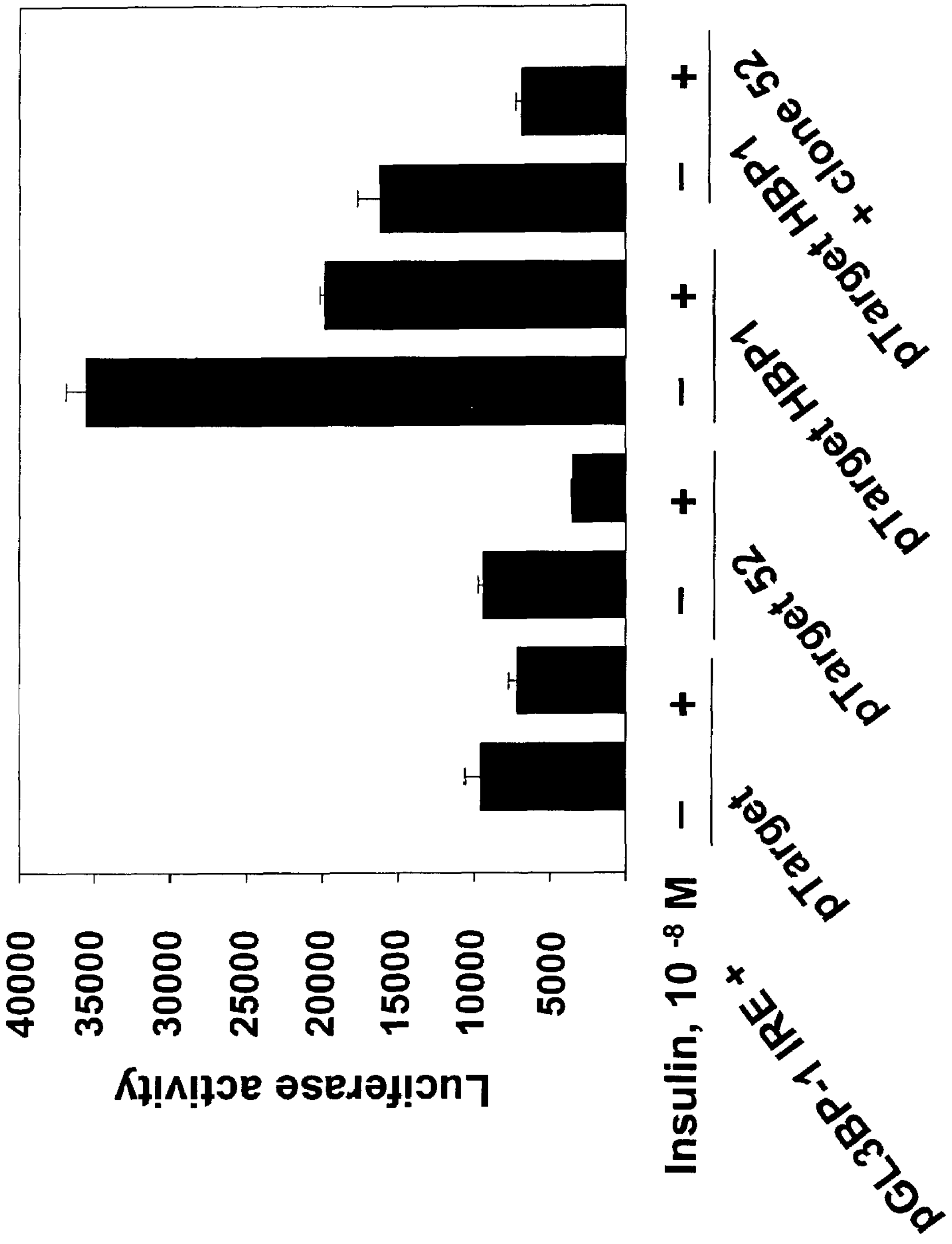
FIG. 23 illustrates IGFBP-1 IRE reporter activity in CHO cells transfected with a vector containing HBP1-encoding sequence or a rat IRDBP-1-encoding sequence (SEQ ID NO: 5 cotransfected with vectors), or the two vectors (each vector having the IRDBP-1 or HBP1-encoding sequence) were cotransfected.

CHO cells were co-transfected with a IGFBP-1 IRE reporter construct and combinations of vectors containing an IRDBP-1 cDNA (SEQ ID NO: 2) or DNA encoding for HBP1. Cells were prepared and transfected as described in Example 7. Luciferase activity was measured as described in Example 7. The IRE identified from the IGFBP-1 is described in Cichy et al. (1998) J. Biol. Chem. 273: 6483-6487; O'Brien et al. (1994) J. Biol. Chem. 269: 30419-30428 and incorporated herein in their entireties. HBP-1 induced the formation of luciferase in the absence of IRDBP-1 or insulin, (as shown in FIG. 23). Cotransfection with the IRDBP-1-encoding cDNA reduced the activation of the IGFBP-1 IRE and decreased the luciferase expression. Induction of cellular IRDBP-1 by insulin reduced luciferase levels still further.

Figure 24:
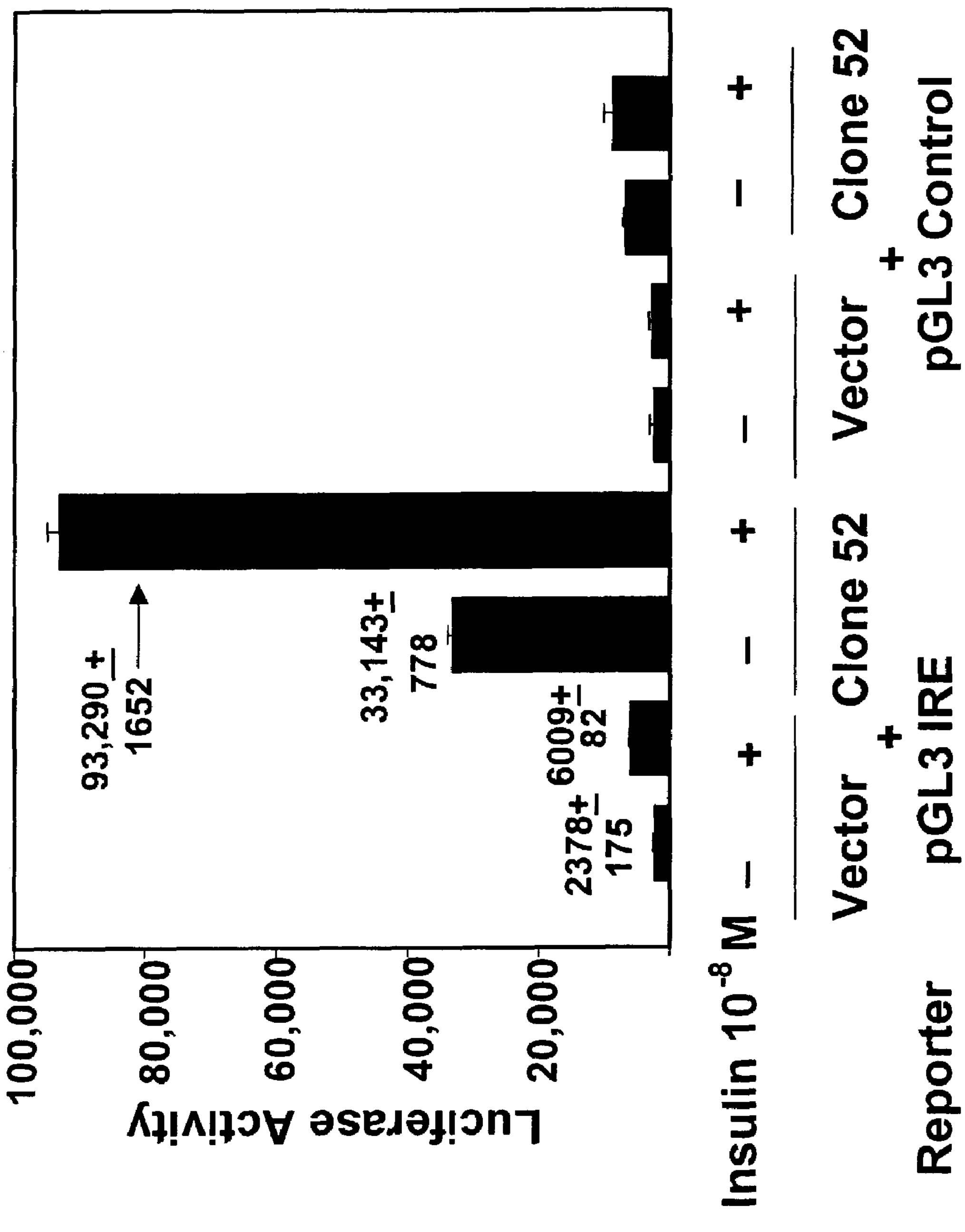
FIG. 24 illustrates the effect of insulin on IGFBP-3 IRE-regulated reporter gene activity in response to the addition of insulin to cultured cells containing either expression vector or expression vector with SEQ ID NO: 5 therein.

The IREs were used to construct multimers as described in Example 1, inserted into the pGL3 promoter vector (Promega., Madison, Wis.) and transfected into COS7 cells. Such cells showed an increase in luciferase reporter activity augmented by the addition of insulin to the media, as shown in FIG. 24.

EXAMPLE 5

Anti-IRDBP-1 Antibodies

Antibodies were developed to oligopeptides corresponding to the carboxy-terminal segment (cAb) and the amino-segment (nAb) of rat IRDBP-1. The C-segment antibody cAb was raised against an epitope of the rat IRDBP-1 protein between amino acids 786-800 of the protein having sequence SEQ ID NO: 47, and had the following sequence: AcetylatedCys-Thr-Ser-Gln-Asn-Thr-Lys-Ser-Arg-Tyr-Ile-Pro-Asn-Gly-Lys-Leu (SEQ ID NO: 15). To develop the N-segment specific antibody nAb, the peptide fragment between IRDBP-1 amino acids 233-247, which had the following sequence: AcetylatedCys-Arg-Asn-Gly-Gly-Thr-Tyr-Lys-Glu-Thr-Gly-Asp-Glu-Tyr-Arg (SEQ ID NO: 46) was used.

In addition, the 1503 bp coding region of the cDNA SEQ ID NO: 44 was expressed in *E. coli* as a His6-tagged thioredoxin (Trx) fusion protein (pET-32, Novagen, Madison, Wis.), and purified with $Ni^{2+}$-nitriloacetate (Qiagen, Valencia, Calif.). The 1.5 kb cDNA was subcloned in-frame into the prokaryotic expression vector pET-32a, transformed into the *E. coli* AD494(DE3) and grown at 37° C. until it reached an $OD_{650}$ of 0.6. IPTG was added to a final concentration of 1 mM three hours before harvest. The fusion protein was purified by affinity chromatography on immobilized His-bind metal chelation resin, and used for gel shift and western analyses.

Figure 25A:
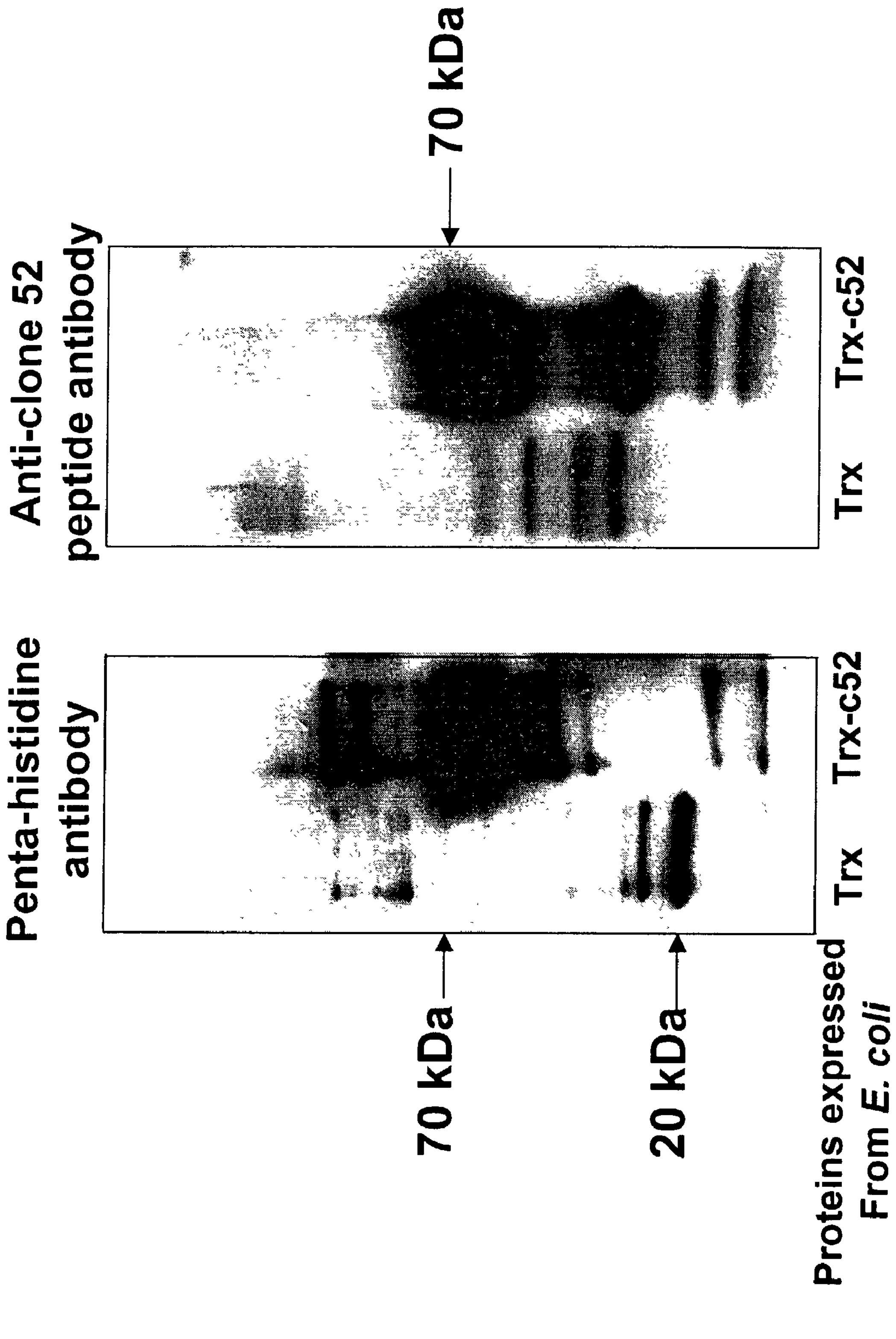
FIG. 25A shows the detection of IRDBP-1 with an attached Trx-His tag using anti-His antibody or anti-IRDBP-1 cAb antibody.
Figure 25B:
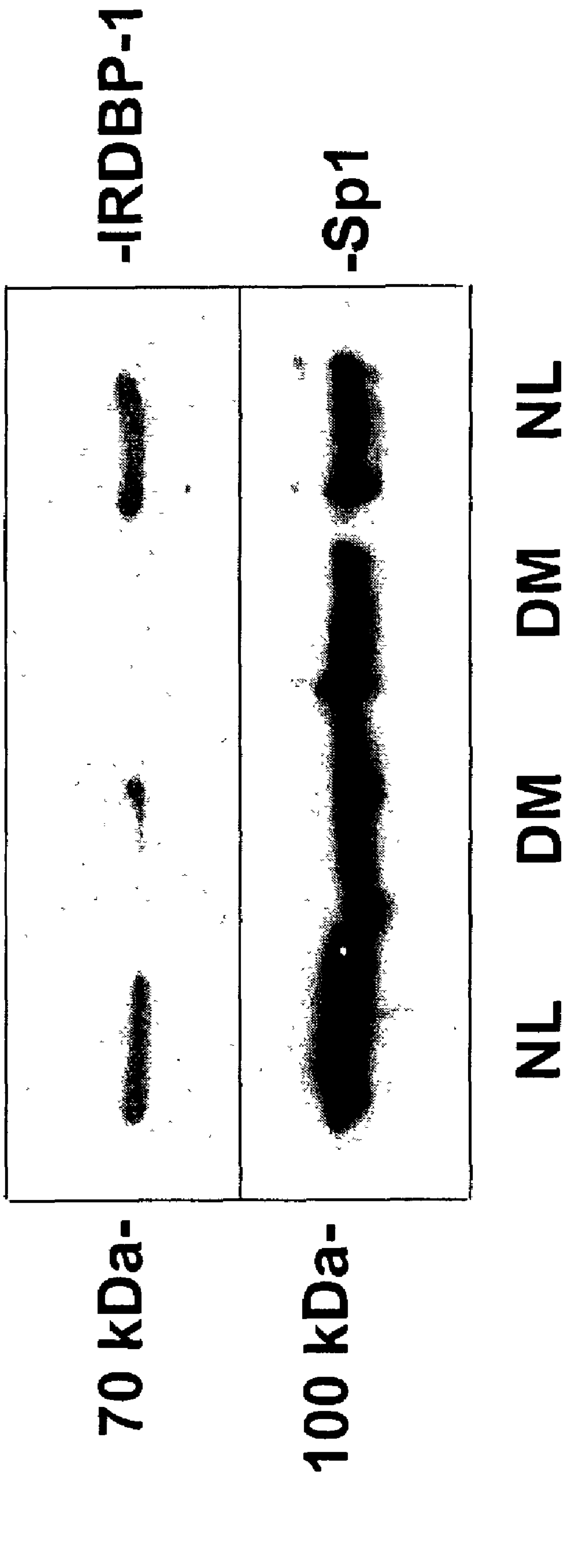
FIG. 25B shows a Western blot of hepatic nuclear extracts from normal and streptozotocin-dibetic rats.

A western blot of the induction control (Trx) and the fusion protein (Trx-IRDBP-1) is shown in FIG. 25A. Both anti-IRDBP-1 cAb and anti-histidine antibodies recognized a 65-70 kDa polypeptide, the size of which is consistent with the predicted size of the fusion protein containing 20 kDa Trx. In western blotting experiments using rat liver nuclear extracts, the anti-IRDBP-1 cAb antibody recognized a 70 kDa protein, as shown in FIG. 25B, consistent with the size of the insulin-responsive protein recognized in southwestern blots by an IGFBP-3 IRE probe. Detectable IRDBP-1-specific band levels were reduced in the livers of streptozotocin-diabetic rats compared to normal rats, indicating insulin-sensitive expression.

Figure 26:
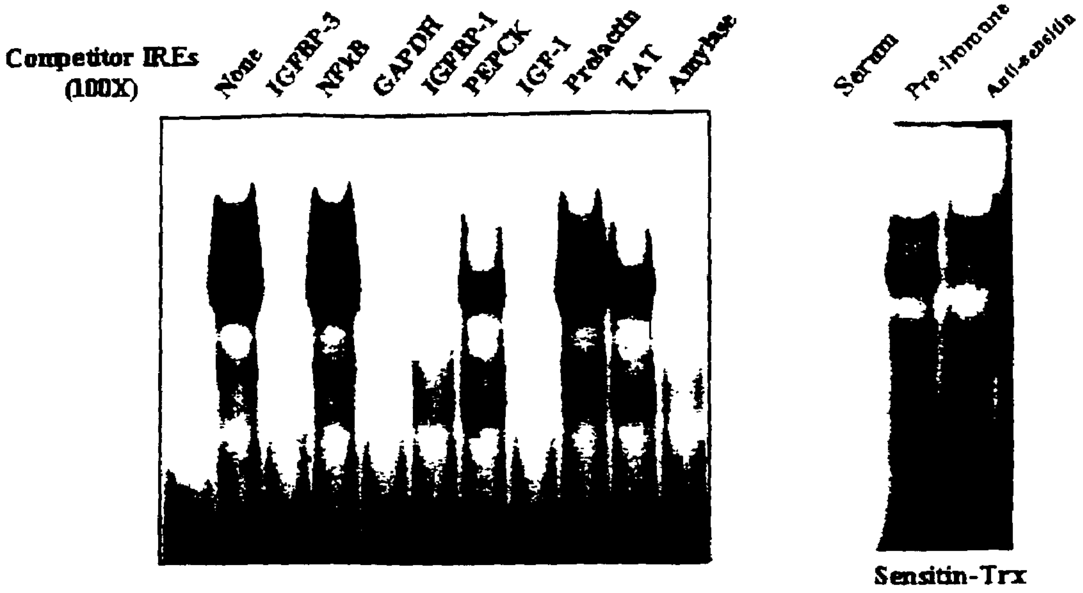
FIG. 26 shows a gel-shift assay with Trx-IRDBP-1 fusion protein and IGFBP-3 IRE.
Figure 27:
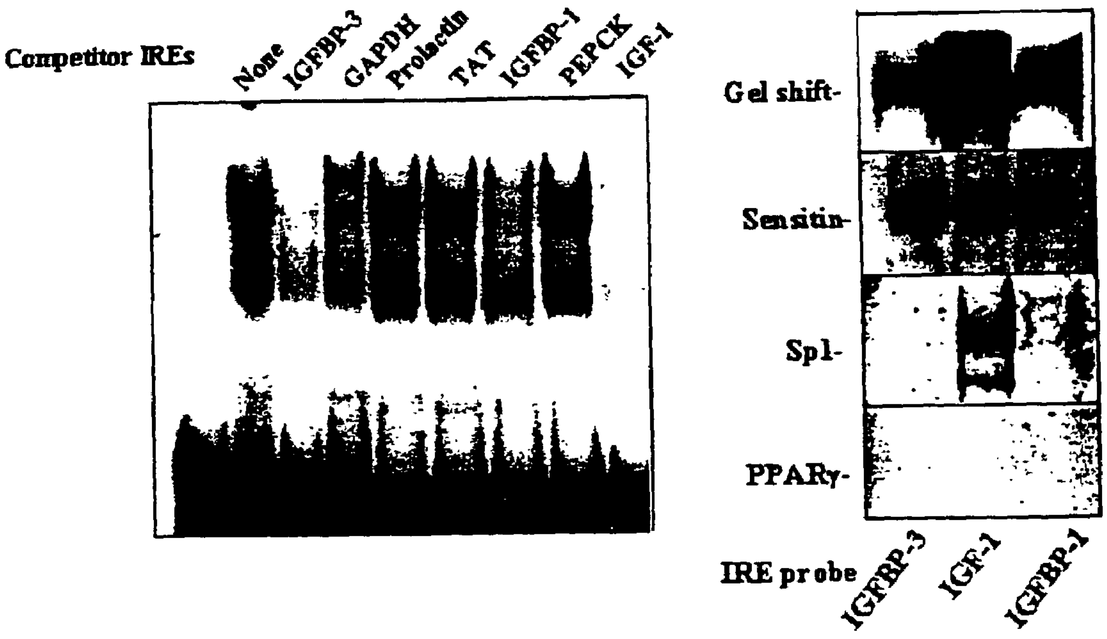
FIG. 27 shows binding of rat hepatic nuclear extracts to IGFBP-3 IRE and secondarily probed with anti-IRDBP-1 cAb or nAb antibody.

The Trx-IRDBP-1 fusion protein also produced a gel shift band with an IGFBP-3 IRE probe, as shown in FIGS. 26 and 27. This band was competed by the IGFBP-3 IRE, but not by the unrelated NFκB oligonucleotide (FIG. 26, left panel). In addition, the gel-shift band was supershifted with the anti-IRDBP-1 cAb antibody, but not with preimmune serum (FIG. 26, right panel).

EXAMPLE 6

Screening of Bacteriophage Human and Rat cDNA Libraries

Because the 952 bp IRDBP-1-encoding clone 52 cDNA (SEQ ID NO: 2) encodes a protein (SEQ ID NO: 3) that contains a binding domain with limited transactivating properties, cDNA sequences (SEQ ID NOS: 5, 6, 14 and 44) were obtained by screening a lambda bacteriophage rat brain cDNA library (Uni-Zap XP library, Stratagene, La Jolla, Calif.) and then extending the cDNAs thus obtained by 5' RACE.

The 952 bp clone 52 cDNA of SEQ ID NO: 2 was used as the nucleic acid probe to screen about $10^8$ plaques. The phage and host *E. coli* were spread on agarose plates and incubated to form plaques, nitrocellulose filters were applied, and the phage particles and unpackaged DNA were adsorbed to the filter to produce a replica of the plate surface. The filters were treated with NaOH to denature the phage DNA, which was then hybridized with the cDNA probe. After isolation of positive plaques that hybridized to the probe, the pBluescript phagemid was rescued with VCSM12 helper phage. The final product is a double-stranded pBluescript phagemid with an inserted DNA. Subsequent rescreening of the library combined with 5' RACE extensions yielded isolated nucleic acids comprising the nucleotide sequence of SEQ ID NO: 5, as shown in FIGS. 4A and 4B, or fragments, variants or derivatives thereof, such as SEQ ID NO: 6 (FIGS. 5A and 5B), SEQ ID NO: 14 (FIGS. 12A and 12B) and SEQ ID NO: 44 (FIG. 13). Automated sequencing confirmed regions within SEQ ID NOS: 5, 6 and 44 having substantially similarity to the nucleotide sequence of rat clone 52 (SEQ ID NO: 2).

To obtain an isolated nucleic acid encoding a region of the human IRDBP-1, the 3404 bp rat cDNA SEQ ID NO: 14 was used to screen a human lambda phage cDNA library (Uni-Zap XR human liver cDNA library, Stratagene, La Jolla, Calif.). Two clones hybridizing to the 3404 bp rat IRDBP-1-specific probe were obtained. One was about 2480 bp long and another clone was about 1700 bp long. Subsequent 5' extensions were obtained by 5' RACE techniques, using the SMART RACE cDNA amplification system from Clontech, Inc, and polyA mRNA isolated from the human cerebellum, until the 4584 bp sequence (SEQ ID NO: 7, shown in FIG. 6A) and the 6331 bp sequence (SEQ ID NO: 45, shown in FIG. 14) were obtained. Overlapping regions of the human IRDBP-1 nucleic acid sequence SEQ ID NO: 45 and the rat IRDBP-1 sequence SEQ ID NO: 44 showed at least 75% similarity when aligned.

Comparison of the human IRDBP-1 nucleic acid sequence SEQ ID NO: 45 with the human genomic DNA sequence Accession Nos. XM059482 and AKO74062 and sequences obtained from Celera Discovery Inc. showed that the human cDNA sequence SEQ ID NO: 45 was derived from at least AIC074062 exons (SEQ ID NOS: 57-62 and 16-41, as shown in Table 1).

TABLE 1

Exon positions of the human IRDBP-1 nucleic acid sequence SEQ ID NO: 45

| Nucleotide Positions of Human cDNA SEQ ID NO: 45 | SEQ ID NO: |
|---|---|
| 1-863 | 57 |
| 864-1151 | 58 |
| 1152-1292 | 59 |
| 1293-1455 | 60 |
| 1456-1581 | 61 |
| 1582-1695 | 62 |
| 1696-1809 | 16 |
| 1810-1924 | 17 |
| 1925-2049 | 18 |
| 2050-2154 | 19 |
| 2155-2268 | 20 |
| 2269-2384 | 21 |
| 2385-2502 | 22 |
| 2503-2620 | 23 |
| 2621-2733 | 24 |
| 2734-2907 | 25 |
| 2908-3021 | 26 |
| 3022-3135 | 27 |
| 3136-3249 | 28 |
| 3250-3363 | 29 |
| 3364-3660 | 30 |
| 3361-3845 | 31 |
| 3846-3957 | 32 |
| 3958-4239 | 33 |
| 4240-4384 | 34 |
| 4385-4467 | 35 |
| 4468-4566 | 36 |
| 4567-4683 | 37 |
| 4684-4772 | 38 |
| 4773-4855 | 39 |
| 4856-4893 | 40 |
| 4894-6331 | 41 |

The N-terminus of the IRDBP-1 of SEQ ID NO: 45 extends 175 amino acids beyond a genomic sequence isolated by the Human Genome Project. Alignmant of the SEQ ID NO: 45 with the Celera, Inc sequence gave four differences at the amino acid positions (of SEQ ID NO: 48) 250 (SS to DD), 369 (P to R), 127 (V deleted) and 1324 (P deleted). Sequences were compared by the "Gapped Blat and PSI-Blast as described by Zhang et al. in Nuc. Acid Res. 25, 3389-3402 (1997) incorporated herein by reference in its entirety.

EXAMPLE 7

IRE Specificity of IRDBP-1

As shown in FIGS. 19 and 27, IREs isolated from GAPDH, IGFBP-1, IGF-1 and amylase genes competed for IRDBP-1 binding to the IGFBP-3 IRE. Competition was weaker with the REs from the PEPCK and TAT genes, and much weaker with the prolactin IRE.

Double-stranded oligonucleotides corresponding to the published sequences of the IREs were used for competition, including the IREs identified from the following genes: IGFBP-3 (5'-AATTCAAGGGTATCCAGGAAAGTCTC-CTTCAAG-3') (SEQ ID NO: 63), Glyceraldehyde-6-phosphate dehydrogenase (5'-AAGTTCCCCAACTTTCCCGC-CTCTCAGCCTTTGAAAG-3') (SEQ ID NO: 49). Insulin-like growth factor binding protein-1 or IGFBP-1 (5'-GTTTGTTTTGCTAGT-3') (SEQ ID NO: 50), Insulin-like growth factor-1 or IGF-I (5'-GCCTCATTATTCCTGC-CCACCAAT-3') (SEQ ID NO: 51) amylase (5'-TATTTTGCGTGAGAGTTTCTAAAAGTCCAT-3') (SEQ ID NO: 52), phosphoenolpyruvate carboxykinase or PEPCK (5'-TGGTGTTTTGACAAC-3') (SEQ ID NO: 53), tyrosine aminotransferase or TAT (5'-GACTAGAACAAACAAGTC-CTGCGTA-3') (SEQ ID NO: 54), prolactin (5'-ATC-TATTTCCGTCATTAAGATA-3') (SEQ ID NO: 55), and the consensus sequence for NFκB binding (5'-GGGACTTTC-CGGGACTTTCC-3') (SEQ ID NO: 56).

A farwestern blot showed that the shifted bands formed between the nuclear extracts and the IREs of IGFBP-3, IGF-I and IGFBP-1 reacted strongly with anti-IRDBP-1 cAb antibody (FIG. 27, right panel). Specificity of this reaction was shown with an anti-SpI antibody that recognized SpI reacting with the IGF-I IRE, and a PPAR gamma antibody used as a negative control.

The shifted band seen with the IRE of the prolactin gene was unreactive with IRDBP-1 cAb. In the farwestem technique, denaturation separates individual proteins and it is possible for IRDBP-1 to bind to cofactors that can interfere with antibody epitope binding, or that the binding of IRDBP-1 to the IRE limits reaction with the antibody. These interactions with multiple genes indicate that IRDBP-1 is involved in coordinating a variety of metabolic responses to insulin.

EXAMPLE 8

Metabolic Activity of the IRDBP-1 Protein

To investigate the biological effects of IRDBP-1, the partial cDNA sequence encoding IRDBP-1 (SEQ ID NO: 14 shown in FIG. 12) was subcloned into the pCMV-Tag epitope tagging mammalian expression vector (Stratagene, La Jolla, Calif.) and transfected into L6 myoblasts to establish IRDBP-1-stably transfected cell lines. G418-resistant clones were isolated and tested for [$^3$H] 2-deoxyglucose uptake (FIG. 28B).

The insulin induction of the expression of the IRDBP-1 gene was shown by Northern analysis wherein from about $10^{-9}$ M to about $10^{-7}$ M insulin increased the formation of IRDBP-1-specific mRNA of about 5.0 kb, as shown in FIG. 20. Normal liver parenchymal cells have elevated levels of the IRSBP1-specific mRNA compared to cells from a rat having diabetes mellitus, also as shown in FIG. 20.

In addition, the 3.4 kb cDNA region SEQ ID NO: 14 (as shown in FIGS. 12A, 12B) (Genbank Accession NO. AF439719) and obtained from the lambda bacteriophage cDNA library screening, was also tested for the ability to induce a luciferase reporter gene expressed under the regulatory control of the IGFBP-3 IRE (FIG. 23). The cDNAs found to produce proteins that bound to IRE sequences were subcloned into plasmid pTARGET, a mammalian expression vector containing Kozak initiation sequences (Promega, Madison, Wis.). The cDNA-containing constructs and a chimeric construct comprising the IGFBP-3 promoter region SEQ ID NO: 1 attached to the firefly luciferase reporter gene of pGL2-Basic (Promega) as described in Villafuerte et al., (1997) J. Biol. Chem. 272: 5024-5030, incorporated herein by reference in its entirety, were co-transfected into chinese hamster ovary (CHO) cells. A chimeric construct also contained three tandem copies of the IRE region of the IGFBP-3 promoter sequence (SEQ ID NO: 1) attached to the pGL3 promoter vector (Promega, Madison, Wis.).

Transient transfections of the IGFBP-3 IRE-luciferase construct together with the cDNA clones in pTARGET were undertaken with CHO cells when the cells reached 60-70% confluence. Lipofectin (Life Technologies, Rockville, Md.) and DNA complexes were mixed at a 15 μg to 2.5 μg ratio and incubated with the cells overnight. Medium was replaced with serum-free DMEM medium, with or without the addition of $10^{-6}$ M human recombinant insulin (Life Technologies, Rockville, Md.) for 24 hours, and cell extracts were assayed for gene activity using a luciferase assay system (Promega, Madison Wis., and following the manufacturer's recommended protocol) and measured using a luminometer.

The cDNA was also subcloned into the mammalian expression vector pCR 3.1 (Invitrogen Corp., Carlsbad, Calif.), and transiently cotransfected into COS 7 cells already containing target IGFBP-3 IRE nucleic acid linked to a luciferase reporter in the pGL3 promoter (Promega, Madison, Wis.).

Figure 29:
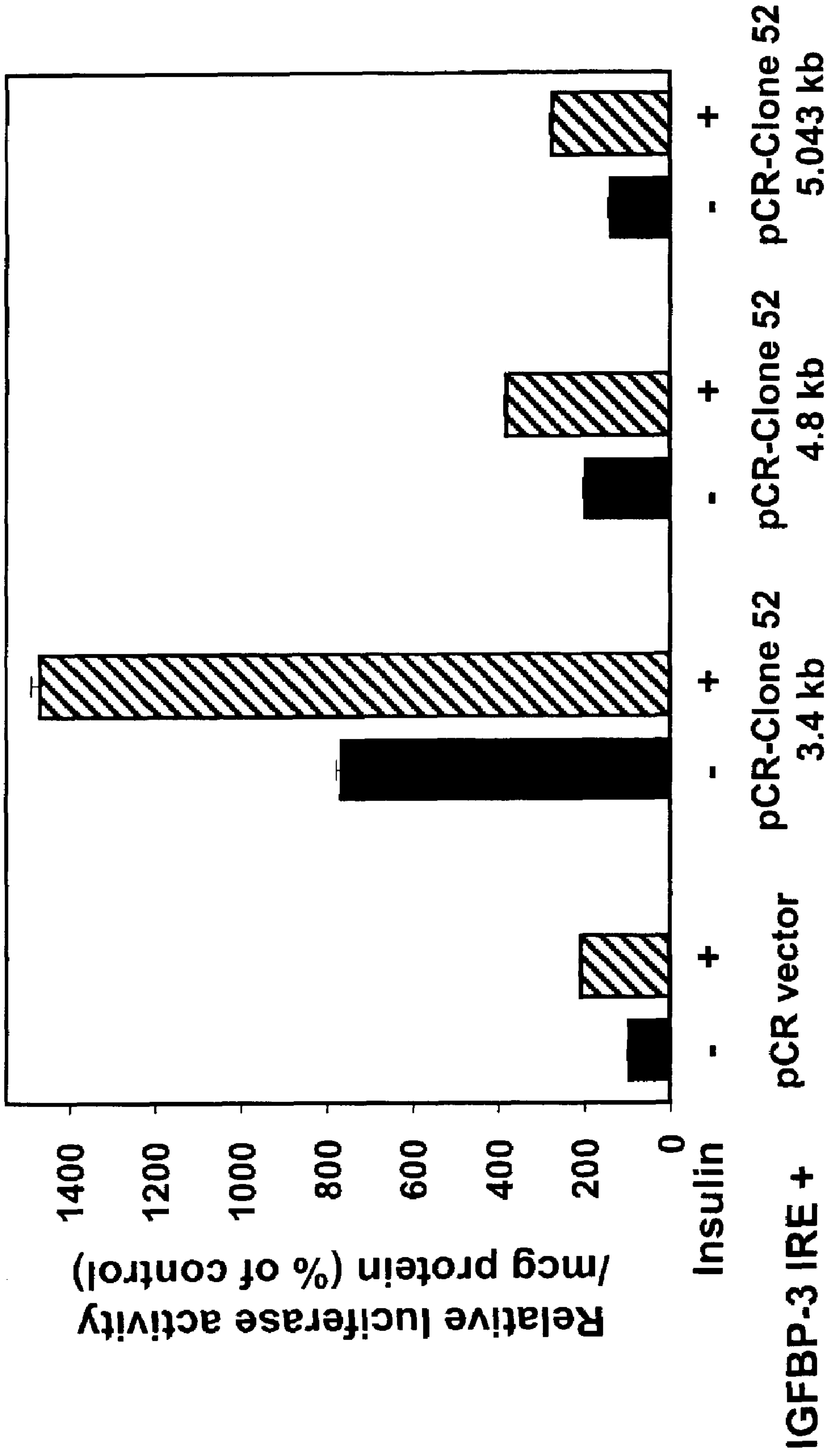
FIG. 29 illustrates cotransfection of COS7 cells with 3.4, 4.8 and 5.043 kb IRDBP-1-encoding cDNA and the IGFBP-3 IRE luciferase reporter.

As shown in FIG. 29, the truncated 3.4 kb IRDBP-1 cDNA, including 1503 bp of translated sequence and 1899 bp of 3'-untranslated sequence, increased IRE-linked reporter activity 15-fold, but had only a 2-fold effect on the control reporter vector. The addition of $10^{-8}$ M insulin had little effect on the control vector but provided 3-fold stimulation of the IRE reporter in the absence or presence of added IRDBP-1. The impact of IRDBP-1 alone was greater than that of insulin alone, and IRDBP-1 and insulin combined were more than additive. Similar findings were obtained with an IRE reporter gene transfected into primary cultures of hepatic nonparenchymal cells.

Extending the 5' end of the expressed 3.4kb IRDBP-1 cDNA reduced stimulation by IRDBP-1 of the IRE reporter as shown in FIG. 29. Since the additional sequence contained mostly the EGF-like repeats, the EGF-like repeats may have a silencing effect. The truncated carboxyl-half of the protein of about 50 kDa appears to be sufficient for transcriptional stimulation.

Figure 28:
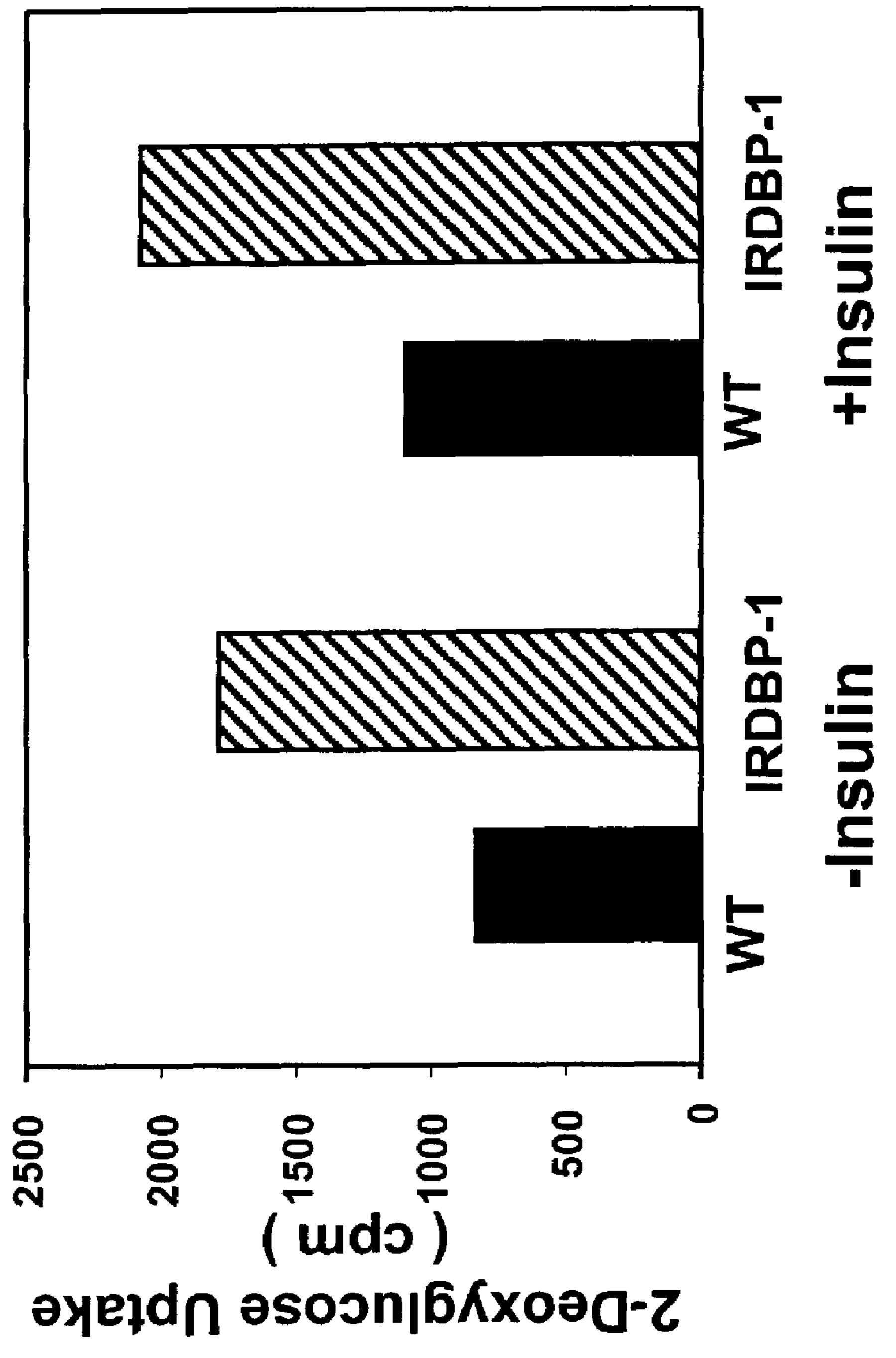
FIG. 28 illustrates the effect of an IRDBP-1 expressing clone (SEQ ID NO: 5) on insulin regulation of glucose uptake in myoblasts.

The expressed 3.4 kb cDNA region SEQ ID NO: 14 increased IGFBP-3 IRE-induced reporter activity 14-fold, and addition of $10^{-6}$ M insulin increased the activity further by 3-fold (FIG. 24). There was a 110% increase in glucose uptake in cells stably transfected with nucleic acid SEQ ID NO 14, as compared to wild type cells, as shown in FIG. 28. With the addition of $10^{-6}$ M insulin, there was a 30% further increase in glucose uptake in wild type cells and a 16% further increase in clone 52-transfected cells. IRDBP-1 is functionally an insulin-mimetic.

EXAMPLE 9

Determination of IRDBP-1 Biological Activity

Figure 30:
FIG. 30 illustrates the effect of IRDBP-1 (SEQ ID NO: 14) on the glycogen content of cultured cells.

To examine the ability of the IRDBP-1 polypeptide to allow storage of substrates related to insulin action, wild type L6 myoblasts and the 3.4 kb IRDBP-1-encoding nucleic acid stably transfected cells were stained with the periodic acid-Schiff base stain specific for glycogen. As shown in FIG. 30, the IRDBP-1-stably transfected cell line showed intense periodic acid Schiff base (+) materials in the cytoplasm, consistent with glycogen accumulation in the IRDBP-1-transfected cells. Thus, IRDBP-1 mediates storage of ingested substrates, and it can act as an insulin substitute at the target organ level.

EXAMPLE 10

IRDBP-1 Expression Correlates to Tissue-specific Glucose Utilization

Northern blotting with a 1503 bp IRDBP-1 specific probe showed that hepatic nonparenchymal cells that exhibit insulin-responsive IGFBP-3 expression, also have insulin-responsive IRDBP-1 expression (FIG. 20, left panel). IRDBP-1 expression was decreased in the livers of streptozotocin-induced diabetic rats (DM) compared to normal rats (FIG. 20, right panel).

In vivo disposition of glucose in various organs and tissues was studied. Following oral glucose load, tracer and forearm catheterization techniques showed that glucose is taken up by splanchnic tissues, including liver and gut (29%), muscle (26%), brain (23%), kidney (7%). heart (4%), fat (3%) and others (8%).

The RNase protection assay used a Kpnl-XhoI fragment (SEQ ID NO: 4, shown in FIG. 3) from clone 52 cDNA (SEQ ID NO: 2) inserted in pGem7Z and transcribed in vitro to give a riboprobe (antisense probe). The assay was carried out using the Hybspeed RPA Kit (Ambion, Inc., Austin, Tex.) according to the manufacturer's directions. RNA extracted from various tissues of the rat was hybridized with the [$^{32}$P] UTP-labeled clone 52 probe-derived RNA at 45° C. in the presence of 40 mM PIPES and 80% formamide. The unhybridized probe was degraded with RNase A and T, and protected RNA was purified and resolved on a sequencing gel.

Figure 21A:
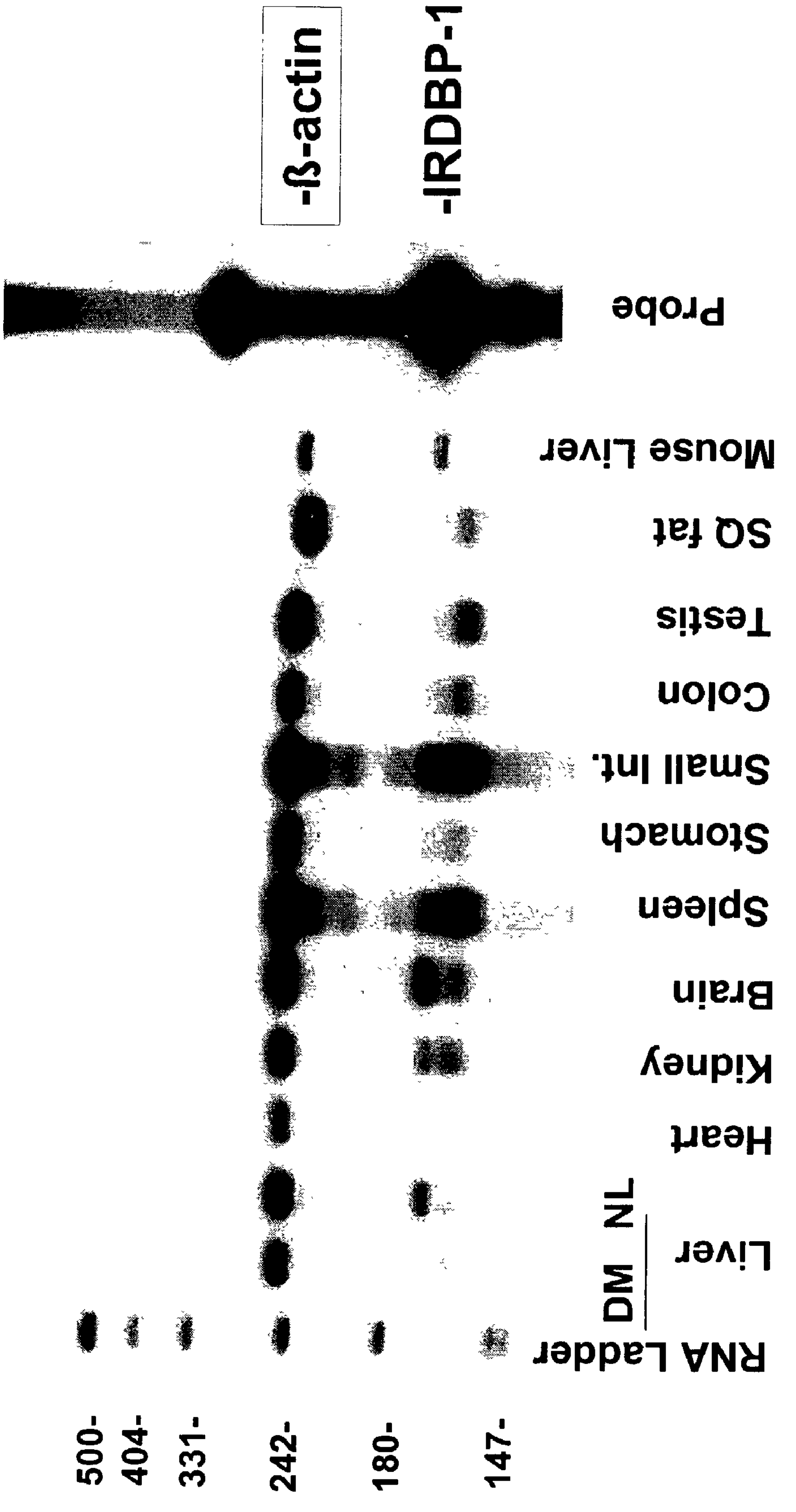
FIG. 21A shows ribonuclease protection assays of rat tissues using the 170 bp (+2270 to +2440 base position) of nucleic acid SEQ ID NO: 5 as the probe.
Figure 21B:
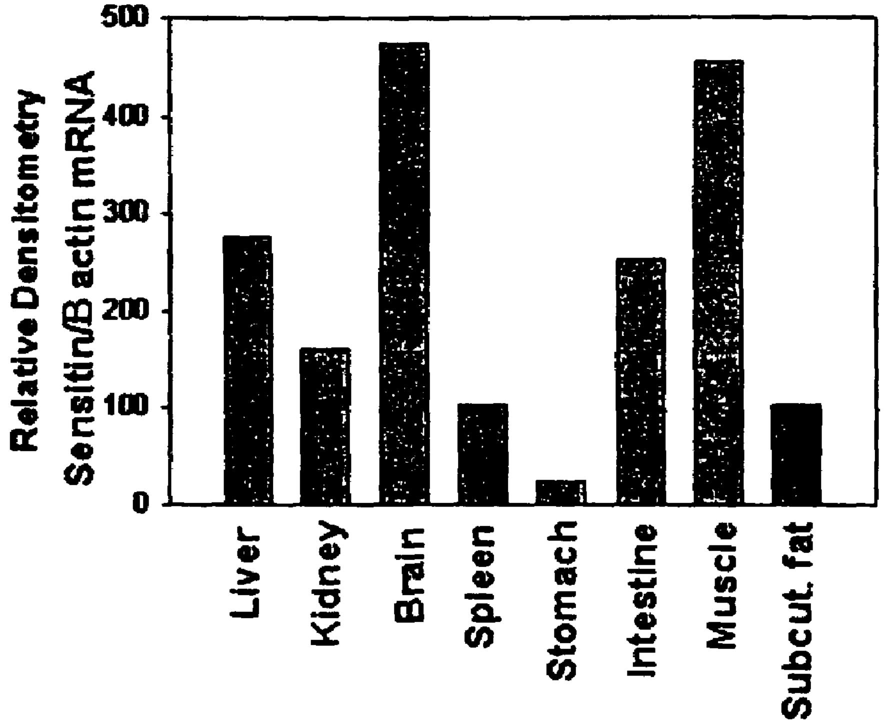
FIG. 21B shows the relative expression of IRDBP-1 mRNA in different rat tissues.
Figure 21C:
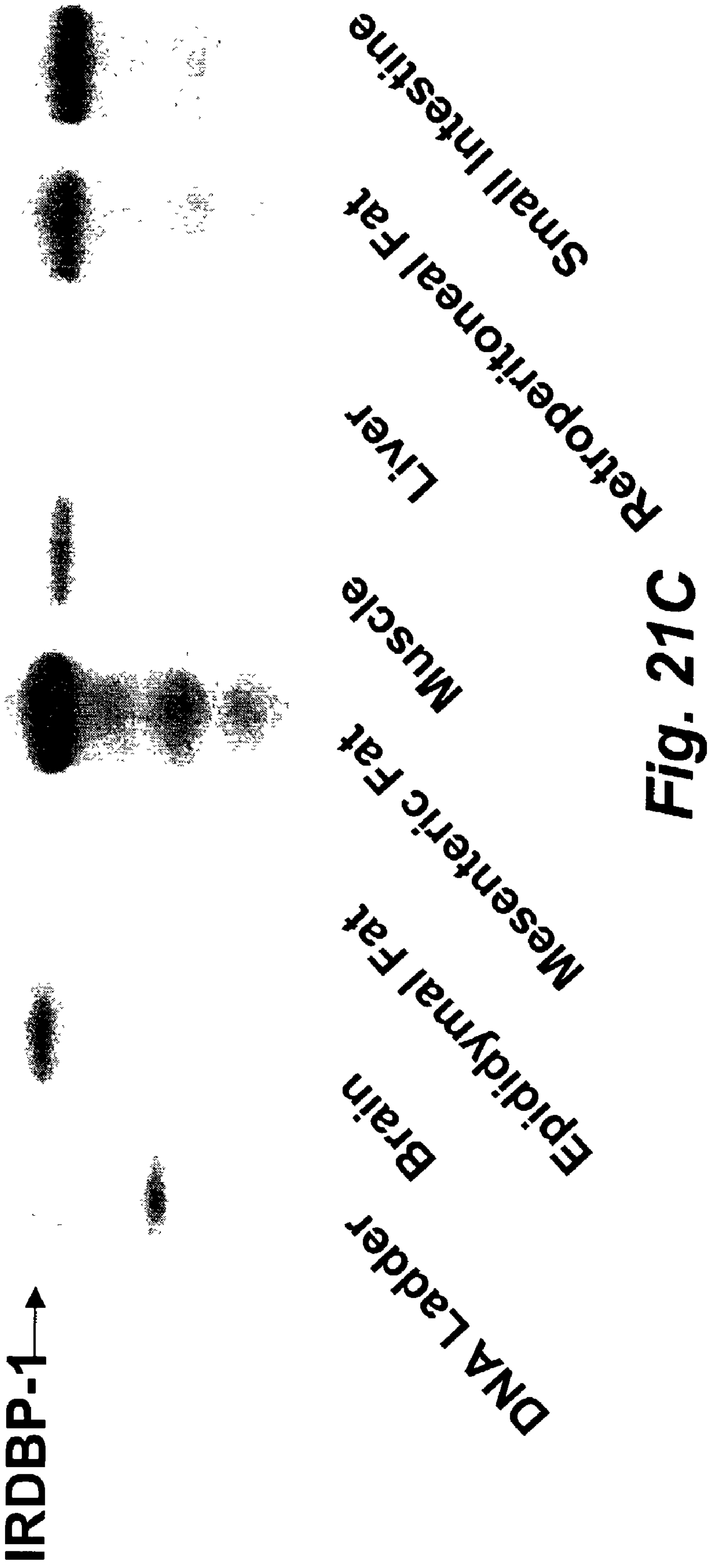
FIG. 21C illustrates the tissue distribution of IRDBP-1-specific mRNA in adipose tissue.
Figure 22:
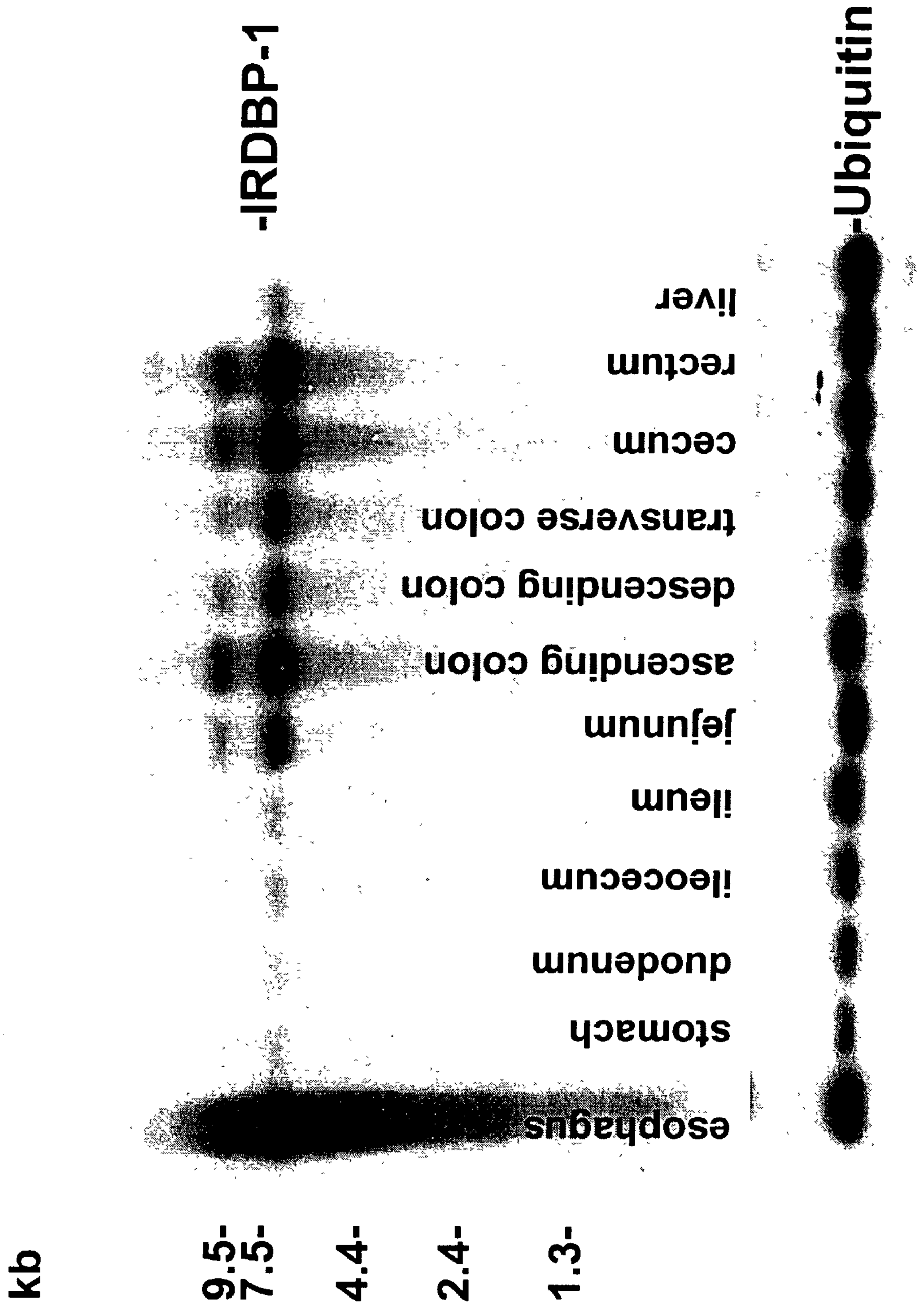
FIG. 22 illustrates the tissue distribution of IRDBP-1-specific mRNA in human digestive tissue.

Using an ribonuclease protection assay, both insulin-dependent (muscles, adipose tissue, liver) and non-insulin dependent tissues or organs in which insulin were shown not to be required for utilization of glucose (brain, kidney, gut) expressed IRDBP-1 mRNA (FIGS. 21A and 22). Thus, the common denominator for IRDBP-1 expression is the dependence of the organ or tissues on glucose for energy utilization.

At the tissue level, studies have shown that when comparing the glucose metabolic rates of different adipose regions, measured as the sum of glucose converted to $CO_2$, triglycerides and lactate, the mesenteric fat cells metabolized significantly more glucose per cell than other fat depots. The hierarchy of the glucose metabolic rate in the different adipose depot is as follows: mesenteric>retroperitoneal>epididymal>subcutaneous fat.

Figure 40:
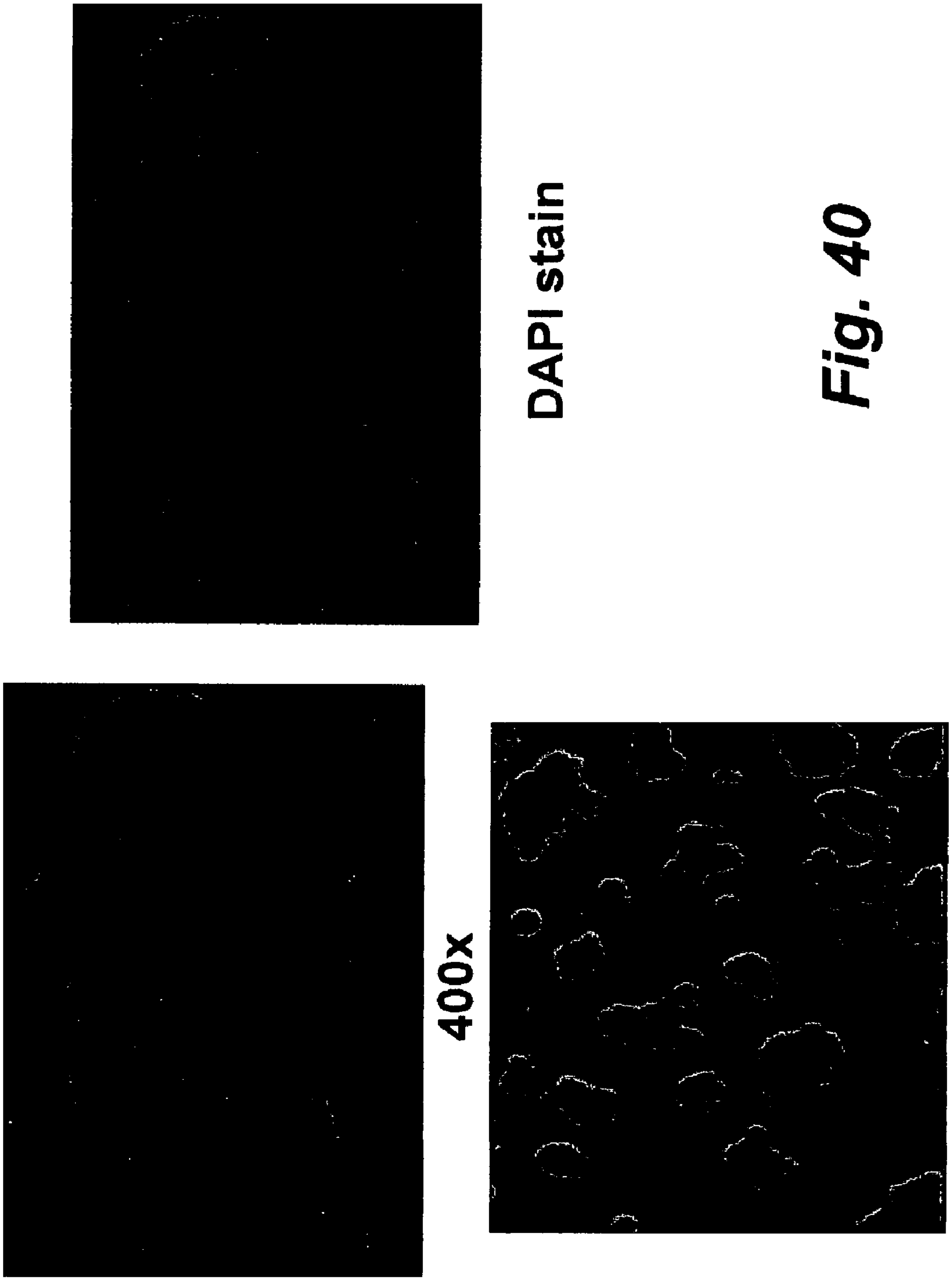
FIG. 40 illustrates immunoflourescent detection of IRDBP-1 in HIT β cells.
Figure 41:
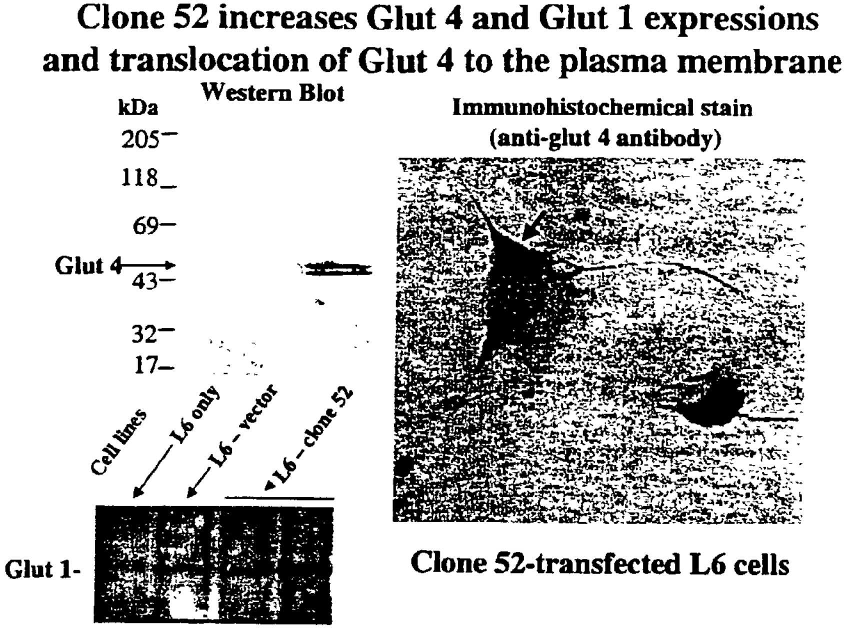
FIG. 41 illustrates the detection of Glut4 and Glut1 expression and the translocation of Glut4 in L6 cells with IRDBP-1 expression.

Cultured beta cells express IRDBP-1, shown in FIG. 40. In cultured adipocytes, IRDBP-1 transfection results in increased Glut4 and Glut1 expression and translocation of Glut 4 to the plasma membrane, as shown in FIG. 41.

As shown in FIGS. 21A and 22, IRDBP-1 expression is highest in mesenteric fat, followed by retroperitoneal, epididymal and subcutaneous fat. Thus, the mRNA abundance of IRDBP-1 in adipose tissues reflects the glucose utilization rates in those tissues. Since diabetes is characterized by resistance to insulin action on glucose uptake and utilization in adipocytes and skeletal muscle, the studies illustrated in FIGS. 18-22, 28-29 indicate that over-expression of IRDBP-1 may overcome the problems of both poor glucose uptake and poor glucose utilization.

EXAMPLE 11

IRDBP-1 Expression is Detected in Many Areas of the Brain, Including Areas Associated with Feedings and Satiety In-situ Hybridization of Rat Brains Using $^{35}$S-labeled IRDBP-1 Riboprobe Rat brains were obtained and fixed by immersion in 4% paraformaldehyde in 0.1 M $NaPO_4$, sectioned on a cryostat to 5-10 μM thickness, and mounted on slides. Sense and antisense $^{35}$S-labeled IRDBP-1 riboprobes were generated by in vitro transcription with $^{35}$S-UTP, and derived from the linearized fragment SEQ ID NO: 4 of IRDBP-1 cDNA. Following proteinase K treatment, prehybridization of the various brain sections was performed for 3 hrs at 42° C., in a buffer containing 10 mM DTT, 0.3 M NaCl, 20 mM Tris pH8, 5 mM EDTA, 1×Denhardt's, 10% Dextran sulfate, and 50% formamide. This was followed by addition of $^{35}$S-labeled probe (600,000 cpm/slide) and tRNA (200 μg/ml) for hybridization. Hybridization was done overnight at 55° C.; slides were then washed, treated with RNAse A, dehydrated, and coated with photographic emulsion. The slides were exposed and developed after 4-12 weeks. Both sagittal (FIG. 31) and coronal (FIG. 32) sections of brains from normal Sprague-Dawley rats, obese fa/fa Zucker rats and lean fa/+ Zucker rats were compared.

EXAMPLE 12

IRDBP-1 is Expressed in the Hypothalamus and Nucleus of the Solitary Tract

Information about the qualities of food are relayed by the primary senses of smell, sight, and taste to the nucleus of the solitary tract in the medulla. The nucleus of the solitary tract (NTS) integrates afferent and efferent information and connects with nearby vagal and sympathetic centers that control metabolism in peripheral organs. The NTS communicates rostrally with the central nucleus of the amygdala. The central nucleus is integrated into the limbic and autonomic systems throughout the brain, including the hypothalamus (paraventricular nucleus-PVN, lateral hypothalamus-LH, ventromedial hypothalamus-VMH) and brainstem. Stimulation of PVN, VMH or LH alters sympathoadrenal and vagal activities.

Brain lesions of the ventromedial hypothalamus produced hyperphagic obesity. Lesions of the lateral hypothalamus caused hypophagia and weight loss. The central administration of insulin also changed the level of defended body weight rather than a simple suppression of food intake. Thus, the hypothalamic pathways that are sensitive to adiposity signals have anatomical connections with caudal brainstem neurons (solitary tract nucleus) that respond to meal-related signals and regulate meal size.

Figure 31:
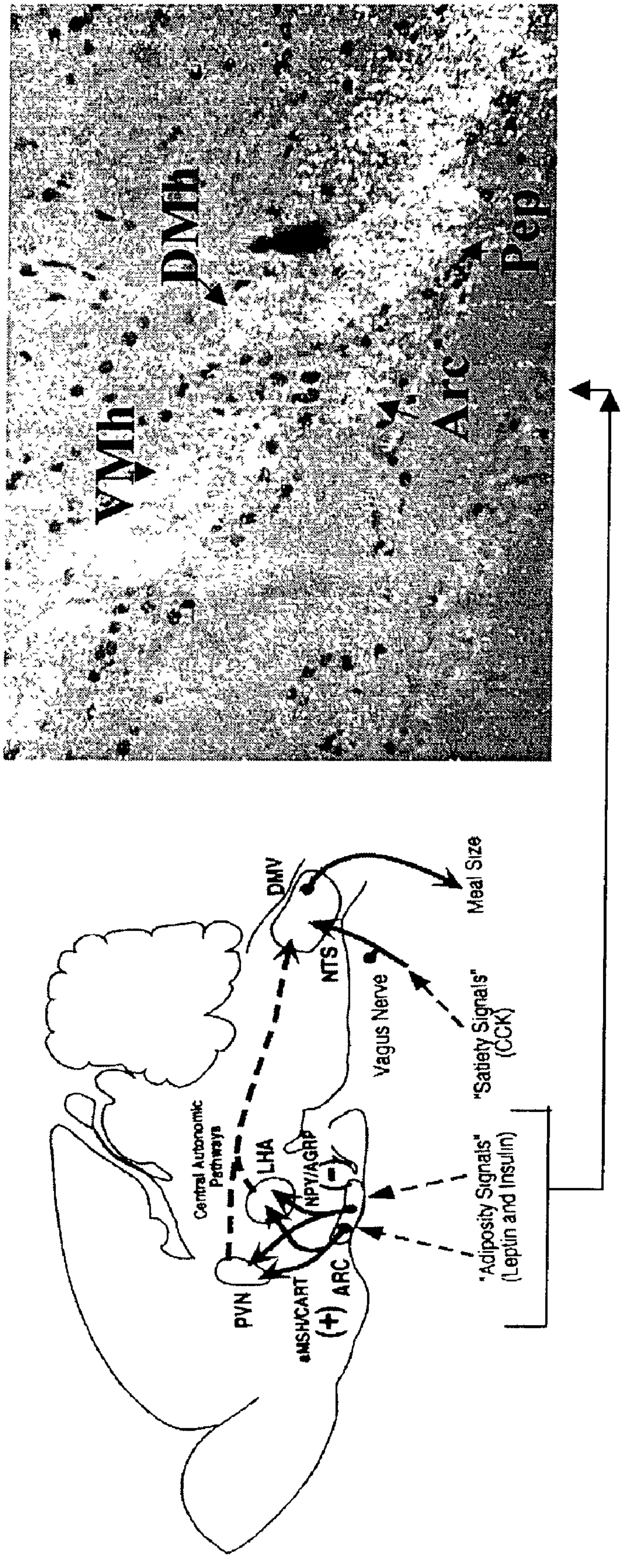
FIG. 31 illustrates the detection of IRDBP-1 mRNA within the hypothalamic portion of the brain by in-situ hybridization.
Figure 32:
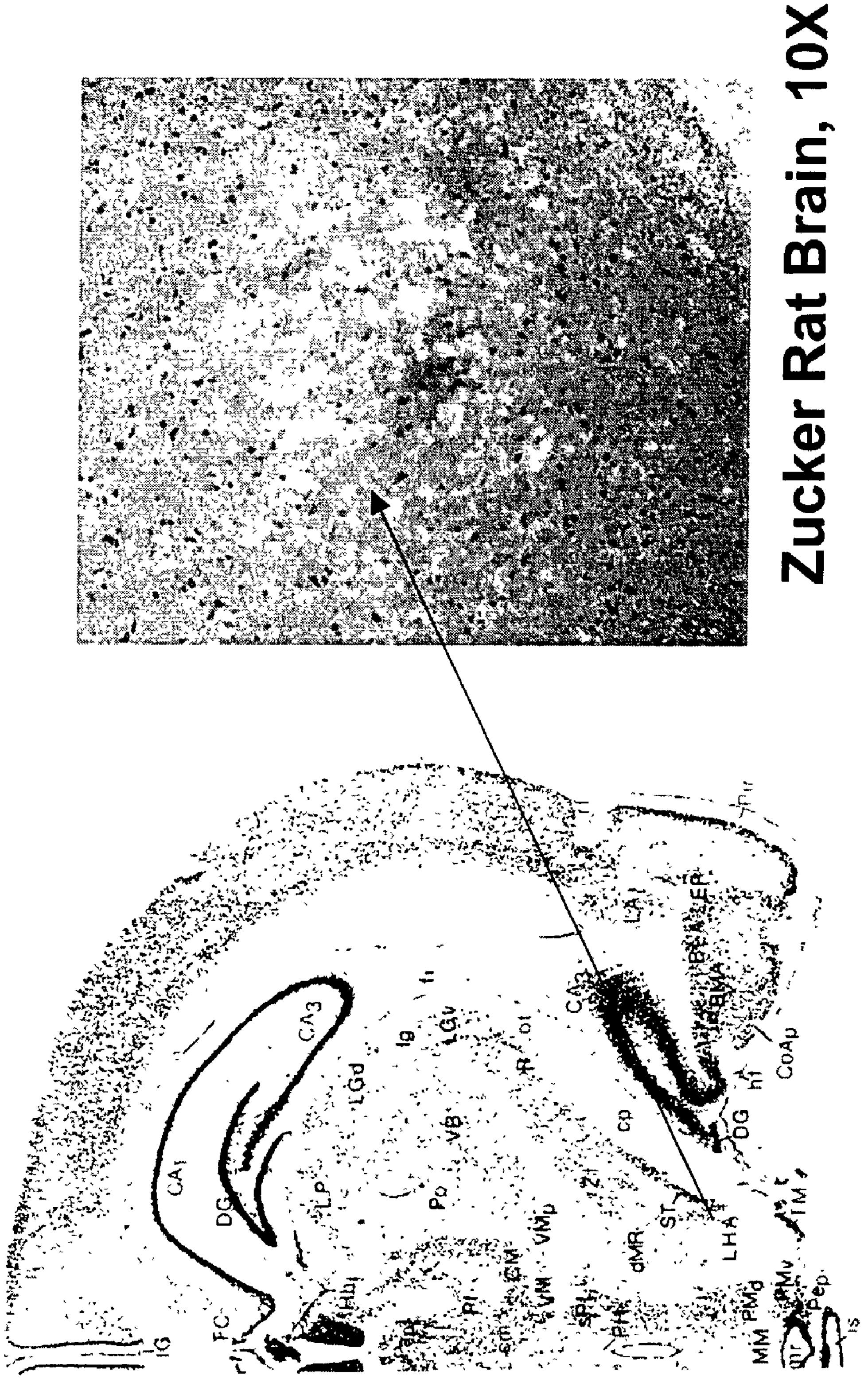
FIG. 32 illustrates the detection of IRDBP-1 mRNA in the lateral hypothalamus by in-situ hybridization.
Figure 33:
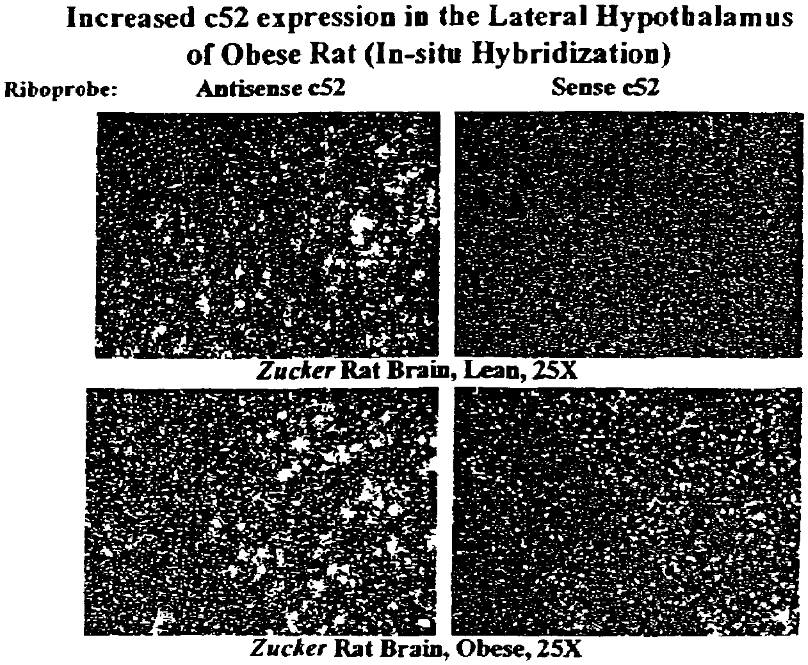
FIG. 33 shows a comparison of IRDBP-1 mRNA in the lateral hypothalamic area of obese and lean rats by in-situ hybridization.

The results from in-situ hybridization with a IRDBP-1 riboprobe indicated that IRDBP-1 mRNA is highly expressed in multiple areas of the hypothalamus. As shown in FIGS. 31-34, a sagittal cut through the thalamic portion of the diencephalon of a normal Sprague Dawley rat showed that IRDBP-1 is expressed in the ventromedial and dorsomedial hypothalamus, arcuate nucleus and periventricular nucleus (FIG. 31). A coronal cut through the thalamic region also showed that IRDBP-1 mRNA is expressed in the lateral hypothalamus (FIG. 32). Furthermore, comparison of the brain sections from obese and lean Zucker rats showed that the number of silver grains, representing IRDBP-1 mRNA, is higher in the obese than the lean rats (FIG. 33), showing that IRDBP-1 is regulated in the feeding center of the brain, and has a potential role in regulating weight of animals.

Figure 34:
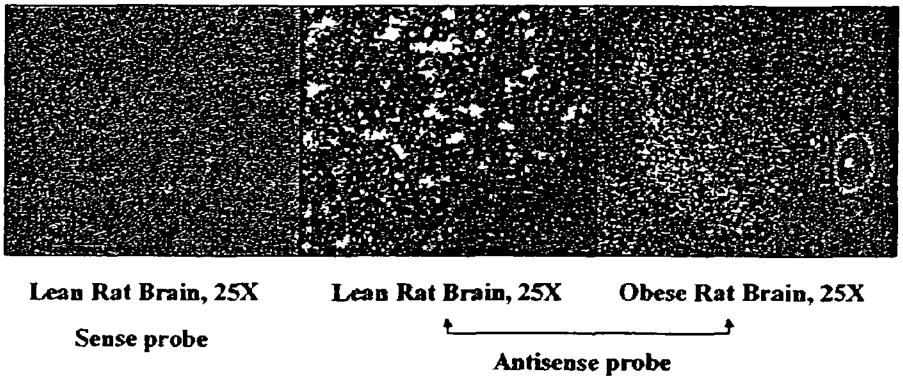
FIG. 34 illustrates IRDBP-1 expression in the solitary tract nuclei of lean and obese rats.

Since all of the information from the neural pathways related to feeding and satiety are integrated in the nucleus of the solitary tract (NTS) of the hindbrain, the expression of IRDBP-1 in the NTS was investigated. As shown in FIG. 34 a sagittal cut through the medullary section of the brain showed that IRDBP-1 mRNA is higher in the NTS of the lean rats, compared to the obese Zucker rats. This further shows that IRDBP-1 is involved not only in altering sympathoadrenal and vagal activities throughout the hypothalamus, but that it has also a potential role in integrating the limbic and autonomic systems involved in maintenance of energy balance.

Figure 35:
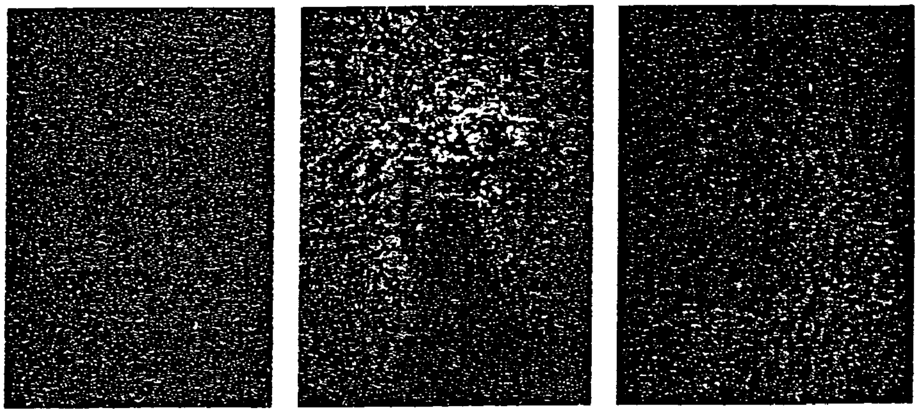
FIG. 35 illustrates an in-situ hybridization analysis of a rat brain section showing that IRDBP-1-specific mRNA is expressed in the pyramidal tract and decussations of the pyramidal tract in obese Zucker rats.
Figure 36:
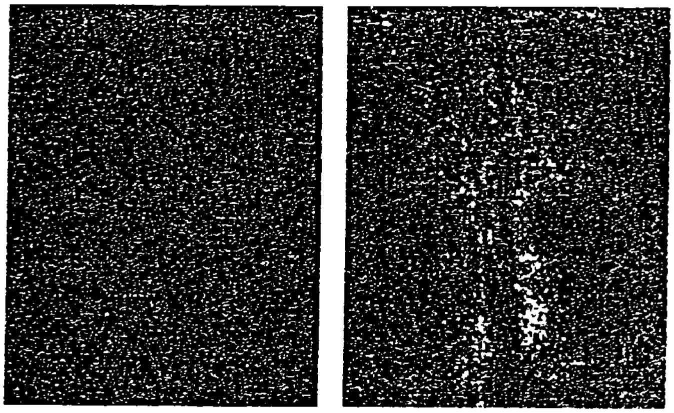
FIG. 36 illustrates an in-situ hybridization analysis showing the expression level of IRDBP-1 in the pyramidal area of the brain of a lean Zucker rat.

Differential IRDBP-1 expression was also seen in the in situ hybridization, with labeled antisense IRDBP-1 probe, of the pyramidal tract and decussations of the pyramidal tract of obese and lean Zucker rats (FIGS. 35 and 36).

EXAMPLE 13

Figure 38:
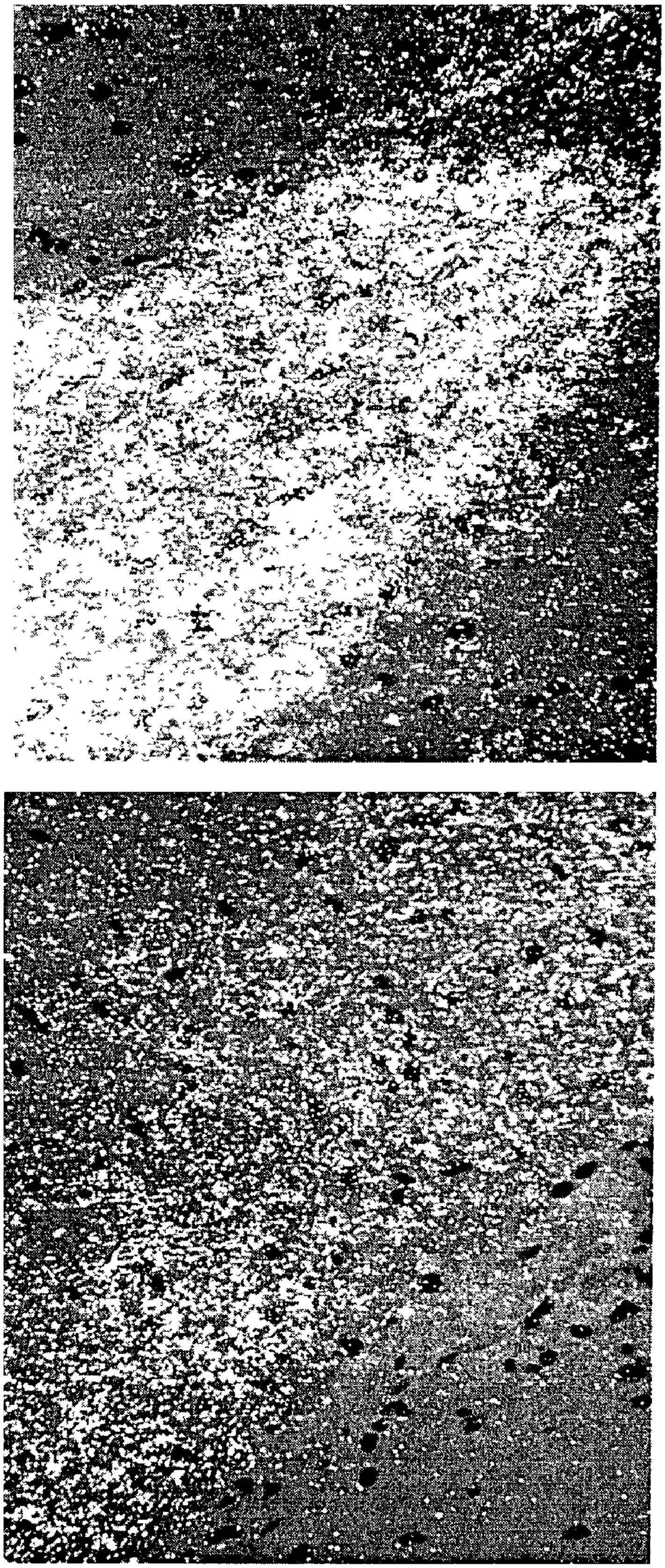
FIG. 38 illustrates IRDBP-1 expression in the amygdala.

Role of IRDBP-1 in the Glucose and Insulin Regulation of Food Intake and Body Weight IRDBP-1 mRNA is highly expressed in the olfactory bulb and amygdala of normal rats, as shown in FIGS. 37 and 38. The glucostatic hypothesis proposed that short-term changes in plasma glucose levels can be detected by the brain and will lead to alterations in food intake. Although virtually all neurons require glucose, only select populations in various areas of the brain respond to changes in glucose concentration by changes in their firing rates. An increase in plasma glucose leads to increased plasma norepinephrine levels and sympathetic nervous system activation, and this is mediated by the glucoresponsive neurons in the hypothalamus.

Since IRDBP-1-specific mRNA appears to be concentrated in selected areas of the hypothalamus, and acts to increase glucose uptake and utilization, as shown in Example 12 above, it is likely that IRDBP-1 has a critical role in mediating the autonomic nervous system activation associated with food intake. With a diet high in fat and sucrose, the plasma norepinephrine response to glucose is predictive of later weight gain, with a high responder becoming obese and a low responder becoming resistant to obesity. IRDBP-1 appears to be a factor that determines basal glucose metabolism in the peripheral tissues, and is concomitantly expressed in regions of the brain that modulate food intake. The efficiency of cellular functions related to IRDBP-1 activity will have a significant impact on overall energy homeostasis.

In addition to the roles of IRDBP-1 in affecting glucose metabolism, synthesis of IRDBP-1 is stimulated by addition of insulin; therefore we also need to consider the effect of insulin action on glucose utilization of the brain. Insulin receptors have been localized to the olfactory bulb, hypothalamus, hippocampus, cerebellum, cerebral cortex, and hindbrain. At the cellular level, insulin modulates expression of hypothalamic neuropeptides, inhibits reuptake of norepinephrine, and enhances endogenous β-adrenergic activity. Central administration of insulin decreases food intake and body weight.

IRDBP-1 mRNA is highly expressed in the olfactory bulb and amygdala of normal rats (FIGS. 37 and 38), and is also expressed in the cerebral cortex, cerebellum and corpus callosum. Lesions of the posterodorsal aspects of the amygdala have been associated with hyperinsulinemia, hyperphagia, and obesity without the preference for particular food that characterized other brain lesion-induced obesity. The involvement of the olfactory system with high levels of expressed IRDBP-1 (FIGS. 37 and 38) in the primary sense of smell, and the affective component associated with eating under the control of the limbic system, including the amygdala and corpus callosum. IRDBP-1 therefore may affect multiple aspects of brain function associated with feeding and satiety.

EXAMPLE 14

IRDBP-1 is Targeted to Pancreatic Beta Cells of the Islets of Langerhans

Glucose is the principal regulator of insulin secretion from pancreatic beta cells, and the kinetic response of insulin to glucose is biphasic in nature. A rapid secretory burst begins within 1 min and decreases over the next 3 to 5 mins. The second phase is characterized by a gradual increase in insulin levels over 5-10 mins, which continues for the next hour. Many type II diabetics have a marked reduction in first phase insulin secretion.

Figure 39:
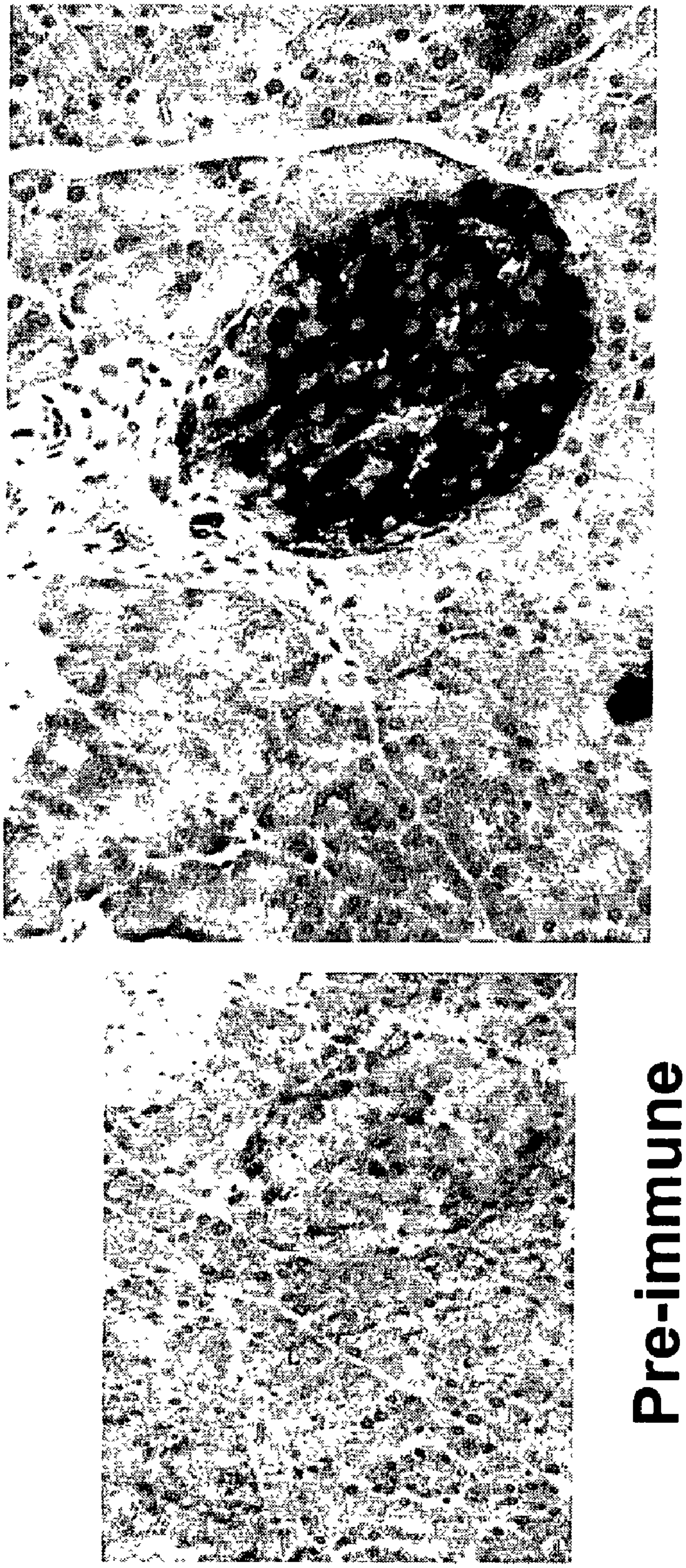
FIG. 39 illustrates immunohistochemical staining with an anti-IRDBP-1 antibody, or with pre-immune serum, of a section of rat pancreas.

A polyclonal antibody raised against the epitopic region SEQ ID NO: 15 of the rat IRDBP-1 polypeptide SEQ ID NO: 11 and capable of detecting the presence of the IRDBP-1 protein from rat or human, was used in immunohistochemical staining of the pancreas to detect the cellular location of IRDBP-1. Insulin acts on beta cells to regulate insulin secretion, insulin synthesis, and glucose sensing/utilization. Functional insulin receptor and IRS-1 have been identified in beta cells. As shown in FIG. 39, IRDBP-1 expression is strongest in the beta cells of the islets of Langerhans.

EXAMPLE 15

Immunodetection of IRDBP-1 Expresson in Pancreatic Renal, Vascular and Neural Tissues Since glucose is the principal regulator of insulin secretion from pancreatic beta cells, and IRDBP-1 mimics insulin action on glucose transport and metabolism, we also determined the expression of IRDBP-1 in the pancreas.

Fixed and paraffin embedded tissue was deparaffinized, rehydrated, treated with proteinase K at 50 μg/ml for 10 min at room temperature, washed with PBS, and blocked with a 1% gelatin/PBS mixture for 20 mins. The primary antibody, anti-rat IRDBP-1 peptide cAb antibody was added at 1:200 dilution in 1% BSA/1×PBS, and the sample was incubated in a humid chamber for 1 hour at room temperature. After washing, a biotinylated secondary antibody was added at 1:400 dilution, and incubated with the sample for 30 min. Color development was performed with the ABC-vector Red complex from an alkaline phosphatase standard kit. The slide was counterstained with Gill's hematoxylin, dehydrated and mounted.

Figure 42A:
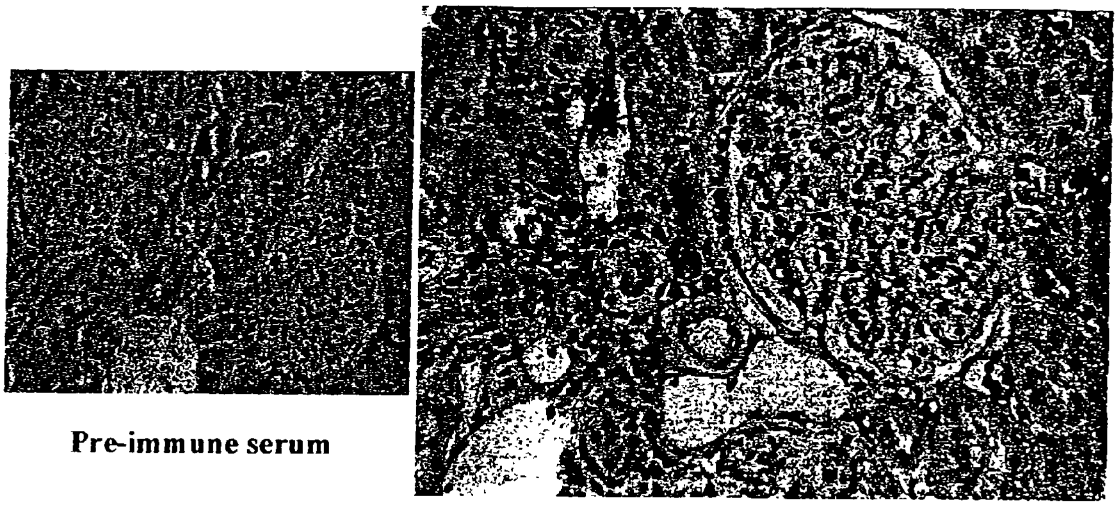
FIG. 42A illustrates immunohistochemical staining of rat kidney mesangial cells, using anti-IRDBP-1 antibody (right) or pre-immune serum (left).
Figure 42B:
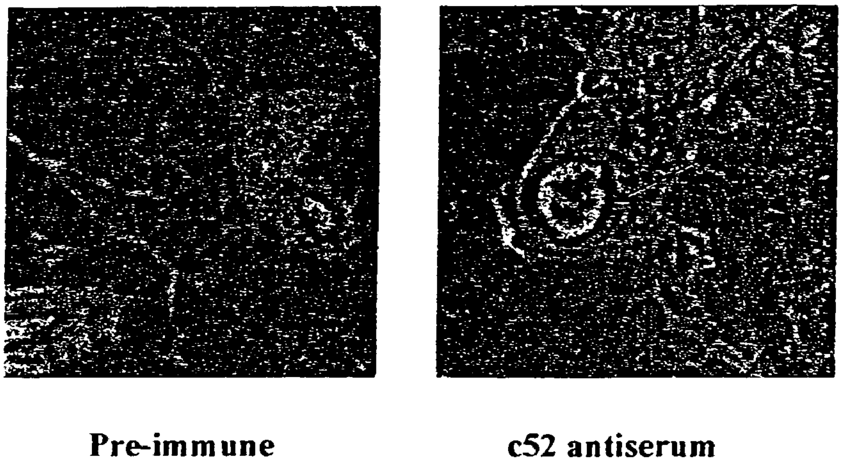
FIG. 42B illustrates immunohistochemical staining of the endothelial lining of blood vessels of the kidney, using anti-IRDBP-1 antibody (right) or pre-immune serum (left).
Figure 42C:
FIG. 42C illustrates immunohistochemical staining of the rat brain, using anti-IRDBP-1 antibody.

As shown in FIG. 39, immunostain of pancreas showed intense accumulation of IRDBP-1 is the cytoplasm of the islet of Langerhans. In particular, the insulin-secreting β cells of the pancreas, which comprised 74% of the islet mass and is central in location, expressed abundant IRDBP-1, as described in Examples 13 and 14 above. IRDBP-1 expression was also detected by immunodetection in the mesangium of the glomerulus of the kidney (FIG. 42A), in vascular endothelial cells (FIG. 42B) and in neuronal cells (FIG. 42C).

Figure 43:
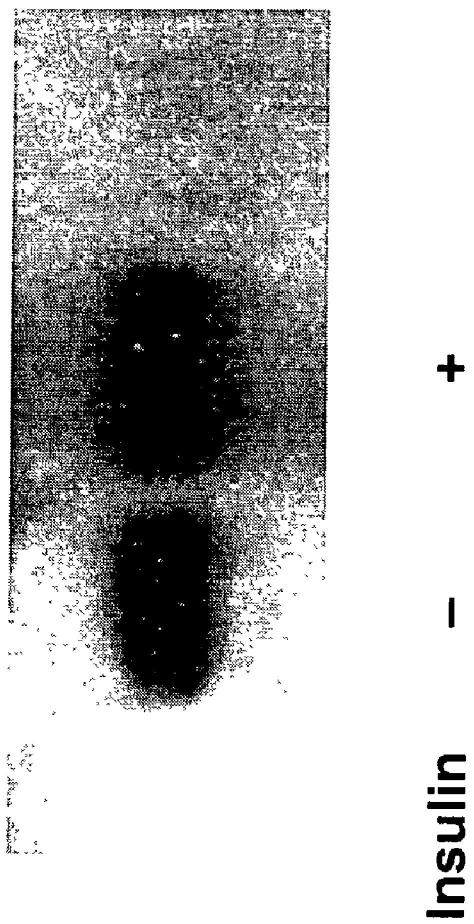
FIG. 43 illustrates a Western blot analysis using anti-rat IRDBP-1 peptide polyclonal antibody and cell extracts from human vascular endothelial cells treated with and without insulin for 6 hours.

A Western blot analysis of the expressed proteins from cultured human vascular endothelial cells, treated or untreated with insulin, probed with a polyclonal anti-rat IRDBP-1 antibody shows that insulin induces the formation of IRDBP-1 in such cells (FIG. 43). This experiment further shows that a rabbit anti-rat IRDBP-1 antibody will cross-react with an IRDBP-1 of a different species. The localization of IRDBP-1 to the endothelium, mesangium and neurons has implications on the development of vascular, renal and neuropathic complications of diabetes. Insulin causes endothelium-derived nitric oxide-dependent vasodilation and modulates vascular tone. Mesangial cell proliferation and expansion is the initial event in the development of diabetic nephropathy. Thus, the action of IRDBP-1 in mediating insulin action in the endothelium will increase the vasodilatory capacity of the blood vessels, and decrease blood pressure and the subsequent onset of atherosclerosis. The antiproliferative action of IRDBP-1 will also decrease the capacity of mesangium to expand and delay the development of diabetic nephropathy.

EXAMPLE 16

Insulin Stimulates Gene Transcription Through Both the Mitogen-activated Protein (MAP) Extracellular Signal-regulated Kinase (Erk) and the P13-kinase/Akt Pathways A. Physical interaction between Akt or Erk and endogenous IRDBP-1 (in COS 7 cells). A pull-down approach was used to establish the position of IRDBP-1 in the insulin signaling cascade, and to show physical contact between IRDBP-1 and signaling antecedents.

Figure 44B:
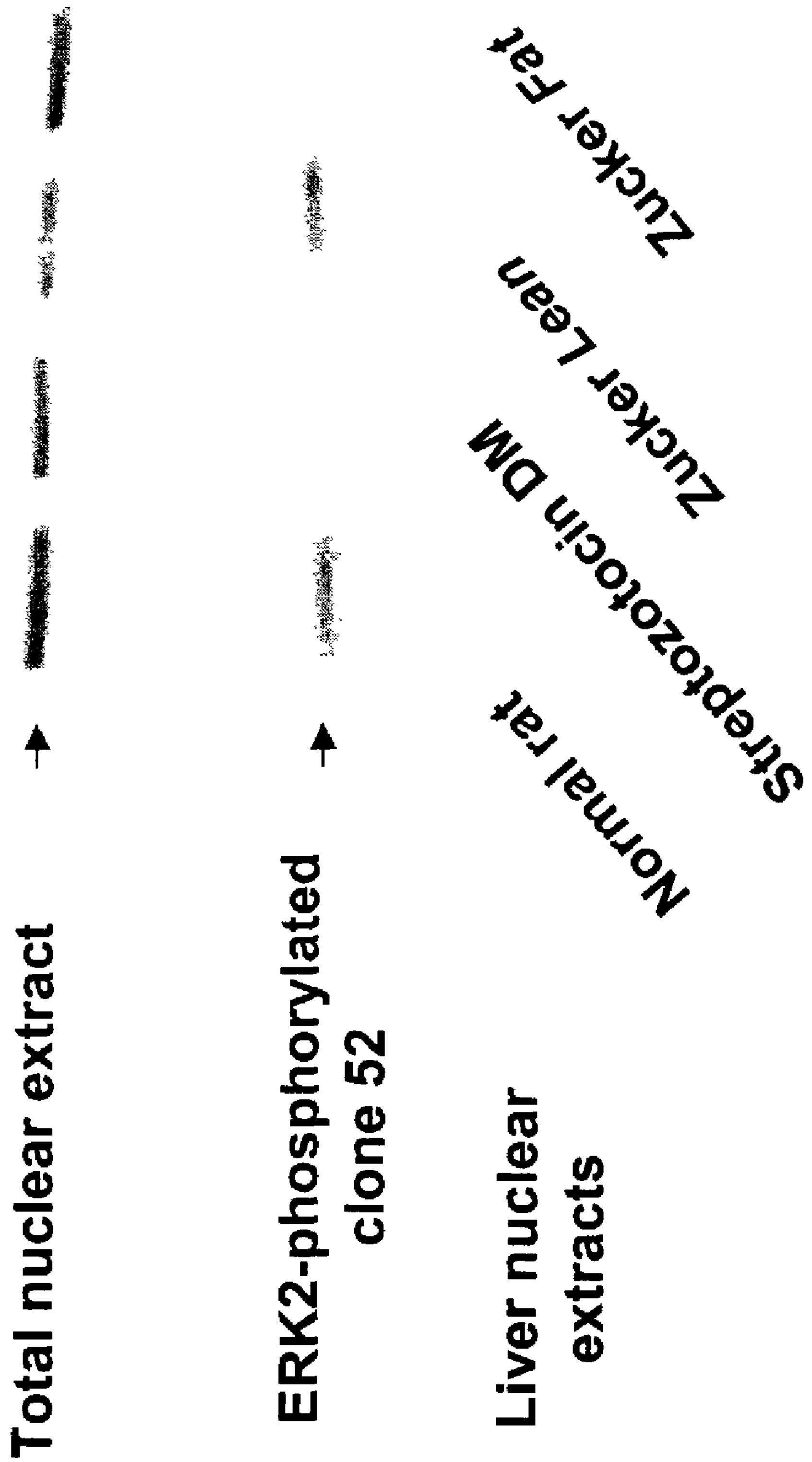
FIG. 44B illustrates differential phosphorylation of IRDBP-1 in normal and streptozotocin-induced diabetic rats, and in Zucker lean and obese rats. Upper panel: western blot; lower panel: Erk2-phosphorylation of IRDBP-1.

As shown in FIG. 44A (left panel), exposure of COS 7 cells to $10^{31}$ 6 M insulin for 24 hr increased the levels of IRDBP-1 and Erk1 detected by immunoblotting of crude lysates (lane 6 vs. 5). IRDBP-1 was coprecipitated by anti-Akt-specific antibodies (lanes 1 and 2) or anti-Erk1/2-specific antibodies (lanes 3 and 4). Erk1 was precipitated by anti Erk-antibody (lanes 3 and 4), but not by the anti-Akt antibody (lanes 1 and 2). SpI, that is not insulin responsive, was not precipitated by either antibody (FIG. 44A, right panel). Decreased Erk-mediated phosphorylation of IRDBP-1 in diabetic and obese rats was also seen (FIG. 44B).

In immunodepletion experiments, prior exposure of COS 7 extracts to an agarose-coupled anti-IRDBP-1 antibody reduced the amount of IRDBP-1 immunoreactivity that coprecipitated with anti-Erk antibody.

Cell lysates from L6 myoblasts stably overexpressing Flag-tagged IRDBP-1 (detected as a 70 kDa protein using anti-Flag antibody)) were also exposed to antibodies specific for Akt and Erk. IRDBP-1 was coprecipitated by anti-Akt and anti-Erk antibodies (as detected by anti-flag antibody), but was not coprecipitated by control IgG. In the control, Akt and Erk were each precipitated by their respective antibodies.

Figure 45A:
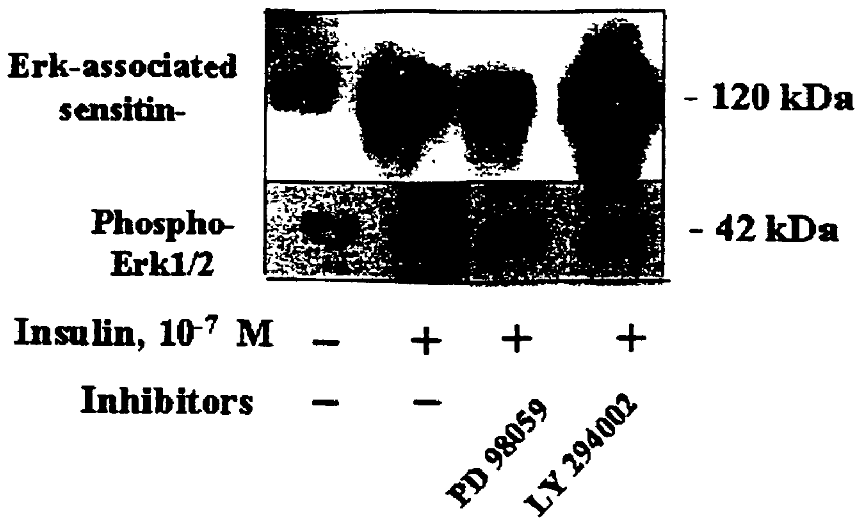
FIG. 45A illustrates probing with anti-IRDBP-1 and anti-phosphoErk antibodies using Western immunoblot of cell extracts from differentated 3T3-L1 adipocytes.

B. IRDBP-1 is situated downstream of the Ras-Mek-Erk kinase signaling enzymes. IRDBP-1 is a target downstream of insulin signaling cascades. Agarose conjugated anti-Erk1/2 antibody was incubated with cell extracts from differentiated 3T3-L1 adipocytes treated with or without PD 98059 (50 μM) and LY 294002 (50 μM), and insulin ($10^{-7}$ M) was added 30 mins later as indicated. Coprecipitated proteins were probed with anti-IRDBP-1 and anti-phospho Erk antibodies using western immunoblots, as shown in FIG. 45A. When 3T3-L1 adipocytes were treated with insulin, nuclear extracts showed increases in IRDBP-1 and Erk1/2 (FIG. 45B) shown with anti-Erk coimmunoprecipitation of cell extracts. Addition of PD 98059 to inhibit Mek 1 that specifically phosphorylates Erk1 and Erk2, reduced insulin-stimulated IRDBP-1 and Erk1 levels compared to insulin-stimulated controls. Inhibition of P13-kinase with LY 294002 increased Erk-associated IRDBP-1. Insulin signaling, therefore, can regulate IRDBP-1 via both the Mek 1 and Erk1 pathways, since blockade of the PI3-kinase-Akt pathway would otherwise be expected to enhance signaling through the Mek-Erk pathway.

Figure 45B:
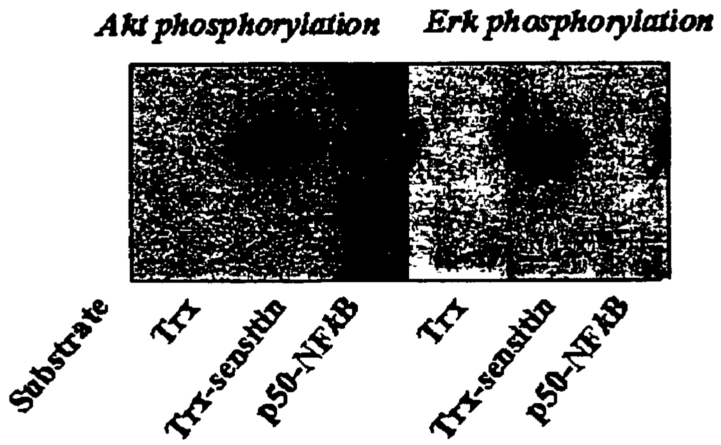
FIG. 45B shows in vitro phosphorylation of IRDBP-1 by Akt and Erk.

C. Akt and Erk phosphorylate IRDBP-1 in vitro. Akt and Erk kinases were immunoprecipitated from insulin-treated COS 7 cells, and kinase reactions performed with the Trx fusion proteins described in Example 1 above. Thioredoxin (Trx) and Trx-IRDBP-1 fusion protein were expressed in *E. coli* (using a pET32 vector), incubated with Akt or Erk in the presence of [γ-$^{32}$P] ATP for 20 mins., and analyzed by SDS-PAGE. *E. coli*-expressed NFκB p50 was used as negative control. Akt phosphorylated the RPRAATF substrate of glycogen synthase kinase 3β, used as a positive control. As shown in FIG. 45B, Akt and Erk did not phosphorylate the controls of Trx alone, and the p50 subunit of NFκB. However, Akt and Erk Trx-IRDBP-1 were capable of phosphorylating Trx-IRDBP-1.

Figure 45C:
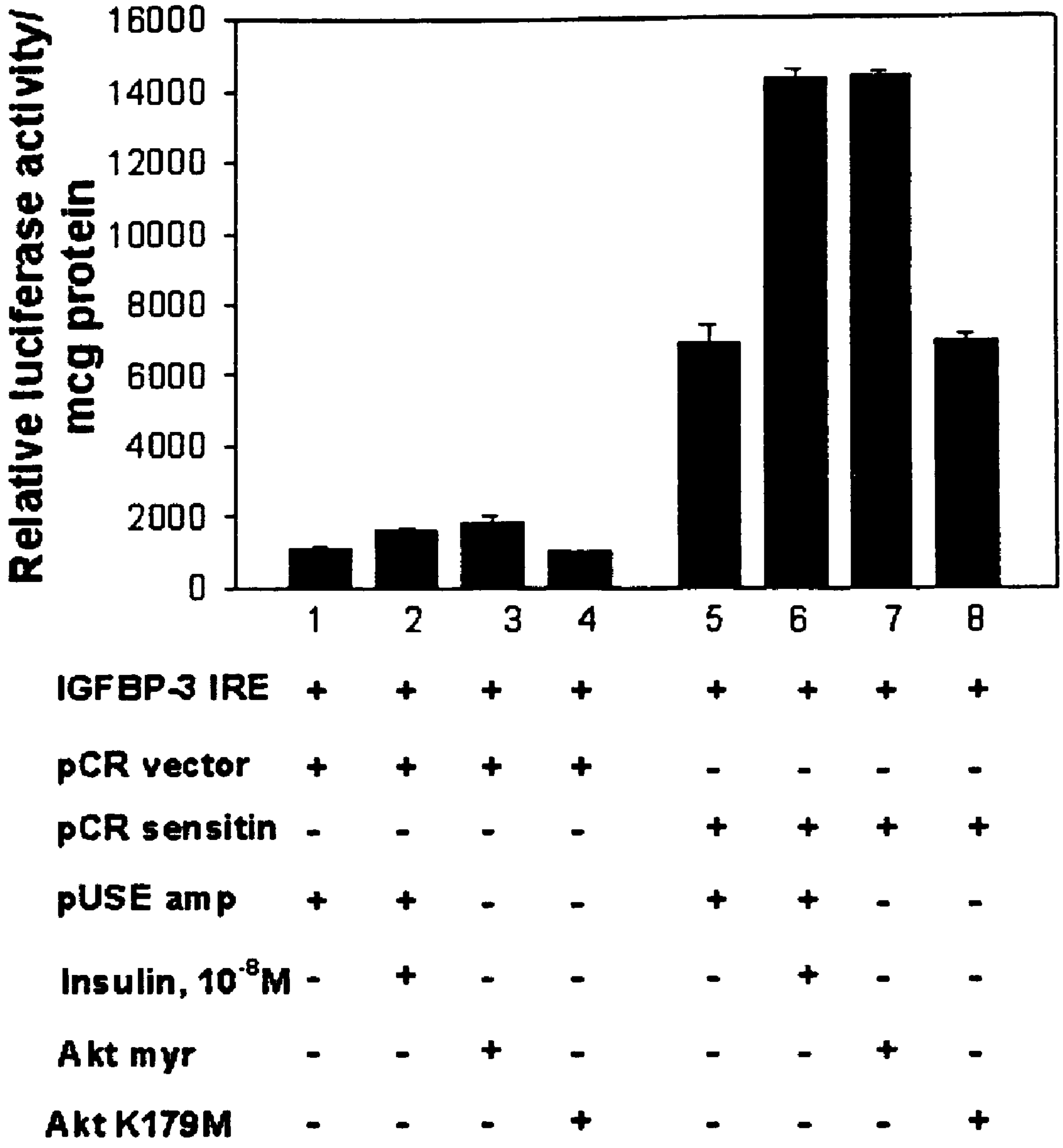
FIG. 45C shows the effects of Akt1 on insulin-mediated IRDBP-1 transcription from the IFGBP-3 IRE

D. The effects of Akt1 on basal and IRDBP-1-induced IRE activity in COS7 cells. COS 7 cells were transfected with either 1 μg of IRDBP-1 (pCR IRDBP-1) or control vector (pCR vector), plus 0.5 μg of Akt1 myr or Akt K179M or the control vector (pUSE amp) as indicated in FIG. 45C. IGFBP-3 IRE-luc expression was normalized to total protein. Activated Akt1 mimics the stimulatory effect of insulin on IRDBP-1, indicating that insulin action on IRDBP-1 may be mediated through phosphorylation by Akt. N-terminal myristoylation of Akt produces a constitutively activated enzyme (Akt myr). Substitution of methionine for lysine at residue 179 of Akt abolishes the kinase activity (Akt K179M). As shown in FIG. 45C, the expression of IRDBP-1 increased transcription of the IRE by 6-fold as compared to the control vector (lane 5 vs. lane 1); insulin treatment of these cells for 24 hours further increased IRDBP-1-activated transcription by 107.7±2% (lane 6 vs. 5). The effect of Akt myr on IRDBP-1 activation was similar to that observed for insulin (lane 7 vs. 6). Akt K179M did not increase IRDBP-1-activated transcription above the level induced by IRDBP-1 alone (lane 8 vs. 5). Control studies without the IRDBP-1 expression construct revealed that insulin and Akt myr stimulated the reporter gene, whereas Akt K179M had no effect (lanes 2, 3, 4 vs. lane 1).

Figure 45D:
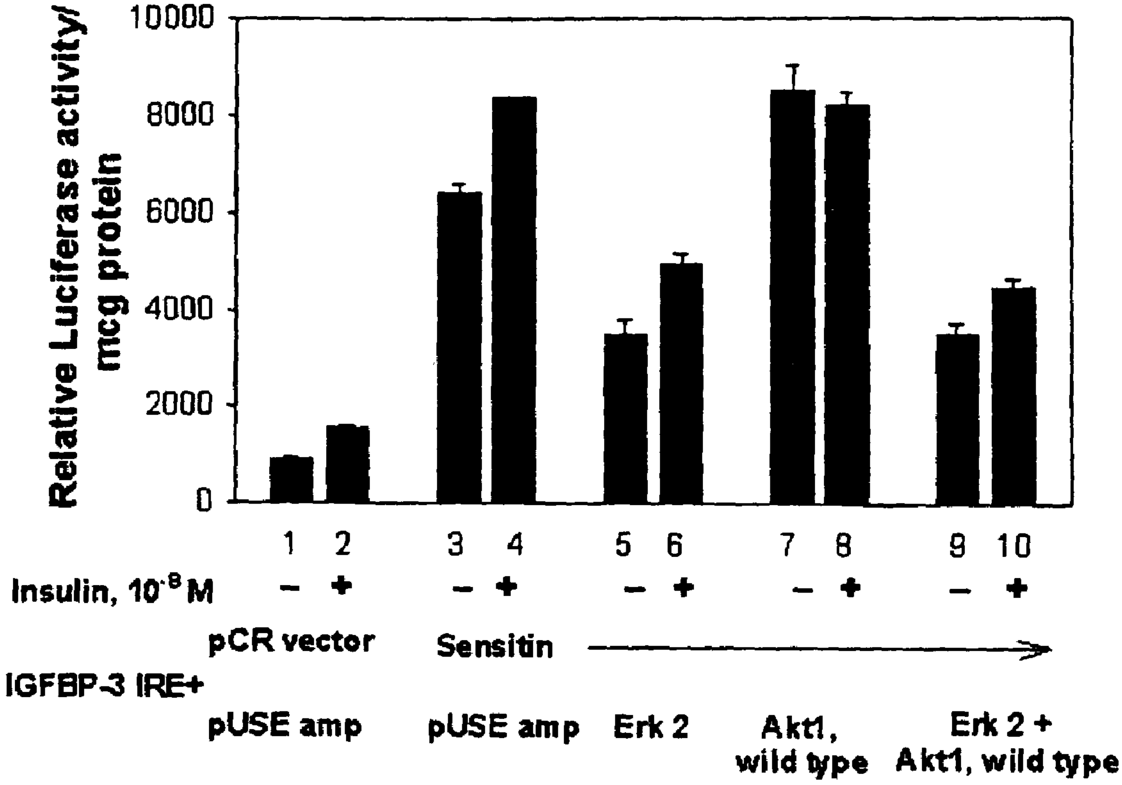
FIG. 45D shows the effects of Erk2 and Akt1 on IGFBP-3 IRE transcription.

E. Differences between the signaling output from Akt and Erk on IRDBP-1 activation. IRDBP-1 -encoding nucleic acid was cotransfected with either wild-type Akt1 and/or Erk2-encoding nucleic acid in pUSEamp expression vectors, and the effect on IRE-mediated transcription was determined. As shown in FIG. 45D, the effect of IRDBP-1 on the IRE was similar to that seen in previous experiments; IRDBP-1 increased IRE activity by 6.8-fold (lane 3 vs. lane 1). Addition of $10^{-8}$ M insulin overnight increased transcription 8.8-fold (lane 4 vs. lane 1). Wild-type Akt1 expression, like Akt myr, stimulated IRDBP-1-induced IRE activity to the same extent as the addition of insulin (lane 7 vs. lane 4). Insulin treatment had no further additive effect on Akt-stimulated transcription (lane 8 vs. lane 7). Thus, Akt1 is sufficient to mediate the effect of insulin on IRDBP-1. In contrast, Erk2 decreased IRDBP-1-induced IRE transcription by 45±4% (lane 5 vs. lane 3), although it did not completely abolish the effect of IRDBP-1. The inhibitory effect of Erk on IRDBP-1 activation was partially reversed with addition of insulin (lane 6 vs. lane 5). When Erk2 and Akt1 were added together, the inhibitory effect of Erk2 predominated over the stimulatory effect of Akt (lane 9 vs lane 7). Therefore, Erk2 stimulates phosphorylation of IRDBP-1 and inhibits its function, while Akt1 stimulates phosphorylation of IRDBP-1 and IRDBP-1 function. The effect of Akt equals the effect of insulin on activation of IRDBP-1.

EXAMPLE 17

Proteolysis and Cell Distribution of IRDBP-1 in Adipocytes, COS 7 and HepG 2 Cells Akt mediates the metabolic actions of insulin by phosphorylating regulatory proteins at the serine or threonine residue.

Both anti-phosphotyrosine and anti-phosphoserine/threonine antibodies immunoprecipitated IRDBP-1 (shown as a about 120 kDa band) and treatment of the cells with insulin increased significantly serine and/or threonine phosporylation of IRDBP-1. A truncated protein of about 50 kDa was detected in insulin-treated, but not in non-insulin-tretaed cells. This lower molecular weight form of IRDBP-1 was detected only in the serine/threonine phospohorylated proteins. Evidence for the proteolytic cleavage of IRDBP-1 is shown below. Therefore, IRDBP-1 can be useful to screen for a specific protease able to cleave IRDBP-1.

A. Proteolytic cleavage of IRDBP-1. IRDBP-1 contains the peptide sequences LSVLS (positions 374-378) and DRSR (positions 603-606) that have been identified as optimal substrates for cleavage of sterol regulatory element binding protein-2 (SREBP-2). Similar cleavage is required for release of SREBP-2 from the endoplasmic reticulum and transit into the nucleus where the truncated SREBP-2 protein modulates the transcription of genes involved in fatty acid and cholesterol synthesis. Similar proteolysis of IRDBP-1 would produce 74- and 49-kDa proteins. A 49 kDa protein is consistent with the size of the transcriptionally active polypeptide that was encoded by the recombinant expression vector.

Figure 46A:
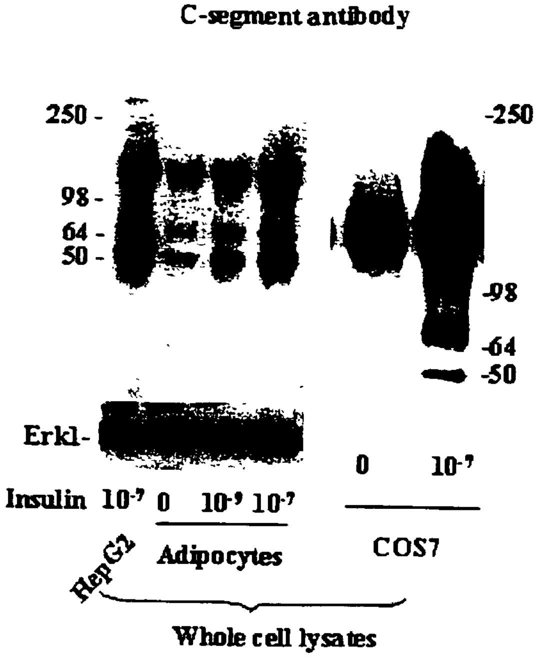
FIGS. 46A and 46B illustrate the proteolysis and cell distribution of IRDBP-1 in adipocytes and COS7 (46A) and HepG2 cells (46B).

Whole-cell extracts (500 μg/lane) were obtained from 3T3-L1 adipocytes (day 5 after differentiation), COS 7 and HepG 2 cells and immunoprecipitated with anti-Erk antibodies as shown in FIG. 46A. Samples were subjected to western blots and probed with the anti-IRDBP-1-cAb anti-IRDBP-1 antibody. The Erk1 level was measured to show equal loading of the protein.

Figure 46B:
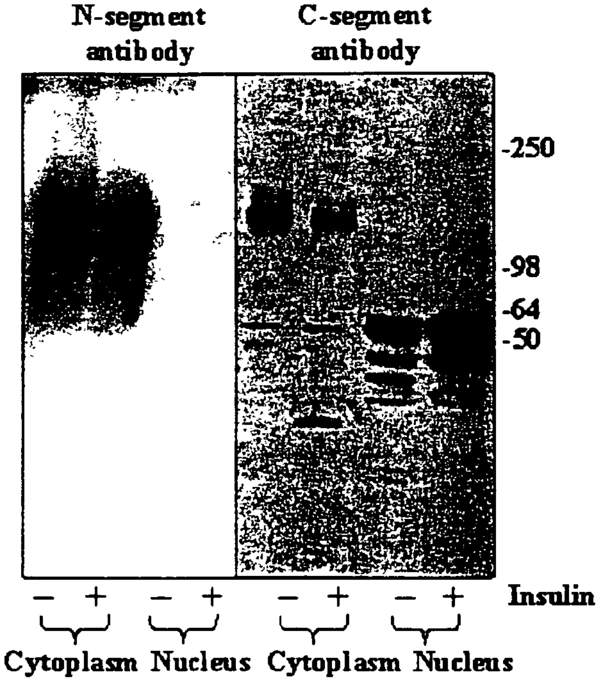

HepG 2 cells were subfractionated into cytosolic and nuclear fractions by detergent disruption of cell membranes and high salt extraction of crude nuclei. Samples were subjected to western blot and probed with anti-IRDBP-1 nAb or cAb antibody, as shown in FIG. 46B.

The cytoplasmic and the nuclear proteins were separated from HepG2 cells, and the fractionated extracts analyzed by western blotting. As shown in FIG. 46B, the anti-IRDBP-1 nAb antibody recognized an approximately 120 kDa band in the cytoplasmic extracts, but reacted poorly with the nuclear extracts. In contrast, the anti-IRDBP-1 cAb antibody recognized both the approximately 120 kDa band in the cytoplasmic extracts, and an approximately 50 kDa band in the nuclear extracts. Exposure of cells to $10^{-7}$ M insulin for 16 hours decreased cytoplasmic IRDBP-1.

Figure 47:
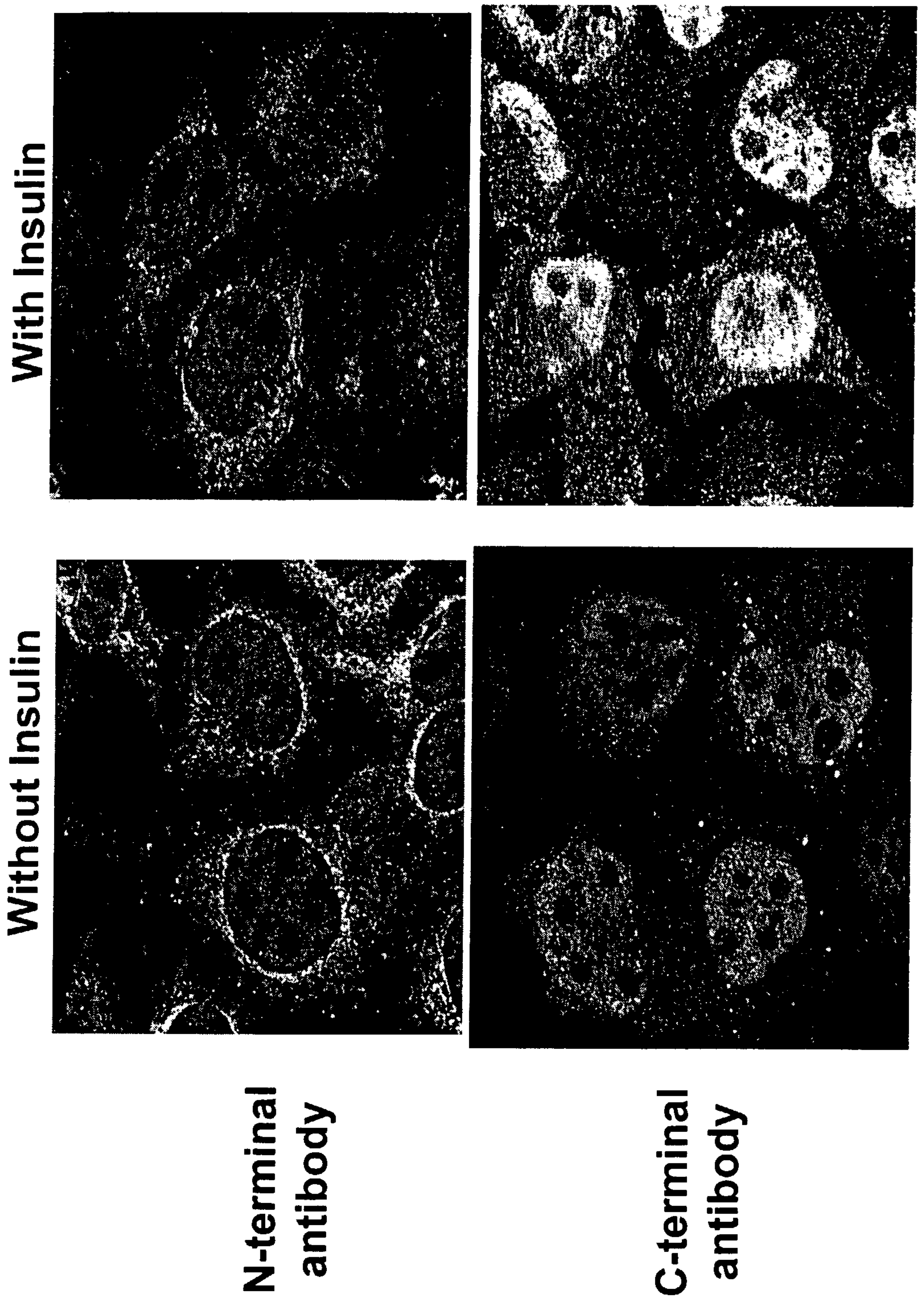
FIG. 47 shows the confocal microscopy of HepG2 cells grown with or without insulin and probed for the n-region or the c-region specific antibodies of IRDBP-1.

B. Confocal microscopy. Confocal microscopy of HepG 2 cells was done on cells grown in the absence or presence of $10^{-8}$ M insulin. Cells were permeabilized, incubated with anti-IRDBP-1 nAb or cAb antibody, and with Oregon green 488 goat anti-rabbit IgG (Molecular Probe) as the secondary antibody. Optical sections in the center of the nuclei were performed with a Zeiss confocal microscope at a magnification of 630×, as shown in FIG. 47.

The nAb immunoreactivity was localized predominantly to the cytoplasm, and tended to aggregate in the perinuclear area. However, cAb immunoreactivity was confined mainly to the nucleus, even in the absence of stimulation by insulin, which is consistent with constitutive basal expression shown by stimulation of the IRE reporter gene in transfection studies. Insulin increased the level of cAb staining in both the cytoplasm and the nucleus. The full-length protein (120 kDa band) is restricted mostly to the cytoplasm, whereas the truncated portion retaining the carboxyl ends (i.e. 70 and 50 kDa bands) was localized predominantly to the nucleus.

EXAMPLE 18

Insulin-induced Phosphorylation of IRDBP-1 at the Serine and/or Threonine Residue is Associated with Proteolytic Cleavage of IRDBP-1

Figure 48:
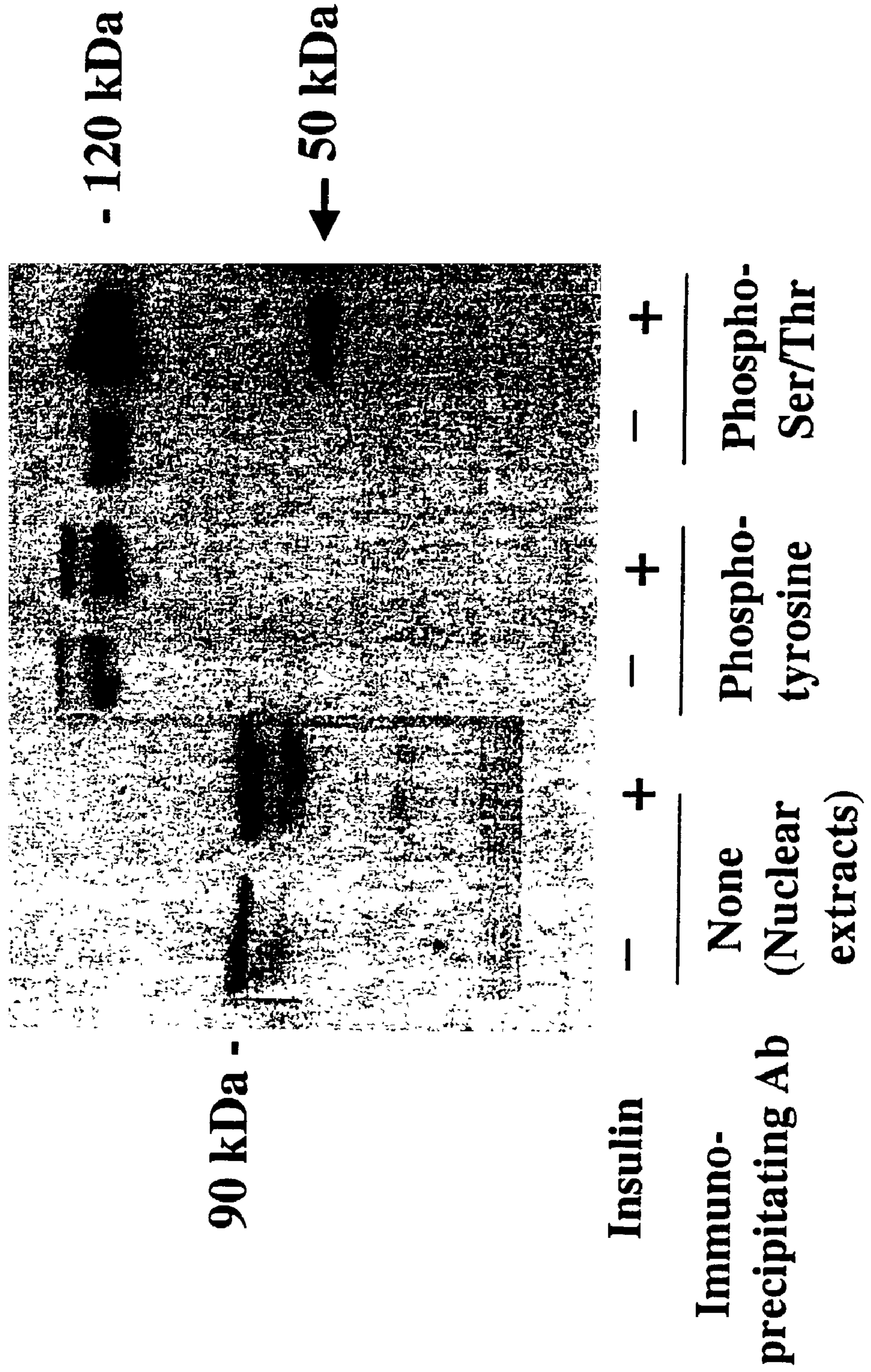
FIG. 48 shows the results of using anti-phospohotyrosine and antiphosphoserine/threonine antibodies to precipitate phosphorylated IRDBP-1 with cell extracts from COS7 cells with and without exposure to insulin.

IRDBP-1 is phosphorylated by Akt at serine/threonine, thereby affecting proteolysis of the protein. Phosphoproteins from COS7 cell extracts were precipitated with phospho-specific antibodies, and the phosphorylated fraction of IRDBP-1 was analyzed by immunoblot analysis. As shown in FIG. 48, both anti-phosphotyrosine and anti-phosphoserine/threonine antibodies immunoprecipitated a IRDBP-1-specific 120 kDa band. Treatment of the cells with insulin significantly increased the serine and/or threonine phosphorylation level of IRDBP-1. Phosphorylation of IRDBP-1 at the serine/threonine residue indicates that IRDBP-1 is a direct substrate for Aktl (FIG. 48). Also, a truncated protein of about 50 kDa size was detected in the insulin-treated, but not in non-insulin treated, cells (indicated by arrow). This lower molecular weight variant of IRDBP-1 was detected only in the serine/threonine-phosphorylated proteins, and not in the tyrosine-phosphorylated proteins.

Figure 49:
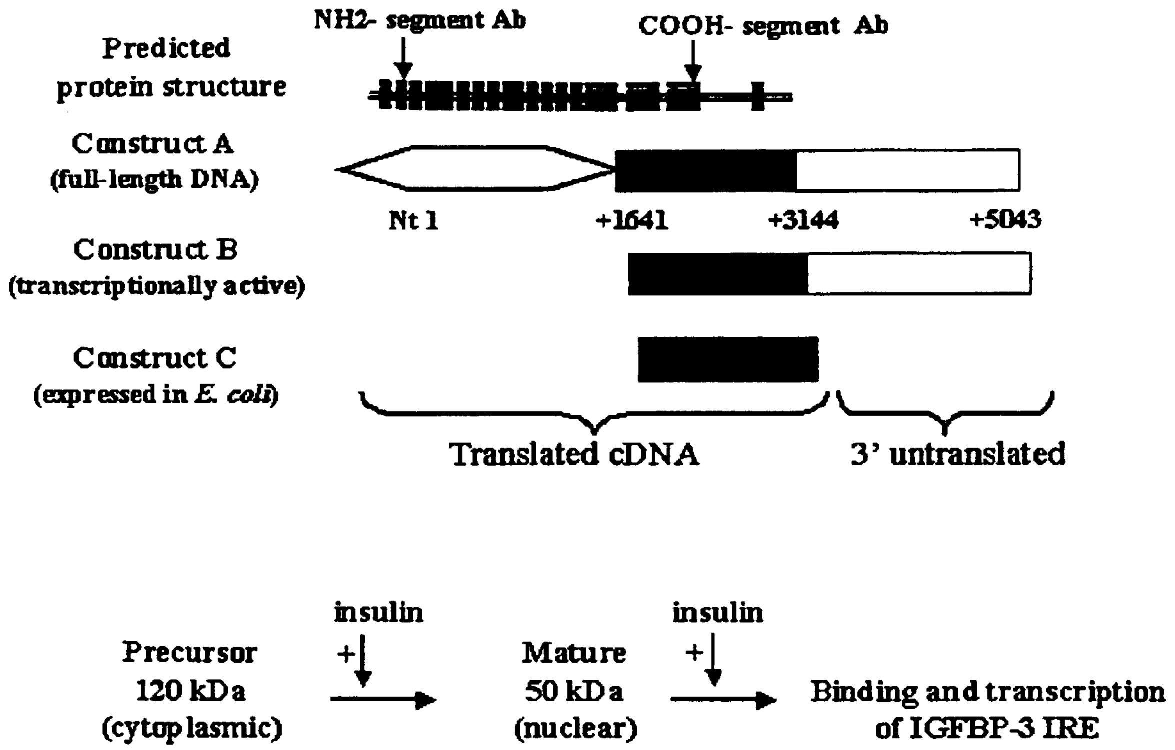
FIG. 49 illustrates the DNA of various constructs. The bottom schema shows the proposed proteolysis of the IRDBP-1 protein.

The size of this truncated protein is similar to the predicted size of the protein encoded by the transcriptionally active expression vector; activation of this vector by insulin, therefore, could involve both nuclear translocation and/or post-translational modifications. A schematic map of the predicted protein structure, the corresponding DNA segments used for functional studies, and a proposed pathway of proteolysis/activation of IRDBP-1 is shown in FIG. 49.

EXAMPLE 19

The Physiologic Relevance of IRDBP-1

An adenoviral recombinant vector containing the transcriptionally active fragment of IRDBP-1 nucleotide positions 1641-3144) of SEQ ID NO: 44 was constructed by subcloning the IRDBP-1-encoding cDNA into the pAdTrack-CMV vector. A 1.5 kb transcriptionally active fragment of rat sensitin cDNA was subcloned into the Hind III/EcoR V sites of the pAdTack-CMV vector plasmid (Clontech, Palo Alto, Calif.). Recombinant adenovirus was generated, amplified and purified by Cesium gradient centrifugation. Purified virus was tittered, and the biological effects compared to that of an equivalent dose of control virus (AdGFP).

Figure 50:
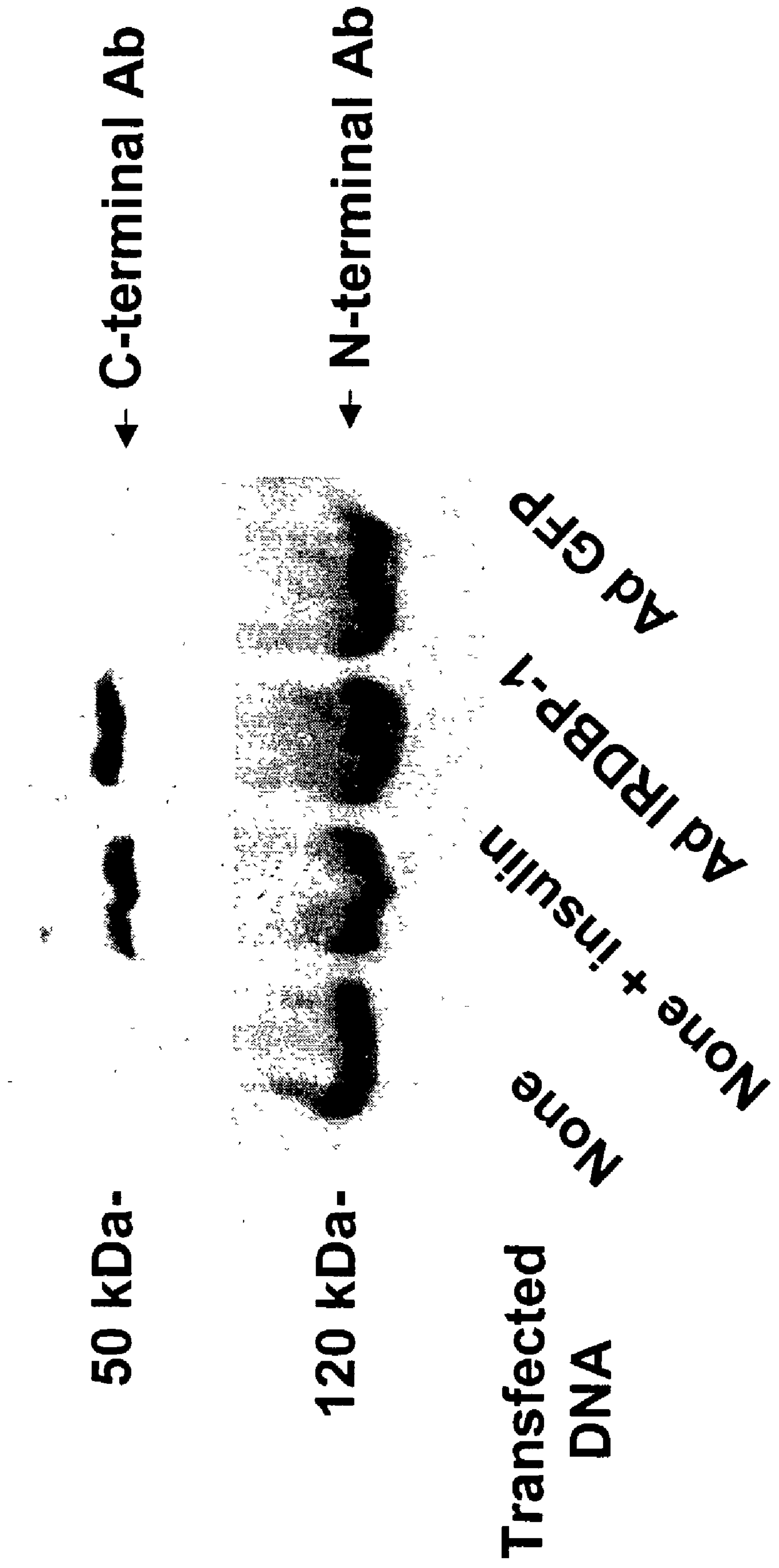
FIG. 50 shows a Western blot wherein recombinant adenovirus encoding IRDBP-1 (Ad-IRDBP-1) and Ad-GFP were transfected into 3T3-L1 cells and cell lysates were probed with anti-IRDBP-1 antibody.
Figure 51A:
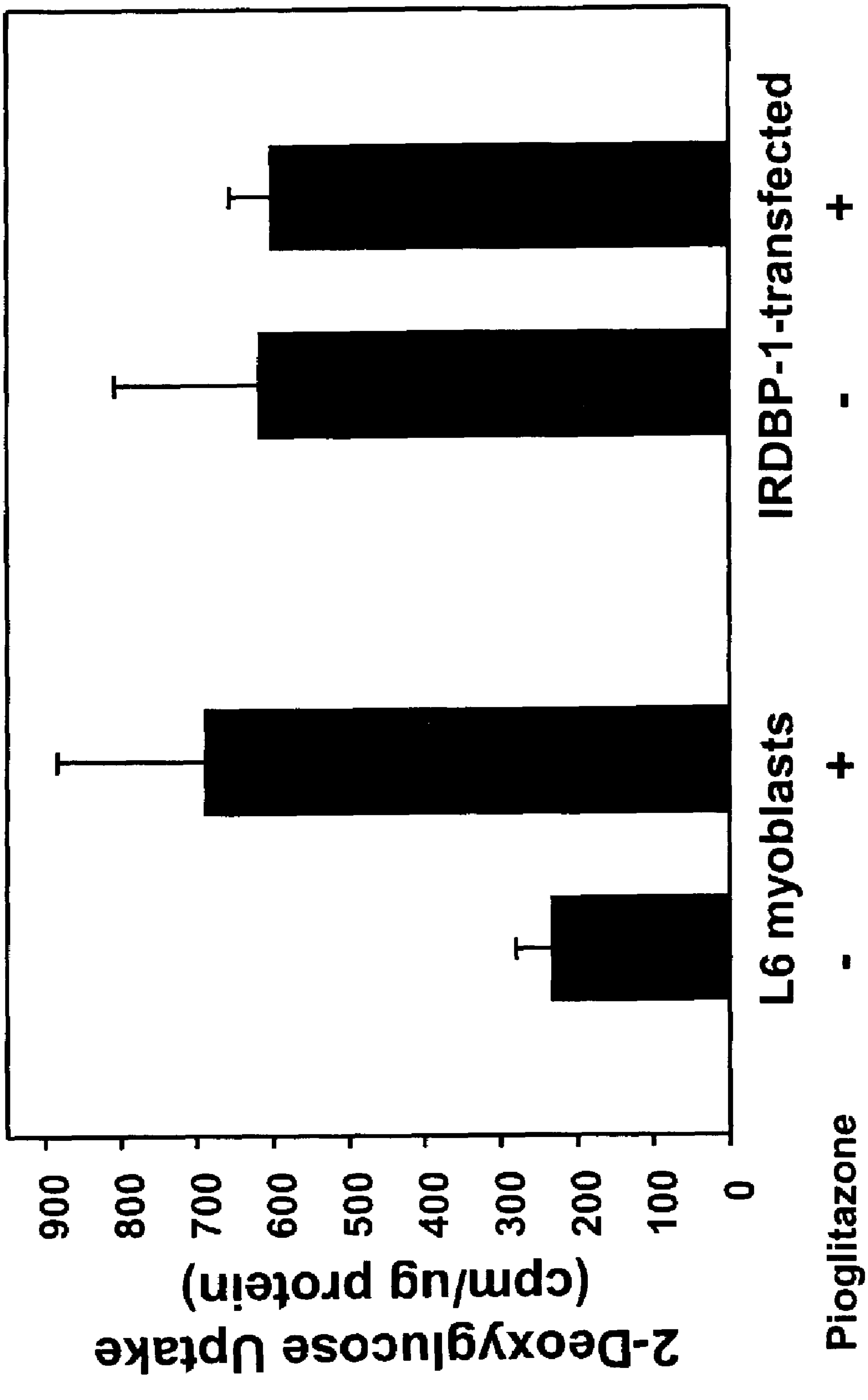
FIG. 51A illustrates IRDBP-1 increases glucose uptake in L6 myoblasts.
Figure 51B:
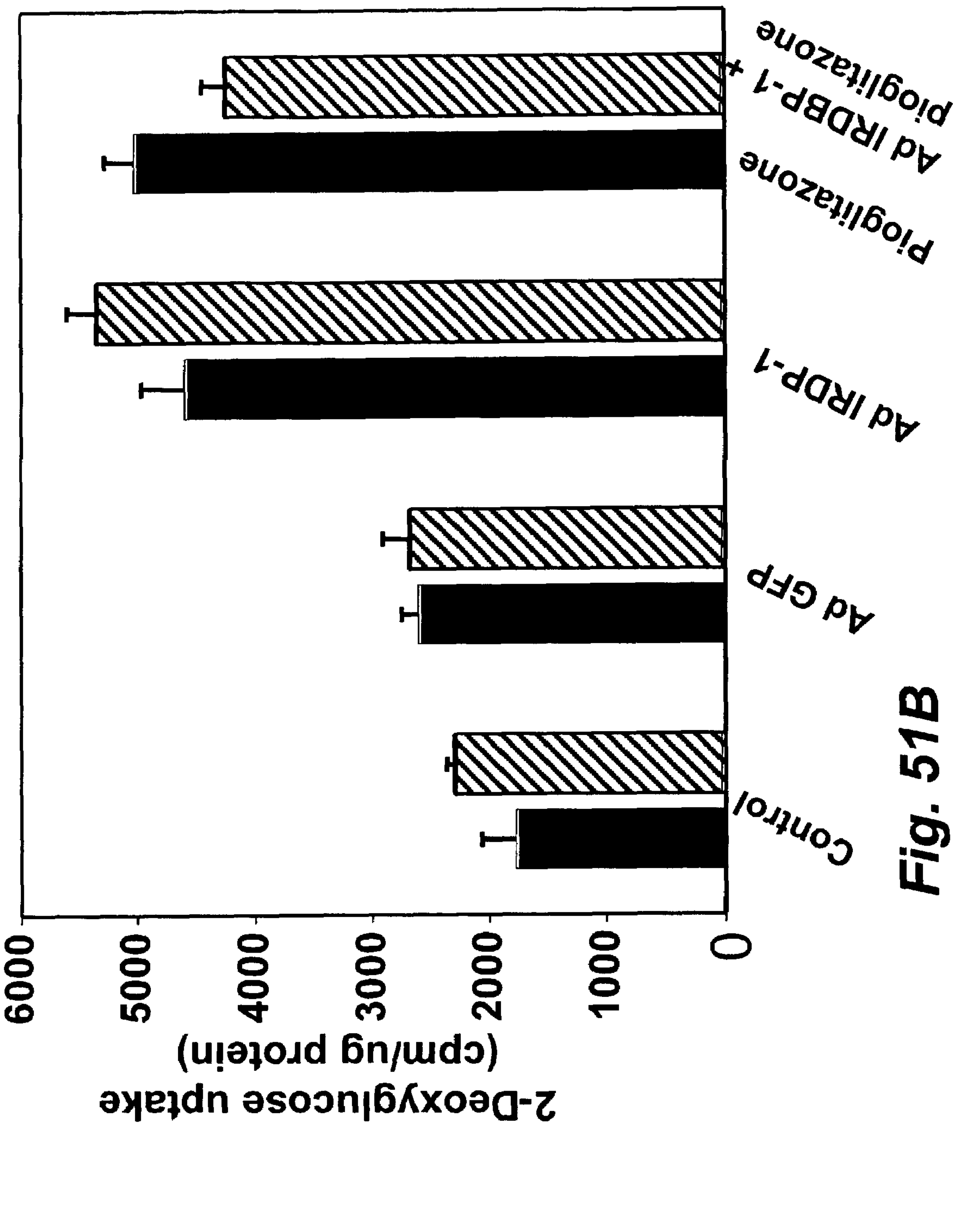
FIG. 51B illustrates IRDBP-1 increases glucose uptake in human adipocytes transfected with Ad-IRDBP-1.

Recombinant adenovirus-encoding IRDBP-1 (Ad-IRDBP-1) and GFP (Ad-GFP) were transfected into 3T3-L1 adipocytes, cell lysates were subjected to western blot analysis and probed with anti-IRDBP-1 cAb or nAb antibody to show that the recombinant Ad-IRDBP-1 vector could express the heterologous IRDBP-1 in the recipient 3T3-L1 cells (FIG. 50). 2.8 μM $[H^3]$ 2-deoxyglucose was added to human adipocytes with or without added $10^{-8}$ M insulin for 15 mins (FIG. 51B). Glucose uptake was compared between control adipocytes and cells transfected with Ad-GFP or Ad-IRDBP-1, and cells treated overnight with or without $10^{-5}$ M pioglitazone. After addition of $10^{-7}$ M insulin for 15 mins, there was a 30±3% increase in glucose uptake in wild type cells, but only a 16±5% increase in IRDBP-1-overexpressing cells.IRDBP-1 confers insulin-like glucose uptake enhancement.

Thiazolidinedione Modulates IRDBP-1 Activity

Figure 52:
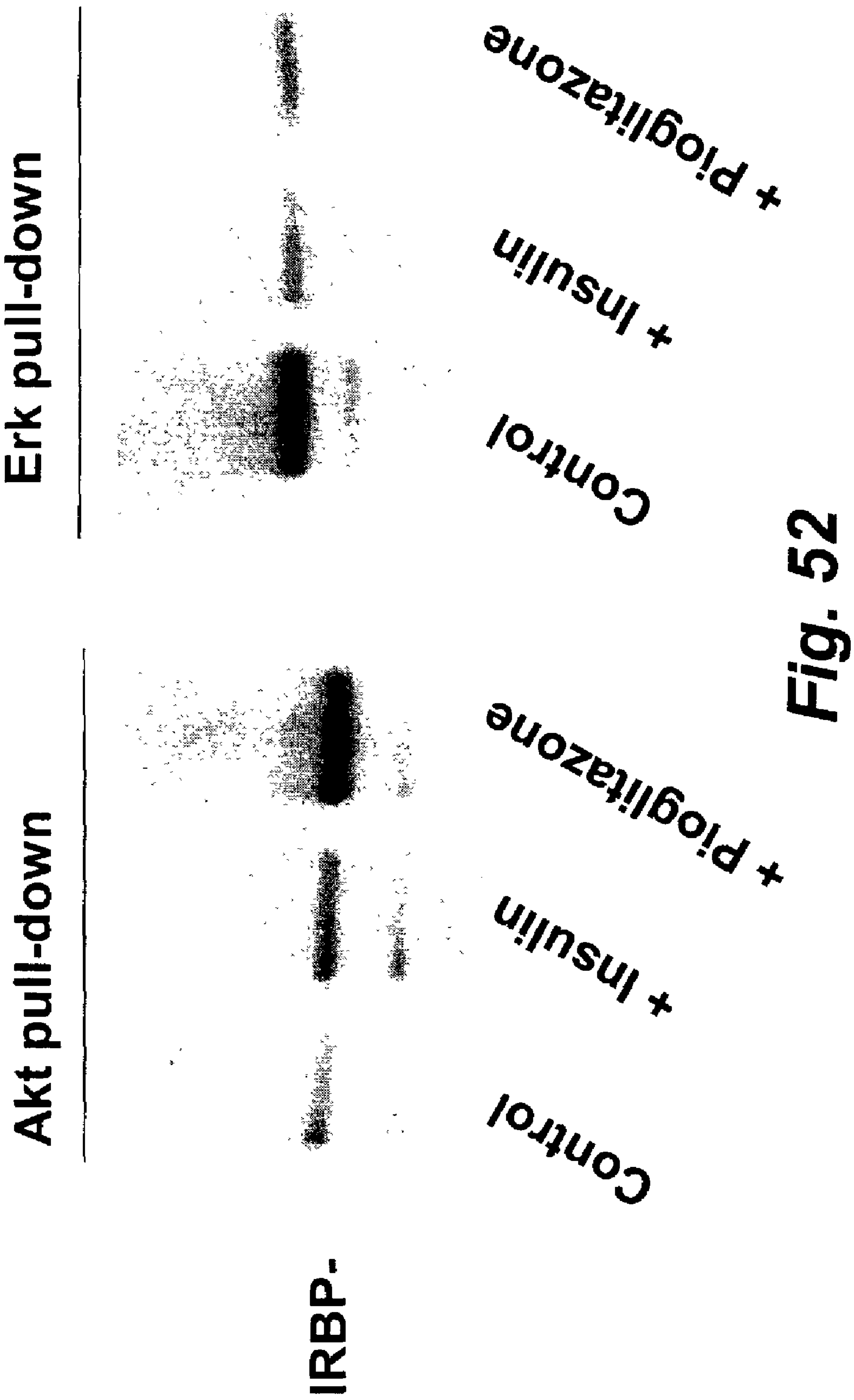
FIG. 52 shows that IRDBP-1 is a target for thiazolidinedione in 3T3-L1 adipocytes.

The effects of IRDBP-1 in the absence and presence of pioglitazone were compared. Pioglitazone is a thiazolidinedione used to increase insulin sensitivity and lower glucose levels in patients with diabetes. Glucose uptake rose by 183±14% in adipocytes treated with pioglitazone for 16 hours, which was comparable to the increased glucose uptake in the Ad-IRDBP-1 cells, as shown in FIG. 51A. However, addition of pioglitazone produced no further increase in glucose uptake in the Ad-IRDBP-1 cells, as shown in FIG. 51B. Pioglitazone and insulin added individually can increase the interaction between Akt1 and IRDBP-1 (FIG. 52). However, the effect of pioglitazone and insulin together is not additive.

EXAMPLE 20

IRDBP-1 Function in Intact Animals

Figure 53A:
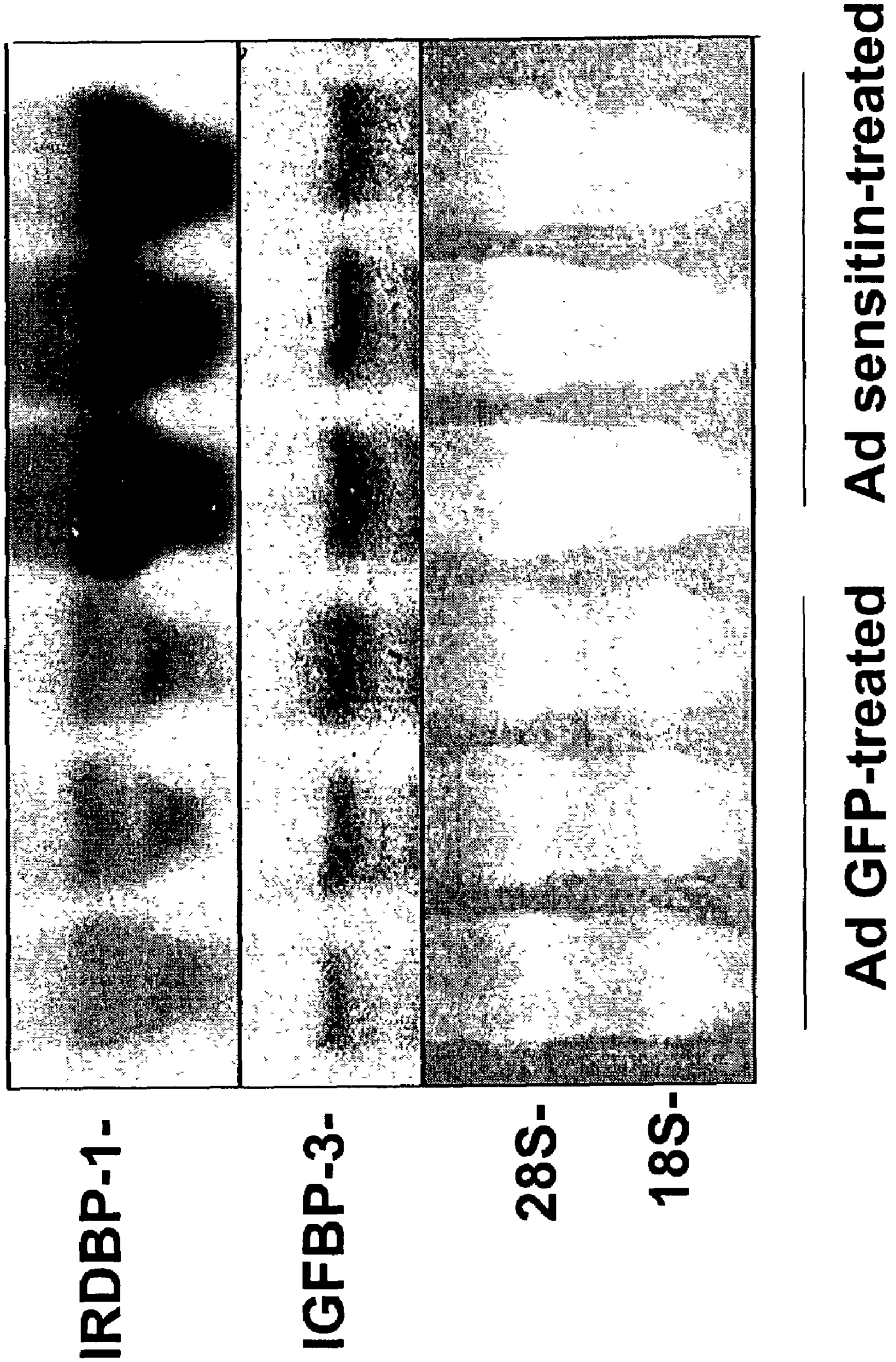
FIG. 53A shows a Northern analysis of hepatic tissues from rats infected with an Ad-IRDBP-1 and Ad-GFP constructs.
Figure 53B:
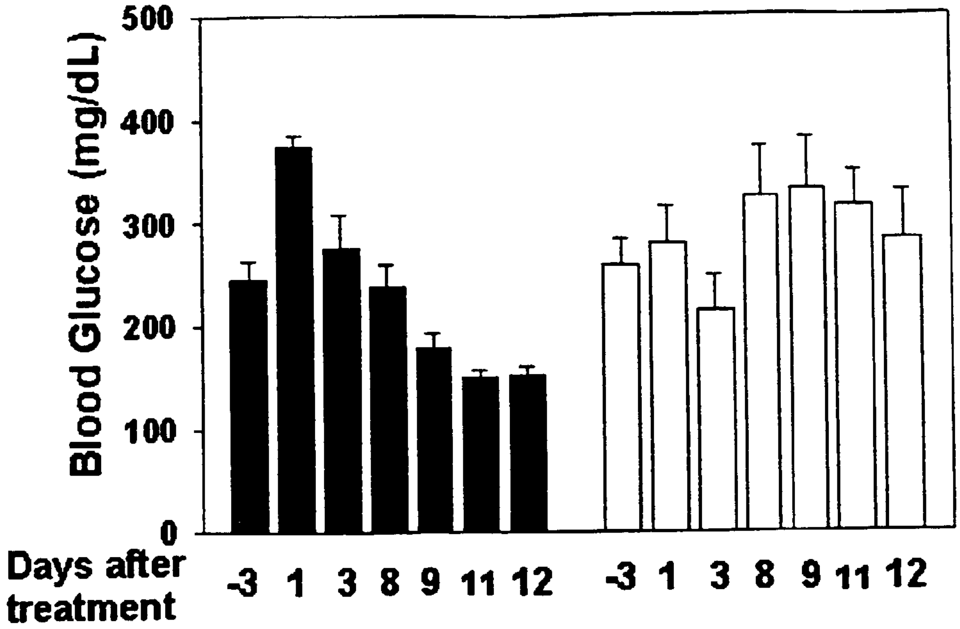
FIG. 53B shows the blood glucose levels of Ad-IRDBP-1 and Ad-GFP injected ZDF rats before and after treatment with the recombinant virus.

The adenoviral constructs were introduced into 10-week old male Zucker diabetic fatty (ZDF) rats via tail vein infusion at a dose of $5.0\times10^7$ plaque forming units (pfu)/gm body weight and resulting in an increase in IRDBP-1 levels in hepatic tissue (FIG. 53A). Control studies included age-matched ZDF rats infused with virus encoding the green fluorescent protein (Ad-GFP), given at a dose equivalent to that of Ad-IRDBP-1. Glucose was measured in blood samples from the tail vein of Ad-IRDBP-1-treated ZDF rats (n=6, black bars) and Ad-GFP-treated ZDF rats (n=6, white bars) before and after treatment with the recombinant adenovirus IRDBP-1 or GFP vector, as shown in FIG. 53B. Values are means ±SEM. Body weight of the Ad-IRDBP-1 transfected ZDF rats was monitored in ad libitum-fed IRDBP-1-treated (n=6, shown as solid line) and GFP-treated rats (n=6, shown as broken line, FIG. 53C).

Figure 53C:
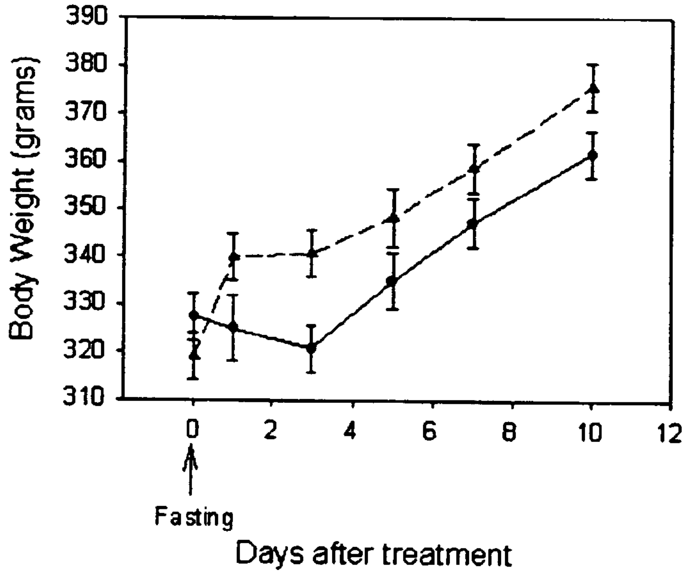
FIG. 53C shows the change in the body weight of Ad-IRDBP-1 injected ZDF rats ad libitum fed.
Figure 53D:
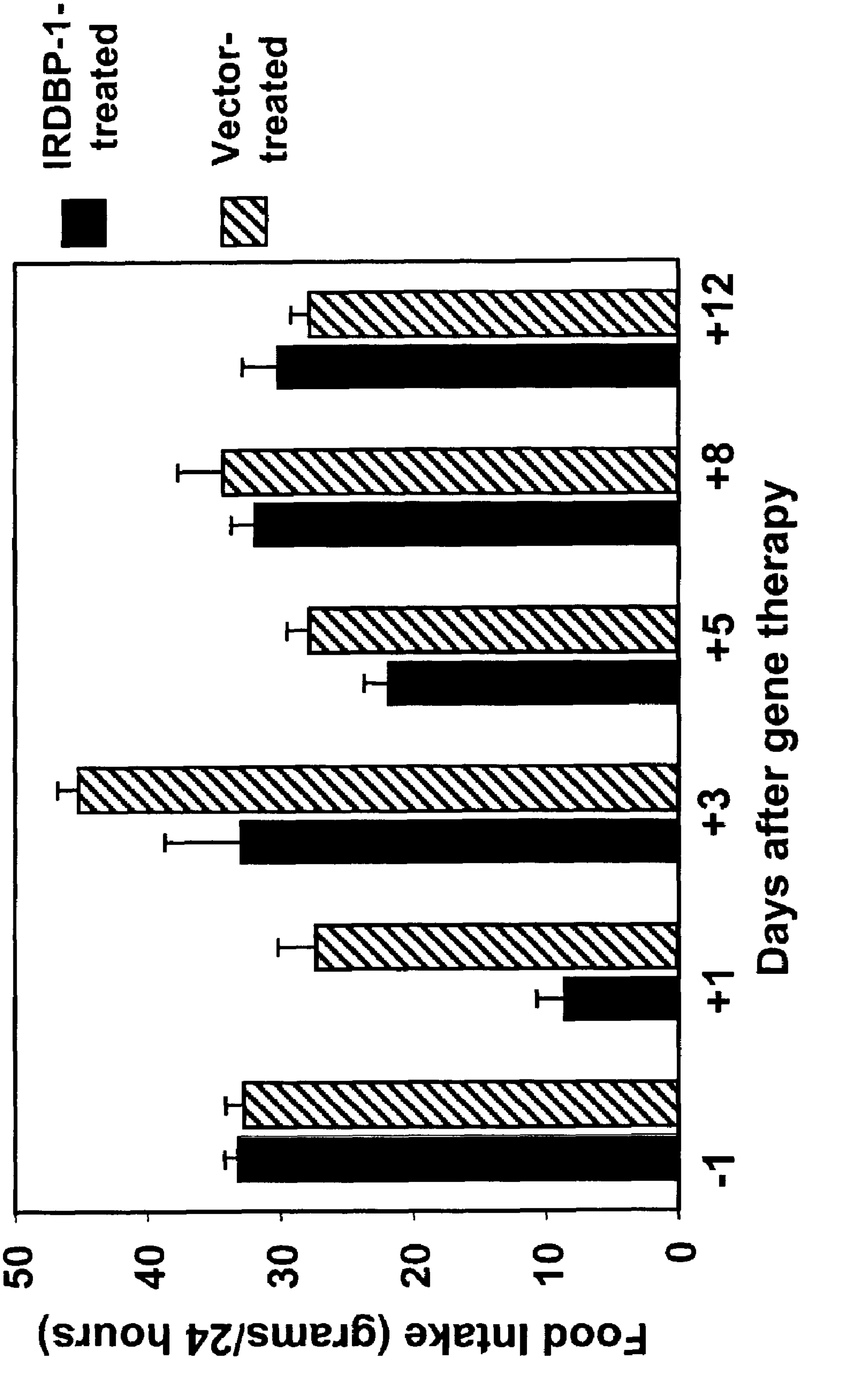
FIG. 53D shows the rate of food uptake of Ad-GFP and Ad-IRDBP-1 treated ZDF rats.
Figure 53E:
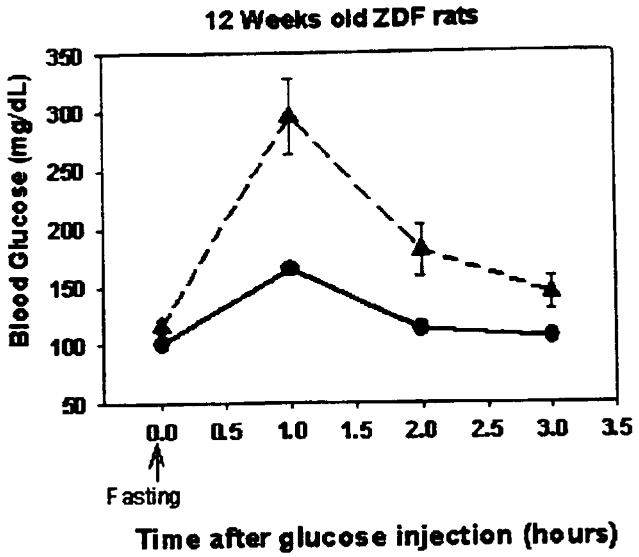
FIG. 53E illustrates the serum glucose levels after gene therapy treatment on 12 week rats injected with Ad-IRDBP-1
Figure 53F:
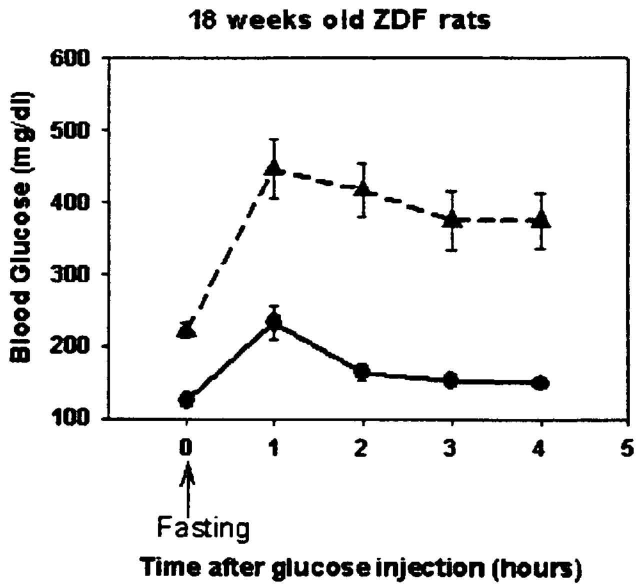
FIG. 53F illustrates the serum glucose levels after gene therapy treatment on 18 week rats injected with Ad-IRDBP-1.

GTT on 12 week and 18 week old rats treated with or without Ad-IRDBP-1 is shown in FIGS. 53E and 53F. Two gms of dextrose/KBW was injected intraperitoneally into Ad-IRDBP-1 and Ad-GFP-treated rats (n=6 in each group), and blood glucose was measured every hour for 3 hours. The results are shown in FIGS. 53E and 53F. Solid line: Ad-IRDBP-1-treated rats; broken line: Ad-GFP-treated rats. Each bar represents mean ±SEM. There was no difference between the effects of normal saline (vehicle) vs. Ad-GFP (viral vector) infusions on glucose levels in the ZDF rats.

The effects of Ad-IRDBP-1 were similar whether the adenovirus was introduced via the portal vein or tail vein. The distribution of IRDBP-1 was traced using immunofluorescence microscopy detection of GFP. Expression of Ad-IRDBP-1 was high in the liver, particularly in hepatocyte nuclei, and also high in mesenteric adipocytes and mesenteric veins. Northern blotting showed that hepatic IRDBP-1 was increased by administration of the transgene (FIG. 53A). An associated increase in IGFBP-3 expression mimicked the ability of insulin to stimulate IGFBP-3 expression. Since ZDF rats are hyperinsulinemic, the findings indicate that IRDBP-1 can have both insulin-mimicking (FIG. 51A) and insulin-sensitizing activity (FIG. 53A).

As shown in FIG. 53B, baseline ~3 pm capillary glucose levels of ad libitum-fed Ad-IRDBP-1 and Ad-GFP rats were not significantly different before treatment (245±17 vs. 258 ±25 mgfdl). However, there was a transient increase in plasma glucose 24 hr after administration of Ad-IRDBP-1, followed by a gradual decline over 10-12 days. After 12 days, there was a significant decrease in the glucose levels of Ad-IRDBP-1 rats (baseline of 245±17 vs. 151±9 mg/dl at 12 days, p<0.05). In contrast, glucose levels remained high in the Ad-GFP rats (baseline of 258±25 vs. 282±48 mg/dl at 12 days, p=NS). The Ad-GFP recipient rats gained weight continuously through the study, while weight was stable in Ad-IRDBP-1 animals for the first 3-5 days (associated with some decrease in food intake), with steady weight gain thereafter (FIGS. 53C, 53D).

On day 11, both groups of animals were fasted overnight. A glucose tolerance test (GTT) was performed with intraperitoneal injection of 2 gm/kg body weight of 50% dextrose. Glycogen was measured by the amyloglucosidase/hexokinase enzymatic assay after acid hydrolysis. Rat insulin was measured by RIA (kit from Linco Research Inc.) Interassay CV=0.20, intraassay CV=0.06.

Figure 54:
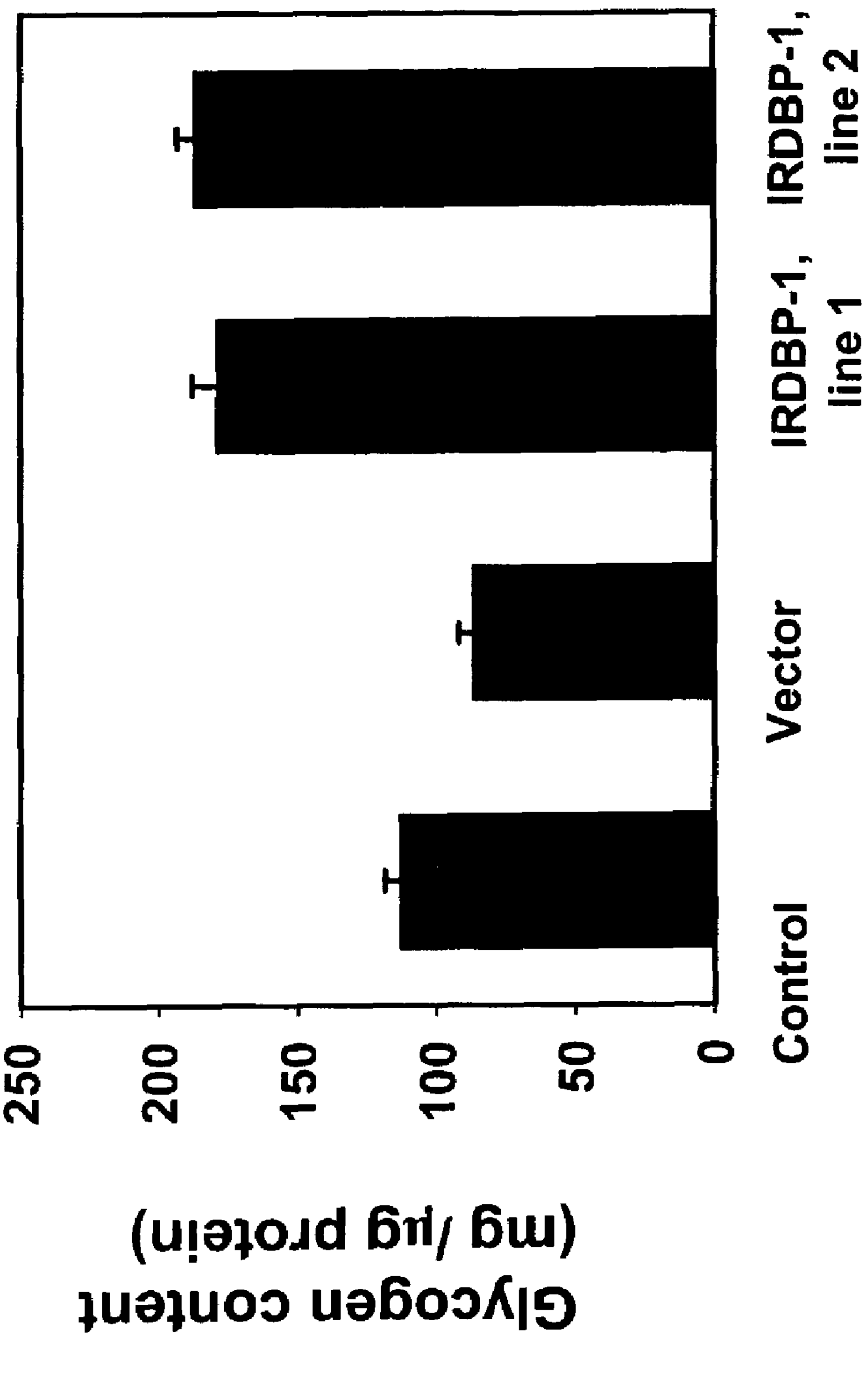
FIG. 54 illustrates the effects of IRDBP-1 on glycogen content in two cell lines with stable expression of IRDBP-1 in transfected L6 cells.

As shown in FIG. 53E, fasting glucose levels were slightly lower in the Ad-IRDBP-1 compared to the Control Ad GDF rats (101±5 vs. 116±6 mg/dl). During the GTT, glucose levels in the Ad-IRDBP-1 rats were 166±6 mg/dl at 1 hour and 113±3 mg/dl at 2 hours, whereas glucose levels in the Ad-GFP rats were 296±31 mg/dl and 181±22 mg/dl, respectively, which was significantly higher than the respective glucose levels in the Ad-IRDBP-1 rats (both p<0.05). Despite lower fasting glucose levels, improved glucose tolerance, and higher liver glycogen (FIG.54), mean fasting insulin levels were also slightly lower in Ad-IRDBP-1 compared to the Ad-GFP rats (0.81±0.06 vs. 0.91±0.12 ng/ml, p=0.5), consistent with increased insulin sensitivity.

The GTTs were repeated with 18 week old ZDF rats with more severe diabetes. Before gene therapy, glucose levels at 3 pm during ad libitum feeding were 395±18 mg/dl in Ad-IRDBP- 1, and 390±18 mg/dl in Ad-GFP rats. Fourteen days after therapy, despite comparable weight (435±gms in Ad-IRDBP-1 rats and 421±14 gms in Ad-GFP rats), the fasting glucose level was significantly lower in Ad-IRDBP-1 rats (125±6 mg/dl vs. 223±10 mg/dl, p<0.005 in Ad-GFP rats) (FIG. 53F). During the GTT, glucose levels in the Ad-IRDBP-1 rats rose to 165±12 and 150±3 mg/dl at 2- and 4-hrs post-challenge, whereas glucose levels in the Ad-GFP rats were 417±38 and 375±38 mg/dl (both p<0.05 vs. values in Ad-IRDBP-1 animals), demonstrating that IRDBP-1 administration decreases fasting glucose and insulin levels, and improves the response to a glucose challenge. Treatment with IRDBP-1 appears to be sufficient to ameliorate hyperglycemia in ZDF rats.

EXAMPLE 21

Administration of IRDBP-1 Sense and Antisense Oligonucleotides to an Animal

Methods & Materials. The methodology was adapted from that of Apostolakis et al, J. Neurosci. 16: 4823-4834) incorporated herein by reference in its entirety. Briefly, ovariectomized (OVX) female rats (200-250 gm) were housed individually and maintained on a 12:12 hour light:dark cycle (lights on at 0700 CST) with rat chow and water in excess ad libitum. After acclimation (7 days), females underwent stereotaxic implantation of third ventricle cannula guides (26 gauge, Plastics One, Roanoke Va.). The experiment started 7 days after surgery. Females were randomly assigned identification numbers and weighed daily between 0900 and 1000 CST for 5 days immediately before experimental treatment, allowing each animal to serve as its own control. Each animal (n=5) received a single intraventricular (icv) injection of antisense (AS, sequence 5'-CTAACTCACAGGTGATGATGTA-GAG-3', SEQ ID NO: 42) oligos (4 nM in 1 μl vol. over 2 min) after weighing on the fifth day. Another group of animals (n=4) served as positive controls and received sense (S, sequence 5'-CTCTACATCATCACCTGTGAGTTAG-3', SEQ ID NO: 43) oligos (4 nM in 1 μl vol. over 2 min). Animals were euthanized under deep anesthesia 8 days after oligonucleotide treatment.

Figure 55A:
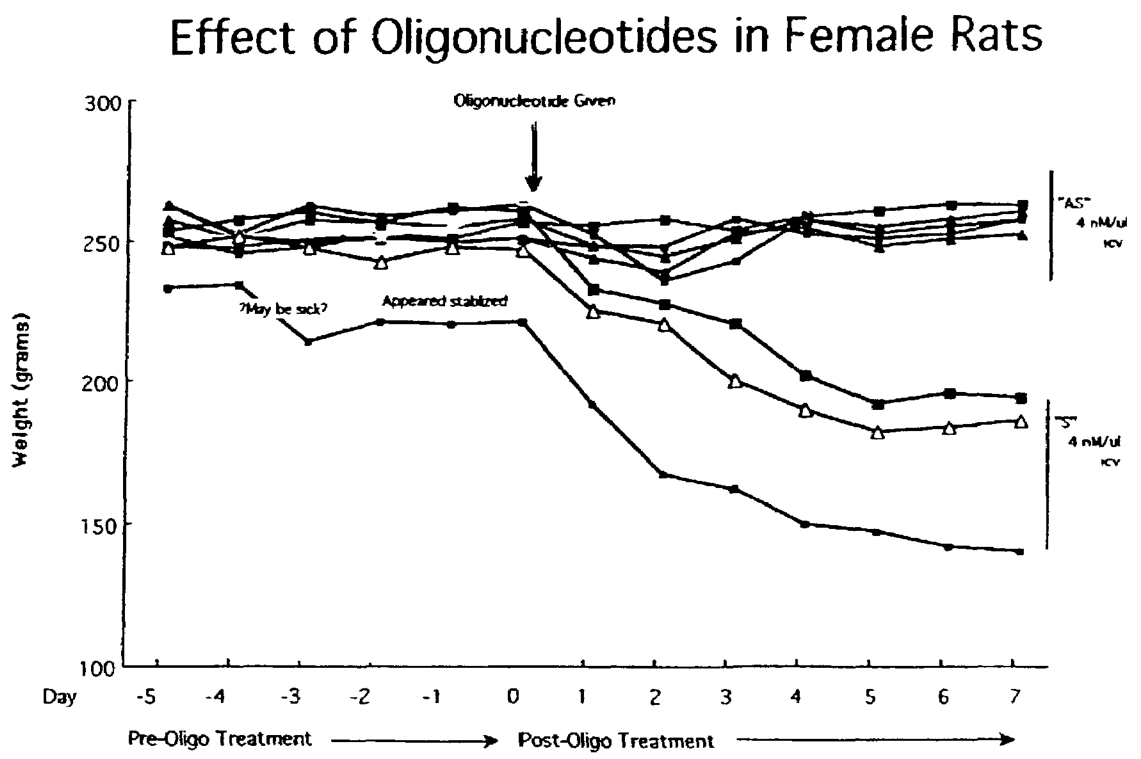
FIG. 55A illustrates the effect of administered IRDBP-1 antisense (AS) or sense (S) oligonucleotides on the body weight of rats.
Figure 55B:
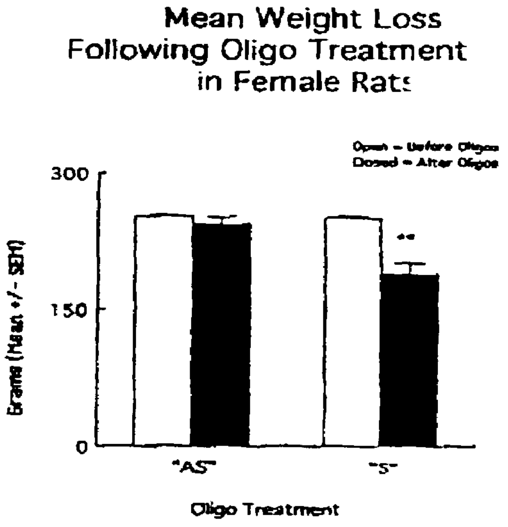
FIG. 55B illustrates the loss in body weight of females rats receiving sense IRDBP-1 DNA.

There was a difference in mean weight loss between those animals following treatment with antisense DNA and sense DNA (FIG. 55A). For the five days prior to oligonucleotide treatment, the animals demonstrated stable weight. Within 24 hours after treatment, animals that received sense DNA began to lose weight with the greatest loss (54±6.4 gm) being attained at 72-96 hours after treatment as shown in FIG. 55A. Antisense DNA had no significant effect on weight (251±2 gm) while sense DNA-treated animals lost weight (54.3±6.2 gm). Individually, the females receiving sense DNA lost 27% of their body weight as compared with either their initial weight, their mean weight during the pretreatment time or mean weight of antisense-treated animals as shown in FIG. 55B.

EXAMPLE 22

Inhibitory Effect of IRDBP-1 on Cell Proliferation

Transfected L6 Cells are Growth Arrested when Transfected with IRDBP-1 Expressing Nucleic Acid.

Figure 56:
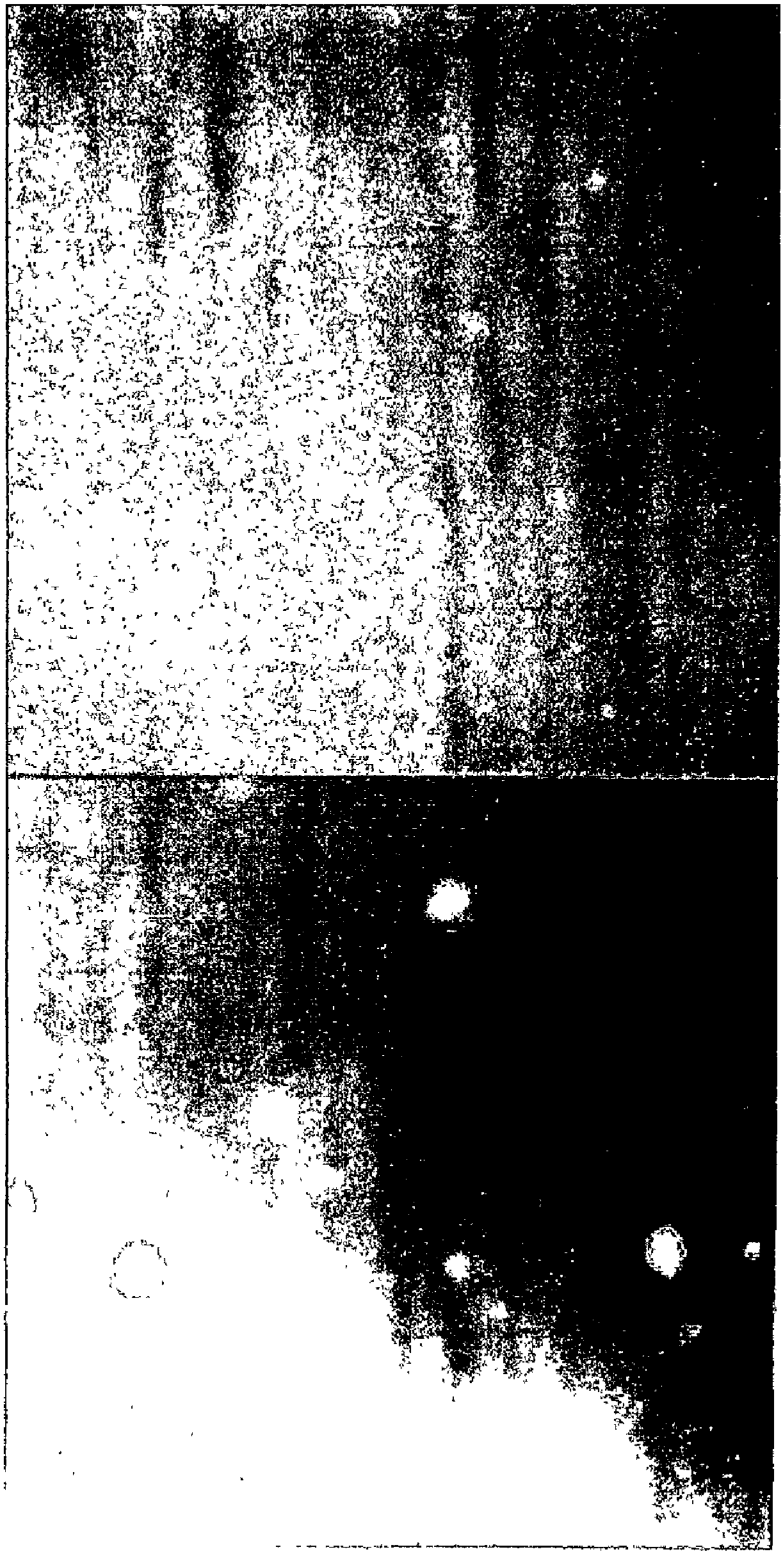
FIG. 56 illustrates phase contrast micrographs of L6 cells stably transfected with control vector alone (left) or with vector containing the IRDBP-1 nucleic acid sequence (right) and grown in soft agar for 4 weeks.

L6 cells stably transfected with the IRDBP-1-encoding cDNA (SEQ ID NO: 14) exhibited significantly reduced proliferation rates when cultured in soft agar, compared to transfection with the vector alone, as shown in FIG. 56.

Figure 57A:
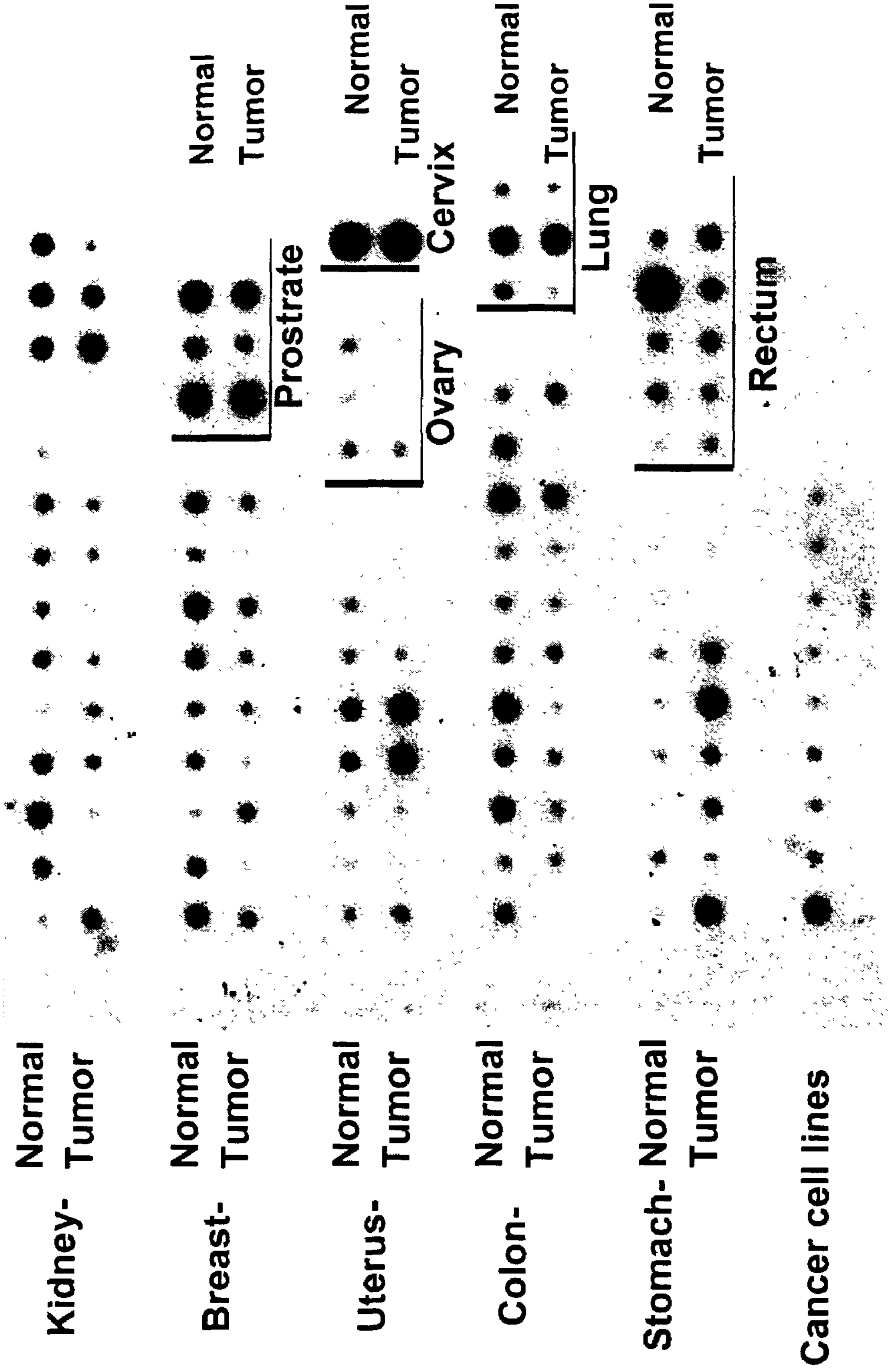
FIG. 57A illustrates the expression of human IRDBP-1 in tumor and normal tissues.
Figure 57B:
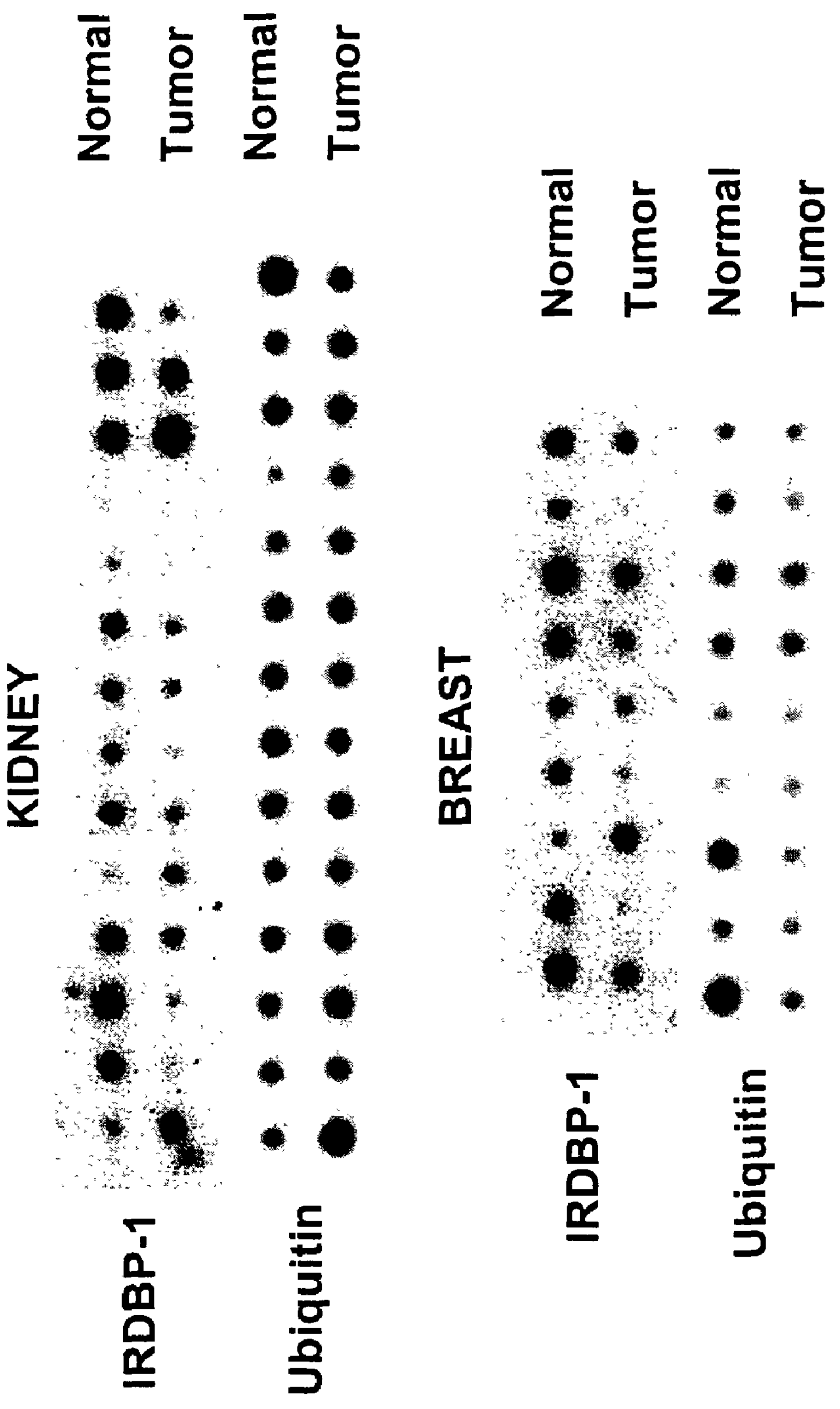
FIG. 57B illustrates the expression of human IRDBP-1 in kidney and breast tumor tissues.
Figure 57C:
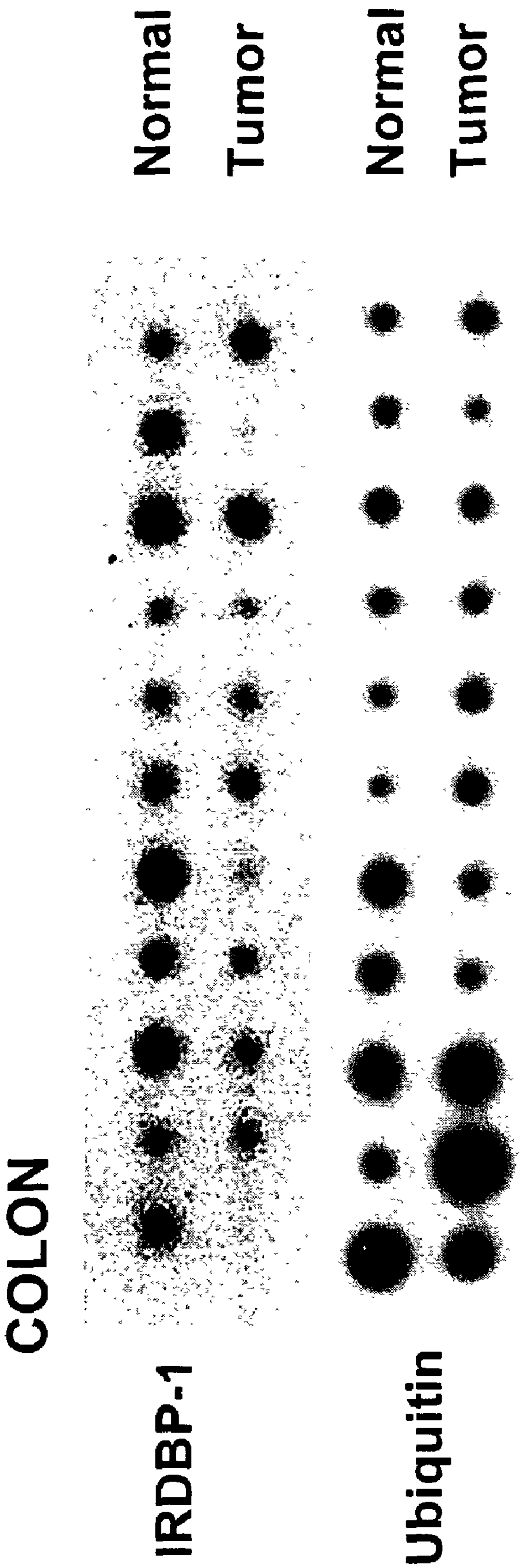
FIG. 57C illustrates the expression of human IRDBP-1 in colon tumor tissues.

Matched tumor/normal expression array analysis showed that in certain cancer types, including breast, rectal, colon, lung and kidney, IRDBP-1 is expressed at higher levels than is found in normal tissues, as shown in FIG. 57A.

RNA was obtained from various normal and tumor tissues, and was converted into cDNA. PCR amplified the cDNA and the samples were blotted onto nylon membranes. cDNAs originating from 68 human tumors and corresponding normal tissues from a single individual were arrayed and immobilized as separate dots. The membrane was hybridized with a human IRDBP-1 probe.

Figure 58:
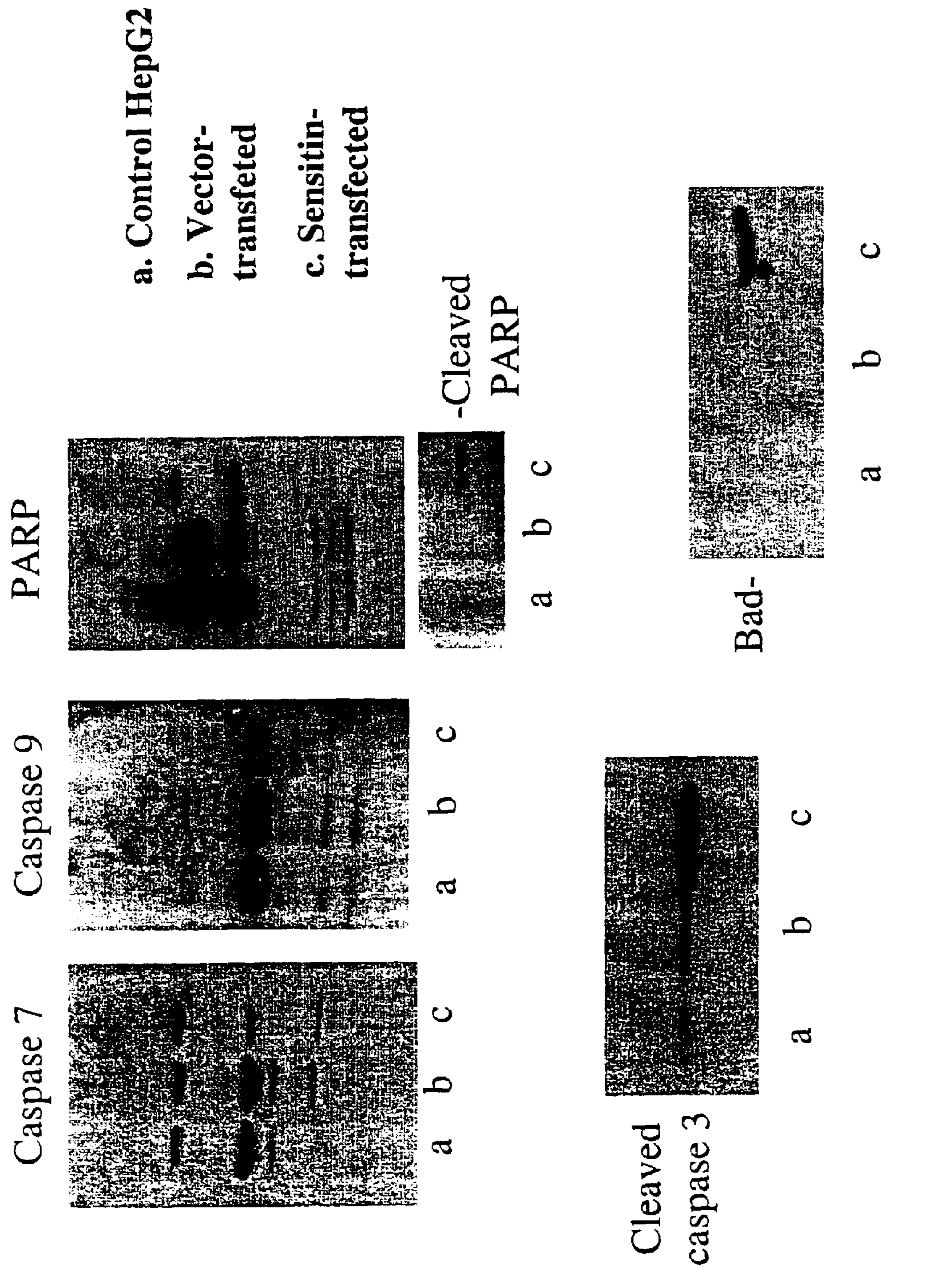
FIG. 58 illustrates IRDBP-1 induces apoptosis in HepG2 cells.
Figure 59:
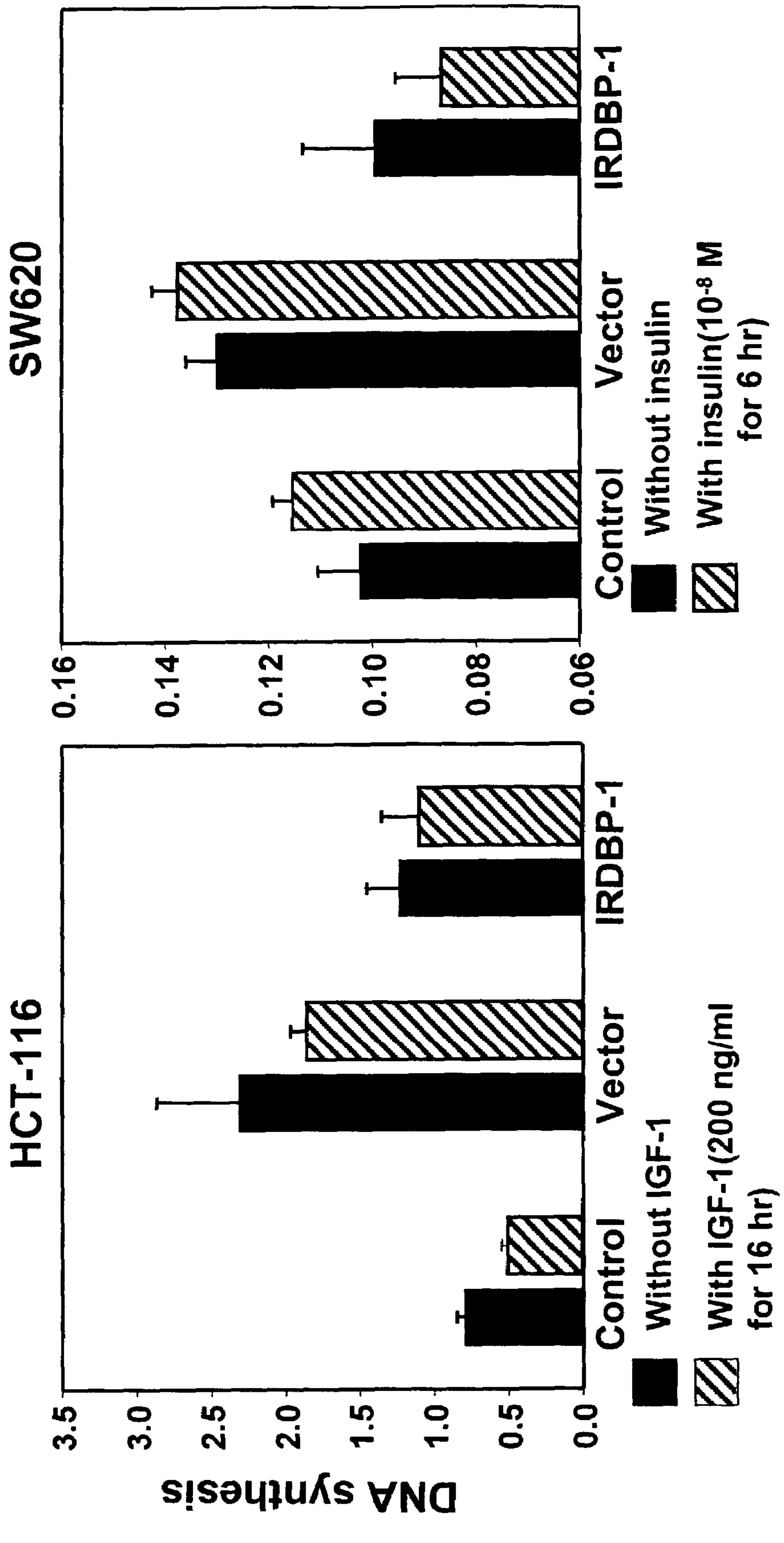
FIG. 59 illustrates the decreased DNA synthesis in HCT-116 and SW620 cells with IRDBP-1 overexpression.
Figure 60:
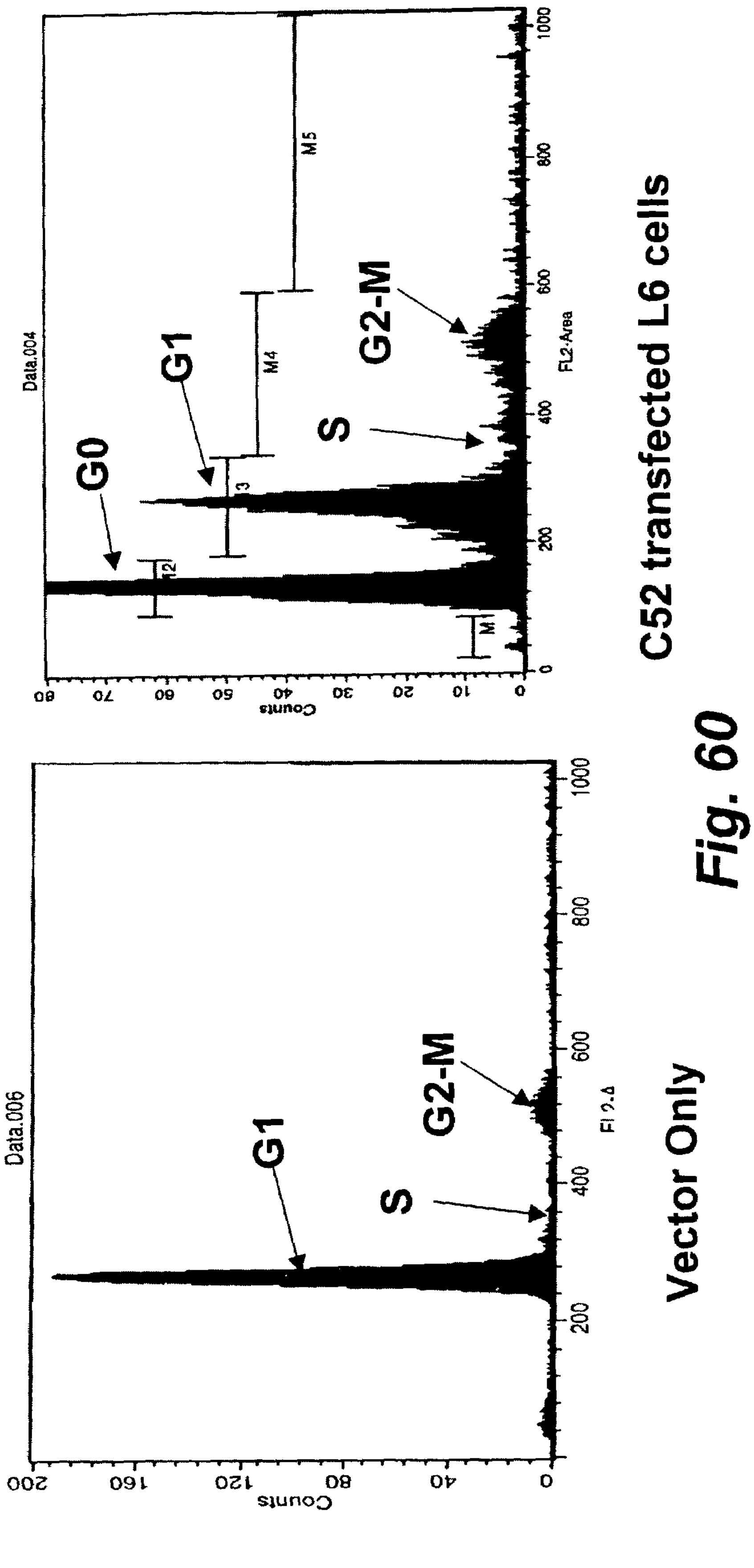
FIG. 60 illustrates analysis by flow cytometry of the cell cycle compartments of L6 cells with (right panel) or without (left panel) over-expression of the IRDBP-1 nucleic acid sequence.
Figure 61:
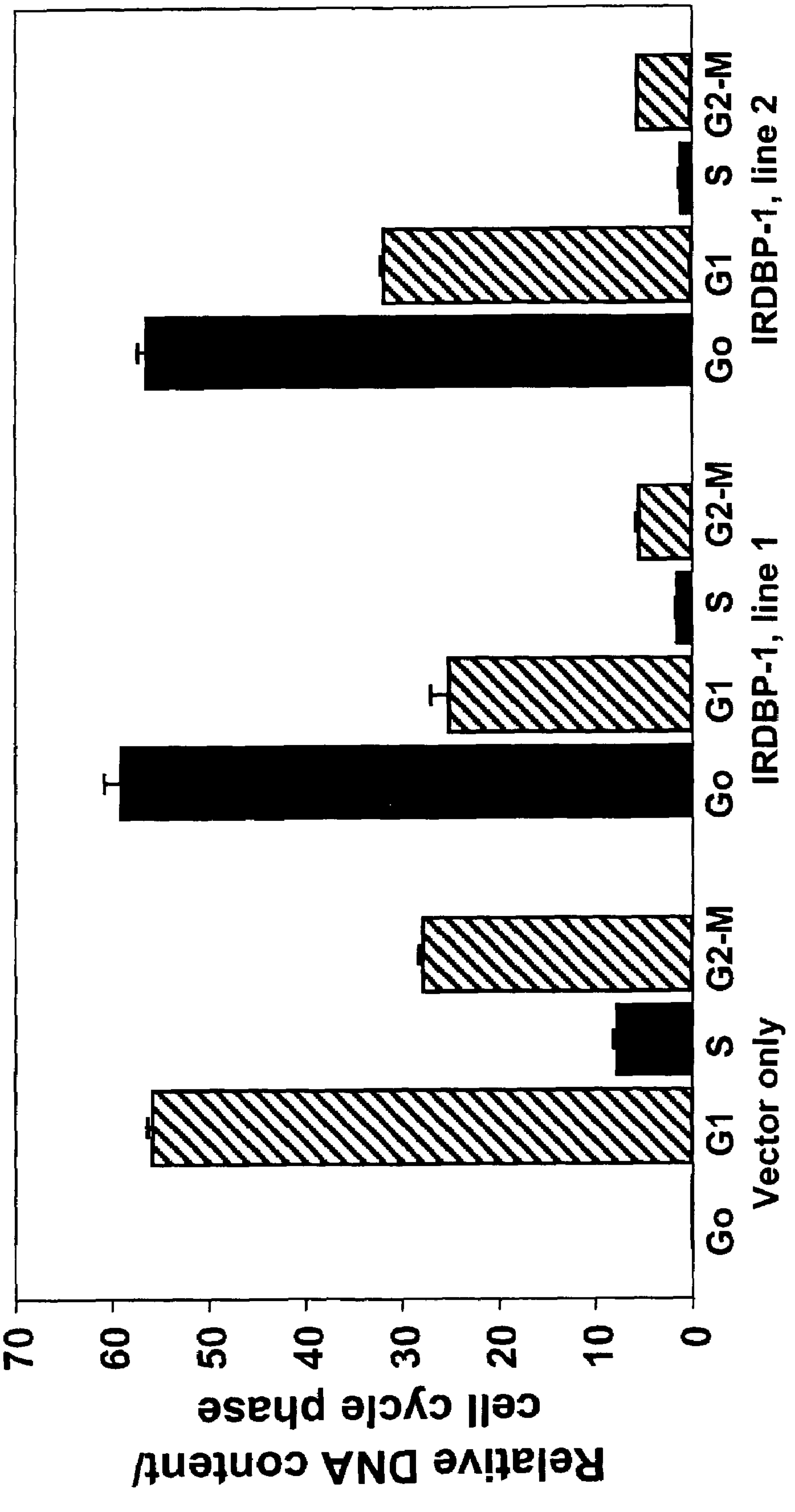
FIG. 61 illustrates the increase in Go cells after expression of IRDBP-1 therein.

Expression of IRDBP-1 in HepG2 cells showed that overexpression of the transfected IRDBP-1 induces apoptopic events (FIG. 58). IRDBP-1 further inhibits DNA synthesis in HCT-116 and SW620 cells (FIG. 59). Overexpression of IRDBP-1 will further induce proliferating cell lines to enter Go stationary phase, as shown in FIGS. 60 and 61.

Flow cytometry Analysis of the Cell Cycle Compartments of L6 Cells with or without Over-expression of the IRDBP-1 Nucleic Acid Sequence.

Flow cytometry was conducted to analyze DNA content and progression through the cell cycle. Stable transfectants were fixed in ice cold 100% ethanol and debris was removed by centrifugation through a cushion of fetal bovine serum. Cell pellets were treated with RNAse solution (500 units/ml of 1.12% (w/v) sodium citrate) at 37° C. for 15 mins, and DNA was stained with propidium iodide (5 mg/100 ml of 1.12% sodium citrate) for 30 minutes at room temperature before analyzing on the flow cytometer.

Stable cell lines transfected with the expression vector pCMV-Tag with and without the IRDBP-1 nucleic acid sequence (SEQ ID NO: 14) were grown to confluence, fixed with ethanol, and stained with propidium iodide. Cell cycle compartment analysis was done by flow cytometry, measuring excitation at 488 nm with argon lasers. The histograms illustrated in FIG. 61 show that cells transfected with the vector alone, 0.2% were in the Go phase, 58% were in the GI phase, 8% in the S phase and 28% in the G2/M phases. With cells transfected with the plasmid comprising the IRDBP-1 sequence (SEQ ID NO: 14), 60% were in the Go phase, 25% of the cells were in the G1 phase, and only 7% of the cells were in S or G2/M phases.

EXAMPLE 23

Generation of IRDBP-1 Knockout Mice Using the IRDBP-1 cDNA Clones of the Present Invention To investigate the function of IRDBP-1, transgenic mice will be generated in which the IRDBP-1 gene is replaced by the $neo^r$ gene. A DNA construct will first be generated that contains $neo^r$ linked to a constitutive promoter. This gene will be flanked on either side by at least 1 kb of genomic IRDBP-1 sequence, which will allow for homologous recombination and integration of $neo^r$ into the endogenous IRDBP-1 gene. Finally, the Herpes Simplex Virus thymidine kinase (HSV-tk) gene will be incorporated into each end of the DNA construct, adjacent to the IRDBP-1 sequences, to allow for selection of homologous recombinants.

Following linearization, the DNA construct described above will be transfected into embryonic stem (ES) cells by electroporation, and these cells will be transferred to culture on gelatin-coated dishes. The addition of G418 will permit selection for cells that contain integration of $neo^r$, while the nucleoside analog gancyclovir will allow for selection of cells in which homologous recombination has occurred; homologous but not heterologous recombination results in removal of the HSV-tk genes from the transfected construct, thus preventing gancyclovir cytotoxicity. ES cell colonies that are resistant to both G418 and gancyclovir will be screened by PCR or Southern analysis for presence and copy number of the $neo^r$ gene, and positive colonies will be subcultured and amplified.

ES cells that have successfully integrated $neo^r$ in place of the IRDBP-1 gene will be used for morula aggregation with 8-cell embryos; aggregates will subsequently be implanted into pseudopregnant female mice. Chimeric mice will be identifiable by their coat color, since the aggregation of ES cells from the 129 strain of agouti mice with 8-cell embryos from an albino strand such as CDI will result in chimeric mice exhibiting white coats with brown splotches. Chimeras will be bred in order to look for germline transmission of the transgene; transgenic offspring will have completely brown coats and will be heterozygous for the transgene. These heterozygous mice will be crossed, resulting in a homozygous line if mutation of the IRDBP-1 is not lethal.

If inactivation of IRDBP-1 proves to be lethal, we will produce tissue-specific knockouts. A transgenic line will be created encoding Cre recombinase in selected tissues using the strategy of targeted transgene expression. A responder “knock-in” mouse will also be created containing a targeting vector that is nearly an exact copy of a segment of genomic IRDBP-1 DNA, except that a critical exon will be flanked by the sites binding the recombinanse (lox-P sites). The mice will be intercrossed, and compound transgenic knockout mice will be produced in which the target gene is excised by Cre recombinase only in the desired cell type ($Cre^{+/+}\times$IRDBP-$1^{-/-}$ or $Cre^{+/-}\times$IRDBP-$1^{-/-}$).

Once IRDBP-1 knockout mice (IRDBP-$1^{-/-}$) are obtained that survive widespread tissue inactivation of IRDBP-1, we will look for tissue-specific, developmental and metabolic changes. Although it is possible that other gene products might be capable of functionally replacing IRDBP-1, our preliminary experiments with stably transfected L6 myoblasts suggest that IRDBP-1 acts at the distal end of the insulin activation pathway and is thus unlikely to be genetically redundant. With tissue-specific knockouts (muscle Cre$^{+/+}$×floxed RDBP-1$^{-/-}$, adipose Cre$^{+/+}$×floxed IRDBP-1$^{-/-}$, and liver Cre$^{+/+}$×floxed IRDBP-1$^{-/-}$), serial crosses of mice will be conducted to allow concurrent inactivation of IRDBP-1 in multiple organs.

Once IRDBP-1 knockout mice are obtained , they will used to test insulin action, and investigate their susceptibility to diabetes and diabetes complications. Growth curves, including intrauterine growth, size and weight of the viscera, and necropsy at various ages to determine for gross histological differences will be determined. We will define the phenotype of the animals in terms of blood glucose, insulin, glucagon, cortisol and leptin measurements at fasted and fed levels. Irnmunohistochemical analysis of the pancreas, kidneys, intestine and organs targeted for knockout studies will be done to confirm the effectiveness of gene ablation and detect presence of changes associated with diabetes. Glucose tolerance tests will be performed by intraperitoneal glucose injection (2 mg/gm body weight), and tail bleed will be at 0, 30, 60 and 120 mins, after injection to check for glucose and insulin levels. Finally, wild-type, IRDBP-1-deficient and heterozygote littermates will be subjected to a diet high in fat (50% of calories from fat) and monitored for parameters of obesity-induced insulin resistance.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part.

What is claimed is:

1. A method of regulating a blood glucose level in a mammal with diabetes mellitus and/or insulin resistance, comprising the step of:

increasing an intracellular IRDBP-1 protein level in cells of the mammal by introducing a DNA construct encoding the IRDBP-1 protein into the cells of the mammal, thereby increasing glucose transport into the cells and resulting in regulation of the blood glucose level in the mammal, wherein the IRDBP-1 protein comprises an amino acid sequence selected from the group consisting of SEQ ID NOs: 11, 12, 13, 47, and 48, and wherein the step of increasing the intracellular IRDBP-1 level is insulin-independent.

2. The method according to claim 1, wherein the DNA construct comprises a nucleic acid sequence selected from the group consisting of SEQ ID NOs: 5, 8, 9, 10, 14, 44, and 45.

3. A method of mimicking an insulin effect on a cell in an insulin-independent manner comprising the step of:

introducing a DNA construct encoding IRDBP-1 protein into the cell, the IRDBP-1-encoding DNA construct being capable of expression of an effective amount of the IRDBP-1 protein in the cell, thereby resulting in an insulin-like effect on the cell in an insulin-independent manner, wherein the IRDBP-1 protein comprises an amino acid sequence selected from the group consisting of SEQ ID NOs: 11, 47, and 48.

4. The method according to claim 3, wherein the insulin-like effect comprises an increase in entry of extracellular glucose into the cell.

5. The method according to claim 3, wherein the insulin-like effect comprises an increase in transcription of an insulin-responsive gene.

6. The method according to claim 5, wherein the insulin-responsive gene encodes a protein selected from the group consisting of IGFBP-3, IGF-1 and IGFBP-1.

7. The method according to claim 6, wherein the insulin-responsive gene encodes the IGFBP-3 protein.

8. The method according to claim 3, wherein the DNA construct comprises a nucleic acid sequence selected from the group consisting of SEQ ID NOs: 5, 8, 9, 10, 14, 44, and 45.

9. The method according to claim 3, wherein the cell is present in a mammal.

10. The method according to claim 9, wherein the mammal is a human.

11. A method of increasing glucose uptake in a cell comprising the step of:

introducing into a cell a DNA construct encoding IRDBP-1 protein, the DNA construct being capable of expression of an effective amount of the IRDBP-1 protein in the cell, thereby increasing the glucose uptake into the cell, wherein the IRDBP-1 protein comprises an amino acid sequence selected from the group consisting of SEQ ID NOs: 11, 47 and 48.

12. The method according to claim 11, wherein the DNA construct comprises a nucleic acid sequence selected from the group consisting of SEQ ID NOs: 5, 8, 9, 10, 14, 44, and 45.

13. The method according to claim 11, wherein the cell is present in a mammal.

14. The method according to claim 13, wherein the mammal is a human.

15. A method of regulating a blood glucose level in a mammal with diabetes mellitus and/or noninsulin-dependent diabetes, comprising the step of:

introducing a DNA construct encoding IRDBP-1 protein into cells of the mammal, the DNA construct being capable of expression of an effective amount of the IRDBP-1 protein in the cells, thereby increasing glucose entry into the cells and resulting in regulation of the blood glucose level in the mammal, wherein the IRDBP-1 protein comprises an amino acid sequence selected from the group consisting of SEQ ID NOs: 11, 47, and 48.

16. The method according to claim 15, wherein the DNA construct comprises a nucleic acid sequence selected from the group consisting of SEQ ID NOs: 5, 8, 9, 10, 14, 44, and 45.

17. The method according to claim 15, wherein the mammal is a human.

* * * * *